(12) United States Patent
Orlandini Von Niessen et al.

(10) Patent No.: US 11,492,628 B2
(45) Date of Patent: Nov. 8, 2022

(54) 3'-UTR SEQUENCES FOR STABILIZATION OF RNA

(71) Applicants: BioNTech SE, Mainz (DE); TRON—Translationale Onkologie an der Universitätsmedizin der Johannes Gutenberg-Universität Mainz gGmbH, Mainz (DE)

(72) Inventors: Alexandra Orlandini Von Niessen, Mainz (DE); Stephanie Fesser, Mannheim (DE); Britta Vallazza, Darmstadt (DE); Tim Beissert, Gross-Gerau (DE); Andreas Kuhn, Mainz (DE); Ugur Sahin, Mainz (DE); Marco Alexander Poleganov, Egelsbach (DE)

(73) Assignees: BioNTech SE, Mainz (DE); TRON—Translationale Onkologie an der Universitätsmedizin der Johannes Gutenberg-Universität Mainz gGmbH, Mainz (DE)

( * ) Notice: Subject to any disclaimer, the term of this patent is extended or adjusted under 35 U.S.C. 154(b) by 563 days.

(21) Appl. No.: 15/763,709

(22) PCT Filed: Oct. 5, 2016

(86) PCT No.: PCT/EP2016/073814
§ 371 (c)(1),
(2) Date: Mar. 28, 2018

(87) PCT Pub. No.: WO2017/060314
PCT Pub. Date: Apr. 13, 2017

(65) Prior Publication Data
US 2019/0071682 A1    Mar. 7, 2019

(30) Foreign Application Priority Data
Oct. 5, 2016 (EP) .................. PCT/EP2015/073814

(51) Int. Cl.
| | | |
|---|---|---|
| C12N 15/67 | (2006.01) |
| A47B 3/00 | (2006.01) |
| A47B 13/02 | (2006.01) |
| A47B 33/00 | (2006.01) |
| A47B 43/00 | (2006.01) |
| A47B 77/02 | (2006.01) |
| A47B 77/06 | (2006.01) |
| A47B 77/08 | (2006.01) |
| A47B 77/16 | (2006.01) |
| A47B 77/18 | (2006.01) |
| A47B 95/00 | (2006.01) |
| A47C 4/00 | (2006.01) |
| A47C 4/08 | (2006.01) |
| A47C 7/00 | (2006.01) |
| A47K 3/28 | (2006.01) |
| B60B 33/00 | (2006.01) |

(Continued)

(52) U.S. Cl.
CPC .............. *C12N 15/67* (2013.01); *A47B 3/002* (2013.01); *A47B 13/02* (2013.01); *A47B 33/00* (2013.01); *A47B 43/00* (2013.01); *A47B 77/022* (2013.01); *A47B 77/06* (2013.01); *A47B 77/08* (2013.01); *A47B 77/16* (2013.01); *A47B 77/18* (2013.01); *A47B 95/00* (2013.01); *A47B 95/008* (2013.01); *A47C 4/00* (2013.01); *A47C 4/08* (2013.01); *A47C 7/002* (2013.01); *A47C 7/006* (2013.01); *A47K 3/284* (2013.01); *B60B 33/00* (2013.01); *C12N 5/0606* (2013.01); *C12N 15/113* (2013.01); *C12N 15/90* (2013.01); *E04H 1/1266* (2013.01); *F16C 11/04* (2013.01); *A47B 2003/006* (2013.01); *A47B 2200/0018* (2013.01); *C12N 2310/113* (2013.01)

(58) Field of Classification Search
CPC .... C12N 15/67; C12N 5/0606; C12N 15/113; C12N 15/90; C12N 2310/113
See application file for complete search history.

(56) References Cited

U.S. PATENT DOCUMENTS

| | | | |
|---|---|---|---|
| 4,897,355 A | 1/1990 | Eppstein et al. |
| 5,264,618 A | 11/1993 | Felgner et al. |

(Continued)

FOREIGN PATENT DOCUMENTS

| | | | |
|---|---|---|---|
| CN | 101855233 A | 10/2010 |
| CN | 104662156 A | 5/2015 |

(Continued)

OTHER PUBLICATIONS

Matoulkova et al in "The role of the 3' untranslated region in post-transcriptional regulation of protein expression in mammalian cells" (RNA Biology May 2012, pp. 563-576). (Year: 2012).*

(Continued)

*Primary Examiner* — Catherine S Hibbert
(74) *Attorney, Agent, or Firm* — Choate, Hall & Stewart LLP; Brenda Herschbach Jarrell; Janet M. Tse

(57) ABSTRACT

The present invention relates to stabilization of RNA, in particular mRNA, and an increase in mRNA translation. The present invention particularly relates to a modification of RNA, in particular in vitro-transcribed RNA, resulting in increased transcript stability and/or translation efficiency. According to the invention, it was demonstrated that certain sequences in the 3'-untranslated region (UTR) of an RNA molecule improve stability and translation efficiency.

73 Claims, 20 Drawing Sheets
Specification includes a Sequence Listing.

(51) Int. Cl.
    *E04H 1/12* (2006.01)
    *F16C 11/04* (2006.01)
    *C12N 5/0735* (2010.01)
    *C12N 15/113* (2010.01)
    *C12N 15/90* (2006.01)

(56) References Cited

U.S. PATENT DOCUMENTS

| | | | |
|---|---|---|---|
| 5,703,055 | A | 12/1997 | Felgner et al. |
| 6,251,399 | B1 | 6/2001 | Diamond et al. |
| 6,472,176 | B2 | 10/2002 | Kovesdi et al. |
| 6,500,641 | B1 | 12/2002 | Chen et al. |
| 6,586,410 | B1 | 7/2003 | Wheeler et al. |
| 7,303,881 | B2 | 12/2007 | Huang et al. |
| 7,462,354 | B2 | 12/2008 | Sette et al. |
| 7,790,696 | B2 | 9/2010 | Gregoriadis |
| 8,017,326 | B2 | 9/2011 | Jan et al. |
| 8,140,270 | B2 | 3/2012 | Kingsmore et al. |
| 8,217,016 | B2 | 7/2012 | Hoerr et al. |
| 8,349,558 | B2 | 1/2013 | Fatho et al. |
| 8,703,142 | B2 | 4/2014 | Diamond et al. |
| 8,853,283 | B2 | 10/2014 | Platscher et al. |
| 8,877,206 | B2 | 11/2014 | Chen et al. |
| 9,115,402 | B2 | 8/2015 | Hacohen et al. |
| 2005/0032730 | A1 | 2/2005 | Von Der Mulbe et al. |
| 2005/0054011 | A1 | 3/2005 | Jan et al. |
| 2007/0025968 | A1 | 2/2007 | Van Der Burg et al. |
| 2009/0055944 | A1 | 2/2009 | Korman et al. |
| 2009/0217401 | A1 | 8/2009 | Korman et al. |
| 2012/0237975 | A1 | 9/2012 | Schrum et al. |
| 2013/0115272 | A1 | 5/2013 | de Fougerolles et al. |
| 2013/0123481 | A1 | 5/2013 | de Fougerolles et al. |
| 2013/0156849 | A1 | 6/2013 | de Fougerolles et al. |
| 2013/0203115 | A1 | 8/2013 | Schrum et al. |
| 2013/0237593 | A1 | 9/2013 | de Fougerolles et al. |
| 2013/0237594 | A1 | 9/2013 | de Fougerolles et al. |
| 2013/0244243 | A1 | 9/2013 | Matsuyama et al. |
| 2013/0244278 | A1 | 9/2013 | de Fougerolles et al. |
| 2013/0244279 | A1 | 9/2013 | de Fougerolles et al. |
| 2013/0245106 | A1 | 9/2013 | de Fougerolles et al. |
| 2013/0245107 | A1 | 9/2013 | de Fougerolles et al. |
| 2013/0255281 | A1 | 10/2013 | Bray |
| 2013/0266640 | A1 | 10/2013 | de Fougerolles et al. |
| 2014/0010861 | A1 | 1/2014 | Bancel et al. |
| 2014/0147454 | A1 | 5/2014 | Chakraborty et al. |
| 2015/0017211 | A1 | 1/2015 | de Fougerolles et al. |
| 2015/0030576 | A1 | 1/2015 | Bancel |
| 2015/0167017 | A1 | 6/2015 | Roy et al. |

FOREIGN PATENT DOCUMENTS

| | | |
|---|---|---|
| DE | 3856241 T2 | 3/1999 |
| DE | 69132916 T2 | 10/2002 |
| DE | 69332803 T2 | 3/2004 |
| EA | 006761 | 4/2006 |
| EA | 011557 | 4/2009 |
| EP | 0292435 A1 | 11/1988 |
| EP | 0839912 A1 | 5/1998 |
| EP | 1242108 A1 | 9/2002 |
| EP | 2569633 A2 | 3/2013 |
| RU | 2126047 C1 | 2/1999 |
| RU | 2148081 C1 | 4/2000 |
| RU | 2152997 C2 | 7/2000 |
| RU | 2307872 C2 | 10/2007 |
| RU | 2491343 C1 | 8/2013 |
| RU | 2535871 C1 | 12/2014 |
| WO | WO-91/19806 A1 | 12/1991 |
| WO | WO-94/14970 A1 | 7/1994 |
| WO | 1994023031 A1 | 10/1994 |
| WO | 1998014464 A1 | 4/1998 |
| WO | 1999024566 A1 | 5/1999 |
| WO | 1999052503 A2 | 10/1999 |
| WO | 2000/20029 A1 | 4/2000 |
| WO | 2000/050592 A1 | 8/2000 |
| WO | 2000067761 A1 | 11/2000 |
| WO | 2001047959 A2 | 7/2001 |
| WO | WO-01/73087 A1 | 10/2001 |
| WO | 2001093902 A2 | 12/2001 |
| WO | 2002048377 A2 | 6/2002 |
| WO | 2002083714 A2 | 10/2002 |
| WO | 02/098443 A2 | 12/2002 |
| WO | WO-03/018760 A1 | 3/2003 |
| WO | 2003051401 A2 | 6/2003 |
| WO | 2003068257 A1 | 8/2003 |
| WO | 2003106692 A2 | 12/2003 |
| WO | 2004004743 A1 | 1/2004 |
| WO | WO-2004/033690 A1 | 4/2004 |
| WO | 2005030250 A2 | 4/2005 |
| WO | 2005039533 A1 | 5/2005 |
| WO | 2005040816 A1 | 5/2005 |
| WO | 2005110338 A2 | 11/2005 |
| WO | WO-2006/082398 A2 | 8/2006 |
| WO | 2006121168 A1 | 11/2006 |
| WO | 2007024708 A2 | 3/2007 |
| WO | 2007025760 A2 | 3/2007 |
| WO | 2007031222 A2 | 3/2007 |
| WO | 2007036366 A2 | 4/2007 |
| WO | 2007/068265 A1 | 6/2007 |
| WO | 2007101227 A2 | 9/2007 |
| WO | WO-2007/122369 A2 | 11/2007 |
| WO | 2008080468 A1 | 7/2008 |
| WO | 2008083174 A2 | 7/2008 |
| WO | 2008085562 A2 | 7/2008 |
| WO | 2008/112127 A2 | 9/2008 |
| WO | 2008116078 A2 | 9/2008 |
| WO | 2008156712 A1 | 12/2008 |
| WO | 2009053041 A2 | 4/2009 |
| WO | WO-2009/042971 A2 | 4/2009 |
| WO | 2009118296 A2 | 10/2009 |
| WO | 2009129227 A1 | 10/2009 |
| WO | WO-2010/037402 A1 | 4/2010 |
| WO | 2010066418 A1 | 6/2010 |
| WO | 2011012316 A2 | 2/2011 |
| WO | WO-2011/075838 A1 | 6/2011 |
| WO | 2011143656 A2 | 11/2011 |
| WO | 2012045075 A1 | 4/2012 |
| WO | 2012045082 A2 | 4/2012 |
| WO | 2012135805 A2 | 10/2012 |
| WO | 2012159729 A1 | 11/2012 |
| WO | 2013040142 A1 | 3/2013 |
| WO | 2013052523 A1 | 4/2013 |
| WO | 2013090648 A1 | 6/2013 |
| WO | 2013/120629 A1 | 8/2013 |
| WO | 2013124701 A2 | 8/2013 |
| WO | 2013143698 A1 | 10/2013 |
| WO | 2013143699 A1 | 10/2013 |
| WO | 2013143700 A2 | 10/2013 |
| WO | 2013151663 A1 | 10/2013 |
| WO | 2013151664 A1 | 10/2013 |
| WO | 2013151665 A2 | 10/2013 |
| WO | 2013151672 A2 | 10/2013 |
| WO | 2014012051 A1 | 1/2014 |
| WO | WO-2014/028295 A2 | 2/2014 |
| WO | 2014071219 A1 | 5/2014 |
| WO | 2014093924 A1 | 6/2014 |
| WO | 2014144039 A1 | 9/2014 |
| WO | 2014144711 A1 | 9/2014 |
| WO | 2014144767 A1 | 9/2014 |
| WO | 2014152027 A1 | 9/2014 |
| WO | 2014152030 A1 | 9/2014 |
| WO | 2014152031 A1 | 9/2014 |
| WO | 2014152211 A1 | 9/2014 |
| WO | 2014159813 A1 | 10/2014 |
| WO | 2014160243 A1 | 10/2014 |
| WO | 2014164253 A1 | 10/2014 |
| WO | 2014168874 A2 | 10/2014 |
| WO | WO-2014/184684 A1 | 11/2014 |
| WO | 2015014375 A1 | 2/2015 |
| WO | 2015034925 A1 | 3/2015 |
| WO | 2015034928 A1 | 3/2015 |
| WO | 2015038892 A1 | 3/2015 |
| WO | 2015043613 A1 | 4/2015 |
| WO | 2015051169 A2 | 4/2015 |
| WO | 2015051173 A2 | 4/2015 |

(56) References Cited

FOREIGN PATENT DOCUMENTS

| | | |
|---|---|---|
| WO | 2015058780 A1 | 4/2015 |
| WO | 2015085318 A2 | 6/2015 |
| WO | 2015089511 A2 | 6/2015 |
| WO | 2015/101414 A2 | 7/2015 |
| WO | 2015/101415 A1 | 7/2015 |
| WO | 2015117620 A1 | 8/2015 |
| WO | WO-2015/138348 A1 | 9/2015 |
| WO | 2015164674 A1 | 10/2015 |
| WO | 2015172843 A1 | 11/2015 |
| WO | 2016/005004 A1 | 1/2016 |
| WO | 2016/005324 A1 | 1/2016 |
| WO | 2016062323 A1 | 4/2016 |
| WO | 2016/091391 A1 | 6/2016 |
| WO | 2016107877 A1 | 7/2016 |
| WO | 2016155809 A1 | 10/2016 |
| WO | WO-2017/059902 A1 | 4/2017 |

OTHER PUBLICATIONS

Jemiely et al (RNA 2003 vol. 9: pp. 1108-1122). (Year: 2003).*
International Preliminary Report on Patentability issued in corresponding International Application No. PCT/EP2016/073814, dated Apr. 19, 2018.
Pon, R and Yu, S., Tandem oligonucleotide synthesis using linker phosphoramidites, Nucleic Acids Res, 33(6):1940-1948 (2005).
Roberts, R. et al., REBASE—enzymes and genes for DNA restriction and modification, Nucleic Acids Research, 35(Database issue):D269-70 (2007).
UniProtKB—P36888 (FLT3_Human), last sequence update: Aug. 21, 2007.
UniProtKB—Q9NVD7 (Parva_Human), last sequence update: Oct. 1, 2000.
UniProtKB—Q5SW79 (CE170_Human), last sequence update: Dec. 21, 2004.
Dolgin, "The Billion-Dollar Biotech," Nature, vol. 522, pp. 26-28, Jun. 4, 2015.
Agrawal et al., Trend in Biotechnology, 14(10):376-387, 1996.
Mayer et al., Anticancer Research 25:3917-3924 (2005).
Bei et al.J Immunother. May 1998;21(3):159-69.
Boczkowski et al. (1996). "Dendritic cells pulsed with RNA are potent antigen-presenting cells in vitro and in vivo," J. Exp. Med. 184: 465-472.
Bowerman, NA. "Engineering the binding properties of the T cell receptor: peptide: MHC ternary complex that governs T cell activity." Mol. Immun. 46: 3000-3008, 2009.
Brickner et al. J. Exp. Med 193(2) 195-205 (2001).
Del Val et al., Cell, vol. 66, Issue 6, Sep. 20, 1991, pp. 1145-1153.
Conry et al. (1994). "Immune response to a carcinoembryonic antigen polynucleotide vaccine," Cancer Res. 54:1164-1168.
Conry et al. (1995). "Characterization of a messenger RNA polynucleotide vaccine vector," Cancer Res. 55:1397-1400.
Coulie et al. (1995). "A mutated intron sequence codes for an antigenic peptide recognized by cytolytic T lymphocytes on a human melanoma," Proc. Natl. Acad. Sci. USA 92: 7976-7980.
Dengjel, J. et al. "Glycan side chains on naturally presented MHC class II ligands" J. Mass Spectrom, 2005.
Ding et al. "Genome remodeling in a basal-like breast cancer metastatis and xenograft." Nature, 464: 999-1005, 2010.
Dolgin, Nature 522:26.
Fritsch, E. F. et al. "HLA-Binding Properties of Tumor Neoepitopes in Humans" Cancer Immunology Research, 2: 522-529, 2014.
Gnirke, A. "Solution hybrid selection with ultra-long oligonucleotides for massively parallel targeted sequencing" Nat. Biotechnol, 2009.
Goya, R. et al. "SNVMix: predicting single nucleotide variants from next-generation sequencing of tumors, Bioinformatics" Bioinformatics, 26: 730-736, 2010.
Gryaznov et al., Biochim. Biophys. Acta, 1489:131-140, 1999.
Guyre et al., Cancer Immunother (1997) 45:146-148.

Hacohen Decl. dated Feb. 16, 14 filed in U.S. Appl. No. 13/108,610, 10 pages.
Hoerr et al. (2000). "In vivo application of RNA leads to induction of specific cytotoxic T lymphocytes and antibodies," Eur. J. Immunol 30:1-7.
Johanning et al. Nucleic Acids Res. May 11, 1995; 23(9): 1495-1501.
Kenter, G. G. et al. "Phase I Immunotherapeutic Trial with Long Peptides Spanning the E6 and E7 sequences of High-risk human papillomavirus 16 in End-stage cervical cancer patients shows low toxicity and robust immunogenicity." Clinical Cancer Research, 14:169-177, 2008.
Keogh, E. et al. "Identification of New Epitopes from Four Different Tumor-Associated Antigens: Recognition of Naturally Processed Epitopes Correlates with HLA-A*0201-Binding Affinity" J Immunol. 167: 787-796, 2001.
Lemmel, Claudia et al., "Differential quantitative analysis of MHC ligands by mass spectrometry using stable isotope labeling" Nat Biotechnol, 2004.
Lennerz et al. (2005). "The response of autologous T cells to a human melanoma is dominated by mutated neoantigens," Proc Natl Acad. Sci USA 102: 16013-16018.
Ley et al. (2008). "DNA sequencing of a cytogenetically normal acute myeloid leukaemia genome," Nature 456: 66-72.
Li et al., Cancer Genome Sequencing and its Implications for Personalized Cancer Vaccine, Cancer 2011, 3, 4191-4211.
Maksyutov and Zagrebelnaya (1993). "ADEPT: a computer program for prediction of protein antigenic determinants," Comput. Appl. Biosci. 9:291-297.
Mandelboim et al. (1995). "Regression of established murine carcinoma metastases following vaccination with tumour-associated antigen peptides," Nature Medicine 1:1179-1183.
Mardis, ER. "Recurring Mutations Found by Seuencing an Acute Myeloid Leukemia Genome" New England J. Med. 361: 1058-1066, 2009.
Margulies, Marcel et al., "Genome Sequencing in Open Microfabricated High Density Picoliter Reactors" Nature, 2005.
Martinon et al. (1993). Induction of virus-specific cytotoxic T lymphocytes in vivo by liposome-entrapped mRNA. Eur. J. Immunol 23, 1719-1722.
Meyerson, M. et al. "Advances in understanding cancer genomes through second-generation sequencing" Nature Rev. Genetics. 11:685-695, 2010.
Monach et al. (1995). "A unique tumor antigen produced by a single amino acid substitution," Immunity 2: 45-59.
Mortazavi (2008). "Mapping and quantifying mammalian transcriptomes by RNA-Seq," Nature Methods 5: 621-628.
Parker et al., J. Immunol. 152 (1994), 163-175.
Parkhurst, MR. et al. "Improved Induction of Melanoma-reactive CTL with peptides from the melanoma antigen gp100 modified at HLA-A*0201-binding residues" J. Immunol. 157: 2549-2548, 1996.
Parmiani, G. et al. "Unique Human Tumor Antigens: Immunobiology and Use in Clinical Trials." The Journal of Immunology, 178: 1975-1979, 2007.
Perissi et al., Electron Spin Resonance and Differential Scanning Calorimetry as Combined Tools for the Study of Liposomes in the Presence of Long Chain Nitroxides, 106 J. of Phys. Chem. B 10468 (2002).
Pfohl et al., Biological Polyelectrolyte Complexes in Solution and Confined on Patterned Surfaces, 198-200 Colloids & Surfaces A: Physicochemical and Eng. Aspects 613 (2002).
Pilla, L. et al. "Multipeptide vaccination in cancer patients" Expert Opinion on Biological Therapy, 9: 1043-1055, 2009.
Pleasance, E. et al. "A comprehensive catalogue of somatic mutaitons from a human cancer genome." Nature, 463: 191-196, 2010.
Pleasance, E. et al. "A small-cell lung cancer genome with complex signatures of tobacco exposure." Nature, 463: 184-190, 2010.
Rammensee (2006). "Some considerations on the use of peptides and mRNA for therapeutic vaccination against cancer," Immunol Cell Biol. 84(3):290-4.
Rammansee 2008, Chapter 50: Cancer Vaccines: Some Basic Considerations, Genomic and Personalized Medicine, Hungtington and Ginsburg E-published on Nov. 11, 2008.

(56) References Cited

OTHER PUBLICATIONS

Rammensee et al. (2002). "Toward patient-specific tumor antigen selection for vaccination," Immunol. Rev. 188: 164-176.
Rammensee et al., Immunogenentics, 50 (1999), 213-219.
Rao (1994). "Epitope-based vaccines: One step at a time," Proc. Indian natn. Sci. Acad. B60: 419-424.
Ressing, M. et al. "Human CTL epitopes encoded by human papillomavirus types 16E6 . . . " J. Immunol. 154:5934-5943, 1995.
Saenz-Badillos et al. (2001). "RNA as a tumor vaccine: a review of the literature," Exp Dermatol. 10(3):143-54.
Segal et al. (2008). "Epitope landscape in breast and colorectal cancer," Cancer Res. 68: 889-892.
Sensi and Aanichini, Unique Tumor Antigens: Evidence for Immune Control of Genome Integrity and Immunogenic Targets for T cell-mediated Patient-Specific Immunotherapy, Clin. Cancer Res. 2006:12(17), 5023.
Sette, A. et al. "Peptide Binding to the Most Frequent HLA-A Class I Alleles Measured by Quantitative Molecular Binding Assays" Mol. Immunol. 31: 813-822, 1994.
Sette, A. et al. "The Relationship Between Class I Binding Affinity and Immunogenicity of Potential Cytotoxic T cell Epitopes." J. Immunol. 153: 5586-5592, 1994.
Shah et al. (2009). "Mutation of FOXL2 in granulosa-cell tumors of the ovary," N. Eng. J. Med. 360: 2719-2729.
Sjöblom et al. (2006). "The consensus coding sequences of human breast and colorectal cancers," Science 314: 268-274.
Stephens et al. (2005). "A screen of the complete protein kinase gene family identifies diverse patterns of somatic mutations in human breast cancer," Nature Genetics, 37: 590-592.
Thomson et al., J. Virology (1998), 72(3):2246-2252.
Toes et al. (1997). "Protective anti-tumor immunity induced by vaccination with recombinant adenoviruses encoding multiple tumor-associated cytotoxic T lymphocyte epitopes in a string-of-beads fashion," Proc. Natl. Acad. Sci. USA 94: 14660-14665.
UniProtKB, "Print-outs from the UniProtKB database concerning the CEP170, PARVA and FLT3 genes".
van der Bruggen et al. (1991). "A gene encoding an antigen recognized by cytolytic T lymphocytes on a human melanoma," Science 254:1643-1647.
Van Laere AS, Nguyen M, Braunschweig M. et al. A regulatory mutation in IGF2 causes a major QTL effect on muscle growth in the pig. Nature. 2003;425(6960):832-836.
Weinschenk et al. (2002). "Integrated functional genomics approach for the design of patient-individual antitumor vaccines," Cancer Res 62: 5818-5827.
Wolff et al. (1990). "Direct gene transfer into mouse muscle in vivo," Science 247:1465-1468.
Wood et al. (2007). "The genomic landscapes of human breast and colorectal cancers," Science 318: 1108-1113.
Wortzel et al. (1983). "Multiple tumour-specific antigens expressed on a single tumour cell," Nature 304: 165-167.
Zhou et al., Hum. Gene Ther., 10(16)12719-24, 1999.
U.S. Appl. No. 61/334,866, filed May 14, 2010.
Dec. 13, 2013 (EP) Office Action—Appl. No. 16778784.5.
Mar. 17, 2017—International Search Report and Written Opinion of PCT/EP2016/073814.
Ledda M et al;"Effect of 3' UTR length on the translatioinal regulation of 5'-terminal oligopyrimidine mRNAs", Gene, vol. 344, Jan. 3, 2004 (Jan. 3, 2004), pp. 213-220, XP027872598, Elsevier, Amsterdam, NL ISSN: 0378-1119 [retrieved on Jan. 3, 2005].
S. Holtkamp et al: "Modification of antigen-encoding RNA increases stability, translational efficacy, and T-cell stimulatory capacity of dendritic cells", Blood, vol. 108, No. 13, Dec. 15, 2006 (Dec. 25, 2006), pp. 4009-4017, XP055044965, ISSN: 0006-4971, DOI: 10.1182/blood-2006-04-015024.
Xia Hongwei et al;:"Suppression of RND3 activity by AES downregulation promotes cancer cell proliferation and invasion ", International Journal of Molecular Medecine, vol. 31, No. 5, May 2013 (May 2013), pp. 1081-1086, XP002767661, ISSN: 1791-244X.
Wang Jun et al:"PLD3 in Alzheimer's disease." Molecular Neurobiology, vol. 51, No. 2, Apr. 2015 (Apr. 2015)m pp. 480-486, XP002767662, ISSN: 1559-1182, DOI: 10.1007/s12035-014-8779-5.
Cao Jingxin et al: "A human homolog of the cavvinia virus HindIII K4L gene is a member of the phospholipase D superfamily", Virus Research, vol. 48, No. 1, Jan. 1, 1997 (Jan. 1, 1997), pp. 11-18, XP002209546, Amsterdam, NL, ISSN: 0168-1702, DOI: 10.1016/S0168-1702(96)01422-0.
Osisami Mary et al: "A role for phospholipase D3 in myotube formation.", PLOS ONE, vol. 7, No. 3, E33341, Mar. 2012 (Mar. 2012), pp. 1-10, XP002767663, ISSN: 1932-6203.
Lee Changhan et al: "The mitochondrial-derived peptide MOTS-c promotes metabolic homeostasis and reduces obesity and insulin resistance.", Cell Metabolism, vol. 21, No. 3, Mar. 3, 2015 (Mar. 3, 2015), pp. 443-454, XP002767664, ISSN: 1932-7420.
Alexandra Gabriela Odandi von Niessen: "Optimization of RNA cancer vaccines using 3' UTR sequence selected for stabilization of RNA (Dissertation)", Sep. 5, 2016 (Sep. 5, 2016), pp. FP-108, I-VII, XP002767665, Fachbereich Biologie der Johannes Gutenberg-Universitat in Mainz; Retrieved from the Internet: URL: https://publications.ub.uni-mains.de/theses/volltexte/2016/100000811/pdf/100000811.pdf [retrieved on Feb. 28, 2017].
Pieper Lisa A et al: "Secretory pathway optimization of CHO producer cells by co-engineering of the mitosRNA-1978 target genes CerS2 and Tbc1D20." Metabolic Engineering, Jan. 11, 2017 (Jan. 11, 2017), XP002767666, ISSN: 1096-7184.
Sep. 6, 2016—International Search Report and Written Opinion of PCT/EP2015/073180.
Mikulska J E et al: "Cloning and analysis of the gene encoding the human neonatal Fc receptor", European Journal of Immunogenetics, vol. 27, No. 4, Aug. 1, 2000 (Aug. 1, 2000), pp. 231-240, XP009093953, Oxford, GB ISSN: 0960-7420, DOI: 10.1046/J. 1365-2370.2000. 00225.X.
GenBank Accession No. FJ376737, pmirGLO Dual-Luciferase miRNA Target Expression Vector Protocol, 2 pages (revised Aug. 2016).
Martinez-Sanchez, A. et al., DICER Inactivation Identifies Pancreatic β-Cell "Disallowed" Genes Targeted by MicroRNAs, Mol. Endocrinol., 29(7):1067-1079 (2015).
PMIR-Report System, miRNA Expression Reporter Vector, Applied Biosystems, 12 pages (Oct. 24, 2008).
Xie, T. et al., MicroRNA-127 Inhibits Lung Inflammation by Targeting IgG Fcγ Receptor I, J. Immunol., 188:2437-2444 (2012).
Kim, J.S. et al., Reprogrammed Pluripotent Stem Cells from Somatic Cells, International Journal of Stem Cells, 4(1): 8 pages (2011).
Krause, A. and Worgall, S., Delivery of antigens by viral vectors for vaccination, Therapeutic Delivery, 2(1):51-70 (2011).

* cited by examiner

```
D2 - | hAg | Firefly Luciferase | Fl  | - A30L70
D2 - | hAg | Firefly Luciferase | 2hBg | - A30L70
Cap   5'UTR        CDS            3'UTR   polyA tail
```

B

|  | RNA integrity | |
|---|---|---|
|  | unmodified | m1Y modified |
| D-2-hAg-Luc-F-I-UTR-[A30-L-A70] | 81 | 84 |
| D-2-hAg-Luc-2hBgUTR-[A30-L-A70] | 82 | 84 |

Figure 10

CUGGUACUGCAUGCACGCAAUGCUAGCUGCCCCUUUCCCGUCCUGGGUACCCCGAGU
CUCCCCCGACCUCGGGUCCCAGGUAUGCUCCCACCUCCACCUGCCCCACUCACCACC
UCUGCUAGUUCAGACACCUCCcaagcacgcagcaaugcagcucaaaacgcuuagcc
uagccacacccccacgggaaacagcagugauuaaccuuuagcauaaacgaaaguuu
aacuaagcuauacuaaccccaggguuggucaauuucgugccagccacacc

D

E

F

SEQUENCE LISTING

<160> NUMBER OF SEQ ID NOS: 235

<210> SEQ ID NO 1
<211> LENGTH: 208
<212> TYPE: RNA
<213> ORGANISM: Homo sapiens

<400> SEQUENCE: 1
cauccugcug cugcugcugc ugcugcugcg ggucuuccug gaaucugacc auucguuguc    60
ugcuaugccc guccucacca agacugacug ccugcugccuu ugcuacugcc cgggccaug   120 agacugacuu cccacugcuc ugccugccuc uccccacugc acuggcacag cccgccuug   180 ccgcugcuga uccauugccg gugugacc                                      208

<210> SEQ ID NO 2
<211> LENGTH: 202
<212> TYPE: RNA
<213> ORGANISM: Homo sapiens

<400> SEQUENCE: 2

```
gcugcugcug cugcugcugc ugcgggucuu ccuggaaucu gaccauucgu ugucugcuau    60
gcccguccuc accaagacug acugccugcu gcuuugcuac ugcccgggcc caugagacug   120
acuucccacu gcucuccug ccucuccca cugcacuggc acagccccgc cuugccgcug    180
cugauccauu gccgguguga cc                                            202
```

<210> SEQ ID NO 3
<211> LENGTH: 210
<212> TYPE: RNA
<213> ORGANISM: Homo sapiens

<400> SEQUENCE: 3

```
uuccugcugc ugcugcugcu gcugcugcug cgggucuucc uagaaucuga ccauucguug    60
ucugcuaugc ccguccucac caagacugac ugccugcugc uuugcuacug cccgggccca   120
ugagacugac uucccacugc ucugccugcc ucucccacu gcacuggcac agccccgccu    180
ugccgcugcu gauccauugc cggugagacc                                    210
```

<210> SEQ ID NO 4
<211> LENGTH: 193
<212> TYPE: RNA
<213> ORGANISM: Homo sapiens

<400> SEQUENCE: 4

```
ugcugcugcu gcugcggguc uuccuggaau cugaccauuc guugucugcu augcccgucc    60
ucaccaagac ugacugccug cugcuuugcu acugcccggg cccaugagac ugacuuccca   120
cugcucugcc ugccucuccc cacugcacug gcacagcccc gccuugccgc ugcugaucca   180
uugccggcgg aca                                                       193
```

<210> SEQ ID NO 5
<211> LENGTH: 186
<212> TYPE: RNA
<213> ORGANISM: Homo sapiens

<400> SEQUENCE: 5

```
gcugcugcgg gucuuccugg aaucugacca uucguugucu gcuaugcccg uccucaccaa    60
gacugacugc cugcugcuuu gcuacugccc gggcccauga cugacuuc ccacugcucu     120 gccugccucu ccccacugca cuggcacagc cccgccuugc cgcugcugau ccauugccgg   180
cguacc                                                              186
```

<210> SEQ ID NO 6
<211> LENGTH: 170
<212> TYPE: RNA
<213> ORGANISM: Homo sapiens

<400> SEQUENCE: 6

```
cuggaaucug accauucguu gucugcuaug cccguccuca ccaagacuga cugccugcug    60
cuuugcuacu gcccgggccc augagacuga cuucccacug cucugccugc cucuccccac   120
ugcacuggca gccccgcc uugccgcugc ugauccauug ccggcggacc                170
```

<210> SEQ ID NO 7
<211> LENGTH: 206
<212> TYPE: RNA
<213> ORGANISM: Homo sapiens

```
<400> SEQUENCE: 7
uccugcugcu gcugcugcug cugcugcggg ucuuccugga aucugaccau ucguugucug      60
cuaugcccgu cccaccaag acugacugcc ugcugcuuug cuacugcccg ggcccaugag      120
acugacuucc cacugcucug ccugccucuc cccacugcac uggcacagcc ccgccuugcc     180
gcugcugauc cauugccggu gggacc                                          206

<210> SEQ ID NO 8
<211> LENGTH: 121
<212> TYPE: RNA
<213> ORGANISM: Homo sapiens

<400> SEQUENCE: 8
cugccugcug cuuugcuacu gcccgggccc augagacuga cuucccacug cucugccugc      60 cucucccac ugcacuggca gcccccgcc uugccgcugc ugauccauug ccgguagaac      120
c                                                                    121

<210> SEQ ID NO 9
<211> LENGTH: 206
<212> TYPE: RNA
<213> ORGANISM: Homo sapiens

<400> SEQUENCE: 9
uccugcugcu gcugcugcug cugcugcggg ucuuccugga aucugaccau uuguugucug      60
cuaugcccgu cccaccaag acugacugcc ugcugcuuug cuacugcccg ggcccaugag      120
acugacuucc cacugcucug ccugccucuc cccacugcac uggcacagcc ccgccuugcc     180
gcugcugauc cauugccggu gggacc                                          206

<210> SEQ ID NO 10
<211> LENGTH: 196
<212> TYPE: RNA
<213> ORGANISM: Homo sapiens

<400> SEQUENCE: 10
gcugcugcug cugcugcggg ucuuccugga aucugaccau ucguugucug cuaugcccgu      60 cccaccaag acugacugcc ugcugcuuug cuacugcccg ggcccaugag acugacuucc      120
cacugcucug ccugccucuc cccacugcac uggcacagcc ccgccuugcc gcugcugauc    180
cauugccggu gugacc                                                    196

<210> SEQ ID NO 11
<211> LENGTH: 276
<212> TYPE: RNA
<213> ORGANISM: Homo sapiens

<400> SEQUENCE: 11
ucuggccuca cugagucuga agagcuguua acuaccaugg ccaguccucc cugagucuga      60
ccaucuucca uccugcugcu gcugcugcug cugcugcggg ucuuccugga aucugaccau    120
ucguugucug cuaugcccgu cccaccaag acugacugcc ugcugcuuug cuacugcccg    180
ggcccaugag acugacuucc cacugcucug ccugccucuc cccacugcac uggcacagcc    240
ccgccuugcc gcugcugauc cauugccggu gugacc                              276

<210> SEQ ID NO 12
<211> LENGTH: 276
<212> TYPE: RNA
<213> ORGANISM: Homo sapiens
```

<400> SEQUENCE: 12

| | |
|---|---|
| ucuggccuca cugagucuga agagcuguua acuaccaugg ccagccuccc cugagucuga | 60 |
| ccaucuucca uccugcugcu gcugcugcug cugcugcggg ucuuccugga aucugaccau | 120 |
| ucguugucug cuaugcccgu ccucaccaag acugacugcc ugcugcuuug cuacugcccg | 180 |
| ggcccaugag acugacuucc cacugcucug ccugccucuc cccacugcac uggcacagcc | 240 |
| ccgccuugcc gcugcugauc cauugccggu gugacc | 276 |

<210> SEQ ID NO 13
<211> LENGTH: 245
<212> TYPE: RNA
<213> ORGANISM: Homo sapiens

<400> SEQUENCE: 13

| | |
|---|---|
| cuaccauggc caguccuccc ugagucugac caucuuccau ccugcugcug cugcugcugc | 60 |
| ugcugcgggu cuuccuggaa ucugaccauu cguugucugc uaugcccguc cucaccaaga | 120 |
| cugacugccu gcugcuuugc uacugcccgg gcccaugaga cugacuuccc acugcucugc | 180 |
| cugccuuucc ccacugcacu ggcacagccc cgccuugccg cugcugaucc auugccggug | 240 |
| ugacc | 245 |

<210> SEQ ID NO 14
<211> LENGTH: 233
<212> TYPE: RNA
<213> ORGANISM: Homo sapiens

<400> SEQUENCE: 14

| | |
|---|---|
| guccucccug agucugacca ucuuccaucc ugcugcugcu gcugcugcug cugcgggucu | 60 |
| uccuggaauc ugaccauucg uugucugcua ugcccgbccu caccaagacu gacugccugc | 120 |
| ugcuuugcua cugcccgggc ccaugagacu gacuucccac ugcucugccu gccucucccc | 180 |
| acugcacugg cacagccccg ccuugccgcu gcugauccau ugccggucug aca | 233 |

<210> SEQ ID NO 15
<211> LENGTH: 232
<212> TYPE: RNA
<213> ORGANISM: Homo sapiens

<400> SEQUENCE: 15

| | |
|---|---|
| guccucccug agucugacca ucuuccaucc ugcugcugcu gcugcugcug cugcgggucu | 60 |
| uccuggaauc ugaccauuug uugucugcua ugccccuccu caccaagacu gacugccugc | 120 |
| ugcuuugcua cugcccgggc ccaugagacu gacuucccac ugcucugccu gccuucccca | 180 |
| cugcacuggc acagccccgc cuugccgcug cugauccauu gccgguguga cc | 232 |

<210> SEQ ID NO 16
<211> LENGTH: 208
<212> TYPE: RNA
<213> ORGANISM: Homo sapiens

<400> SEQUENCE: 16

| | |
|---|---|
| ccauccugcu gcugcugcug cugcugcugc gggucuuccu ggaaucugac cauucguugu | 60 |
| cugcuaugcc cguccucacc aagacugacu gccugcugcu ugcuacugcc cgggcccaug | 120 |
| agacugacuu cccacugcuc ugccugccuc uccccacugc acuggcacag ccccgccuug | 180 |
| ccgcugcuga uccauugccg gugugacc | 208 |

<210> SEQ ID NO 17
<211> LENGTH: 237
<212> TYPE: RNA
<213> ORGANISM: Homo sapiens

<400> SEQUENCE: 17
gccaguccuc ccugagucug accaucuucc auccugcugc ugcugcugcu gcugcugcgg      60
gucuuccugg aaucugacca uucguugucu gcuaugcccg uccucaccaa gacugacugc     120
cugcugauuu gcuacugccc gggcccauga gacugacuuc ccacugcucu gccugccucu     180
ccccacugca cuggcacagc cccgccuugc cgcugcugau ccauugccgg ugugacc       237

<210> SEQ ID NO 18
<211> LENGTH: 297
<212> TYPE: RNA
<213> ORGANISM: Homo sapiens

<400> SEQUENCE: 18
ugccuuccgu cuccugcugc uucuggccuc acugagucug aagagcuguu aacuaccaug      60
gccaguccuc ccugagucug accaucuucc auccugcugc ugcugcugcu gcugcugcgg     120
gucuuccugg aaucugacca uucguugucu gcuaugcccg uccucaccaa gacugacugc     180
cugcugcuuu gcuacugccc gggcccauga gacugacuuc ccacugcucu gccugccucu     240
ccccacugca cuggcacagc cccgccuugc cgcugcugau ccauugccgg ugugacc       297

<210> SEQ ID NO 19
<211> LENGTH: 238
<212> TYPE: RNA
<213> ORGANISM: Homo sapiens

<400> SEQUENCE: 19
ggccaguccu cccugagucu gaccaucuuc cauccugcug cugcugcugc ugcugcugcg      60
ggucuuccug gaaucugacc auucguuguc ugcuaugccc guccucacca agacugacug     120
ccugcugcuu ugcuacugcc cgggcccaug agacugacuu cccacugcuc ugccugccuc     180
uccccacugc acuggcacag ccccgccuug ccgcugcuga uccauugccg gugugacc      238

<210> SEQ ID NO 20
<211> LENGTH: 238
<212> TYPE: RNA
<213> ORGANISM: Homo sapiens

<400> SEQUENCE: 20
ggccaguccu cccugagucu gaccaucuuc cauccugcug cugcugcugc ugcugcugcg      60
ggucuuccug gaaucugacc auucguuguc ugcuaugccc guccucacca agacugacug     120
ccugcugcuu ugcuacugcc cgggcccaug agacugacuu cccacugcuc ugccugccuc     180
uccccacugc acuggcacag ccccgccuug ccgcugcuga uccauugccg gugugacc      238

<210> SEQ ID NO 21
<211> LENGTH: 219
<212> TYPE: RNA
<213> ORGANISM: Homo sapiens

<400> SEQUENCE: 21
ugaccaucuu ccauccugcu gcugcugcug cugcugcugc gggucuuccu ggaaucugac      60
cauucguugu cugcuaugcc cguccucacc aagacugacu gccugcugcu uugcuacugc     120
ccgggcccau gagacugacu ucccacugcu cugccugccu cuccccacug cacuggcaca     180

```
gccccgccuu gccgcugcug auccauugcc ggugugacc                    219

<210> SEQ ID NO 22
<211> LENGTH: 237
<212> TYPE: RNA
<213> ORGANISM: Homo sapiens

<400> SEQUENCE: 22
ccaguccucc cugagucuga ccaucuucca uccugcugcu gcugcugcug cugcugcggg    60
ucuuccugga aucugaccau cguugucug cuaugcccgu ccucaccaag acugacugcc   120
ugcugcuuug cuacugcccg ggcccaugag acugacuucc cucugcucug ccugccucuc   180
cccacugcac uggcacagcc ccgccuugcc gcugcugauc cauugccugu gugacca     237

<210> SEQ ID NO 23
<211> LENGTH: 214
<212> TYPE: RNA
<213> ORGANISM: Homo sapiens

<400> SEQUENCE: 23
ugaccaucuu ccauccugcu gcugcugcug cugcgggucu ccuggaauc ugaccauucg    60 uugucugcua ugcccguccu uaccaagacu gacugccugc ugcuuugcua cugcccgggc   120
ccaugagacu gacuuccac ugcucugccu gccucucccc acugcacugg cacagccccg   180
ccuugucgcu gcugauccau ugccggugug acac                            214

<210> SEQ ID NO 24
<211> LENGTH: 128
<212> TYPE: RNA
<213> ORGANISM: Homo sapiens

<400> SEQUENCE: 24
gacugacugc cugcugcuuu gcuacugccc gggcccauga gacugacuuc ccacugcucu    60
gccugccucu cccacugcac uggcacagc cccgccuugc cgcugcugau ccauugccgg   120
ugugaccc                                                          128

<210> SEQ ID NO 25
<211> LENGTH: 230
<212> TYPE: RNA
<213> ORGANISM: Homo sapiens

<400> SEQUENCE: 25
cucccugagu cugaccaucu uccauccugc ugcugcugcu gcugcugcug cgggucuucc    60
uggaaucuga ccauucguug ucugcuaugc ccguccucac caagacugac ugccugcugc   120
uuugcuacug cccgggccca ugagacugac uucccacugc ucugccugcc ucucccacu   180 gcacuggcac agccccgccu ugccgcugcu gauccauugc cggugugacc             230

<210> SEQ ID NO 26
<211> LENGTH: 211
<212> TYPE: RNA
<213> ORGANISM: Homo sapiens

<400> SEQUENCE: 26
uuccauccug cugcugcugc ugcugcugcu gcgggucuuc cuggaaucug accauucguu    60
gucugcuaug cccguccuca ccaagacuga cugccugcug cuuugcuacu gcccgggccc   120
augagacuga cuucccacug cucugccugc cucucccac ugcacuggca cagccccgcc   180
```
uugccgcugc ugauccauug ccggugugac c          211

<210> SEQ ID NO 27
<211> LENGTH: 143
<212> TYPE: RNA
<213> ORGANISM: Homo sapiens

<400> SEQUENCE: 27
ugcccguccu caccaagacu gacugccugc ugcuuugcua cugcccgggc ccaugagacu    60
gacuucccac ugcucugccu gccucucccc acugcacugg cacagcccg ccuugccgcu   120 gcugauccau ugccggugug acc                                          143

<210> SEQ ID NO 28
<211> LENGTH: 143
<212> TYPE: RNA
<213> ORGANISM: Homo sapiens

<400> SEQUENCE: 28
ugcccguccu caccaagacu gacugccugc ugcuuugcua cugcccgggc ccaugagacu    60
gacuucccac ugcucugccu gccucucccc acugcacugg cacagcccg ccuugccgcu   120 gcugauccau ugccggugug acc                                          143

<210> SEQ ID NO 29
<211> LENGTH: 181
<212> TYPE: RNA
<213> ORGANISM: Homo sapiens

<400> SEQUENCE: 29
gcgggucuuc cuggaaucug aacauucguu gucugcuaug cccguccuca ccaagacuga    60
cugccugcug cuuugcuacu gcccgggccc augagacuga cuucccacug cucugccugc   120 cucucccac ugcacuggca gccccgcc uugccgcugc ugauccauug ccggugugac     180
c                                                                  181

<210> SEQ ID NO 30
<211> LENGTH: 154
<212> TYPE: RNA
<213> ORGANISM: Homo sapiens

<400> SEQUENCE: 30
guugucugcu augcccgucc ucaccaagac ugacugccug cugcuuugcu acugcccggg    60
cccaugagac ugacuuccca cugcucugcc ugcucucccc acugcacug gcacagcccc   120 gccuugccgc ugcugaucca uugccggugu gacc                              154

<210> SEQ ID NO 31
<211> LENGTH: 130
<212> TYPE: RNA
<213> ORGANISM: Homo sapiens

<400> SEQUENCE: 31
caagacugac ugccugcugc uuugcuacug cccgggccca ugagacugac uucccacugc    60
ucugccugcc ucucccacu gcacuggcac agccccgccu ugccgcugcu gauccauugc   120
cggugugacc                                                         130

<210> SEQ ID NO 32
<211> LENGTH: 138
<212> TYPE: RNA
<213> ORGANISM: Homo sapiens

```
<400> SEQUENCE: 32
ccucaccaag acugacugcc ugcugcuuug cuacugcccg gacccaugag acugacuucc    60
cacugcucug ccugccucuc cccacugcac uggcacagcc ccgccuugcc gcugcugauc   120
cauugccggu gugacugc                                                 138

<210> SEQ ID NO 33
<211> LENGTH: 214
<212> TYPE: RNA
<213> ORGANISM: Homo sapiens

<400> SEQUENCE: 33
cuuccauccu gcugcugcug cugcugcugc ugcgggucuu ccuggaaucu gaccauucgu    60
ugucugcuau gcccguccuc accaagacug acugccugcu gcuuugcuac ugcccgggcc   120
caugagacug acuucccacu gcucugccug ccucucccca cugcacuggc acagcccgc   180 cuugccgcug cugauccauu gccgguguga cccc                               214

<210> SEQ ID NO 34
<211> LENGTH: 135
<212> TYPE: RNA
<213> ORGANISM: Homo sapiens

<400> SEQUENCE: 34
cucaccaaga cugacugccu gcugcuuugc uacugcccgg gcccaugaga cugacuuccc    60
acugcucugc cugccucucc ccacugcacu ggcacagccc cgccuugccg cugcugaucc   120
auugccggug ugacc                                                    135

<210> SEQ ID NO 35
<211> LENGTH: 129
<212> TYPE: RNA
<213> ORGANISM: Homo sapiens

<400> SEQUENCE: 35
aagacugacu gccugcugcu uugcuacugc ccgggcccau gagacugacu ucccacugcu    60
cugccugccu cucccacugc acuggcacag ccccgccuu gccgcugcug auccauugcc   120
ggugugacc                                                           129

<210> SEQ ID NO 36
<211> LENGTH: 541
<212> TYPE: RNA
<213> ORGANISM: Homo sapiens

<400> SEQUENCE: 36
cuccagcucg cuuccauuug cuugcagaag uucgcgcugu gcacgaag cuugcgcucc      60 uuggaggccu cagcaacagc aucaucaagc ugagcuucca gcucuuuccu gagcuucuca   120
gcucuccgca uuccugccg cauggcguca ccuucugcg uggccaccuc caucucccuc    180
uccuugucuc gcagcugccg ggacaccuuc ugcgcuaaga ugggauacgg cauugaggga   240
ucaaugugua aggauccgau cugcuucugg cccacugag ucugaagagc uguuaacuac   300
cauggccagu cucccugag ucugaccauc uuccauccug cugcugcugc ugcugcugcu   360
gcgggucuuc cuggaaucug accauucguu gucugcuaug uccguccuca ccaagacuga   420
cugccugcug cuuugcuacu gcccgggccc augagacuga cuucccacug cucugccugc   480 cucucccac ugcacuggca cagccccgcc uugccgcugc ugauccauug ccgguggac    540
```

```
<210> SEQ ID NO 37
<211> LENGTH: 125
<212> TYPE: RNA
<213> ORGANISM: Homo sapiens

<400> SEQUENCE: 37
cugacugccu gcugcuuugc uacugcccgg gcccaugaga cugacuuccc acugcucugc    60
cugccucucc ccacugcacu ggcacagccc cgccuugccg cugcugaucc auugccggug   120
ugacc                                                               125

<210> SEQ ID NO 38
<211> LENGTH: 131
<212> TYPE: RNA
<213> ORGANISM: Homo sapiens

<400> SEQUENCE: 38
ccaagacuga cugccugcug cuuugcuacu gcccgggccc augagacuga cuucccacug    60
cucugccugc cucuccccac ugcacuggca gccccgcc uugccgcugc ugauccauug    120
acggugugac c                                                        131

<210> SEQ ID NO 39
<211> LENGTH: 245
<212> TYPE: RNA
<213> ORGANISM: Homo sapiens

<400> SEQUENCE: 39
uaacuaccau ggccaguccu cccugagucu gaccaucuuc cauccugcug cugcugcugc    60
ugcugcgggu cuuccuggaa ucugaccauu cguugcucgc uaugcccguc cucaccaaga   120
cugacugccu gcugcuuugc uacugcccgg gcccaugaga cugacuuccc acugcucugc   180
cugccucucc ccacugcacu ggcacagccc cgccuugccg cuguugaucc auugccggug   240
ugacc                                                               245

<210> SEQ ID NO 40
<211> LENGTH: 131
<212> TYPE: RNA
<213> ORGANISM: Homo sapiens

<400> SEQUENCE: 40
ccaagacuga cugccugcug cuuugcuacu gcccgggccc augagacuga cuucccacug    60
cucugccugc cucuccccac ugcacuggca gccccgcc uugccgcugu ugauccauug    120
ucggugugac c                                                        131

<210> SEQ ID NO 41
<211> LENGTH: 131
<212> TYPE: RNA
<213> ORGANISM: Homo sapiens

<400> SEQUENCE: 41
ccaagacuga cugccugcug cuuugcuacu gcccgggccc augagacuga cuucccacug    60
cucugccugc cucuccccac ugcacuggca gccccgcc uugccgcugc ugauccauug    120
ccggugugac c                                                        131

<210> SEQ ID NO 42
<211> LENGTH: 149
```

```
<212> TYPE: RNA
<213> ORGANISM: Homo sapiens

<400> SEQUENCE: 42
cugcuaugcc uguccucacc aagacugacu gccugcugcu uugcuacugc ccgggcccau     60
gagacugacu ucccacugcu cugccugccu cuccccaaug cacuggcaca gccccgccuu    120
gccgcugcug auccauugcc ggugugacc                                      149

<210> SEQ ID NO 43
<211> LENGTH: 149
<212> TYPE: RNA
<213> ORGANISM: Homo sapiens

<400> SEQUENCE: 43
cugcuaugcc cguccucacc aagacugacu gccugcugcu uugcuacugc ccgggcccau     60
gagacugacu ucccacugcu cugccugccu cuccccacug cacuggcaca gccccgccuu    120
gccgcugcug auccauugcc ggugugacc                                      149

<210> SEQ ID NO 44
<211> LENGTH: 147
<212> TYPE: RNA
<213> ORGANISM: Homo sapiens

<400> SEQUENCE: 44
gcuaugcccg uccucaccaa gacugacugc cugcugcuuu gcuacugccc gggcccauga     60
gacugacuuc ccacugcucu gccugccucu cccacugca cuggcacagc cccgccuugc     120
cgcugcugau ccauugccgg ugugacc                                        147

<210> SEQ ID NO 45
<211> LENGTH: 176
<212> TYPE: RNA
<213> ORGANISM: Homo sapiens

<400> SEQUENCE: 45
ucuuccugga aucugaccau ucguugucug cuaugcccgu ccucaccaag acugacugcc     60
ugcugcuuug cuacugcccg ggcccaugag acugacuucc cacugcucug ccugccucuc    120
cccacugcac uggcacagcc ccgccuugcc gcugcugauc cauugccggu gugacc        176

<210> SEQ ID NO 46
<211> LENGTH: 171
<212> TYPE: RNA
<213> ORGANISM: Homo sapiens

<400> SEQUENCE: 46
cuggaaucug accauucguu gucugcuaug cccguccuca ccaagacuga cugccugcug     60
cuuugcuacu gcccggggcc augagacuga cuucccacug cucugccugc cucuccccac    120
ugcacuggca gccccgcc uugccgcugc ugauccauug ccggugugac c                171

<210> SEQ ID NO 47
<211> LENGTH: 171
<212> TYPE: RNA
<213> ORGANISM: Homo sapiens

<400> SEQUENCE: 47
cuggaaucug accauucguu gucugcuaug cccguccuca ccaagacuga cugccugcug     60
cuuugcuacu gcccggggcc augagacuga cuucccacug cucugccugc cucuccccac    120
```

```
ugcacuggca cagccccgcc uugccgcugc ugauccauug ccggugugac c        171
```

<210> SEQ ID NO 48
<211> LENGTH: 169
<212> TYPE: RNA
<213> ORGANISM: Homo sapiens

<400> SEQUENCE: 48

```
ggaaucugac cauucguugu cugcuaugcc cguccucacc aagacugacu gccugcugcu    60
uugcuacugc ccgggcccau gagacugacu ucccacugcu cugccugccu cucccacug    120
cacuggcaca gccccgccuu gccgcugcug auccauugcc ggugugacc                169
```

<210> SEQ ID NO 49
<211> LENGTH: 131
<212> TYPE: RNA
<213> ORGANISM: Homo sapiens

<400> SEQUENCE: 49

```
ccaagacuga cugccugcug cuuugcuacu gcccgggccc augagacuga cuucccacug    60
cucugccugc cucuccccac ugcacuggca uagccccgcc uugccgcugc ugauccauug    120
ccggugugac c                                                         131
```

<210> SEQ ID NO 50
<211> LENGTH: 175
<212> TYPE: RNA
<213> ORGANISM: Homo sapiens

<400> SEQUENCE: 50

```
cuuccuggaa ucugaccauu cguugucugc uaugcccguc ucaccaagac ugacugccu    60
gcugcuuugc uacugcccgg gcccaugaga cugacuuccc acugcucugc cugccucucc    120
ccacugcacu ggcauagccc cgccuugccg cugcugaucc auuccggug ugacc           175
```

<210> SEQ ID NO 51
<211> LENGTH: 140
<212> TYPE: RNA
<213> ORGANISM: Homo sapiens

<400> SEQUENCE: 51

```
cagacacccg ccccccggcc cuggcuaaga auuugcuucc uguugccagc augaccuacc    60
cucgccucuu ugaugccauc cgcugccacc uccuuuugcu ccuggacccu uuagccucuc    120
ugcccuucca cucucugacc                                                140
```

<210> SEQ ID NO 52
<211> LENGTH: 149
<212> TYPE: RNA
<213> ORGANISM: Homo sapiens

<400> SEQUENCE: 52

```
uuccagccag acacccgccc ccggcccug gcuaagaagu ugcuuccugu ugccagcaug     60
accuacccuc gccucuuuga ugccauccgc ugccaccucc uuugucccu ggacccuuua    120
gccucucugc ccuuccacuc ucugacccc                                     149
```

<210> SEQ ID NO 53
<211> LENGTH: 212
<212> TYPE: RNA
<213> ORGANISM: Homo sapiens

<400> SEQUENCE: 53

```
cucgcuuccu gggucugcag guccagccgg cuggcacccu ccauguaccc aggggagauu    60
ccagccagac acccgccccc cggcccuggc uaagaaguug cuuccuguug ccagcaugac   120
cuacccucgc ucuuugaug ccauccgcug ccaccuccuu uugcuccugg acccuuuagc   180
cucucugccu uuccacucuc ugaccaccgc cc                                 212

<210> SEQ ID NO 54
<211> LENGTH: 144
<212> TYPE: RNA
<213> ORGANISM: Homo sapiens

<400> SEQUENCE: 54
uccagccaga cacccgcccc ccggcccugg cuaagaaguu gcuuccuguu ccagcauga    60 ccuacccucg ccucuuugau gccauccgcu gccaccuccu uuugcuccug gacccuuuag  120
cuucucugcc cuuccacucu cugg                                          144

<210> SEQ ID NO 55
<211> LENGTH: 207
<212> TYPE: RNA
<213> ORGANISM: Homo sapiens

<400> SEQUENCE: 55
cgcuuccugg gucugcaggu ccagccggcu ggcacccucc acguacccag gggagauucc    60
agccagacac ccgcccccg gcccuggcua agaaguugcu uccuguugcc agcaugaccu   120
acccucgccu cuuugaugcc auccgcugcc accuccuuuu gcuccuggac ccuuuagccu   180
cucugcccuu ccacucucug accaccg                                       207

<210> SEQ ID NO 56
<211> LENGTH: 158
<212> TYPE: RNA
<213> ORGANISM: Homo sapiens

<400> SEQUENCE: 56
cauguaccca ggggagauuc cagccagaca cccgccccc ggcccuggcu aagaaguugc     60
uuccuguugc cagcaugacc uacccucgcc ucuuugaugc cauccgcugc caccuccuuu   120
ugcuccugga cccuuuagcc ucucugcccu uccacucg                           158

<210> SEQ ID NO 57
<211> LENGTH: 197
<212> TYPE: RNA
<213> ORGANISM: Homo sapiens

<400> SEQUENCE: 57
cucgcuuccu gggucugcag guccagccgg cuggcacccu ccauguaccc aggggagauu    60
ccagccagac acccgccccc cggcccuggc uaagaaguug cuuccuguug ccagcaugac   120
cuacccucgc ucuuugaug ccauccgcug ccaccuccuu uugcuccugg acccuuuagc   180
cucucugccc ccccgau                                                  197

<210> SEQ ID NO 58
<211> LENGTH: 236
<212> TYPE: RNA
<213> ORGANISM: Homo sapiens

<400> SEQUENCE: 58
cccagcuccc uaggcguccc aucucgcuuc cugggucugc agguccagcc ggcuggcacc    60
```

```
cuccauguac ccaggggaga uuccagccag acacccgccc cccggcccug gcuaagaagu      120
ugcuuccugu ugccagcaug accuacccuc gccucuuuga ugccauccgc ugccaccucc      180
uuuugcuccu ggacccuuua gccucucugc ccuuccacuc uuugacccccc aucuua         236
```

```
<210> SEQ ID NO 59
<211> LENGTH: 273
<212> TYPE: RNA
<213> ORGANISM: Homo sapiens

<400> SEQUENCE: 59
ggccaccggg caugggaagu augagaaggu gcuugugaa ggggggcccgg cucccuaggc       60 gucccaucuc gcuccuggg ucugcagguc cagccggcug gcaccuucca uguacccagg      120
gagauuccag ccagacaccc gccccccggc ccuggcuaag aaguugcuuc cuguugccag     180
caugaccuac ccucgccucu uugaugccau ccgcugccac cuccuuuugc uccggaccc     240 uuuagccucu cugccuucc acucucugac ccc                                   273
```

```
<210> SEQ ID NO 60
<211> LENGTH: 171
<212> TYPE: RNA
<213> ORGANISM: Homo sapiens

<400> SEQUENCE: 60
uguacccagg ggagauucca gccagacacc cgccccccgg cccuggcuaa gaaguugcuu       60
ccuguugcca gcaugaccua cccucgccuc uuugaugcca uccgcugcca ccuccuuuug     120
cuccuggacc cuuuagccuc ucugccuuc cacucucuga ccaccacccc c               171
```

```
<210> SEQ ID NO 61
<211> LENGTH: 134
<212> TYPE: RNA
<213> ORGANISM: Homo sapiens

<400> SEQUENCE: 61
ccggcccugg cuaagaaguu gcuuccuguu gccagcauga ccuacccucg ccucuuugau       60
gccauccgcu gccaccuccu uuugcuccug gacccuuuag ccucucugcc cuuccacucu     120
cugaccacag cccc                                                        134
```

```
<210> SEQ ID NO 62
<211> LENGTH: 140
<212> TYPE: RNA
<213> ORGANISM: Homo sapiens

<400> SEQUENCE: 62
ccccggcccu ggcuaagaag uugcuuccug uugccagcau gaccuacccu cgccucuuug       60
augccauccg cugccaccuc cuuuugcucc uggacccuuu agccucucug cccuuccacu     120
cucugaccac cgccccgcc                                                   140
```

```
<210> SEQ ID NO 63
<211> LENGTH: 188
<212> TYPE: RNA
<213> ORGANISM: Homo sapiens

<400> SEQUENCE: 63
ccggcuggca ccuccaugu acccagggga gauuccagcc agacaccgc ccccggccc          60 uggcuaagaa guugcuuccu guugccagca ugaccuaccc ucgccucuuu gaugccaucc     120
gcugccaccu ccuuuugcuc cuggacccuu agccucucu gcccuuccac ucucugacca     180
``` ccgccccc 188

<210> SEQ ID NO 64
<211> LENGTH: 190
<212> TYPE: RNA
<213> ORGANISM: Homo sapiens

<400> SEQUENCE: 64
gccggcuggc acccuccaug uacccagggg agauuccagc cagacacccg cccccccggcc    60 cuggcuaaga aguugcuucc uguugccagc augaccuacc cuagccucuu ugaugccauc   120
cgcugccacc uccuuuugc uccggacccu uuuagccucu ugcccuucc acucucugac    180 caccgccccc                                                          190

<210> SEQ ID NO 65
<211> LENGTH: 154
<212> TYPE: RNA
<213> ORGANISM: Homo sapiens

<400> SEQUENCE: 65
uccagccaga cacccgcccc ccggcccugg cuaagaaguu gcuuccuguu gccagcauga    60
ccuacccucg ccucuuugau gccauccgcu gccaccuccu uuugcuccug gacccuuuag   120
ccucucugcc cuuccacucu cugaccacca cccc                               154

<210> SEQ ID NO 66
<211> LENGTH: 146
<212> TYPE: RNA
<213> ORGANISM: Homo sapiens

<400> SEQUENCE: 66
gccagacacc cgcccccggg ccuggcuaa gaaguugcuu ccuguugcca gcaugaccua    60
cccucgccuc uuugaugcca uccgcugcca ccuccuuuug cuccuggacc cuuuagccuc   120
ucugcccuuc cacucucuga cccccc                                        146

<210> SEQ ID NO 67
<211> LENGTH: 150
<212> TYPE: RNA
<213> ORGANISM: Homo sapiens

<400> SEQUENCE: 67
uccagccaga cacccgcccc ccggcccugg cuaagaaguu gcuuccuguu gccagcauga    60
ccuacccucg ccucuuugau gccauccgcu gccaccuccu uuugcuccug gacccuuuag   120
ccucucugcc cuuccacucu cugaccccccc                                   150

<210> SEQ ID NO 68
<211> LENGTH: 233
<212> TYPE: RNA
<213> ORGANISM: Homo sapiens

<400> SEQUENCE: 68
cggcucccua ggcgucccau cucgcuuccu gggucugcag guccagccgg cuggcacccu    60
ccauguaccc aggggagauu ccagccagac acccgccccc cggcccuggc uaagaaguug   120
cuuccuguug ccagcaugac cuacccucgc cucuuugaug ccauccgcug ccaccuccuu   180
uugcuccugg acccuuuagc cucucugccc uuccacucuc ugaccacugc ccc          233

<210> SEQ ID NO 69

```
<211> LENGTH: 197
<212> TYPE: RNA
<213> ORGANISM: Homo sapiens

<400> SEQUENCE: 69
ugcaggucca gccggcuggc acccuccaug uacccagggg agauuccagc cagacaccca      60 cccccggcc cuggcuaaga aguugcuccu guugccagca ugaccuaccc ucgccucuuu      120
gaugccaucc gcugccaccu ccuuuugcuc cuggacccuu uagccucucu gcccuuccac     180
ucucugacca cuacccc                                                    197

<210> SEQ ID NO 70
<211> LENGTH: 155
<212> TYPE: RNA
<213> ORGANISM: Homo sapiens

<400> SEQUENCE: 70
uuccagccag acacccgccc cccggcccug gcuaagaagu ugcuuccugu ugccagcaug      60
accuacccuc gccucuuuga ugccauccgc ugccaccucc uuuugcuccu ggacccuuua    120
gccucucugc ccuuccacuc ucugaccacu gcccc                                155

<210> SEQ ID NO 71
<211> LENGTH: 134
<212> TYPE: RNA
<213> ORGANISM: Homo sapiens

<400> SEQUENCE: 71 cccgccccc ggcccuggcu aagaaguugc uuccuguugc cagcaugacc uaccucgcc       60 ucuuugaugc cauccgcugc caccuccuuu ugcuccugga cccuuagcc ucucugcccu      120 uccacucucu gacc                                                       134

<210> SEQ ID NO 72
<211> LENGTH: 147
<212> TYPE: RNA
<213> ORGANISM: Homo sapiens

<400> SEQUENCE: 72
cagccagaca cccgccccc ggcccuggcu aagaaguugc uuccuguugc cagcaugacc      60
uacccucgcc ucuuugaugc cauccgcugc caccuccuuu ugcuccugga cccuuuagcc    120
ucucugcccu uccacucucu gaacacc                                         147

<210> SEQ ID NO 73
<211> LENGTH: 192
<212> TYPE: RNA
<213> ORGANISM: Homo sapiens

<400> SEQUENCE: 73
gagccuacuc ugaugaccgu ggccuuggcu ccuccaggaa ggcucaggag cccuaccucc      60
cugccauuau agcugcuccc cgccagaagc cugugccaac ucucugcauu cccgaucuc    120 cuguggcugu cacccuuggu caccuccgug cugucacugc caucuccccc cugacccuc     180 gaacccaucc ua                                                         192

<210> SEQ ID NO 74
<211> LENGTH: 191
<212> TYPE: RNA
<213> ORGANISM: Homo sapiens

<400> SEQUENCE: 74
```

```
gagccuacuc ugaugaccgu ggccuuggcu ccuccaggaa ggcucaggcg cccuaccucc     60
cugccauuau agcugcuccc cgccagaagc cugugccaac ucucugcauu cccugaucuc    120
caucccugug gcugucaccc uuggucaccu ccgugcuguc acugccaucu cccccccugac   180 cccucuaacc c                                                         191
```

<210> SEQ ID NO 75
<211> LENGTH: 162
<212> TYPE: RNA
<213> ORGANISM: Homo sapiens

<400> SEQUENCE: 75

```
gccuacucug augaccgugg ccuuggcucc uccaggaagg cucaggagcc cuaccucccu     60
gccauuauag cugcuccccg ccagaagccu gugccaacuc ucugcauucc cugaucuccu   120 ucccugugge ugucacccuu ggccacugec caucccccc cc                       162
```

<210> SEQ ID NO 76
<211> LENGTH: 183
<212> TYPE: RNA
<213> ORGANISM: Homo sapiens

<400> SEQUENCE: 76

```
gagccuacuc ugaugaccgu ggccuuggcu ccuccaggaa ggcucaggag cccuaccucc     60
cugccauuau agcugcuccc cgccagaagc cugugccaac ucucugcauu cccugaucuc    120
caucccugug gcugucaccc uuggucaccu ccgugcuguu acugccaucu cccccccugac   180 ccc                                                                 183
```

<210> SEQ ID NO 77
<211> LENGTH: 240
<212> TYPE: RNA
<213> ORGANISM: Homo sapiens

<400> SEQUENCE: 77

```
gaagagccua cucugaugac cguggccuug gcuccuccag gaaggcucag gagcccuacc     60
ucccugccau uauagcugcu ccccgccaga agccugugcc aacucucugc auucccugau   120
cuccaucccu guggcuguca ccuugguca ccccgugcu gucacugcca ucuccccccu     180
gaccccucua acccauccuc ugccucccuc ccugcaguca gagggucccug uucccaacca  240
```

<210> SEQ ID NO 78
<211> LENGTH: 166
<212> TYPE: RNA
<213> ORGANISM: Homo sapiens

<400> SEQUENCE: 78

```
uguggccuug gcuccuccag gaaggcuaag gagcccuacc ucccugccau uauagcugcu    60
ccccgccaga agccugugcc aacucucugc auucccugau cuccaucccu guggcuguca   120 cccuuggcuca ccuccgugcu gucacugcca ucuccccccu gacccc                 166
```

<210> SEQ ID NO 79
<211> LENGTH: 155
<212> TYPE: RNA
<213> ORGANISM: Homo sapiens

<400> SEQUENCE: 79

```
gccuuggcuc cuccaggaag gcucaggagc ccuaccuccc ugccauuaua gcugcuccccc    60
```

```
gccagaagcc ugugccaacu cucugcauuc ccugaucucc aucccugugg cugucacccu    120
uggucaccuc cgugcuguca cugccaucuc ccccc                              155

<210> SEQ ID NO 80
<211> LENGTH: 310
<212> TYPE: RNA
<213> ORGANISM: Homo sapiens

<400> SEQUENCE: 80
agagccuacu cugaugaccg uggccuuggc uccuccagga aggcucagga gcccaccuc     60 ccugccauua uagcgcucc ccgccagaag ccugugccaa cucucugcau cccugaucu    120 ccaucccugu ggcugucacc cuuggucacc uccgugcugu cacugccauc ucccccuga   180 ccccucuaac ccauccucug ccuccccccc ugcagucaga ggguccuguu cccaucagcg   240 auucccugc uuaaacccuu ccaugacccc ccacugcccu aagcugaggu cagucccca    300 agccugacau                                                         310

<210> SEQ ID NO 81
<211> LENGTH: 204
<212> TYPE: RNA
<213> ORGANISM: Homo sapiens

<400> SEQUENCE: 81
uauagcugcu ccccgccaga agccugugcc aacucucugc auucccugau cuccaucccu    60
guggcuguca cccuuggguca ccuccgugcu gucacugcca ucccccccu gaccccucua   120 acccauccuc ugcccucccu ccugcagucca gagggccuug uucccaucag cgauucccc   180 gcuuaaaccc uuccaugaca gccc                                         204

<210> SEQ ID NO 82
<211> LENGTH: 169
<212> TYPE: RNA
<213> ORGANISM: Homo sapiens

<400> SEQUENCE: 82
ucugcauucc cugaucucca ucccugugggc ugucacccuu ggucaccucc gugcugucac    60
ugccaucucc ccccugaccc cucuaaccca uccucugccu ccccccugc agucagaggg    120 uccuguuccc aucagcgauu ccccugcuua agcccuucca ugacucccc                169

<210> SEQ ID NO 83
<211> LENGTH: 217
<212> TYPE: RNA
<213> ORGANISM: Homo sapiens

<400> SEQUENCE: 83
cucccugcca uuauagcugc uccccgccag aagccugugc caacucucug cauucccuga    60
ucuccauccc uguggcuguc acccuugguc accuccgugc ugucacugcc aucccccc    120 ugaccccucu aacccauccu cugcuccccu cccugcaguc agaggguccu guucccauca   180 gcgauuccc ugcuuaaacc cuuccaugac ucccccaa                           217

<210> SEQ ID NO 84
<211> LENGTH: 272
<212> TYPE: RNA
<213> ORGANISM: Homo sapiens

<400> SEQUENCE: 84
gccuacucug augaccgugg ccuuggguc uccaggaagg cucaggagcc cuaccuccu      60
```

```
gccauuauag cugcuccccg ccagaagucu gugccaacuc ucugcauucc cugaucucca    120
ucccuguggc ugucacccuu ggucaccucc gugcugucac ugccaucucc cccugaccc     180 cucuaaccca uccucugccu ccucccugc agucagaggg uccuguccc aucagcgauu      240 ccccugcuua aacccuucca ugacuccccu cu                                  272

<210> SEQ ID NO 85
<211> LENGTH: 131
<212> TYPE: RNA
<213> ORGANISM: Homo sapiens

<400> SEQUENCE: 85
cuaccucccu gccauuauag cugcuccccg ccagaagccu gugccaacuc ucugcauucc    60
cugaucucca ucccuguggc ugucacccuu ggucacccuc gugcugucac ugccaucucc   120
ccccugaccc c                                                        131

<210> SEQ ID NO 86
<211> LENGTH: 136
<212> TYPE: RNA
<213> ORGANISM: Homo sapiens

<400> SEQUENCE: 86
cugguacugc augcacgcaa ugcuagcugc cccuuucccg uccuggguac cccgagucuc    60
ccccgaccuc ggguccccagg uaugcuccca ccuccaccug cccacucac caccucugcu  120 aguuccagac accucc                                                   136

<210> SEQ ID NO 87
<211> LENGTH: 203
<212> TYPE: RNA
<213> ORGANISM: Homo sapiens

<400> SEQUENCE: 87
ccggcccuuc ccccguuuug aacaugugua accgacaguc ugccugggcc acagcccucu    60
cacccuggua cugcaugcac gcaaugcuag cugcccuuu ccguccugg gcaccccgag    120 ucuccccga ccccggguccc cagguaugcu cccaccucca ccugcccac ucaccaccuc   180 ugcuaguucc agacaccccc gcg                                           203

<210> SEQ ID NO 88
<211> LENGTH: 197
<212> TYPE: RNA
<213> ORGANISM: Homo sapiens

<400> SEQUENCE: 88 ccuuccccg uuugaacau guguaaccga cagucugccu gggccacagc ccucaccc       60 ugguacugca ugcacgcaau gcuagcugcc ccuuucccgc ccugggcacc ccgagucucc   120
cccgaccccg ggucccaggu augcucccac cuccaccugc ccacucacc accucugcua   180 guuccagaca ccuccac                                                  197

<210> SEQ ID NO 89
<211> LENGTH: 273
<212> TYPE: RNA
<213> ORGANISM: Homo sapiens

<400> SEQUENCE: 89
ucugccuggg ccacagcccu cucacccugg uacugcaugc acgcaaugcu agcugccccu    60
```

| | |
|---|---|
| uucccguccu gggcacccccg agucuccccc gaccccgggu cccagguaug cucccaccuc | 120 |
| caccugcccc acuccaccacc ucugcuaguu ccagacaccu ccacgcccac cugguccucu | 180 |
| cccaucgccc acaaaagggg gggcacgagg gacgagcuua gcugagcugg gaggagcagg | 240 |
| gugagggugg gcgacccagg auuccccac ccc | 273 |

<210> SEQ ID NO 90
<211> LENGTH: 199
<212> TYPE: RNA
<213> ORGANISM: Homo sapiens

<400> SEQUENCE: 90

| | |
|---|---|
| ugacaccuca gcugacagcg ugggcaacgc cugccgccug cucugaggcc cgauccagug | 60 |
| ggcaggccaa ggccugcugg gccccgcgg acccaggugc ucggguacc ggucccuguc | 120 |
| cccgcacccc cgcuucuguc ugccccauug uggcuccuca ggcucucucc ccugcucucc | 180 |
| caccucuacc uccacccca | 199 |

<210> SEQ ID NO 91
<211> LENGTH: 193
<212> TYPE: RNA
<213> ORGANISM: Homo sapiens

<400> SEQUENCE: 91

| | |
|---|---|
| cucagcugac agcgugggca acgccugccg ccugcucuga ggcccgaucc agugggcagg | 60 |
| ccaaggccug cugggccccc gcggaccccag gugcucuggg ucacggucc ugucccgca | 120 |
| cccccgcuuc ugucugcccc auuguggcuc cucaggcucu cucccugcu ucccaccuc | 180 |
| uaccuccacu ccc | 193 |

<210> SEQ ID NO 92
<211> LENGTH: 158
<212> TYPE: RNA
<213> ORGANISM: Homo sapiens

<400> SEQUENCE: 92

| | |
|---|---|
| ucugaggccc gauccagugg gcaggccaag gccugcuggg ccccgcgga cccaggugcu | 60 |
| cuggguacg gucccugucc ccgcacccc gcuucugucu gccccauugu ggcuccucag | 120 |
| gcucucuccc cugcucuccc accucuaccu ccaccccc | 158 |

<210> SEQ ID NO 93
<211> LENGTH: 153
<212> TYPE: RNA
<213> ORGANISM: Homo sapiens

<400> SEQUENCE: 93

| | |
|---|---|
| ggcccgaucc agugggcagg ccaaggccug cugggccccc gcggacccag gugcucuggg | 60 |
| ucacggucccc ugucccgca ccccgcuuc ugucugcccc auuguggcuc cucaggcucu | 120 |
| cuccccugcu ucccaccuc uaccuccacc ccc | 153 |

<210> SEQ ID NO 94
<211> LENGTH: 128
<212> TYPE: RNA
<213> ORGANISM: Homo sapiens

<400> SEQUENCE: 94

| | |
|---|---|
| gccugcuggg ccccgcgga cccaggugcu cuggguacg gucccugucc ccgcacccc | 60 |
| gcuucugucu gccccauugu ggcuccucag gcucucuccc cugcucuccc accucuaccu | 120 |

```
ccgcccccc                                                              128

<210> SEQ ID NO 95
<211> LENGTH: 116
<212> TYPE: RNA
<213> ORGANISM: Homo sapiens

<400> SEQUENCE: 95
cgcggaccca ggugucucugg gucacgglucc cugucccgc accccgcuu cugucugccc        60 cauuguggcu ccuuaggcuc ucuccccugc ucucccaccu uuaccuccac cccuac          116

<210> SEQ ID NO 96
<211> LENGTH: 190
<212> TYPE: RNA
<213> ORGANISM: Homo sapiens

<400> SEQUENCE: 96
cugacagcgu gggcaacgcc ugccgccugc ucugaggccc gauccagugg gcaggccaag        60
gccugcuggg ccccgcgga cccaggugcu cugggucacg gucccugucc cgcaccccc        120 gcuucugucu gccccauugu ggcuccucag gcucucuccc cugcucuccc accucuaccu      180
ccaccccac                                                              190

<210> SEQ ID NO 97
<211> LENGTH: 191
<212> TYPE: RNA
<213> ORGANISM: Homo sapiens

<400> SEQUENCE: 97
cugacagcgu gggcaacgcc ugccgccugc ucugaggccc gauccagugg gcaggccaag        60
gccugcuggg ccccgcgga cccaggugcu cugggucacg gucccugucc cgcaccccc        120 gcuucugucu gccccauugu ggcuccucag gcucucuccc cugcucuccc accucuaccu      180 ccaccccaa c                                                            191

<210> SEQ ID NO 98
<211> LENGTH: 191
<212> TYPE: RNA
<213> ORGANISM: Homo sapiens

<400> SEQUENCE: 98
cugacagcgu gggcaacgcc ugccgccugc ucugaggccc gauccagugg gcaggccaag        60
gccugcuggg ccccgcgga cccaggugcu cugggucacg gucccugucc cgcaccccc        120 gcuucugucu gccccauugu ggcuccucag gcucucuccc cugcucuccc accucuaccu      180 ccaccccaa c                                                            191

<210> SEQ ID NO 99
<211> LENGTH: 184
<212> TYPE: RNA
<213> ORGANISM: Homo sapiens

<400> SEQUENCE: 99
cgugggcaac gccugccgcc ugcucugagg cccgauccag ugggcaggcc aaggccugcu        60 gggccccgc ggaccaggu gcucggguc acggucccug ucccgcacc cccgcuucug         120 ucugccccau uguggcuccu caggcucucu ccccugcucu cccaccucua ccuccaccca      180
cacc                                                                   184
```

<210> SEQ ID NO 100
<211> LENGTH: 238
<212> TYPE: RNA
<213> ORGANISM: Homo sapiens

<400> SEQUENCE: 100

```
uccugaggga cuggacuccc ccuuacagcc augaccuuga caccucagcu gacagcgugg      60
gcaacgccug ccgccugcuc ugaggcccga uccagugggc aggccaaggc cugcugggcc     120
cccgcggacc caggugcucu ggucacggu cccugucccc gcaccccgc uucugucugc       180
cccauugugg cuccucaggc ucucucccu gcucucccac cucuaccucc acgcccac       238
```

<210> SEQ ID NO 101
<211> LENGTH: 234
<212> TYPE: RNA
<213> ORGANISM: Homo sapiens

<400> SEQUENCE: 101

```
cugagggacu gggacucccc uuacagccau gaccuugaca ccucagcuga cagcgugggc      60
aacgccugcc gccugcucug aggcccgauc cagugggcag gccaaggccu gcugggcccc     120
cgcggaccca ggugcucugg gucacggucc cugucccgc accccgcuu cugucugcc       180
cauuggcu ccucaggcuc ucuccccgc ucucccaccu cuaccuccac accu              234
```

<210> SEQ ID NO 102
<211> LENGTH: 258
<212> TYPE: RNA
<213> ORGANISM: Homo sapiens

<400> SEQUENCE: 102

```
ugcggagcca gcuggaggcc auuuccuga gggacuggga cuccccuuac agccaugacc      60
uugacaccuc agcugacagc gugggcaacg ccugccgccu gcucugaggc ccgauccagu     120
gggcaggcca aggccugcug gccccgcg acccaggug cucuggguca cggucccugu       180
ccccgcaccc ccgcuucugu cugccccauu guggcuccuc aggcucucuc cccugcucuc     240
ccaccucuac cuccaccc                                                   258
```

<210> SEQ ID NO 103
<211> LENGTH: 249
<212> TYPE: RNA
<213> ORGANISM: Homo sapiens

<400> SEQUENCE: 103

```
cuggaggcca uuuccugag ggacugggac uccccuuaca gccaugaccu ugacaccuca       60
gcugacagcg uggggcaacgc cugccgccug cucugaggcc cgauccagug ggcaggccaa    120
ggccugcugg gccccgcgg acccaggugc ucuggucac ggucccuguc ccgcacccc       180
cgcuucuguc ugccccauug uggcucucuca ggcucucucc ccugcucucc caccucuacc    240
uccccccac                                                             249
```

<210> SEQ ID NO 104
<211> LENGTH: 226
<212> TYPE: RNA
<213> ORGANISM: Homo sapiens

<400> SEQUENCE: 104

```
cugggacucc ccuuacagcc augaccuuga caccucagcu gacagcgugg gcaacgccug      60
ccgccugcuc ugaggcccaa uccagugggc aggccaaggc cugcugggcc ccgcggacc     120
```

```
caggugcucu ggguccacggu cccugucccc gcaccccgc uucugucugc cccauugugc    180
cuccuuaggc ucucucccu gcucccac cucaccucc accccc                      226

<210> SEQ ID NO 105
<211> LENGTH: 133
<212> TYPE: RNA
<213> ORGANISM: Homo sapiens

<400> SEQUENCE: 105
gcagcaaugc agcucaaaac gcuuagccua gccacacccc cacgguaaac agcagugauu    60 aacuuuagc auaaacgaa aguuaacua agcuauacua acccccagggu uggucaauuu     120 cgugccagcc acc                                                      133

<210> SEQ ID NO 106
<211> LENGTH: 233
<212> TYPE: RNA
<213> ORGANISM: Homo sapiens

<400> SEQUENCE: 106
cuuucuauua gcucuuagua agauuacaca ugcaagcauc cccguccag ugaguucacc     60 cucuaaauca ccacgauaaa aagggacaag caucaagcac gcagcaaugc agcucaaaac    120
gcuuagccua gccacacccc cacgggaaac agcagugauu aacuuuagc auaaacgaa     180 aguuaacua agcuauacua acccccagggu uggucaauuu cgugccagcu acc          233

<210> SEQ ID NO 107
<211> LENGTH: 190
<212> TYPE: RNA
<213> ORGANISM: Homo sapiens

<400> SEQUENCE: 107
guuccaguga guuccccuc uaaaucacca cgaucaaaag ggacaagcau caagcacgca     60
gcaaugcagc ucaaaacgcu uagccuagcc acaccccac gggaaacagc agugauuaac    120
cuuuagcaau aaacgaaagu uuaacuaagc uauacuaacc ccagggguugg caauuucgu    180 gccagccacc                                                          190

<210> SEQ ID NO 108
<211> LENGTH: 154
<212> TYPE: RNA
<213> ORGANISM: Homo sapiens

<400> SEQUENCE: 108
aaagggacaa gcaucaagca cgcagcaaug cagcucaaaa cgcuuagccu agccacaccc    60
ccacgggaaa cagcagugau uaaccuuuag caauaaacga aguuaacu aagcuauacu     120 aacccaggg uuggucaauu ucgugccagc cacc                                154

<210> SEQ ID NO 109
<211> LENGTH: 158
<212> TYPE: RNA
<213> ORGANISM: Homo sapiens

<400> SEQUENCE: 109
ucaaagggaa caagcaucaa gcacgcaaca augcagcuca aaaacgcuua gccuagccac    60
acccccacgg gaaacagcag ugauuaaccu uuagcaauaa acgaaaguuu aacuaagcua    120 cacuaaccccc agguuggguc aauuucgugc cagccacc                          158
```

```
<210> SEQ ID NO 110
<211> LENGTH: 210
<212> TYPE: RNA
<213> ORGANISM: Homo sapiens

<400> SEQUENCE: 110
uacacaugca agcaucccccg uuccagugag uucacccucu aaaucaccac gaucaaaagg      60
gacaagcauc aagcacgcag caaugcagcu caaaaacgcu uagccuagcc acaccccccac    120 gggaaacagc agugauuaac cuuuagcaau aaacgaaagu uuaacuaagc uauacuaacc    180
ccaggguugg ucaauuucgu gccagccacc                                      210

<210> SEQ ID NO 111
<211> LENGTH: 143
<212> TYPE: RNA
<213> ORGANISM: Homo sapiens

<400> SEQUENCE: 111
caucaagcac gcagcaaugc agcucaaaac gcuuagccua gccacacccc cacgggaaac      60
agcagugauu aaccuuuagc aauaaacgaa aguuuaacua agcuauacua accccagggu    120
uggucaauuu cgugccaacc acc                                             143

<210> SEQ ID NO 112
<211> LENGTH: 154
<212> TYPE: RNA
<213> ORGANISM: Homo sapiens

<400> SEQUENCE: 112
aaagggacaa gcaucaagca cgcagcaaug cagcucaaaa cgcuuagccu agccacaccc      60
ccacgggaaa cagcagugau uaaccuuuag caauaaacga aguuuaacu aagcuauacu     120 aaccccaggg uuggucaauu ucgugccaac cacc                                 154

<210> SEQ ID NO 113
<211> LENGTH: 140
<212> TYPE: RNA
<213> ORGANISM: Homo sapiens

<400> SEQUENCE: 113
caagcacgca acaaugcagc ucaaaacgcu uagccuagcc acaccccccac gggaaacagc     60 agugauuaac cuuuagcaau aaacgaaagu uuaacuaagc uauacuaacc ccaggguugg    120
ucaauuucgu gccaaccacc                                                 140

<210> SEQ ID NO 114
<211> LENGTH: 144
<212> TYPE: RNA
<213> ORGANISM: Homo sapiens

<400> SEQUENCE: 114
caucaagcac gcagcaaugc agcucaaaac gcuuagccua gccacacccc caugggaaac      60
agcagugauu aaccuuuagc aauaaacgaa aguuuaacua agcuauacua accccagggu    120
uggucaauuu cgugccagcu cacc                                            144

<210> SEQ ID NO 115
<211> LENGTH: 142
<212> TYPE: RNA
<213> ORGANISM: Homo sapiens

<400> SEQUENCE: 115
```

```
caagcacgca gcaaugcagc ucaaaacgcu uagccuagcc acaccccac gggaaacagc      60 agugauuaac cuuuagcaau aaacgaaagu uuaacuaagc uauacuaacc ccaggguugg    120
ucaauuucgu gccagccaca cc                                             142

<210> SEQ ID NO 116
<211> LENGTH: 140
<212> TYPE: RNA
<213> ORGANISM: Homo sapiens

<400> SEQUENCE: 116
caagcacgca gcaaugcagc ucaaaacgcu uagccuagcc acaccccac gggaaacagc      60 agugauuaac cuuuagcaau aaacgaaagu uuaacuaagc uauacuaacc ccaggguugg    120
ucaauuucgu gccagccacc                                                140

<210> SEQ ID NO 117
<211> LENGTH: 162
<212> TYPE: RNA
<213> ORGANISM: Homo sapiens

<400> SEQUENCE: 117
cacgaucaaa agggacaagc aucaagcacg cagcaaugca gcucaaaacg cuuagccuag     60
ccacaccccc acgggaaaca gcagugauua accuuuagca auaaacgaaa guuuaacuaa    120
gcuauacuaa ccccaggguu ggucaauuuc gugccagcca cc                       162

<210> SEQ ID NO 118
<211> LENGTH: 170
<212> TYPE: RNA
<213> ORGANISM: Homo sapiens

<400> SEQUENCE: 118
uaaaucacca cgaucaaaag ggacaagcau caagcacgca gcaaugcagc ucaaaacgcu     60
uagccuagcc acaccccac gggaaacagc agugauuaac cuuuagcaau aaacgaaagu    120
uuaacuaagc uauacuaacc ccaggguugg ucaauuucgu gccagccacc               170

<210> SEQ ID NO 119
<211> LENGTH: 236
<212> TYPE: RNA
<213> ORGANISM: Homo sapiens

<400> SEQUENCE: 119
agccuuucua uuagcucuua guaagauuac acaugcaagc auccccguuc cagugaguuc     60
acccucuaaa ucaccacgau caaagggac aagcaucaag cacgcagcaa ugcagcucaa    120
aacgcuuagc cuagccacac ccccacggga aacagcagug auuaaccuuu agcaauaaac    180
gaaaguuuaa cuaagcuaua cuaaccccag gguuggucaa uuucgugcca gccacc         236

<210> SEQ ID NO 120
<211> LENGTH: 151
<212> TYPE: RNA
<213> ORGANISM: Homo sapiens

<400> SEQUENCE: 120
gggacaagca ucaagcacgc agcaaugcag cucaaaacgc uuagccuagc cacacccca      60 cgggaaacag cagugauuaa ccuuuagcaa uaaacgaaag uuuaacuaag cuauacuaac    120
cccaggguug gucaauuucg ugccagccac c                                   151
```

```
<210> SEQ ID NO 121
<211> LENGTH: 151
<212> TYPE: RNA
<213> ORGANISM: Homo sapiens

<400> SEQUENCE: 121
gggacaagca ucaagcacgc agcaaugcag cucaaaacgc uuagccuagc cacaccccca    60
cgggaaacag cagugauuaa ccuuuagcaa uaaacgaaag uuuaacuaag cuauacuaac   120 cccagggüug gucaauuucg ugccagccac c                                  151

<210> SEQ ID NO 122
<211> LENGTH: 253
<212> TYPE: RNA
<213> ORGANISM: Homo sapiens

<400> SEQUENCE: 122
uucugcccca gcuuugcagg augaaacacu uccccgcuug gcucucauuc uuccacaaga    60
gagaccuuuc uccggaccug guugcuacug guucagcaac ucugcagaaa auguccuccc   120
cuguggcugc cucagcucau gccuuuggcc ugaagucccca gcaugaugg cagcccccuca   180 ucuuccaagu uuugcgcucc ccuuuaccua acgcuuccug ccucccaugc aucuguacuc   240
cuucugugcc acu                                                      253

<210> SEQ ID NO 123
<211> LENGTH: 253
<212> TYPE: RNA
<213> ORGANISM: Homo sapiens

<400> SEQUENCE: 123
uucugcccca gcuuugcagg augaaacacu uccccgcuug gcucucauuc uuccacaaga    60
gagaccuuuc uccggaccug guugcuacug guucagcaac ucugcagaaa auguccuccc   120
cuguggcugc cucagcucau gccuuuggcc ugaagucccca gcaugaugg cagcccccuca   180 ucuuccaagu uuugcgcucc ccuuuaccua acgcuuccug ccucccaugc aucuguacuc   240
cuucugugcc acu                                                      253

<210> SEQ ID NO 124
<211> LENGTH: 250
<212> TYPE: RNA
<213> ORGANISM: Homo sapiens

<400> SEQUENCE: 124 cccccagcuuu gcaggaugaa acacuucccc gcuuggcucu cauucuucca caagagagac    60
cuuucuccgg accugguugc uacugguuca gcaacucugc agaaaauguc cuccccugug   120
gcugccucag cucaugccuu uggccugaag ucccagcauu gauggcagcc ccucaucuuc   180
caaguuuugu gcucccccuuu accuaacgcu uccugccucc caugcaucug uacuccuccu   240
gugccacaaa                                                          250

<210> SEQ ID NO 125
<211> LENGTH: 250
<212> TYPE: RNA
<213> ORGANISM: Homo sapiens

<400> SEQUENCE: 125 cccccagcuuu gcaggaugaa acacuucccc gcuuggcucu cauucuucca caagagagac    60
cuuucuccgg accugguugc uacugguuca gcaacucugc agaaaauguc cuccccugug   120
```

```
gcugccucag cucaugccuu uggccugaag ucccagcauu gauggcagcc ccucaucuuc    180
caaguuuugu gcuccccuuu accaacgcu uccugccucc caugcaucug uacuccuccu    240
gugccacaaa                                                          250

<210> SEQ ID NO 126
<211> LENGTH: 233
<212> TYPE: RNA
<213> ORGANISM: Homo sapiens

<400> SEQUENCE: 126
cuuugcagga ugaaacacuu ccccgcuugg cucucauucu uccacaagag agaccuuucu    60
ccggaccugg uugcuacugg uucagcaacu cugcagaaaa uguccucccc uguggcugcc   120
ucagcucaug ccuuuggccu gaagucccag cauugauggc agccccucau cuuccaaguu   180
uugugcuccc cuuuaccuaa cgcuuccugc ucccaugca ucuguacucc ucc            233

<210> SEQ ID NO 127
<211> LENGTH: 228
<212> TYPE: RNA
<213> ORGANISM: Homo sapiens

<400> SEQUENCE: 127
ugcaggauga aacacuuccc cgcuuggcuc ucauucuucc acaggagaga ccuuucuccg    60 gaccgguug cuacgguuc agcaacucug cagaaaaugu cccccugu ggcugccuca      120 gcucaugccu uuggccugaa gucccagcau ugauggcagc cccucaucu ccaaguuug    180 ugcucccccuu uaccaacgc uuccugccuc ccaugcaucu guaccca                 228

<210> SEQ ID NO 128
<211> LENGTH: 280
<212> TYPE: RNA
<213> ORGANISM: Homo sapiens

<400> SEQUENCE: 128
gugaagauga ccacauucaa ggaagaaccu cugccccag cuuugcagga ugaaacacuu     60
ccccgcuugg cucuccuucu uccacaagag agaccuuucu ccggaccugg uugcuacugg   120
uucagcagcu cugcagaaaa uguccucccu uguggcugcc ucagcucgua ccuuuggccu   180
gaagucccag cauuaauggc agccccucau cuuccaaguu uugugcuccc cuuuaccuaa   240
ugcuuccugc ucccaugca ucuguacucc ugcugugcca                          280

<210> SEQ ID NO 129
<211> LENGTH: 207
<212> TYPE: RNA
<213> ORGANISM: Homo sapiens

<400> SEQUENCE: 129
uccacaagag agaccuuucu ccggaccugg cugcuacugg uucagcagcu cugcagaaaa    60
uguccucccu uguggcugcc ucagcucgua ccuuuggccu gaagucccag cauuaauggc   120
agccccucau cuuccaaguu uugugcuccc cuuuaccuaa ugcuuccugc ucccaugca   180 ucuguacucc ugcugugcca caaacac                                      207

<210> SEQ ID NO 130
<211> LENGTH: 207
<212> TYPE: RNA
<213> ORGANISM: Homo sapiens
```

<400> SEQUENCE: 130

```
uccacaagag agaccuuucu ccggaccugg cugcuacugg uucagcagcu cugcagaaaa      60
ugucccuccu uguggcugcc ucagcucgua ccuuuggccu gaagucccag cauuaauggc     120
agccccucau cuuccaaguu uugugcuccc cuuuaccuaa ugcuuccugc cucccaugca     180
ucuguacucc ugcugugcca caaacac                                         207
```

<210> SEQ ID NO 131
<211> LENGTH: 163
<212> TYPE: RNA
<213> ORGANISM: Homo sapiens

<400> SEQUENCE: 131

```
gcuacugguu cagcagcucu gcagaaaaug uccucccuug uggcugccuc agcucguacc      60
uuuggccuga agucccagca uuaauggcag ccccucaucu ccaaguuuug ugucccccu      120
uuaccuaaug cuuccugccu cccaugcauc uguacuccug cgu                       163
```

<210> SEQ ID NO 132
<211> LENGTH: 249
<212> TYPE: RNA
<213> ORGANISM: Homo sapiens

<400> SEQUENCE: 132

```
agaaccuucu gccccagcuu ugcaggauga aacacuuccc cgcuuggcuc ucauucuucc      60
acaagagaga ccuuucuccg gaccugguug cuacugguuc agcagcucug cagaaaaugu     120
ccucccuugu ggcugccuca gcucguaccu uuggccugaa gucccagcau aauggcagc     180
cccucaucuu ccaaguuuug cucccccuu accuaaugc uuccugccuc ccaugcaucu      240
guacuccug                                                             249
```

<210> SEQ ID NO 133
<211> LENGTH: 249
<212> TYPE: RNA
<213> ORGANISM: Homo sapiens

<400> SEQUENCE: 133

```
agaaccuucu gccccagcuu ugcaggauga aacacuuccc cgcuuggcuc ucauucuucc      60
acaagagaga ccuuucuccg gaccugguug cuacugguuc agcagcucug cagaaaaugu     120
ccucccuugu ggcugccuca gcucguaccu uuggccugaa gucccagcau aauggcagc     180
cccucaucuu ccaaguuuug cucccccuu accuaaugc uuccugccuc ccaugcaucu      240
guacuccug                                                             249
```

<210> SEQ ID NO 134
<211> LENGTH: 264
<212> TYPE: RNA
<213> ORGANISM: Homo sapiens

<400> SEQUENCE: 134

```
ugaagaugac cacauucaag gaagaaccuu cugccccagc uuugcaggau gaaacacuuc      60
cccgcuuggc ucucauucuu ccacaagaga ccuuucuc cggaccuggu uguucagcag     120
cucugcagaa aauguccucc cuuguggcug ccucagcucu accuuuggc cugaagcccc      180
agcauuaaug gcagccccuc aucuccaag uuugugcuc cccuuaccu aaugcuuccu      240
gccucccaug caucuguacu ccug                                            264
```

<210> SEQ ID NO 135
<211> LENGTH: 270
<212> TYPE: RNA
<213> ORGANISM: Homo sapiens

<400> SEQUENCE: 135
ugaagaugac cacauucaag gaagaaccuu cugccccagc uuugcaggau gaaacacuuc    60
cccgcuuggc ucucauucuu ccacaagaga gaccuuucuc cggaccuggu ugcuacuggu   120
ucagcagcuc ugcagaaaau guccuccccu guggcugccu cagcucguac cuuuggccug   180
aagucccagc auuaauggca gccccucauc uuccaaguuu ugugcucccc uuuaccuaau   240
gcuuccugcc ucccaugcau cuguacuccc                                   270

<210> SEQ ID NO 136
<211> LENGTH: 245
<212> TYPE: RNA
<213> ORGANISM: Homo sapiens

<400> SEQUENCE: 136
ccacauucaa ggaagaaccu ucugcccag cuuugcagga ugaaacacuu ccccgcuugg    60
cucucauucu uccacaagag agaccuuucu ccggaccugg uugcuacugg uucagcagcu   120
cugcagaaaa uguccucccu guggcugcc ucagcucgua ccuuuggccu gaagucccag    180
cauuaauggc agccccucau cuuccaaguu uugugcuccc cuuuaccuaa ugcuuccugc   240
ccccc                                                               245

<210> SEQ ID NO 137
<211> LENGTH: 257
<212> TYPE: RNA
<213> ORGANISM: Homo sapiens

<400> SEQUENCE: 137
gugaagauga ccacauucaa ggaagaaccu ucugccccag cuuugcagga ugaaacacuu    60
ccccgcuugg cucucauucu uccacaagag agaccuuucu ccggaccugg uugcuacugg   120
uucagcagcu cugcagaaaa uguccucccu guggcugcc ucagcucgua ccuuuggccu    180
gaagucccag cauuaauggc agccccucau cuuccaaguu uugugcuccc cuuuaccuaa   240
ugcuuccugc cccccau                                                 257

<210> SEQ ID NO 138
<211> LENGTH: 209
<212> TYPE: RNA
<213> ORGANISM: Homo sapiens

<400> SEQUENCE: 138
agaaccuucu gccccagcuu ugcaggauga aacacuuccc cgcuuggcuc ucauucucc    60 acaagagaga ccuuucuccg gaccugguug cuacugguuc agcagcucug cagaaaaugu   120 ccuccuugu ggcugccuca gcucguaccu uuggccugaa gucccagcau uaauggcagc   180
cccucaucuu ccaaguuuug ugcuccccc                                    209

<210> SEQ ID NO 139
<211> LENGTH: 276
<212> TYPE: RNA
<213> ORGANISM: Homo sapiens

<400> SEQUENCE: 139
cugaagugaa gaugaccaca uucaaggaag aaccuucugc cccagcuuug caggaugaaa    60

| | | |
|---|---|---|
| cacuuccccg cuuggcucuc auucuuccac aagagagacc uuucuccgga ccugguugcu | 120 | |
| acugguucag cagcucugca gaaaaugucc ucccugugg cugccucagc ucguaccuuu | 180 | |
| ggccugaagu cccagcauua auggcagccc cucaucuucc aaguuugug cuccccuuua | 240 | |
| ccuaaugcuu ccugccuccc augcaucugu acuccu | 276 | |

```
<210> SEQ ID NO 140
<211> LENGTH: 276
<212> TYPE: RNA
<213> ORGANISM: Homo sapiens

<400> SEQUENCE: 140
```

| | | |
|---|---|---|
| cugaagugaa gaugaccaca uucaaggaag aaccuucugc cccagcuuug caggaugaaa | 60 | |
| cacuuccccg cuuggcucuc auucuuccac aagagagacc uuucuccgga ccugguugcu | 120 | |
| acugguucag cagcucugca gaaaaugucc ucccugugg cugccucagc ucguaccuuu | 180 | |
| ggccugaagu cccagcauua auggcagccc cucaucuucc aaguuugug cuccccuuua | 240 | |
| ccuaaugcuu ccugccuccc augcaucugu acuccu | 276 | |

```
<210> SEQ ID NO 141
<211> LENGTH: 270
<212> TYPE: RNA
<213> ORGANISM: Homo sapiens

<400> SEQUENCE: 141
```

| | | |
|---|---|---|
| aagaugacca cauucaagga agaaccuucu gccccagcuu ugcaggauga aacacuuccc | 60 | |
| cgcuuggcuc ucauucuucc acaagagaga ccuuucuccg gaccugguug cuacugguuc | 120 | |
| agcagcucug cagaaaaugu ccucccuugu ggcugccuca gcucguaccu uuggccugaa | 180 | |
| gucccagcau uaauggcagc ccccaucucu ccaaguuuug cucccccuu uaccaaugc | 240 | |
| uuccugccuc ccaugcaucu guacuccugc | 270 | |

```
<210> SEQ ID NO 142
<211> LENGTH: 211
<212> TYPE: RNA
<213> ORGANISM: Homo sapiens

<400> SEQUENCE: 142
```

| | | |
|---|---|---|
| ccccgcuugg cucucauucu uccacaagag agaccuuucu ccggaccugg uugcuacugg | 60 | |
| uucagcagcu cugcagaaaa uguccucccu uguggcugcc ucagcucgua ccuuuggccu | 120 | |
| gaagucccag cauuaauggc agccccucau cuuccaaguu uugugcuccc cuuuaccuaa | 180 | |
| ugcuuccugc cucccaugca ucuguacucc u | 211 | |

```
<210> SEQ ID NO 143
<211> LENGTH: 211
<212> TYPE: RNA
<213> ORGANISM: Homo sapiens

<400> SEQUENCE: 143
```

| | | |
|---|---|---|
| ccccgcuugg cucucauucu uccacaagag agaccuuucu ccggaccugg uugcuacugg | 60 | |
| uucagcagcu cugcagaaaa uguccucccu uguggcugcc ucagcucgua ccuuuggccu | 120 | |
| gaagucccag cauuaauggc agccccucau cuuccaaguu uugugcuccc cuuuaccuaa | 180 | |
| ugcuuccugc cucccaugca ucuguacucc u | 211 | |

```
<210> SEQ ID NO 144
<211> LENGTH: 286
```

```
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 144
ugcccguccu caccaagacu gacugccugc ugcuuugcua cugcccgggc ccaugagacu        60
gacuucccac ugcucugccu gccucucccc acugcacugg cacagcccg ccuugccgcu       120 gcugauccau ugccggugug accugcccgu ccucaccaag acugacugcc ugcugcuuug      180
cuacugcccg ggcccaugag acugacuucc cacugcucug ccugcccucu cccacugcac      240
uggcacagcc ccgccuugcc gcugcugauc cauugccggu gugacc                     286

<210> SEQ ID NO 145
<211> LENGTH: 292
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 145
ugcccguccu caccaagacu gacugccugc ugcuuugcua cugcccgggc ccaugagacu        60
gacuucccac ugcucugccu gccucucccc acugcacugg cacagcccg ccuugccgcu       120 gcugauccau ugccggugug accuuccagc cagacacccg cccccggcc cuggcuaaga       180 aguugcuucc uguugccagc augaccuacc cucgccucuu ugaugccauc cgcugccacc      240
uccuuuugcu ccuggacccu uuagccucuc ugcccuucca cucucugacc cc              292

<210> SEQ ID NO 146
<211> LENGTH: 298
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 146
ugcccguccu caccaagacu gacugccugc ugcuuugcua cugcccgggc ccaugagacu        60
gacuucccac ugcucugccu gccucucccc acugcacugg cacagcccg ccuugccgcu       120 gcugauccau ugccggugug accgccuugg cuccuccagg aaggcucagg agcccuaccu      180
cccugccauu auagcugcuc cccgccagaa gccugugcca acucucugca uucccugauc      240 uccauccug uggcugucac ccuuggucac cuccgugcug ucacugccau cucccccc         298

<210> SEQ ID NO 147
<211> LENGTH: 279
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 147
ugcccguccu caccaagacu gacugccugc ugcuuugcua cugcccgggc ccaugagacu        60
gacuucccac ugcucugccu gccucucccc acugcacugg cacagcccg ccuugccgcu       120 gcugauccau ugccggugug acccuggac ugcaugcacg caaugcuagc ugccccuuuc       180
ccguccuggg uacccccgagu cuccccccgac cucggguccc agguaugcuc ccaccuccac    240
```
cugccccacu caccaccucu gcuaguucca gacaccucc        279

<210> SEQ ID NO 148
<211> LENGTH: 333
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 148
ugcccguccu caccaagacu gacugccugc ugcuuugcua cugcccgggc ccaugagacu        60
gacuucccac ugcucugccu gccucucccc acugcacugg cacagcccg ccuugccgcu       120 gcugauccau ugccggugug acccugacag cgugggcaac gccugccgcc ugcucugagg      180
cccgauccag ugggcaggcc aaggccugcu gggcccccgc ggacccaggu gcucugggguc     240 acgguccug ucccgcacc cccgcuucug ucugcccau uguggcuccu caggcucucu        300
ccccugcucu cccaccucua ccuccacccc cac                                    333

<210> SEQ ID NO 149
<211> LENGTH: 285
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 149
ugcccguccu caccaagacu gacugccugc ugcuuugcua cugcccgggc ccaugagacu        60
gacuucccac ugcucugccu gccucucccc acugcacugg cacagcccg ccuugccgcu       120 gcugauccau ugccggugug accgagagcu cgcuuucug cuguccaauu ucuauuaaag      180
guuccuuugu ucccuaaguc caacuacuaa acuggggau auuaugaagg gccuugagca        240
ucuggauucu gccuaauaaa aaacauuuau uuucauugcu gcguc                       285

<210> SEQ ID NO 150
<211> LENGTH: 285
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 150
ugcccguccu caccaagacu gacugccugc ugcuuugcua cugcccgggc ccaugagacu        60
gacuucccac ugcucugccu gccucucccc acugcacugg cacagcccg ccuugccgcu       120 gcugauccau ugccggugug acccaagcac gcagcaaugc agcucaaaac gcuuagccua      180
gccacacccc cacgggaaac agcagugauu aaccuuuagc aauaaacgaa aguuuaacua       240
agcuauacua accccagggu uggucaauuu cgugccagcc acacc                       285

<210> SEQ ID NO 151
<211> LENGTH: 376
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 151
ugcccguccu caccaagacu gacugccugc ugcuuugcua cugcccgggc ccaugagacu        60

```
gacuucccac ugcucugccu gccucuccccc acugcacugg cacagcccccg ccuugccgcu     120 gcugauccau ugccggugug acccuuugca ggaugaaaca cuuccccgcu uggcucucau      180
ucuuccacaa gagagaccuu ucuccggacc ugguugcuac ugguucagca acucugcaga      240 aaaugccuc cccugugggcu gccucagcuc augccuuugg ccugaagucc cagcauugau      300 ggcagcccccu caucuuccaa guuuugugcu ccccuuuacc uaacgcuucc ugccucccau    360
gcaucuguac uccucc                                                      376
```

```
<210> SEQ ID NO 152
<211> LENGTH: 292
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 152
uuccagccag acacccgccc cccggcccug gcuaagaagu ugcuuccugu ugccagcaug       60
accuacccuc gccucuuuga ugccauccgc ugccaccucc uuuugcuccu ggacccuuua     120
gccucucugc ccuuccacuc ucugaccccu gcccguccuc accaagacug acugccugcu     180
gcuuugcuac ugcccgggcc caugagacug acuucccacu gcucugccug ccucuccccca    240 cugcacuggc acagccccgc cuugccgcug cugauccauu gccgguguga cc              292
```

```
<210> SEQ ID NO 153
<211> LENGTH: 298
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 153
uuccagccag acacccgccc cccggcccug gcuaagaagu ugcuuccugu ugccagcaug       60
accuacccuc gccucuuuga ugccauccgc ugccaccucc uuuugcuccu ggacccuuua     120
gccucucugc ccuuccacuc ucugaccccu uccagccaga cacccgcccc ccggcccugg     180
cuaagaaguu gcuuccuguu gccagcauga ccuacccucg ccucuuugau gccauccgcu     240
gccaccuccu uuugcuccug gacccuuuag ccucucugcc cuuccacucu cugacccc       298
```

```
<210> SEQ ID NO 154
<211> LENGTH: 304
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 154
uuccagccag acacccgccc cccggcccug gcuaagaagu ugcuuccugu ugccagcaug       60
accuacccuc gccucuuuga ugccauccgc ugccaccucc uuuugcuccu ggacccuuua     120
gccucucugc ccuuccacuc ucugacccccg ccuuggcucc uccaggaagg cucaggagcc    180
cuaccucccu gccauuauag cugcucccccg ccagaagccu gugccaacuc ucugcauucc    240 cugauccca ucccugugggc ugucacccuu ggucaccucc gugcugucac ugccaucucc    300
cccc                                                                   304
```

```
<210> SEQ ID NO 155
<211> LENGTH: 285
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 155
uuccagccag acacccgccc cccggcccug gcuaagaagu ugcuuccugu ugccagcaug      60
accuacccuc gccucuuuga ugccauccgc ugccaccucc uuuugcuccu ggacccuuua     120
gccucucugc ccuuccacuc ucugaccccc ugguacugca ugcacgcaau gcuagcugcc     180
ccuuucccgu ccugggacc ccgagucucc cccgaccucg ggucccaggu augcucccac      240
cuccaccugc cccacucacc accucugcua guuccagaca ccucc                    285

<210> SEQ ID NO 156
<211> LENGTH: 339
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 156
uuccagccag acacccgccc cccggcccug gcuaagaagu ugcuuccugu ugccagcaug      60
accuacccuc gccucuuuga ugccauccgc ugccaccucc uuuugcuccu ggacccuuua     120
gccucucugc ccuuccacuc ucugaccccc ugacagcgug ggcaacgccu gccgccugcu     180
cugaggcccg auccaguggg caggccaagg ccugcugggc cccgcggac ccaggugcuc      240 ugggucacgg ucccugnccc cgcaccccg cuucugucug cccauugug gcuccucagg       300 cucucucccc ugcucuccca ccucuaccuc cacccccac                           339

<210> SEQ ID NO 157
<211> LENGTH: 291
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 157
uuccagccag acacccgccc cccggcccug gcuaagaagu ugcuuccugu ugccagcaug      60
accuacccuc gccucuuuga ugccauccgc ugccaccucc uuuugcuccu ggacccuuua     120
gccucucugc ccuuccacuc ucugaccccg agagcucgcu uucuugcugu ccaauuucua     180
uuaaagguuc cuuuguuccc uaaguccaac uacuaaacug ggggauauua ugaagggccu     240
ugagcaucug gauucugccu aauaaaaaac auuuauuuuc auugcugcgu c              291

<210> SEQ ID NO 158
<211> LENGTH: 291
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 158
uuccagccag acacccgccc cccggcccug gcuaagaagu ugcuuccugu ugccagcaug      60
accuacccuc gccucuuuga ugccauccgc ugccaccucc uuuugcuccu ggacccuuua     120
```

```
gccucucugc ccuuccacuc ucugacccc  aagcacgcag caaugcagcu caaaacgcuu    180
agccuagcca caccccacg  ggaaacagca gugauuaacc uuuagcaaua aacgaaaguu    240
uaacuaagcu auacuaaccc cagggguuggu caauuucgug ccagccacac c             291
```

<210> SEQ ID NO 159
<211> LENGTH: 382
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 159

```
uuccagccag acacccgccc cccggcccug gcuaagaagu ugcuuccugu ugccagcaug    60
accuacccuc gccucuuuga ugccauccgc ugccaccucc uuuugcuccu ggacccuuua   120
gccucucugc ccuuccacuc ucugacccc  uuugcaggau gaaacacuuc cccgcuuggc   180
ucucauucuu ccacaagaga gaccuuucuc cggaccuggu ugcuacuggu ucagcaacuc   240
ugcagaaaau guccuccccu guggcugccu cagcucaugc cuuuggccug aaguccagc    300 auugauggca gccccucauc uuccaaguuu ugugcucccc uuuaccuaac gcuuccugcc   360
ucccaugcau cuguacuccu cc                                            382
```

<210> SEQ ID NO 160
<211> LENGTH: 298
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 160

```
gccuuggcuc cuccaggaag gcucaggagc ccuaccuccc ugccauuaua gcugcuccc    60 gccagaagcc ugugccaacu cucugcauuc ccugaucucc aucccugugg cugucacccu   120
uggucaccuc cgugcuguca cugccaucuc cccccugccc guccucacca agacugacug   180
ccugcugcuu ugcuacugcc cgggcccaug agacugacuu cccacugcuc ugccugccuc   240
uccccacugc acuggcacag ccccgccuug ccgcugcuga uccauugccg gugugacc     298
```

<210> SEQ ID NO 161
<211> LENGTH: 304
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 161

```
gccuuggcuc cuccaggaag gcucaggagc ccuaccuccc ugccauuaua gcugcuccc    60 gccagaagcc ugugccaacu cucugcauuc ccugaucucc aucccugugg cugucacccu   120
uggucaccuc cgugcuguca cugccaucuc ccccuucca  gccagacacc cgcccccgg    180 cccuggcuaa gaaguugcuu ccuguugcca gcaugaccua cccucgccuc uuugaugcca   240
uccgcugcca ccuccuuuug cuccuggacc cuuuagccuc ucugcccuuc cacucucuga   300
cccc                                                                304
```

<210> SEQ ID NO 162
<211> LENGTH: 310
<212> TYPE: RNA

-continued

```
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 162
gccuuggcuc cuccaggaag gcucaggagc ccuaccuccc ugccauuaua gcugcuccccc    60 gccagaagcc ugugccaacu cucugcauuc ccugaucucc aucccugugg cugucacccu   120
uggucaccuc cgugcuguca cugccaucuc cccccgccuu ggcuccucca ggaaggcuca   180
ggagcccuac cucccugcca uuauagcugc uccccgccag aagccugugc caacucucug   240
cauucccuga ucccauccc uguggcuguc acccuugguc accuccgugc ugucacugcc   300 aucuccccccc                                                         310

<210> SEQ ID NO 163
<211> LENGTH: 291
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 163
gccuuggcuc cuccaggaag gcucaggagc ccuaccuccc ugccauuaua gcugcuccccc    60 gccagaagcc ugugccaacu cucugcauuc ccugaucucc aucccugugg cugucacccu   120
uggucaccuc cgugcuguca cugccaucuc cccccuggu acugcaugca cgcaaugcua   180 gcugcccuu ucccguccug gguacccga gucccccg accugggcuc caggcuaugc     240
ucccaccucc accugcccca cucaccaccu cugcuaguuc cagacaccuc c             291

<210> SEQ ID NO 164
<211> LENGTH: 345
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 164
gccuuggcuc cuccaggaag gcucaggagc ccuaccuccc ugccauuaua gcugcuccccc    60 gccagaagcc ugugccaacu cucugcauuc ccugaucucc aucccugugg cugucacccu   120
uggucaccuc cgugcuguca cugccaucuc cccccugac agcgugggca acgccugccg   180
ccugcucuga ggcccgaucc agugggcagg ccaaggccug cugggccccc gcggacccag   240
gugcucuggg ucacggucc uguccccgca ccccgcuuc ugucugcccc auuguggcuc     300
cucaggcucu cuccccugcu cucccaccuc uaccuccacc cccac                   345

<210> SEQ ID NO 165
<211> LENGTH: 297
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 165
gccuuggcuc cuccaggaag gcucaggagc ccuaccuccc ugccauuaua gcugcuccccc    60 gccagaagcc ugugccaacu cucugcauuc ccugaucucc aucccugugg cugucacccu   120
uggucaccuc cgugcuguca cugccaucuc ccccgagag cucgcuuucu ugcuguccaa   180
```

```
uuucuauuaa agguuccuuu guucccuaag uccaacuacu aaacuggggg auauuaugaa    240
gggccuugag caucuggauu cugccuaaua aaaaacauuu auuuucauug cugcguc       297

<210> SEQ ID NO 166
<211> LENGTH: 297
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 166
gccuuggcuc cuccaggaag gcucaggagc ccuaccuccc ugccauuaua gcugcuccccc   60 gccagaagcc ugugccaacu cucugcauuc ccugaucucc aucccugugg cugucacccu    120
uggucaccuc cgugcuguca cugccaucuc cccccaagc acgcagcaau gcagcucaaa    180
acgcuuagcc uagccacacc cccacgggaa acagcaguga uuaaccuuua gcauaaaacg    240
aaaguuuaac uaagcuauac uaaccccagg guuggucaau uucgugccag ccacacc       297

<210> SEQ ID NO 167
<211> LENGTH: 388
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 167
gccuuggcuc cuccaggaag gcucaggagc ccuaccuccc ugccauuaua gcugcuccccc   60 gccagaagcc ugugccaacu cucugcauuc ccugaucucc aucccugugg cugucacccu    120
uggucaccuc cgugcuguca cugccaucuc ccccccuuug caggaugaaa cacuuccccg    180
cuuggcucuc auucuuccac aagagagacc uuucuccgga ccugguugcu acugguucag    240
caacucugca gaaaaugucc uccccugugg cugccucagc ucaugccuuu ggccugaagu    300
cccagcauug auggcagccc cucaucuucc aaguuuugug cuccccuuua ccuaacgcuu    360
ccugccuccc augcaucugu acuccucc                                       388

<210> SEQ ID NO 168
<211> LENGTH: 279
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 168
cugguacugc augcacgcaa ugcuagcugc cccuuucccg uccugggac cccgagucuc     60 ccccgaccuc ggguccagg uaugcuccca ccuccaccug ccccacucac caccucugcu    120
aguuccagac accuccugcc cguccucacc aagacugacu gccugcugcu uugcuacugc    180
ccggccccau gagacugacu ucccacugcu cugccugccu cuccccacug cacuggcaca    240
gccccgccuu gccgcugcug auccauugcc ggugugacc                           279

<210> SEQ ID NO 169
<211> LENGTH: 285
<212> TYPE: RNA
<213> ORGANISM: Artificial Sequence
<220> FEATURE:
<223> OTHER INFORMATION: Description of Artificial Sequence: Synthetic
```

Combination of 3'-UTR sequence elements

<400> SEQUENCE: 169

| | | | | | |
|---|---|---|---|---|---|
| cugguacugc | augcacgcaa | ugcuagcugc | cccuucccg | uccuggguac | cccgagucuc | 60 |
| ccccgaccuc | ggguccccagg | uaugcuccca | ccuccaccug | ccccacucac | caccucugcu | 120 |
| aguuccagac | accuccuucc | agccagacac | ccgcccccg | gcccuggcua | agaaguugcu | 180 |
| uccuguugcc | agcaugaccu | acccucgccu | cuuugaugcc | auccgcugcc | accuccuuuu | 240 |
| gcuccuggac | ccuuuagccu | cucugcccuu | ccacucucug | acccc | | 285 |

<210> SEQ ID NO 170
<211> LENGTH: 291
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 170

| | | | | | |
|---|---|---|---|---|---|
| cugguacugc | augcacgcaa | ugcuagcugc | cccuucccg | uccuggguac | cccgagucuc | 60 |
| ccccgaccuc | ggguccccagg | uaugcuccca | ccuccaccug | ccccacucac | caccucugcu | 120 |
| aguuccagac | accuccgccu | uggcuccucc | aggaaggcuc | aggagcccua | ccucccugcc | 180 |
| auuauagcug | cuccccgcca | gaagccugug | ccaacucucu | gcauccccug | aucccauccc | 240 |
| cuguggcugu | cacccuuggu | caccuccgug | cugucacugc | caucucccc | c | 291 |

<210> SEQ ID NO 171
<211> LENGTH: 272
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 171

| | | | | | |
|---|---|---|---|---|---|
| cugguacugc | augcacgcaa | ugcuagcugc | cccuucccg | uccuggguac | cccgagucuc | 60 |
| ccccgaccuc | ggguccccagg | uaugcuccca | ccuccaccug | ccccacucac | caccucugcu | 120 |
| aguuccagac | accucccugg | uacugcaugc | acgcaaugcu | agcugccccu | uucccguccu | 180 |
| ggguaccccg | agucuccccc | gaccucgggu | cccagguaug | ucccaccuc | caccugcccc | 240 |
| acucaccacc | ucugcuaguu | ccagacaccu | cc | | | 272 |

<210> SEQ ID NO 172
<211> LENGTH: 326
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 172

| | | | | | |
|---|---|---|---|---|---|
| cugguacugc | augcacgcaa | ugcuagcugc | cccuucccg | uccuggguac | cccgagucuc | 60 |
| ccccgaccuc | ggguccccagg | uaugcuccca | ccuccaccug | ccccacucac | caccucugcu | 120 |
| aguuccagac | accucccuga | cagcgugggc | aacgccugcc | gccugcucug | aggcccgauc | 180 |
| caguggggcag | gccaaggccu | gcugggcccc | cgcggaccca | ggugcucugg | gucacggucc | 240 |
| cugucccccgc | accccgcuu | cugucugccc | cauugugggcu | cccaggcuc | ucuccccugc | 300 |
| ucucccaccu | cuaccuccac | ccccac | | | | 326 |

<210> SEQ ID NO 173
<211> LENGTH: 278
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 173
cugguacugc augcacgcaa ugcuagcugc cccuucccg uccggguac cccgagucuc      60 ccccgaccuc gggucccagg uaugcuccca ccuccaccug ccccacucac caccucugcu     120
aguuccagac accuccgaga gcucgcuuuc uugcugucca auucuauua aagguuccuu      180 uguucccuaa guccaacuac uaaacugggg gauauuauga agggccuuga gcaucuggau     240
ucugccuaau aaaaaacauu uauuucauu gcugcguc                              278

<210> SEQ ID NO 174
<211> LENGTH: 278
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 174
cugguacugc augcacgcaa ugcuagcugc cccuucccg uccggguac cccgagucuc       60 ccccgaccuc gggucccagg uaugcuccca ccuccaccug ccccacucac caccucugcu    120
aguuccagac accucccaag cacgcagcaa ugcagcucaa aacgcuuagc cuagccacac    180
ccccacggga aacagcagug auuaaccuuu agcaauaaac gaaaguuuaa cuaagcuaua    240
cuaaccccag gguuggucaa uuucgugcca gccacacc                             278

<210> SEQ ID NO 175
<211> LENGTH: 369
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 175
cugguacugc augcacgcaa ugcuagcugc cccuucccg uccggguac cccgagucuc       60 ccccgaccuc gggucccagg uaugcuccca ccuccaccug ccccacucac caccucugcu    120
aguuccagac accuccuuu gcaggaugaa acacuuccc gcuuggcucu cauucuucca      180
caagagagac cuuucuccgg accugguugc uacgguuca gcaacucugc agaaaaugc      240 cuccccugug gcugcucag cucaugccuu uggccugaag uccagcauu gauggcagcc      300 ccucaucuuc caaguuuugu gcuccccuuu accaacgcu uccugccucc caugcaucug     360
uacuccucc                                                             369

<210> SEQ ID NO 176
<211> LENGTH: 333
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 176
cugacagcgu gggcaacgcc ugccgccugc ucugaggccc gauccagugg gcaggccaag     60

```
gccugcuggg ccccgcgga cccaggugcu cugggucacg gucccuguccc ccgcaccccc    120 gcuucugucu gccccauugu ggcuccucag gcucucuccc cugcucuccc accucuaccu    180 ccaccccac ugcccguccu caccaagacu gacugccugc ugcuuugcua cugcccgggc    240
ccaugagacu gacuucccac ugcucugccu gccucuccc acugacugg cacagccccg     300 ccuugccgcu gcugauccau ugccggugug acc                                333
```

<210> SEQ ID NO 177
<211> LENGTH: 339
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 177

```
cugacagcgu gggcaacgcc ugccgccugc ucugaggccc gauccagugg gcaggccaag    60
gccugcuggg ccccgcgga cccaggugcu cugggucacg gucccuguccc ccgcaccccc    120 gcuucugucu gccccauugu ggcuccucag gcucucuccc cugcucuccc accucuaccu    180 ccaccccac uuccagccag acacccgccc cccggcccug gcuaagaagu ugcuuccugu    240
ugccagcaug accuacccuc gccucuuuga ugccauccgc ugccaccucc uuuugcuccu    300
ggacccuuua gccucucugc ccuuccacuc ucugacccc                          339
```

<210> SEQ ID NO 178
<211> LENGTH: 345
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 178

```
cugacagcgu gggcaacgcc ugccgccugc ucugaggccc gauccagugg gcaggccaag    60
gccugcuggg ccccgcgga cccaggugcu cugggucacg gucccuguccc ccgcaccccc    120 gcuucugucu gccccauugu ggcuccucag gcucucuccc cugcucuccc accucuaccu    180 ccaccccac gccuuggcuc cuccaggaag gcucaggagc ccuaccuccc ugccauuaua    240
gcugcucccc gccagaagcc ugugccaacu cucugcauuc ccugaucucc aucccugugg    300
cugucacccu uggucacccuc cgugcuguca cugccaucuc ccccc                  345
```

<210> SEQ ID NO 179
<211> LENGTH: 326
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 179

```
cugacagcgu gggcaacgcc ugccgccugc ucugaggccc gauccagugg gcaggccaag    60
gccugcuggg ccccgcgga cccaggugcu cugggucacg gucccuguccc ccgcaccccc    120 gcuucugucu gccccauugu ggcuccucag gcucucuccc cugcucuccc accucuaccu    180 ccaccccac cugguacugc augcacgcaa ugcuagcugc cccuuucccg uccugggguac   240 cccgagcucu ccccgaccuc gggucccagg uaugcuccca ccuccaccug ccccacucac    300
caccucugcu aguuccagac accucc                                        326
```

<210> SEQ ID NO 180
<211> LENGTH: 380
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 180

```
cugacagcgu gggcaacgcc ugccgccugc ucugaggccc gauccagugg gcaggccaag      60
gccugcuggg ccccgcgga cccaggugcu cugggucacg gucccugucc ccgcaccccc     120
gcuucugucu gccccauugu ggcuccucag gcucucuccc cugcucuccc accucuaccu    180
ccacccccac cugacagcgu gggcaacgcc ugccgccugc ucugaggccc gauccagugg    240
gcaggccaag gccugcuggg ccccgcgga cccaggugcu cugggucacg gucccugucc    300
ccgcaccccc gcuucugucu gccccauugu ggcuccucag gcucucuccc cugcucuccc    360
accucuaccu ccacccccac                                                380
```

<210> SEQ ID NO 181
<211> LENGTH: 332
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 181

```
cugacagcgu gggcaacgcc ugccgccugc ucugaggccc gauccagugg gcaggccaag      60
gccugcuggg ccccgcgga cccaggugcu cugggucacg gucccugucc ccgcaccccc     120
gcuucugucu gccccauugu ggcuccucag gcucucuccc cugcucuccc accucuaccu    180
ccacccccac gagagcucgc uuucuugcug uccaauuucu auuaaagguu ccuuuguucc    240
cuaaguccaa cuacuaaacu gggggauauu augaagggcc uugagcaucu ggauucugcc    300
uaauaaaaaa cauuuauuuu cauugcugcg uc                                  332
```

<210> SEQ ID NO 182
<211> LENGTH: 332
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 182

```
cugacagcgu gggcaacgcc ugccgccugc ucugaggccc gauccagugg gcaggccaag      60
gccugcuggg ccccgcgga cccaggugcu cugggucacg gucccugucc ccgcaccccc     120
gcuucugucu gccccauugu ggcuccucag gcucucuccc cugcucuccc accucuaccu    180
ccacccccac caagcacgca gcaaugcagc ucaaaacgcu uagccuagcc acacccccac    240
gggaaacagc agugauuaac cuuuagcaau aaacgaaagu uuaacuaagc uauacuaacc    300
ccaggguugg ucaauuucgu gccagccaca cc                                  332
```

<210> SEQ ID NO 183
<211> LENGTH: 423
<212> TYPE: RNA
<213> ORGANISM: Artificial Sequence
<220> FEATURE:
<223> OTHER INFORMATION: Description of Artificial Sequence: Synthetic Combination of 3'-UTR sequence elements

<400> SEQUENCE: 183

| | |
|---|---|
| cugacagcgu gggcaacgcc ugccgccugc ucugaggccc gauccagugg gcaggccaag | 60 |
| gccugcuggg cccccgcgga cccaggugcu cugggucacg gucccugucc ccgcaccccc | 120 |
| gcuucugucu gccccauugu ggcuccucag gcucucuccc cugcucuccc accucuaccu | 180 |
| ccacccccac cuuugcagga ugaaacacuu ccccgcuugg cucucauucu uccacaagag | 240 |
| agaccuuucu ccggaccugg uugcuacugg uucagcaacu cugcagaaaa uguccucccc | 300 |
| uguggcugcc ucagcucaug ccuuuggccu gaagucccag cauugauggc agccccucau | 360 |
| cuuccaaguu uugugcuccc cuuuaccuaa cgcuuccugc ucccaugca ucuguacucc | 420 |
| ucc | 423 |

<210> SEQ ID NO 184
<211> LENGTH: 285
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 184

| | |
|---|---|
| gagagcucgc uuucuugcug uccaauuucu auuaaagguu ccuuuguucc cuaaguccaa | 60 |
| cuacuaaacu gggggauauu augaaggggcc uugagcaucu ggauucugcc uaauaaaaaa | 120 |
| cauuuauuuu cauugcugcg ucugcccguc cucaccaaga cugacugccu gcugcuuugc | 180 |
| uacugcccgg gcccaugaga cugacuuccc acugcucugc cugccucucc ccacugcacu | 240 |
| ggcacagccc cgccuugccg cugcugaucc auugccggug ugacc | 285 |

<210> SEQ ID NO 185
<211> LENGTH: 291
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 185

| | |
|---|---|
| gagagcucgc uuucuugcug uccaauuucu auuaaagguu ccuuuguucc cuaaguccaa | 60 |
| cuacuaaacu gggggauauu augaaggggcc uugagcaucu ggauucugcc uaauaaaaaa | 120 |
| cauuuauuuu cauugcugcg ucuuccagcc agacacccgc ccccggccc uggcuaagaa | 180 |
| guugcuuccu guugccagca ugaccuaccc ucgccucuuu gaugccaucc gcugccaccu | 240 |
| ccuuuugcuc cuggacccuu uagccucucu gcccuuccac ucucugaccc c | 291 |

<210> SEQ ID NO 186
<211> LENGTH: 297
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 186

| | |
|---|---|
| gagagcucgc uuucuugcug uccaauuucu auuaaagguu ccuuuguucc cuaaguccaa | 60 |
| cuacuaaacu gggggauauu augaaggggcc uugagcaucu ggauucugcc uaauaaaaaa | 120 |
| cauuuauuuu cauugcugcg ucgccuuggc uccuccagga aggcucagga gcccuaccuc | 180 |

```
ccugccauua uagcugcucc ccgccagaag ccugugccaa cucucugcau ucccugaucu    240
ccaucccugu ggcugucacc cuuggucacc uccgugcugu cacugccauc ucccccc       297
```

<210> SEQ ID NO 187
<211> LENGTH: 278
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 187

```
gagagcucgc uuucuugcug uccaauuucu auuaaagguu ccuuuguucc cuaaguccaa    60
cuacuaaacu gggggauauu augaagggcc uuagcaucu ggauucugcc uaauaaaaaa    120
cauuuauuuu cauugcugcg uccugguacu gcaugcacgc aaugcuagcu gccccuuucc   180
cguccugggu accccgaguc uccccgacc ucgguccca gguaugcucc caccuccacc    240
ugccccacuc accaccucug cuaguccag acaccucc                            278
```

<210> SEQ ID NO 188
<211> LENGTH: 332
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 188

```
gagagcucgc uuucuugcug uccaauuucu auuaaagguu ccuuuguucc cuaaguccaa    60
cuacuaaacu gggggauauu augaagggcc uuagcaucu ggauucugcc uaauaaaaaa    120
cauuuauuuu cauugcugcg uccugacagc gugggcaacg ccugccgccu gcucugaggc   180
ccgauccagu gggcaggcca aggccugcug ggccccgcg gacccaggug cucuggguca    240 cgguccugu ccccgcaccc ccgcuucugu cugccccauu guggcuccuc aggcucucuc   300
cccugcucuc ccaccucuac cuccaccccc ac                                 332
```

<210> SEQ ID NO 189
<211> LENGTH: 284
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 189

```
gagagcucgc uuucuugcug uccaauuucu auuaaagguu ccuuuguucc cuaaguccaa    60
cuacuaaacu gggggauauu augaagggcc uuagcaucu ggauucugcc uaauaaaaaa    120
cauuuauuuu cauugcugcg ucgagagcuc gcuuucuugc uguccaauuu cauuuaaagg   180
uuccuuuguu cccuaaguccc aacuacuaaa cuggggauua uuaugaaggg ccuugagcau   240
cuggauucug ccuaauaaaa aacauuuauu uucauugcug cguc                    284
```

<210> SEQ ID NO 190
<211> LENGTH: 284
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 190

```
gagagcucgc uuucuugcug uccaauuucu auuaaagguu ccuuuguucc cuaaguccaa     60
cuacuaaacu gggggauauu augaagggcc uugagcaucu ggauucugcc uaauaaaaaa    120
cauuuauuuu cauugcugcg uccaagcacg cagcaaugca gcucaaaacg cuuagccuag    180
ccacaccccc acgggaaaca gcagugauua accuuuagca auaaacgaaa guuuaacuaa    240
gcuauacuaa ccccaggguu ggucaauuuc ugccagcca cacc                      284
```

<210> SEQ ID NO 191
<211> LENGTH: 375
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 191

```
gagagcucgc uuucuugcug uccaauuucu auuaaagguu ccuuuguucc cuaaguccaa     60
cuacuaaacu gggggauauu augaagggcc uugagcaucu ggauucugcc uaauaaaaaa    120
cauuuauuuu cauugcugcg uccuuugcag gaugaaacac uuccccgcuu ggcucucauu    180 cuccacaag agagaccuuu cuccggaccu gguugcuacu gguucagcaa cucugcagaa    240 aaugccucc ccuguggcug ccucagcuca ugccuuuggc cugaagucc agcauugaug     300 gcagccccuc aucuuccaag uuuugugcuc cccuuuaccu aacgcuuccu gccucccaug   360
caucuguacu ccucc                                                     375
```

<210> SEQ ID NO 192
<211> LENGTH: 285
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 192

```
caagcacgca gcaaugcagc ucaaaacgcu uagccuagcc acacccccac gggaaacagc     60
agugauuaac cuuuagcaau aaacgaaagu uuaacuaagc uauacuaacc ccaggguugg    120
ucaauuucgu gccagccaca ccugcccguc cucaccaaga cugacugccu gcugcuuugc    180
uacugcccgg gccaugaga cugacuuccc acugcucgc cugccucucc ccacugcacu     240
ggcacagccc cgccuugccg cugcugaucc auugccggug ugacc                    285
```

<210> SEQ ID NO 193
<211> LENGTH: 291
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 193

```
caagcacgca gcaaugcagc ucaaaacgcu uagccuagcc acacccccac gggaaacagc     60
agugauuaac cuuuagcaau aaacgaaagu uuaacuaagc uauacuaacc ccaggguugg    120
ucaauuucgu gccagccaca ccuuccagcc agacacccgc ccccggcccc uggcuaagaa    180
guugcuuccu guugccagca ugaccuaccc ucgccucuuu gaugccaucc gcugccaccu    240
ccuuuugcuc cuggacccuu uagccucucu gcccuuccac ucucugaccc c             291
```

```
<210> SEQ ID NO 194
<211> LENGTH: 297
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 194
caagcacgca gcaaugcagc ucaaaacgcu uagccuagcc acaccccac gggaaacagc    60 agugauuaac cuuuagcaau aaacgaaagu uuaacuaagc uauacuaacc ccaggguugg   120
ucaauuucgu gccagccaca ccgccuuggc uccuccagga aggcucagga gcccuaccuc   180
ccugccauua uagcugcucc ccgccagaag ccugugccaa cucucugcau ucccugaucu   240
ccaucccugu ggcugucacc cuuggucacc uccgugcugu cacugccauc uccccc       297

<210> SEQ ID NO 195
<211> LENGTH: 278
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 195
caagcacgca gcaaugcagc ucaaaacgcu uagccuagcc acaccccac gggaaacagc    60 agugauuaac cuuuagcaau aaacgaaagu uuaacuaagc uauacuaacc ccaggguugg   120
ucaauuucgu gccagccaca cccugguacu gcaugcacgc aaugcuagcu gccccuuucc   180
cguccugggu accccgaguc uccccgaccu cgggucccca gguaugcucc caccuccacc   240
ugccccacuc accaccucug cuaguuccag acaccucc                           278

<210> SEQ ID NO 196
<211> LENGTH: 332
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 196
caagcacgca gcaaugcagc ucaaaacgcu uagccuagcc acaccccac gggaaacagc    60 agugauuaac cuuuagcaau aaacgaaagu uuaacuaagc uauacuaacc ccaggguugg   120
ucaauuucgu gccagccaca ccugacagc gugggcaacg ccugccgccu gcucugaggc    180
ccgauccagu gggcaggcca aggccugcug ggccccgcg gacccaggug cucuggguca    240
cggucccugu ccccgcaccc cgcuucugu cugcccauu guggcuccuc aggcucucuc     300
cccugcucuc ccaccucuac cuccaccccc ac                                 332

<210> SEQ ID NO 197
<211> LENGTH: 284
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 197
caagcacgca gcaaugcagc ucaaaacgcu uagccuagcc acaccccac gggaaacagc    60 agugauuaac cuuuagcaau aaacgaaagu uuaacuaagc uauacuaacc ccaggguugg   120
```

```
ucaauuucgu gccagccaca ccgagagcuc gcuuucuugc uguccaauuu cuauuaaagg    180
uuccuuuguu cccuaaguce aacuacuaaa cuggggggaua uuaugaaggg ccuugagcau    240
cuggauucug ccuaauaaaa aacauuuauu uucauugcug cguc                     284

<210> SEQ ID NO 198
<211> LENGTH: 284
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 198
caagcacgca gcaaugcagc ucaaaacgcu uagccuagcc acaccccac ggaaacagc      60 agugauuaac cuuuagcaau aaacgaaagu uuaacuaagc uauacuaacc ccagggguugg   120 ucaauuucgu gccagccaca cccaagcacg cagcaaugca gcucaaaacg cuuagccuag    180
ccacaccccc acgggaaaca gcagugauua accuuuagca auaaacgaaa guuuaacuaa    240
gcuauacuaa ccccaggguu ggucaauuuc gugccagcca cacc                     284

<210> SEQ ID NO 199
<211> LENGTH: 375
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 199
caagcacgca gcaaugcagc ucaaaacgcu uagccuagcc acaccccac ggaaacagc      60 agugauuaac cuuuagcaau aaacgaaagu uuaacuaagc uauacuaacc ccagggguugg   120 ucaauuucgu gccagccaca cccuuugcag gaugaaacac uuccccgcuu ggcucucauu    180 cuccacaag agagaccuuu uccggaccu gguugcuacu gguucagcaa cucugcagaa      240
aauguccucc ccuguggcug ccucagcuca ugccuuuggc cugaagucc agcauugaug     300 gcagcccuc aucuuccaag uuuugugcuc cccuuuaccu aacgcuuccu gccucccaug    360
caucuguacu ccucc                                                     375

<210> SEQ ID NO 200
<211> LENGTH: 376
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 200
cuuugcagga ugaaacacuu ccccgcuugg cucucauucu uccacaagag agaccuuucu    60
ccggaccugg uugcuacugg uucagcaacu cugcagaaaa uguccucccc uguggcugcc    120
ucagcucaug ccuuuggccu gaagucccag cauugauggc agccccucau cuccaaguu    180 uugugcuccc cuuuaccuaa cgcuuccugc cucccaugca ucuguacucc ucugcccgu    240 ccucaccaag acugacugcc ugcugcuuug cuacugcccg ggcccaugag acugacuucc    300
cacugcucug ccugccucuc cccacugcac uggcacagcc ccgccuugcc gcugcugauc    360
cauugccggu gugacc                                                    376

<210> SEQ ID NO 201
```

```
<211> LENGTH: 382
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 201
cuuugcagga ugaaacacuu ccccgcuugg cucucauucu uccacaagag agaccuuucu      60
ccggaccugg uugcuacugg uucagcaacu cugcagaaaa uguccucccc uguggcugcc     120
ucagcucaug ccuuuggccu gaagucccag cauugauggc agccccucau cuccaaguu     180 uugugcuccc cuuuaccuaa cgcuccugc ucccaugca ucuguacucc uccuuccagc      240
cagacacccg cccccccggcc cuggcuaaga aguugcuucc uguugccagc augaccuacc    300
cucgccucuu ugaugccauc cgcugccacc uccuuuugcu ccuggacccu uuagccucuc    360
ugcccuucca cucucugacc cc                                              382

<210> SEQ ID NO 202
<211> LENGTH: 388
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 202
cuuugcagga ugaaacacuu ccccgcuugg cucucauucu uccacaagag agaccuuucu      60
ccggaccugg uugcuacugg uucagcaacu cugcagaaaa uguccucccc uguggcugcc     120
ucagcucaug ccuuuggccu gaagucccag cauugauggc agccccucau cuccaaguu     180 uugugcuccc cuuuaccuaa cgcuccugc ucccaugca ucuguacucc uccgccuugg      240
cuccuccagg aaggcucagg agcccuaccu cccugccauu auagcugcuc cccgccagaa    300
gccugugcca cucucugca uucccugauc uccaucccug uggcugucac ccuuggucac    360
cuccgugcug ucacugccau cucccccc                                        388

<210> SEQ ID NO 203
<211> LENGTH: 369
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 203
cuuugcagga ugaaacacuu ccccgcuugg cucucauucu uccacaagag agaccuuucu      60
ccggaccugg uugcuacugg uucagcaacu cugcagaaaa uguccucccc uguggcugcc     120
ucagcucaug ccuuuggccu gaagucccag cauugauggc agccccucau cuccaaguu     180 uugugcuccc cuuuaccuaa cgcuccugc ucccaugca ucuguacucc ucccugguac      240
ugcaugcacg caaugcuagc ugcccuuuc ccguccuggg uaccccgagu cuccccgac      300 cucgggucc agguaugcuc ccaccuccac cugccccacu caccaccucu gcuaguucca    360
gacaccucc                                                             369

<210> SEQ ID NO 204
<211> LENGTH: 423
<212> TYPE: RNA
<213> ORGANISM: Artificial Sequence
<220> FEATURE:
```

<223> OTHER INFORMATION: Description of Artificial Sequence: Synthetic
      Combination of 3'-UTR sequence elements

<400> SEQUENCE: 204
cuuugcagga ugaaacacuu ccccgcuugg cucucauucu uccacaagag agaccuuucu     60
ccggaccugg uugcuacugg uucagcaacu cugcagaaaa uguccucccc uguggcugcc    120
ucagcucaug ccuuuggccu gaagucccag cauugauggc agccccucau cuuccaaguu    180
uugugcuccc cuuuaccuaa cgcuuccugc ucccaugca ucuguacucc cccugacag      240 cgugggcaac gccugccgcc ugcucugagg cccgauccag ugggcaggcc aaggccugcu    300
gggcccccgc ggaccaggu gcucggguc acgguccug uccccgcacc cccgcuucug      360
ucugccccau uguggcuccu caggcucucu ccccugcucu cccaccucua ccuccacccc    420
cac                                                                 423

<210> SEQ ID NO 205
<211> LENGTH: 375
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 205
cuuugcagga ugaaacacuu ccccgcuugg cucucauucu uccacaagag agaccuuucu     60
ccggaccugg uugcuacugg uucagcaacu cugcagaaaa uguccucccc uguggcugcc    120
ucagcucaug ccuuuggccu gaagucccag cauugauggc agccccucau cuuccaaguu    180
uugugcuccc cuuuaccuaa cgcuuccugc ucccaugca ucuguacucc ccgagagcu     240 cgcuuucuug cuguccaauu ucuauuaaag guuccuuugu cccuaaguc caacuacuaa    300 acuggggau auuaugaagg gccuugagca ucuggauucu gccuaauaaa aaacauuuau    360
uuucauugcu gcguc                                                    375

<210> SEQ ID NO 206
<211> LENGTH: 375
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 206
cuuugcagga ugaaacacuu ccccgcuugg cucucauucu uccacaagag agaccuuucu     60
ccggaccugg uugcuacugg uucagcaacu cugcagaaaa uguccucccc uguggcugcc    120
ucagcucaug ccuuuggccu gaagucccag cauugauggc agccccucau cuuccaaguu    180
uugugcuccc cuuuaccuaa cgcuuccugc ucccaugca ucuguacucc ucccaagcac    240
gcagcaaugc agcucaaaac gcuuagccua gccacacccc cacgggaaac agcagugauu    300
aaccuuuagc aauaaacgaa aguuuaacua agcuauacua accccagggu uggucaauuu    360
cgugccagcc acacc                                                    375

<210> SEQ ID NO 207
<211> LENGTH: 466
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 207

| | | | | | |
|---|---|---|---|---|---|
| cuuugcagga | ugaaacacuu | ccccgcuugg | cucucauucu | uccacaagag | agaccuuucu | 60 |
| ccggaccugg | uugcuacugg | uucagcaacu | cugcagaaaa | uguccucccc | uguggcugcc | 120 |
| ucagcucaug | ccuuuggccu | gaagucccag | cauugauggc | agccccucau | cuuccaaguu | 180 |
| uugugcuccc | cuuuaccuaa | cgcuuccugc | cucccaugca | ucuguacucc | ucccuuugca | 240 |
| ggaugaaaca | cuuccccgcu | uggcucucau | ucuuccacaa | gagagaccuu | ucccggacc | 300 |
| ugguugcuac | ugguucagca | acucugcaga | aaaugccuc | cccguggcu | gccucagcuc | 360 |
| augccuuugg | ccugaagucc | cagcauugau | ggcagccccu | caucuuccaa | guuuugugcu | 420 |
| ccccuuuacc | uaacgcuucc | ugccucccau | gcaucuguac | uccucc | | 466 |

<210> SEQ ID NO 208
<211> LENGTH: 278
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 208

| | | | | | |
|---|---|---|---|---|---|
| cugguacugc | auggacgcaa | ugcuagcugc | cccuuucccg | uccuggguac | cccgagucac | 60 |
| ccccgaccuc | ggguccccagg | uaucguccca | ccuccaccug | ccccacucac | caccucugcu | 120 |
| aguuccagac | accucccaag | cacgcagcaa | ugcagcucaa | aacgcuuagc | auagccacac | 180 |
| ccccacggga | aacagcagug | auuaaccuuu | agcaauaauc | gaauguuuaa | cuaagcuaua | 240 |
| cuaaccccag | gguuggucaa | uuucgugcca | gccacacc | | | 278 |

<210> SEQ ID NO 209
<211> LENGTH: 278
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 209

| | | | | | |
|---|---|---|---|---|---|
| cucguacugc | auggacgcaa | ugcuagcugc | cccuuucccg | uccuggguac | cccgagucac | 60 |
| caccgaccuc | ggguccccagg | uaucguccca | ccuccacgug | ccccacucac | caccucugcu | 120 |
| aguuccagac | accucccaag | cacgcagcaa | ugcagcucaa | aacgcuuagc | auagccacac | 180 |
| ccccacggga | aacaguagug | auuaaccuuu | agcaauaauc | gaaugucuaa | cuaagcuaua | 240 |
| cuaaccccag | gguugaucaa | uuacgugcca | gccacacc | | | 278 |

<210> SEQ ID NO 210
<211> LENGTH: 278
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 210

| | | | | | |
|---|---|---|---|---|---|
| cucguacugc | auggacgcaa | ugcuagcugc | cccuuucccg | uccuggguac | cccgagucac | 60 |
| caccgaccuc | ggguccccagg | uaucguccca | ccuccacgug | ccccacucac | caccuuugcu | 120 |
| aguuccagac | accucccaug | cacgcagcaa | ugcagaucaa | aacgcuuagc | auagccacac | 180 |
| ccccacggga | aacaguagug | auuaaccuuu | agcaauaauc | gaaugucuaa | cuaagcuaua | 240 |

```
cuaaccccag gguugaucaa uuacgugcca gccacacc                                    278
```

<210> SEQ ID NO 211
<211> LENGTH: 278
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 211

```
gucguacugc auggacgcaa ugcuagcagc accuuucccg uccugggua cccgagucac            60
caccgaccuc gggucccagg uaucguccca ccuccacgug ccccacccac caccuuugcu          120
aguuccagag accucccaug cacgcagcaa ugcagaucaa aacgcuuagc auagccacac          180
cgccacggga aacaguagug aucaaccuuu agcuauaauc gaaugcuaa cuaagcuauu           240
cuaaccacag gguugaucaa uuacgugcca gccagacc                                  278
```

<210> SEQ ID NO 212
<211> LENGTH: 278
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 212

```
cugguacugc augcacgcaa ugcuagcugc cccaaagggc uccugggua cccgagucuc            60
ccccgaccuc gggucccagg uaugcuccca ccuccaccug cccacucac caccucugcu          120
aguuccagac accucccaag cacgcagcaa ugcagcucaa aacgcuuagc cuagccacac          180
ccccacggga aacagcagug auuaaccuuu agcaauaaac gaaaguuuaa cuaagcuaua         240
cuaaccccag gguuggucaa uuucgugcca gccacacc                                  278
```

<210> SEQ ID NO 213
<211> LENGTH: 278
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 213

```
cugguacugc augcacgcgc ugcuagcugc cccuuucccg ugguccguac cccgagucuc           60
ccccgaccuc gggucccagg uaugcuccca ccuccaccug cccacucac caccucugcu          120
aguuccagac accucccaag cacgcagcaa ugcagcucaa aacgcuuagc cuagccacac          180
ccccacggga aacagcagug auuaaccuuu agcaauaaac gaaaguuuaa cuaagcuaua         240
cuaaccccag gguuggucaa uuucgugcca gccacacc                                  278
```

<210> SEQ ID NO 214
<211> LENGTH: 278
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 214

```
cugguacugc augcacgcaa ugcuagcugc cccuuucccg uggaccguac ggcgagucuc           60
```

```
cccgaccuc ggguccccagg uaugcuccca ccuccaccug cccacucac caccucugcu    120 aguuccagac accucccaag cacgcagcaa ugcagcucaa aacgcuuagc cuagccacac    180
ccccacggga aacagcagug auuaaccuuu agcaauaaac gaaaguuuaa cuaagcuaua    240
cuaaccccag gguuggucaa uuucgugcca gccacacc                           278
```

<210> SEQ ID NO 215
<211> LENGTH: 278
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 215

```
cugguacugc augcacgcaa ugcuagcugc cccuuugccg uggaccguac gggcugucuc     60 cccgaccuc ggguccccagg uaugcuccca ccuccaccug cccacucac caccucugcu    120 aguuccagac accucccaag cacgcagcaa ugcagcucaa aacgcuuagc cuagccacac    180
ccccacggga aacagcagug auuaaccuuu agcaauaaac gaaaguuuaa cuaagcuaua    240
cuaaccccag gguuggucaa uuucgugcca gccacacc                           278
```

<210> SEQ ID NO 216
<211> LENGTH: 278
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 216

```
cugguacugc augcacgcaa ugcuagcugc cccuuugggc uggaccguac gggcugucuc     60 cccgaccuc ggguccccagg uaugcuccca ccuccaccug cccacucac caccucugcu    120 aguuccagac accucccaag cacgcagcaa ugcagcucaa aacgcuuagc cuagccacac    180
ccccacggga aacagcagug auuaaccuuu agcaauaaac gaaaguuuaa cuaagcuaua    240
cuaaccccag gguuggucaa uuucgugcca gccacacc                           278
```

<210> SEQ ID NO 217
<211> LENGTH: 278
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 217

```
cugguacugc augcacgcaa ugcuagcugc cccuuucccg ugguccguac cccgagucuc     60 cccgaccuc gggucggacc uaugcuccca ccuccaccug cccacucac caccucugcu    120 aguuccagac accucccaag cacgcagcaa ugcagcucaa aacgcuuagc cuagccacac    180
ccccacggga aacagcagug auuaaccuuu agcaauaaac gaaaguuuaa cuaagcuaua    240
cuaaccccag gguuggucaa uuucgugcca gccacacc                           278
```

<210> SEQ ID NO 218
<211> LENGTH: 278
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 218
cugguacugc augcacgcaa ugcuagcugc cccuuucccg uggaccguac ggcgagucuc      60
ccccgaccuc gccucggucc uaugcuccca ccuccaccug ccccacucac caccucugcu     120
aguuccagac accucccaag cacgcagcaa ugcagcucaa aacgcuuagc cuagccacac     180
ccccacggga aacagcagug auuaaccuuu agcaauaaac gaaaguuuaa cuaagcuaua     240
cuaaccccag gguuggucaa uuucgugcca gccacacc                             278

<210> SEQ ID NO 219
<211> LENGTH: 278
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 219
cugguacugc augcacgcaa ugcuagcugc cccuuugccg uggaccguac gggcugucuc      60
ccccgaccag cccucggucc uaugcuccca ccuccaccug ccccacucac caccucugcu     120
aguuccagac accucccaag cacgcagcaa ugcagcucaa aacgcuuagc cuagccacac     180
ccccacggca aacagcagug auuaaccuuu agcaauaaac gaaaguuuaa cuaagcuaua     240
cuaaccccag gguuggucaa uuucgugcca gccacacc                             278

<210> SEQ ID NO 220
<211> LENGTH: 278
<212> TYPE: RNA
<213> ORGANISM: Artificial Sequence
<220> FEATURE:
<223> OTHER INFORMATION: Description of Artificial Sequence: Synthetic
      Combination of 3'-UTR sequence elements

<400> SEQUENCE: 220
cugguacugc augcacgcaa ugcuagcugc cccuuugggc uggaccguac gggcugucuc      60
ccccgaccag cccucggucc uaugcuccca ccuccaccug ccccacucac caccucugcu     120
aguuccagac accucccaag cacgcagcaa ugcagcucaa aacgcuuagc cuagccacac     180
ccccagccca aacagcagug auuaaccuuu agcaauaaac gaaaguuuaa cuaagcuaua     240
cuaaccccag gguuggucaa uuucgugcca gccacacc                             278

<210> SEQ ID NO 221
<211> LENGTH: 142
<212> TYPE: RNA
<213> ORGANISM: Artificial Sequence
<220> FEATURE:
<223> OTHER INFORMATION: Description of Artificial Sequence: Synthetic
      3'-UTR sequence element

<400> SEQUENCE: 221
gagagcucgc uuucuugcug uccaauuucu auuaaagguu ccuuuguucc cuaaguccaa      60
cuacuaaacu gggggauauu augaagggcc uugagcaucu ggauucugcc uauaaaaaa     120 cauuuauuuu cauugcugcg uc                                              142

<210> SEQ ID NO 222
<211> LENGTH: 120
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 222
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa       120

<210> SEQ ID NO 223
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
aaaaaaaaaa aaaaaaaaaa aaaaaaaaaa aaaaaaaaaa aaaaaaaaaa aaaaaaaaaa        60

<210> SEQ ID NO 224
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
tttttttttt tttttttttt tttttttttt tttttttttt tttttttttt tttttttttt        60

<210> SEQ ID NO 225
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
aaaaaaaaaa aaaaaaaaaa aaaaaaaaaa aaaaaaaaaa aaaaaaaaaa                   50

<210> SEQ ID NO 226
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(80)
<223> OTHER INFORMATION: This sequence may encompass 1-80 nucleotides
<220> FEATURE:
<223> OTHER INFORMATION: See specification as filed for detailed
      description of substitutions and preferred embodiments

<400> SEQUENCE: 226
aaaaaaaaaa aaaaaaaaaa aaaaaaaaaa aaaaaaaaaa aaaaaaaaaa aaaaaaaaaa        60
aaaaaaaaaa aaaaaaaaaa                                                    80

<210> SEQ ID NO 227
<211> LENGTH: 100
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature

```
<222> LOCATION: (1)..(100)
<223> OTHER INFORMATION: This sequence may encompass 1-100 nucleotides
<220> FEATURE:
<223> OTHER INFORMATION: See specification as filed for detailed
      description of substitutions and preferred embodiments

<400> SEQUENCE: 227
aaaaaaaaaa aaaaaaaaaa aaaaaaaaaa aaaaaaaaaa aaaaaaaaaa aaaaaaaaaa       60
aaaaaaaaaa aaaaaaaaaa aaaaaaaaaa aaaaaaaaaa                            100

<210> SEQ ID NO 228
<211> LENGTH: 80
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(80)
<223> OTHER INFORMATION: This sequence may encompass 30-80 nucleotides
<220> FEATURE:
<223> OTHER INFORMATION: See specification as filed for detailed
      description of substitutions and preferred embodiments

<400> SEQUENCE: 228
aaaaaaaaaa aaaaaaaaaa aaaaaaaaaa aaaaaaaaaa aaaaaaaaaa aaaaaaaaaa       60
aaaaaaaaaa aaaaaaaaaa                                                   80

<210> SEQ ID NO 229
<211> LENGTH: 500
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(500)
<223> OTHER INFORMATION: This sequence may encompass 20-500 nucleotides
<220> FEATURE:
<223> OTHER INFORMATION: See specification as filed for detailed
      description of substitutions and preferred embodiments

<400> SEQUENCE: 229
aaaaaaaaaa aaaaaaaaaa aaaaaaaaaa aaaaaaaaaa aaaaaaaaaa aaaaaaaaaa       60
aaaaaaaaaa aaaaaaaaaa aaaaaaaaaa aaaaaaaaaa aaaaaaaaaa aaaaaaaaaa      120
aaaaaaaaaa aaaaaaaaaa aaaaaaaaaa aaaaaaaaaa aaaaaaaaaa aaaaaaaaaa      180
aaaaaaaaaa aaaaaaaaaa aaaaaaaaaa aaaaaaaaaa aaaaaaaaaa aaaaaaaaaa      240
aaaaaaaaaa aaaaaaaaaa aaaaaaaaaa aaaaaaaaaa aaaaaaaaaa aaaaaaaaaa      300
aaaaaaaaaa aaaaaaaaaa aaaaaaaaaa aaaaaaaaaa aaaaaaaaaa aaaaaaaaaa      360
aaaaaaaaaa aaaaaaaaaa aaaaaaaaaa aaaaaaaaaa aaaaaaaaaa aaaaaaaaaa      420
aaaaaaaaaa aaaaaaaaaa aaaaaaaaaa aaaaaaaaaa aaaaaaaaaa aaaaaaaaaa      480
aaaaaaaaaa aaaaaaaaaa                                                  500

<210> SEQ ID NO 230
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 230
tttttttttt tttttttt                                                 18

<210> SEQ ID NO 231
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(50)
<223> OTHER INFORMATION: This sequence may encompass 20-50 nucleotides
<220> FEATURE:
<223> OTHER INFORMATION: See specification as filed for detailed
      description of substitutions and preferred embodiments

<400> SEQUENCE: 231
aaaaaaaaaa aaaaaaaaaa aaaaaaaaaa aaaaaaaaaa aaaaaaaaaa              50

<210> SEQ ID NO 232
<211> LENGTH: 120
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: See specification as filed for detailed
      description of substitutions and preferred embodiments

<400> SEQUENCE: 232
aaaaaaaaaa aaaaaaaaaa aaaaaaaaaa aaaaaaaaaa aaaaaaaaaa aaaaaaaaaa   60
aaaaaaaaaa aaaaaaaaaa aaaaaaaaaa aaaaaaaaaa aaaaaaaaaa aaaaaaaaaa   120

<210> SEQ ID NO 233
<211> LENGTH: 50
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: See specification as filed for detailed
      description of substitutions and preferred embodiments

<400> SEQUENCE: 233
aaaaaaaaaa aaaaaaaaaa aaaaaaaaaa aaaaaaaaaa aaaaaaaaaa              50

<210> SEQ ID NO 234
<211> LENGTH: 70
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: See specification as filed for detailed
      description of substitutions and preferred embodiments

<400> SEQUENCE: 234
aaaaaaaaaa aaaaaaaaaa aaaaaaaaaa aaaaaaaaaa aaaaaaaaaa aaaaaaaaaa   60
aaaaaaaaaa                                                          70

<210> SEQ ID NO 235
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: See specification as filed for detailed
      description of substitutions and preferred embodiments

<400> SEQUENCE: 235
aaaaaaaaaa aaaaaaaaaa                                            20
```

3'-UTR SEQUENCES FOR STABILIZATION OF RNA

SEQUENCE LISTING

The instant application contains a Sequence Listing which has been submitted electronically in ASCII format and is hereby incorporated by reference in its entirety. Said ASCII copy, created on Feb. 24, 2020, is named 2013237-0054SL.txt and is 106,811 bytes in size.

The use of RNA offers an attractive alternative to DNA in order to circumvent the potential safety risks connected with the therapeutic use of DNA. In vitro-transcribed RNA (IVT-RNA) is of particular interest in therapeutic approaches. The advantages of a therapeutic use of RNA include transient expression and a non-transforming character. RNA does not need to enter the nucleus in order to be expressed and moreover cannot integrate into the host genome, thereby eliminating the risk of oncogenesis. When used for vaccination, injection of RNA can induce both cellular and humoral immune responses in vivo. However, the use of RNA for clinical applications is greatly restricted especially by the short half life of RNA.

IVT vectors may be used in a standardized manner as template for in vitro transcription. Such IVT vectors may have the following structure: a 5' RNA polymerase promoter enabling RNA transcription, followed by a gene of interest which is flanked either 3' and/or 5' by untranslated regions (UTR), and a 3' polyadenyl cassette containing A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript.

Human immature dendritic cells (hiDCs) are widely used to develop and improve immunotherapies for cancer treatment. Loaded with in vitro transcribed (IVT)-mRNA encoding a specific tumor antigen (TA), hiDCs are able to induce an effective anti-tumor response. However, a prerequisite for an effective immune response using RNA-based cancer vaccines is high stability and translation efficiency of the RNA. Both can be improved by structural modifications of the 5'-CAP, the 3' poly(A)-tail as well as the 5' and 3' untranslated regions (UTRs). Sequence elements within the UTRs affect translational efficiency (mainly 5'-UTR) and RNA stability (mainly 3'-UTR).

In previous work we have demonstrated that two consecutive copies of the human beta-globin 3'-UTR (now called 2hBg; previously also 2βgUTR) contribute to higher transcript stability and translational efficiency (Holtkamp (2006) Blood 108:4009-4017). However, the presence of two identical copies of the human beta-globin 3'-UTR sequence in the plasmid DNA, which is ultimately used as template for the in vitro transcription of RNA, bears the risk of recombination during its propagation in E. coli. Similarly, any cloning approach, especially using PCR-based amplification, is very difficult. The same holds true for PCR-based amplification of the RNA-encoding region with the 2hBg at the 3'-end to be used as template for the in vitro transcription, because here mispriming, which leads to omission of one copy of the human beta-globin 3'-UTR, has been observed. To avoid these problems we sought to identify novel sequences that have a stabilizing effect on in vitro transcribed mRNA at least similar to, ideally even better than, the 2hBg sequence.

It was the object of the present invention to provide RNA with increased stability and/or translation efficiency and means for obtaining such RNA. It should be possible to obtain increased grades of expression by using said RNA in therapy.

This object is achieved according to the invention by the subject matter of the claims.

The present invention relates to stabilization of RNA, in particular mRNA, and an increase in mRNA translation. The present invention particularly relates to a modification of RNA, in particular in vitro-transcribed RNA, resulting in increased transcript stability and/or translation efficiency.

According to the invention, it was demonstrated that certain sequences in the 3'-untranslated region (UTR) of an RNA molecule improve stability and translation efficiency.

Using RNA modified according to the invention in the transfection of dendritic cells (DCs), it will be possible, for example, to increase the density of antigen-specific peptide/MHC complexes on the transfected cells and their ability to stimulate and expand antigen-specific $CD4^+$ and $CD8^+$ T cells. The invention therefore, in one embodiment, relates to a strategy for optimizing RNA vaccines for transfecting DC or RNA-transfected DC vaccines by using RNA which has been modified by the RNA modifications described according to the invention.

According to the invention, modification, and thereby stabilization and/or increase in translation efficiency, of RNA is preferably achieved by genetically modifying expression vectors which preferably serve as template for RNA transcription in vitro. These expression vectors allow transcription of RNA with a 3'-untranslated region described according to the invention, and preferably between the sequence coding for a peptide or protein (open reading frame) and the poly(A) sequence.

These vectors may also allow transcription of RNA with a poly(A) sequence which preferably has an open end in said RNA, i.e. no nucleotides other than A nucleotides flank said poly(A) sequence at its 3' end. An open-ended poly(A) sequence in the RNA can be achieved by introducing a type IIS restriction cleavage site into an expression vector which allows RNA to be transcribed under the control of a 5' RNA polymerase promoter and which contains a polyadenyl cassette, wherein the recognition sequence is located 3' of the polyadenyl cassette, while the cleavage site is located upstream and thus within the polyadenyl cassette. Restriction cleavage at the type IIS restriction cleavage site enables a plasmid to be linearized within the polyadenyl cassette. The linearized plasmid can then be used as template for in vitro transcription, the resulting transcript ending in an unmasked poly(A) sequence. Furthermore, an optional disruption of the 3' polyadenyl cassette by a random nucleotide sequence, with an equal distribution of the 4 nucleotides (linker), increases the stability of the 3' polyadenyl cassette in E. coli.

SUMMARY OF THE INVENTION

In one aspect, the invention relates to a nucleic acid molecule comprising in the 5'→3' direction of transcription:
 (a) a promoter;
 (b) a transcribable nucleic acid sequence or a nucleic acid sequence for introducing a transcribable nucleic acid sequence; and
 (c) a nucleic acid sequence which, when transcribed under the control of the promoter (a), codes for a 3'-untranslated region in the transcript, said 3'-untranslated region comprising a nucleic acid sequence which is selected from the group consisting of:

(c-1) the nucleic acid sequence of the 3'-untranslated region of FCGRT, a fragment thereof, or a variant of said nucleic acid sequence or fragment, (c-2) the nucleic acid sequence of the 3'-untranslated region of LSP1, a fragment thereof, or a variant of said nucleic acid sequence or fragment, (c-3) the nucleic acid sequence of the 3'-untranslated region of CCL22, a fragment thereof, or a variant of said nucleic acid sequence or fragment, (c-4) the nucleic acid sequence of the 3'-untranslated region of AES, a fragment thereof, or a variant of said nucleic acid sequence or fragment, (c-5) the nucleic acid sequence of the 3'-untranslated region of PLD3, a fragment thereof, or a variant of said nucleic acid sequence or fragment, (c-6) the nucleic acid sequence of the non-coding RNA of MT-RNR1, a fragment thereof, or a variant of said nucleic acid sequence or fragment, (c-7) the nucleic sequence of the 3'-untranslated region of HLA-DRB4, a fragment thereof, or a variant of said nucleic acid sequence or fragment, and (c-8) any combination of two or more of the nucleic acid sequences, fragments and/or variants under (c-1), (c-2), (c-3), (c-4), (c-5), (c-6) and (c-7).

In one embodiment, the nucleic acid sequences (b) and (c) under the control of the promoter (a) can be transcribed to give a common transcript in which the nucleic acid sequence transcribed from the nucleic acid sequence (c) is active so as to increase the translation efficiency and/or the stability of the nucleic acid sequence transcribed from the transcribable nucleic acid sequence (b).

In one embodiment, the nucleic acid sequences (b) and (c) are not naturally linked.

In one embodiment, (c-4) the nucleic acid sequence of the 3'-untranslated region of AES, a fragment thereof, or a variant of said nucleic acid sequence or fragment comprises a nucleic acid sequence selected from the group consisting of a nucleic acid sequence selected from SEQ ID NOs: 86 to 89, a fragment thereof, or a variant of said nucleic acid sequence or fragment.

In one embodiment, (c-4) the nucleic acid sequence of the 3'-untranslated region of AES, a fragment thereof, or a variant of said nucleic acid sequence or fragment comprises a nucleic acid sequence selected from the group consisting of the nucleic acid sequence of SEQ ID NO: 86, a fragment thereof, or a variant of said nucleic acid sequence or fragment.

In one embodiment, (c-6) the nucleic acid sequence of the non-coding RNA of MT-RNR1, a fragment thereof, or a variant of said nucleic acid sequence or fragment comprises a nucleic acid sequence selected from the group consisting of a nucleic acid sequence selected from SEQ ID NOs: 105 to 121, a fragment thereof, or a variant of said nucleic acid sequence or fragment.

In one embodiment, (c-6) the nucleic acid sequence of the non-coding RNA of MT-RNR1, a fragment thereof, or a variant of said nucleic acid sequence or fragment comprises a nucleic acid sequence selected from the group consisting of the nucleic acid sequence of SEQ ID NO: 115, a fragment thereof, or a variant of said nucleic acid sequence or fragment.

In one embodiment, the nucleic acid sequence (c-8) comprises a combination of two or more identical or different nucleic acid sequences, fragments and/or variants under (c-1), (c-2), (c-3), (c-4), (c-5), (c-6) and (c-7). In various embodiments, the nucleic acid sequence (c-8) comprises a combination of (c-i) and (c-2), (c-1) and (c-3), (c-1) and (c-4), (c-1) and (c-5), (c-1) and (c-6), (c-1) and (c-7), (c-2) and (c-3), (c-2) and (c-4), (c-2) and (c-5), (c-2) and (c-6), (c-2) and (c-7), (c-3) and (c-4), (c-3) and (c-5), (c-3) and (c-6), (c-3) and (c-7), (c-4) and (c-5), (c-4) and (c-6), (c-4) and (c-7), (c-5) and (c-6), (c-5) and (c-7), or (c-6) and (c-7).

In one embodiment, the nucleic acid sequence (c-8) comprises a combination of (c-4) the nucleic acid sequence of the 3'-untranslated region of AES, a fragment thereof, or a variant of said nucleic acid sequence or fragment, and (c-6) the nucleic acid sequence of the non-coding RNA of MT-RNR1, a fragment thereof, or a variant of said nucleic acid sequence or fragment. In one embodiment, (c-4) the nucleic acid sequence of the 3'-untranslated region of AES, a fragment thereof, or a variant of said nucleic acid sequence or fragment is located 5' to (c-6) the nucleic acid sequence of the non-coding RNA of MT-RNR1, a fragment thereof, or a variant of said nucleic acid sequence or fragment. In one embodiment, the combination of (c-4) the nucleic acid sequence of the 3'-untranslated region of AES, a fragment thereof, or a variant of said nucleic acid sequence or fragment, and (c-6) the nucleic acid sequence of the non-coding RNA of MT-RNR1, a fragment thereof, or a variant of said nucleic acid sequence or fragment comprises a nucleic acid sequence selected from the group consisting of the nucleic acid sequence of SEQ ID NO: 174, a fragment thereof, or a variant of said nucleic acid sequence or fragment.

In one embodiment, the nucleic acid molecule of the invention further comprises (d) a nucleic acid sequence which, when transcribed under the control of the promoter (a), codes for a nucleic acid sequence which is a polyadenyl sequence optionally comprising within the polyadenyl sequence a sequence of one or more consecutive nucleotides containing nucleotides other than A nucleotides. In one embodiment, said polyadenyl sequence comprises at least 20 A nucleotides, preferably at least 40, at least 80, at least 100 or at least 120 A nucleotides, preferably consecutive A nucleotides (SEQ ID NO: 232). In one embodiment, said sequence of one or more consecutive nucleotides containing nucleotides other than A nucleotides is a sequence, preferably an arbitrary sequence, of 2 or more consecutive nucleotides, wherein the first and the last nucleotide of said sequence of 2 or more consecutive nucleotides is a nucleotide other than an A nucleotide. In one embodiment, said nucleic acid sequence (d) is a nucleic acid sequence which, when transcribed under the control of the promoter (a), codes for a nucleic acid sequence which is a polyadenyl sequence comprising within the polyadenyl sequence a sequence of one or more consecutive nucleotides containing nucleotides other than A nucleotides and which exhibits higher stability upon propagation of said nucleic acid molecule in *Escherichia coli* compared to a nucleic acid molecule which 'comprises instead of said nucleic acid sequence (d) a nucleic acid sequence (d)' which, when transcribed under the control of the promoter (a), codes for a polyadenyl sequence of the same length as said nucleic acid sequence which is a polyadenyl sequence comprising within the polyadenyl sequence a sequence of one or more consecutive nucleotides containing nucleotides other than A nucleotides. In one embodiment, said nucleic acid sequence which is a polyadenyl sequence optionally comprising within the polyadenyl sequence a sequence of one or more consecutive nucleotides containing nucleotides other than A nucleotides comprises at least 80 nucleotides, preferably at least 90 or 100 nucleotides. In one embodiment, said nucleic acid sequence which is a polyadenyl sequence optionally comprising within the polyadenyl sequence a sequence of one or more consecutive nucleotides containing nucleotides other than A nucleotides comprises at least 90 nucleotides, preferably at least 100 nucleotides, preferably at least 110 nucleotides. In one embodiment, said nucleic acid sequence which is a polyadenyl sequence optionally comprising within the polyadenyl sequence a sequence of one or more consecutive nucleotides containing nucleotides other than A nucleotides comprises about 120 nucleotides. In particular embodiments, said nucleic acid sequence which is a polyadenyl sequence optionally comprising within the polyadenyl sequence a sequence of one or more consecutive nucleotides containing nucleotides other than A nucleotides comprises up to 200, preferably up to 150, and, in particular, up to 130 nucleotides. In one embodiment, at least 90%, preferably at least 92%, preferably at least 95%, 97% or 98% of the nucleotides of said nucleic acid sequence which is a polyadenyl sequence optionally comprising within the polyadenyl sequence a sequence of one or more consecutive nucleotides containing nucleotides other than A nucleotides are A nucleotides in said polyadenyl sequence (not including A nucleotides in said sequence of one or more consecutive nucleotides containing nucleotides other than A nucleotides).

In one embodiment, said sequence of one or more consecutive nucleotides containing nucleotides other than A nucleotides is located within a region from position 21 to position 80, preferably from position 21 to position 60, more preferably from position 31 to position 50 of said polyadenyl sequence.

In one embodiment, said sequence of one or more consecutive nucleotides containing nucleotides other than A nucleotides is preceeded by at least 20 A residues, preferably at least 30, 40 or 50 A residues (SEQ ID NO: 233) in said polyadenyl sequence. In particular embodiments, said sequence of one or more consecutive nucleotides containing nucleotides other than A nucleotides is preceeded by up to 80 A residues, preferably up to 70 or 60 A residues in said polyadenyl sequence (SEQ ID NO: 226).

In one embodiment, said sequence of one or more consecutive nucleotides containing nucleotides other than A nucleotides is followed by at least 20 A residues, preferably at least 30, 40, 50, 60 or 70 A residues (SEQ ID NO: 234) in said polyadenyl sequence. In particular embodiments, said sequence of one or more consecutive nucleotides containing nucleotides other than A nucleotides is followed by up to 100 A residues, preferably up to 80 A residues in said polyadenyl sequence (SEQ ID NO: 227).

In one embodiment, said sequence of one or more consecutive nucleotides containing nucleotides other than A nucleotides is preceeded by 20 to 50, preferably 30 to 40 A residues (SEQ ID NO: 231) in said polyadenyl sequence and is followed by 30 to 80, preferably 40 to 70 A residues (SEQ ID NO: 228) in said polyadenyl sequence.

In one embodiment, said sequence of one or more consecutive nucleotides containing nucleotides other than A nucleotides has a length of at least 3, at least 4, at least 5, at least 6, at least 8, preferably at least 10, more preferably at least 15 nucleotides.

In one embodiment, said sequence of one or more consecutive nucleotides containing nucleotides other than A nucleotides has a length of no more than 50, preferably no more than 30, more preferably no more than 20 nucleotides.

In one embodiment, said sequence of one or more consecutive nucleotides containing nucleotides other than A nucleotides does not comprise more than 3, preferably no more than 2, preferably no consecutive A residues.

In one embodiment, the nucleic acid sequences (b), (c) and (d) under the control of the promoter (a) can be transcribed to give a common transcript. In one embodiment, the nucleic acid sequences transcribed from the nucleic acid sequences (c) and optionally (d) are active so as to increase the translation efficiency and/or the stability of the nucleic acid sequence transcribed from the transcribable nucleic acid sequence (b).

In one embodiment, in the transcript said nucleic acid sequence which is a polyadenyl sequence optionally comprising within the polyadenyl sequence a sequence of one or more consecutive nucleotides containing nucleotides other than A nucleotides is located at the 3' end.

In one embodiment, the nucleic acid molecule of the invention is a DNA molecule. In one embodiment, said nucleic acid molecule is an expression vector or plasmid such as an IVT vector.

In one embodiment, the nucleic acid molecule of the invention is a closed circular molecule or a linear molecule.

In one embodiment, the transcribable nucleic acid sequence comprises a nucleic acid sequence coding for a peptide or protein and the nucleic acid sequence for introducing a transcribable nucleic acid sequence is a multiple cloning site.

In one embodiment, the nucleic acid molecule of the invention further comprises one or more members selected from the group consisting of: (i) a reporter gene; (ii) a selectable marker; and (iii) an origin of replication.

In one embodiment, the nucleic acid molecule of the invention is suitable, in particular after linearization, for in vitro transcription of RNA, in particular mRNA.

Prior to in vitro transcription, circular IVT vectors are generally linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. However, it was found that RNA having an open-ended poly(A) sequence is translated more efficiently than RNA having a poly(A) sequence with a masked terminus.

Accordingly, nucleic acid molecules of the invention when used as expression vectors preferably allow transcription of RNA with a poly(A) sequence which preferably has an open end in said RNA, i.e. no nucleotides other than A nucleotides flank said poly(A) sequence at its 3' end. An open-ended poly(A) sequence in the RNA can be achieved by introducing a type IIS restriction cleavage site into an expression vector which allows RNA to be transcribed under the control of a 5' RNA polymerase promoter and which contains a polyadenyl cassette, wherein the recognition sequence is located downstream of the polyadenyl cassette, while the cleavage site is located upstream and thus within the polyadenyl cassette. Restriction cleavage at the type IIS restriction cleavage site enables a plasmid to be linearized within the polyadenyl cassette. The linearized plasmid can then be used as template for in vitro transcription, the resulting transcript ending in an unmasked poly(A) sequence.

Accordingly, in one embodiment, it is preferred that the nucleic acid molecule of the invention can be cleaved, preferably enzymatically or in another biochemical way, within the nucleic acid sequence (d) in such a way that said cleavage results in a nucleic acid molecule which comprises, in the 5'→3' direction of transcription, the promoter (a), the nucleic acid sequences (b) and (c), and at least a part of the nucleic acid sequence (d), wherein the at least a part of the nucleic acid sequence (d), when transcribed under the control of the promoter (a), codes for said nucleic acid sequence which is a polyadenyl sequence optionally comprising within the polyadenyl sequence a sequence of one or more consecutive nucleotides containing nucleotides other than A nucleotides and wherein in the transcript the 3'-terminal nucleotide is an A nucleotide of said nucleic acid sequence which is a polyadenyl sequence optionally comprising within the polyadenyl sequence a sequence of one or more consecutive nucleotides containing nucleotides other than A nucleotides.

Preferably, after cleavage, the nucleic acid molecule, at the end of the strand that serves as template for the nucleic acid sequence which is a polyadenyl sequence optionally comprising within the polyadenyl sequence a sequence of one or more consecutive nucleotides containing nucleotides other than A nucleotides, has a T nucleotide which is part of the nucleic acid sequence which serves as template for the nucleic acid sequence which is a polyadenyl sequence optionally comprising within the polyadenyl sequence a sequence of one or more consecutive nucleotides containing nucleotides other than A nucleotides.

The nucleic acid molecule of the invention is preferably a closed circular molecule prior to cleavage and a linear molecule after cleavage.

Preferably, cleavage is carried out with the aid of a restriction cleavage site which is preferably a restriction cleavage site for a type IIS restriction endonuclease.

In one embodiment, the recognition sequence for the type IIS restriction endonuclease is located 5-26 base pairs, preferably 24-26 base pairs, downstream of the 3' end of the nucleic acid sequence (d).

In one embodiment, a nucleic acid molecule according to the invention is in a closed circular conformation and preferably suitable for in vitro transcription of RNA, in particular mRNA, in particular after linearization.

In further aspects, the invention relates to a nucleic acid molecule obtainable by linearization of an above-described nucleic acid molecule, preferably by cleavage within the nucleic acid sequence (d), and to RNA obtainable by transcription, preferably in vitro transcription, with above-described nucleic acid molecules under the control of the promoter (a).

Thus, the invention in one aspect relates to RNA comprising in the 5'→3' direction:
(a) a 5'-untranslated region;
(b) a nucleic acid sequence coding for a peptide or protein; and
(c) a 3'-untranslated region, said 3'-untranslated region comprising a nucleic acid sequence which is selected from the group consisting of:
(c-1) the nucleic acid sequence of the 3'-untranslated region of FCGRT, a fragment thereof, or a variant of said nucleic acid sequence or fragment,
(c-2) the nucleic acid sequence of the 3'-untranslated region of LSP1, a fragment thereof, or a variant of said nucleic acid sequence or fragment,
(c-3) the nucleic acid sequence of the 3'-untranslated region of CCL22, a fragment thereof, or a variant of said nucleic acid sequence or fragment,
(c-4) the nucleic acid sequence of the 3'-untranslated region of AES, a fragment thereof, or a variant of said nucleic acid sequence or fragment,
(c-5) the nucleic acid sequence of the 3'-untranslated region of PLD3, a fragment thereof, or a variant of said nucleic acid sequence or fragment,
(c-6) the nucleic acid sequence of the non-coding RNA of MT-RNR1, a fragment thereof, or a variant of said nucleic acid sequence or fragment,
(c-7) the nucleic sequence of the 3'-untranslated region of HLA-DRB4, a fragment thereof, or a variant of said nucleic acid sequence or fragment,
and
(c-8) any combination of two or more of the nucleic acid sequences, fragments and/or variants under (c-1), (c-2), (c-3), (c-4), (c-5), (c-6) and (c-7).

In one embodiment, the nucleic acid sequences (b) and (c) are not naturally linked.

In one embodiment, the RNA further comprises (d) a nucleic acid sequence which is a polyadenyl sequence optionally comprising within the polyadenyl sequence a sequence of one or more consecutive nucleotides containing nucleotides other than A nucleotides. In one embodiment, said nucleic acid sequence (d) is located at the 3' end of said RNA.

In one embodiment, the nucleic acid sequences (c) and optionally (d) are active so as to increase the translation efficiency and/or the stability of the nucleic acid sequence coding for a peptide or protein.

In one embodiment, the RNA further comprises (e) a 5' Cap.

Embodiments of the 3'-untranslated region and the nucleic acid sequence which is a polyadenyl sequence optionally comprising within the polyadenyl sequence a sequence of one or more consecutive nucleotides containing nucleotides other than A nucleotides are as described above for the nucleic acid molecules of the invention.

In a further aspect, the invention relates to a method of obtaining RNA, comprising:
(i) providing a nucleic acid molecule of the invention, and
(ii) transcribing RNA using the nucleic acid molecule as a template.

In a further aspect, the invention relates to a method of obtaining a peptide or protein, comprising:
(i) obtaining RNA encoding the peptide or protein according to the method of obtaining RNA of the invention, and
(ii) translating the RNA.

In one embodiment, the method of obtaining RNA or the method of obtaining a peptide or protein further comprises, prior to transcription of the nucleic acid molecule, cleavage of the nucleic acid molecule.

In a further aspect, the invention relates to a method of obtaining RNA, comprising:
(i) coupling a nucleic acid sequence (b) which, when transcribed, codes for a 3'-untranslated region, at the 3' end of a transcribable nucleic acid sequence (a) comprising a nucleic acid sequence coding for a peptide or protein, and
(ii) transcribing the nucleic acid obtained, said 3'-untranslated region comprising a nucleic acid sequence which is selected from the group consisting of:
(b-1) the nucleic acid sequence of the 3'-untranslated region of FCGRT, a fragment thereof, or a variant of said nucleic acid sequence or fragment,
(b-2) the nucleic acid sequence of the 3'-untranslated region of LSP1, a fragment thereof, or a variant of said nucleic acid sequence or fragment,
(b-3) the nucleic acid sequence of the 3'-untranslated region of CCL22, a fragment thereof, or a variant of said nucleic acid sequence or fragment,
(b-4) the nucleic acid sequence of the 3'-untranslated region of AES, a fragment thereof, or a variant of said nucleic acid sequence or fragment, (b-5) the nucleic acid sequence of the 3'-untranslated region of PLD3, a fragment thereof, or a variant of said nucleic acid sequence or fragment, (b-6) the nucleic acid sequence of the non-coding RNA of MT-RNR1, a fragment thereof, or a variant of said nucleic acid sequence or fragment, (b-7) the nucleic sequence of the 3'-untranslated region of HLA-DRB4, a fragment thereof, or a variant of said nucleic acid sequence or fragment, and (b-8) any combination of two or more of the nucleic acid sequences, fragments and/or variants under (b-1), (b-2), (b-3), (b-4), (b-5), (b-6) and (b-7).

In one embodiment, the nucleic acid sequences (a) and (b) can be transcribed to give a common transcript in which the nucleic acid sequence transcribed from the nucleic acid sequence (b) is active so as to increase the translation efficiency and/or the stability of the nucleic acid sequence transcribed from the transcribable nucleic acid sequence (a).

In one embodiment, the nucleic acid sequences (a) and (b) are not naturally linked.

In one embodiment, the method further comprises coupling a nucleic acid sequence (c) which, when transcribed, codes for a nucleic acid sequence which is a polyadenyl sequence optionally comprising within the polyadenyl sequence a sequence of one or more consecutive nucleotides containing nucleotides other than A nucleotides, at the 3' end of the nucleic acid sequence (b).

In one embodiment, the nucleic acid sequences (a), (b), and (c) can be transcribed to give a common transcript in which the nucleic acid sequences transcribed from the nucleic acid sequences (b) and, optionally, (c) are active so as to increase the translation efficiency and/or the stability of the nucleic acid sequence transcribed from the transcribable nucleic acid sequence (a).

Embodiments of the 3'-untranslated region and the nucleic acid sequence which is a polyadenyl sequence optionally comprising within the polyadenyl sequence a sequence of one or more consecutive nucleotides containing nucleotides other than A nucleotides are as described above for the nucleic acid molecules of the invention.

In a further aspect, the invention relates to a method of obtaining a peptide or protein, comprising:

(i) obtaining RNA by the method of obtaining RNA of the invention, and (ii) translating the RNA.

The methods of the invention may be performed in vitro or in vivo. In one embodiment of any of the methods of the invention, transcription is carried out in vitro.

In one embodiment, the method of obtaining RNA or the method of obtaining a peptide or protein further comprises, prior to transcription of the nucleic acid molecule, cleavage of the nucleic acid molecule.

In one embodiment, cleavage is within the nucleic acid sequence which, when transcribed, codes for a nucleic acid sequence which is a polyadenyl sequence optionally comprising within the polyadenyl sequence a sequence of one or more consecutive nucleotides containing nucleotides other than A nucleotides in such a way that transcription of the nucleic acid obtained in this way generates a transcript which has at its 3'-terminal end said nucleic acid sequence which is a polyadenyl sequence optionally comprising within the polyadenyl sequence a sequence of one or more consecutive nucleotides containing nucleotides other than A nucleotides, wherein the 3'-terminal nucleotide of said transcript is an A nucleotide of the nucleic acid sequence which is a polyadenyl sequence optionally comprising within the polyadenyl sequence a sequence of one or more consecutive nucleotides containing nucleotides other than A nucleotides.

In all aspects of the methods according to the invention, cleavage is preferably carried out with the aid of a restriction cleavage site which is preferably a restriction cleavage site for a type IIS restriction endonuclease.

In one embodiment, the recognition sequence for the type IIS restriction endonuclease is 5-26 base pairs, preferably 24-26 base pairs, downstream of the 3' end of the nucleic acid sequence which, when transcribed, codes for a nucleic acid sequence which is a polyadenyl sequence optionally comprising within the polyadenyl sequence a sequence of one or more consecutive nucleotides containing nucleotides other than A nucleotides.

The invention also relates to RNA obtainable by the methods according to the invention of obtaining RNA.

The invention may be utilized, for example, for increasing expression of recombinant proteins in cellular transcription and expression. More specifically, it is possible, when producing recombinant proteins, to use expression vectors of the invention for transcription of recombinant nucleic acids and expression of recombinant proteins in cell-based systems. This includes, for example, the preparation of recombinant antibodies, hormones, cytokines, enzymes, and the like. This allows inter alia production costs to be reduced.

It is also possible to use the nucleic acid molecules of the invention for gene therapy applications. Accordingly, a nucleic acid molecule of the invention may be a gene therapy vector and used for expression of a transgene. To this end, any nucleic acid (DNA/RNA)-based vector systems (for example plasmids, adenoviruses, poxvirus vectors, influenza virus vectors, alphavirus vectors, and the like) may be used. Cells can be transfected with these vectors in vitro, for example in lymphocytes or dendritic cells, or else in vivo by direct administration.

RNA of the invention (e.g. obtained using a nucleic acid molecule described herein as a transcription template) may be employed, for example, for transient expression of genes, with possible fields of application being RNA-based vaccines which are transfected into cells in vitro or administered directly in vivo, transient expression of functional recombinant proteins in vitro, for example in order to initiate differentiation processes in cells or to study functions of proteins, and transient expression of functional recombinant proteins such as erythropoietin, hormones, coagulation inhibitors, etc., in vivo, in particular as pharmaceuticals.

RNA of the invention may be used in particular for transfecting antigen-presenting cells and thus as a tool for delivering the antigen to be presented and for loading antigen-presenting cells, with said antigen to be presented corresponding to the peptide or protein expressed from said RNA or being derived therefrom, in particular by way of intracellular processing such as cleavage, i.e. the antigen to be presented is, for example, a fragment of the peptide or protein expressed from the RNA. Such antigen-presenting cells may be used for stimulating T cells, in particular CD4+ and/or CD8+ T cells.

Accordingly, in a further aspect, the invention relates to a use of the RNA of the invention for transfecting a host cell. In one embodiment, the host cell is an antigen-presenting cell, in particular a dendritic cell, a monocyte or a macrophage.

In a further aspect, the invention relates to a use of the RNA of the invention for therapy, in particular for vaccination.

In a further aspect, the invention relates to a pharmaceutical composition such as a vaccine composition comprising the RNA of the invention.

In a further aspect, the invention relates to the RNA of the invention for the uses described herein.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in a preferred embodiment a sequence of one or more consecutive nucleotides containing nucleotides other than A nucleotides is preceeded by at least 20 A residues (SEQ ID NO: 235) in said polyadenyl sequence and if in another preferred embodiment a sequence of one or more consecutive nucleotides containing nucleotides other than A nucleotides is followed by at least 20 A residues (SEQ ID NO: 235) in said polyadenyl sequence, it is a contemplated preferred embodiment that a sequence of one or more consecutive nucleotides containing nucleotides other than A nucleotides is preceeded and followed by at least 20 A residues (SEQ ID NO: 235) in said polyadenyl sequence.

Preferably, the terms used herein are defined as described in "A multilingual glossary of biotechnological terms: (IUPAC Recommendations)", H. G. W. Leuenberger, B. Nagel, and H. Kolbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The present invention describes nucleic acid molecules such as DNA plasmids useful as RNA expression vectors comprising nucleic acid sequences encoding modified 3' untranslated regions (UTRs) in the RNA having a stabilizing effect on the RNA and/or increasing translational efficiency of the RNA.

The term "nucleic acid sequence which, when transcribed, codes for a 3'-untranslated region in the transcript" relates to a nucleic acid sequence containing a template strand coding for said 3'-untranslated region. Preferably, said nucleic acid sequence comprises a coding strand comprising the same nucleic acid sequence as said 3'-untranslated region of the RNA transcript produced (although with thymine replaced for uracil). Thus, according to the invention a "nucleic acid sequence which, when transcribed, codes for a 3'-untranslated region in the transcript", in one embodiment, comprises a coding strand comprising a 3'-untranslated region as specified herein (although with thymine replaced for uracil).

The term "FCGRT" relates to Fc fragment of IgG, receptor, transporter, alpha and includes the FCGRT gene. This gene encodes a receptor that binds the Fc region of monomeric immunoglobulin G. The encoded protein transfers immunoglobulin G antibodies from mother to fetus across the placenta. This protein also binds immunoglobulin G to protect the antibody from degradation.

The term "nucleic acid sequence of the 3'-untranslated region of FCGRT, a fragment thereof, or a variant of said nucleic acid sequence or fragment" relates to a nucleic acid sequence comprising, preferably consisting of a nucleic acid sequence selected from the group consisting of SEQ ID NOs: 1 to 50 of the sequence listing or a fragment thereof, or a variant of said nucleic acid sequence or fragment. In one embodiment, the term relates to a nucleic acid sequence comprising, preferably consisting of a nucleic acid sequence which is at least 90%, preferably at least 95%, more preferably at least 98% identical to a nucleic acid sequence selected from the group consisting of SEQ ID NOs: 1 to 50. In one particularly preferred embodiment, the term relates to a nucleic acid sequence comprising, preferably consisting of the nucleic acid sequence of SEQ ID NO: 27 or comprising, preferably consisting of a nucleic acid sequence which is at least 90%, preferably at least 95%, more preferably at least 98% identical to the nucleic acid sequence of SEQ ID NO: 27.

The term "LSP1" relates to Lymphocyte-Specific Protein and includes the LSP1 gene. This gene encodes an intracellular F-actin binding protein. The protein is expressed in lymphocytes, neutrophils, macrophages, and endothelium and may regulate neutrophil motility, adhesion to fibrinogen matrix proteins, and transendothelial migration.

The term "nucleic acid sequence of the 3'-untranslated region of LSP1, a fragment thereof, or a variant of said nucleic acid sequence or fragment" relates to a nucleic acid sequence comprising, preferably consisting of a nucleic acid sequence selected from the group consisting of SEQ ID NOs: 51 to 72 of the sequence listing or a fragment thereof, or a variant of said nucleic acid sequence or fragment. In one embodiment, the term relates to a nucleic acid sequence comprising, preferably consisting of a nucleic acid sequence which is at least 90%, preferably at least 95%, more preferably at least 98% identical to a nucleic acid sequence selected from the group consisting of SEQ ID NOs: 51 to 72. In one particularly preferred embodiment, the term relates to a nucleic acid sequence comprising, preferably consisting of the nucleic acid sequence of SEQ ID NO: 52 or comprising, preferably consisting of a nucleic acid sequence which is at least 90%, preferably at least 95%, more preferably at least 98% identical to the nucleic acid sequence of SEQ ID NO: 52.

The term "CCL22" relates to Chemokine (C-C Motif) Ligand 22 and includes the CCL22 gene. The product of this gene binds to chemokine receptor CCR4. This chemokine may play a role in the trafficking of activated T lymphocytes to inflammatory sites and other aspects of activated T lymphocyte physiology.

The term "nucleic acid sequence of the 3'-untranslated region of CCL22, a fragment thereof, or a variant of said nucleic acid sequence or fragment" relates to a nucleic acid sequence comprising, preferably consisting of a nucleic acid sequence selected from the group consisting of SEQ ID NOs: 73 to 85 of the sequence listing or a fragment thereof, or a variant of said nucleic acid sequence or fragment. In one embodiment, the term relates to a nucleic acid sequence comprising, preferably consisting of a nucleic acid sequence which is at least 90%, preferably at least 95%, more preferably at least 98% identical to a nucleic acid sequence selected from the group consisting of SEQ ID NOs: 73 to 85. In one particularly preferred embodiment, the term relates to a nucleic acid sequence comprising, preferably consisting of the nucleic acid sequence of SEQ ID NO: 79 or comprising, preferably consisting of a nucleic acid sequence which is at least 90%, preferably at least 95%, more preferably at least 98% identical to the nucleic acid sequence of SEQ ID NO: 79.

The term "AES" relates to Amino-Terminal Enhancer Of Split and includes the AES gene. The protein encoded by this gene belongs to the groucho/TLE family of proteins, can function as a homooligomer or as a heteroologimer with other family members to dominantly repress the expression of other family member genes.

The term "nucleic acid sequence of the 3'-untranslated region of AES, a fragment thereof, or a variant of said nucleic acid sequence or fragment" relates to a nucleic acid sequence comprising, preferably consisting of a nucleic acid sequence selected from the group consisting of SEQ ID NOs: 86 to 89 of the sequence listing or a fragment thereof, or a variant of said nucleic acid sequence or fragment. In one embodiment, the term relates to a nucleic acid sequence comprising, preferably consisting of a nucleic acid sequence which is at least 90%, preferably at least 95%, more preferably at least 98% identical to a nucleic acid sequence selected from the group consisting of SEQ ID NOs: 86 to 89. In one particularly preferred embodiment, the term relates to a nucleic acid sequence comprising, preferably consisting of the nucleic acid sequence of SEQ ID NO: 86 or comprising, preferably consisting of a nucleic acid sequence which is at least 90%, preferably at least 95%, more preferably at least 98% identical to the nucleic acid sequence of SEQ ID NO: 86. In one particularly preferred embodiment, the term relates to a nucleic acid sequence comprising, preferably consisting of the nucleic acid sequence of positions 1 to 68, positions 1 to 102, positions 35 to 102, positions 35 to 136, or positions 68 to 136 of SEQ ID NO: 86 or comprising, preferably consisting of a nucleic acid sequence which is at least 90%, preferably at least 95%, more preferably at least 98% identical to the nucleic acid sequence of positions 1 to 68, positions 1 to 102, positions 35 to 102, positions 35 to 136, or positions 68 to 136 of SEQ ID NO: 86.

The term "PLD3" relates to Phospholipase D Family, Member 3 and includes the PLD3 gene. This gene encodes a member of the phospholipase D (PLD) family of enzymes that catalyze the hydrolysis of membrane phospholipids.

The encoded protein is a single-pass type II membrane protein and contains two PLD phosphodiesterase domains. This protein influences processing of amyloid-beta precursor protein. Mutations in this gene are associated with Alzheimer disease risk.

The term "nucleic acid sequence of the 3'-untranslated region of PLD3, a fragment thereof, or a variant of said nucleic acid sequence or fragment" relates to a nucleic acid sequence comprising, preferably consisting of a nucleic acid sequence selected from the group consisting of SEQ ID NOs: 90 to 104 of the sequence listing or a fragment thereof, or a variant of said nucleic acid sequence or fragment. In one embodiment, the term relates to a nucleic acid sequence comprising, preferably consisting of a nucleic acid sequence which is at least 90%, preferably at least 95%, more preferably at least 98% identical to a nucleic acid sequence selected from the group consisting of SEQ ID NOs: 90 to 104. In one particularly preferred embodiment, the term relates to a nucleic acid sequence comprising, preferably consisting of the nucleic acid sequence of SEQ ID NO: 96 or comprising, preferably consisting of a nucleic acid sequence which is at least 90%, preferably at least 95%, more preferably at least 98% identical to the nucleic acid sequence of SEQ ID NO: 96.

The term "MT_RNR1" relates to Mitochondrially Encoded 12S RNA and includes the MT RNR1 gene. This RNA gene belongs to the Mt_rRNA class. Diseases associated with MT-RNR1 include restrictive cardiomyopathy and auditory neuropathy. Among its related pathways are Ribosome biogenesis in eukaryotes and CFTR translational fidelity (class I mutations).

The term "nucleic acid sequence of the 3'-untranslated region of MT RNR1, a fragment thereof, or a variant of said nucleic acid sequence or fragment" relates to a nucleic acid sequence comprising, preferably consisting of a nucleic acid sequence selected from the group consisting of SEQ ID NOs: 105 to 121 of the sequence listing or a fragment thereof, or a variant of said nucleic acid sequence or fragment. In one embodiment, the term relates to a nucleic acid sequence comprising, preferably consisting of a nucleic acid sequence which is at least 90%, preferably at least 95%, more preferably at least 98% identical to a nucleic acid sequence selected from the group consisting of SEQ ID NOs: 105 to 121. In one particularly preferred embodiment, the term relates to a nucleic acid sequence comprising, preferably consisting of the nucleic acid sequence of SEQ ID NO: 115 or comprising, preferably consisting of a nucleic acid sequence which is at least 90%, preferably at least 95%, more preferably at least 98% identical to the nucleic acid sequence of SEQ ID NO: 115. In one particularly preferred embodiment, the term relates to a nucleic acid sequence comprising, preferably consisting of the nucleic acid sequence of positions 1 to 71, positions 1 to 107, positions 37 to 107, positions 37 to 142, or positions 71 to 142 of SEQ ID NO: 115 or comprising, preferably consisting of a nucleic acid sequence which is at least 90%, preferably at least 95%, more preferably at least 98% identical to the nucleic acid sequence of positions 1 to 71, positions 1 to 107, positions 37 to 107, positions 37 to 142, or positions 71 to 142 of SEQ ID NO: 115.

The term "HLA-DRB4" relates to Major Histocompatibility Complex, Class II, DR Beta 4 and includes the HLA-DRB4 gene. HLA-DRB4 belongs to the HLA class II beta chain paralogues. This class II molecule is a heterodimer consisting of an alpha (DRA) and a beta (DRB) chain, both anchored in the membrane. It plays a central role in the immune system by presenting peptides derived from extracellular proteins. Class II molecules are expressed in antigen presenting cells (APC: B lymphocytes, dendritic cells, macrophages).

The term "nucleic acid sequence of the 3'-untranslated region of HLA-DRB4, a fragment thereof, or a variant of said nucleic acid sequence or fragment" relates to a nucleic acid sequence comprising, preferably consisting of a nucleic acid sequence selected from the group consisting of SEQ ID NOs: 122 to 143 of the sequence listing or a fragment thereof, or a variant of said nucleic acid sequence or fragment. In one embodiment, the term relates to a nucleic acid sequence comprising, preferably consisting of a nucleic acid sequence which is at least 90%, preferably at least 95%, more preferably at least 98% identical to a nucleic acid sequence selected from the group consisting of SEQ ID NOs: 122 to 143. In one particularly preferred embodiment, the term relates to a nucleic acid sequence comprising, preferably consisting of the nucleic acid sequence of SEQ ID NO: 126 or comprising, preferably consisting of a nucleic acid sequence which is at least 90%, preferably at least 95%, more preferably at least 98% identical to the nucleic acid sequence of SEQ ID NO: 126.

The term "any combination of two or more of the nucleic acid sequences, fragments and/or variants" with respect to the nucleic acid sequences of the 3'-untranslated regions of certain genes, fragments thereof, or variants of said nucleic acid sequences or fragments means that 2 or more, 3 or more or 4 or more and preferably up to 6 or up to 5 of said nucleic acid sequences, fragments and/or variants are lined up head-to-tail, optionally spaced by linkers. In one embodiment, the combination of two or more of the nucleic acid sequences, fragments and/or variants comprises two or more different and/or two or more identical nucleic acid sequences, fragments and/or variants. In one embodiment, the combination of two or more of the nucleic acid sequences, fragments and/or variants comprises two or more different nucleic acid sequences, fragments and/or variants of the 3'-untranslated region of the same and/or different genes.

In one embodiment, the term relates to a nucleic acid sequence comprising, preferably consisting of a nucleic acid sequence which is at least 90%, preferably at least 95%, more preferably at least 98% identical to a nucleic acid sequence selected from the group consisting of SEQ ID NOs: 144 to 220, preferably SEQ ID NOs: 174 and 208 to 220. In one embodiment, the term relates to a nucleic acid sequence comprising, preferably consisting of a nucleic acid sequence selected from the group consisting of SEQ ID NOs: 144 to 220, preferably SEQ ID NOs: 174 and 208 to 220 or a fragment thereof, or a variant of said nucleic acid sequence or fragment. In one particularly preferred embodiment, the term relates to a nucleic acid sequence comprising, preferably consisting of the nucleic acid sequence of SEQ ID NO: 174 or comprising, preferably consisting of a nucleic acid sequence which is at least 90%, preferably at least 95%, more preferably at least 98% identical to the nucleic acid sequence of SEQ ID NO: 174.

The term "linker" according to the invention relates to a nucleic acid sequence added between two nucleic acid sequences to connect said two nucleic acid sequences. There is no particular limitation regarding the linker sequence.

According to the invention, a nucleic acid molecule or a nucleic acid sequence refers to a nucleic acid which is preferably deoxyribonucleic acid (DNA) or ribonucleic acid (RNA). According to the invention, nucleic acids comprise genomic DNA, cDNA, mRNA, recombinantly prepared and chemically synthesized molecules. According to the invention, a nucleic acid may be in the form of a single-stranded or double-stranded and linear or covalently closed circular molecule.

In the context of the present invention, the term "RNA" relates to a molecule which comprises ribonucleotide residues and preferably being entirely or substantially composed of ribonucleotide residues. The term "ribonucleotide" relates to a nucleotide with a hydroxyl group at the 2'-position of a β-D-ribofuranosylgroup. The term "RNA" comprises double-stranded RNA, single stranded RNA, isolated RNA such as partially or completely purified RNA, essentially pure RNA, synthetic RNA, and recombinantly generated RNA such as modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs, particularly analogs of naturally-occurring RNAs. According to the invention, RNA includes mRNA.

The term "mRNA" means "messenger-RNA" and relates to a transcript which is generated by using a DNA template and encodes a peptide or protein. Typically, mRNA comprises a 5'-UTR, a protein coding region, a 3'-UTR, and a poly(A) sequence. mRNA may be generated by in vitro transcription from a DNA template. The in vitro transcription methodology is known to the skilled person. For example, there is a variety of in vitro transcription kits commercially available. According to the invention, mRNA may be modified by further stabilizing modifications and capping, in addition to the modifications according to the invention.

In one embodiment of the present invention, RNA is self-replicating RNA, such as single stranded self-replicating RNA. In one embodiment, the self-replicating RNA is single stranded RNA of positive sense. In one embodiment, the self-replicating RNA is viral RNA or RNA derived from viral RNA. In one embodiment, the self-replicating RNA is alphaviral genomic RNA or is derived from alphaviral genomic RNA. In one embodiment, the self-replicating RNA is a viral gene expression vector. In one embodiment, the virus is Semliki forest virus. In one embodiment, the self-replicating RNA contains one or more transgenes. In one embodiment, if the RNA is viral RNA or derived from viral RNA, the transgenes may partially or completely replace viral sequences such as viral sequences encoding structural proteins. In one embodiment, the self-replicating RNA is in vitro transcribed RNA.

The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA if attached thereto, preferably in vivo and/or in a cell. Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be generated post-transcriptionally using capping enzymes, for example, capping enzymes of vaccinia virus.

The term "nucleic acid" according to the invention also comprises a chemical derivatization of a nucleic acid on a nucleotide base, on the sugar or on the phosphate, and nucleic acids containing non-natural nucleotides and nucleotide analogs.

"Fragment" or "fragment of a nucleic acid sequence" relates to a part of a nucleic acid sequence, i.e. a sequence which represents the nucleic acid sequence shortened at the 5'- and/or 3'-end(s). Preferably, a fragment when it replaces said nucleic acid sequence in an RNA molecule retains RNA stability and/or translational efficiency. Preferably, a fragment of a nucleic acid sequence comprises at least 80%, preferably at least 90%, 95%, 96%, 97%, 98%, or 99% of the nucleotide residues from said nucleic acid sequence.

The term "variant" with respect to, for example, nucleic acid and amino acid sequences, according to the invention includes any variants, in particular mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence.

According to the invention, nucleic acid variants include single or multiple nucleotide deletions, additions, mutations and/or insertions in comparison with the reference nucleic acid. Deletions include removal of one or more nucleotides from the reference nucleic acid. Addition variants comprise 5'- and/or 3'-terminal fusions of one or more nucleotides, such as 1, 2, 3, 5, 10, 20, 30, 50, or more nucleotides. Mutations can include but are not limited to substitutions, wherein at least one nucleotide in the sequence is removed and another nucleotide is inserted in its place (such as transversions and transitions), abasic sites, crosslinked sites, and chemically altered or modified bases. Insertions include the addition of at least one nucleotide into the reference nucleic acid.

With respect to nucleic acid molecules, the term "variant" includes degenerate nucleic acid sequences, wherein a degenerate nucleic acid according to the invention is a nucleic acid that differs from a reference nucleic acid in codon sequence due to the degeneracy of the genetic code.

Preferably the degree of identity between a given nucleic acid sequence and a nucleic acid sequence which is a variant of said given nucleic acid sequence will be at least 70%, preferably at least 75%, preferably at least 80%, more preferably at least 85%, even more preferably at least 90% or most preferably at least 95%, 96%, 97%, 98% or 99%. The degree of identity is preferably given for a region of at least about 30, at least about 50, at least about 70, at least about 90, at least about 100, at least about 150, at least about 200, at least about 250, at least about 300, or at least about 400 nucleotides. In preferred embodiments, the degree of identity is given for the entire length of the reference nucleic acid sequence.

"Sequence similarity" indicates the percentage of amino acids that either are identical or that represent conservative amino acid substitutions. "Sequence identity" between two polypeptide or nucleic acid sequences indicates the percentage of amino acids or nucleotides that are identical between the sequences.

The term "% identical" is intended to refer, in particular, to a percentage of nucleotides which are identical in an optimal alignment between two sequences to be compared, with said percentage being purely statistical, and the differences between the two sequences may be randomly distributed over the entire length of the sequence and the sequence to be compared may comprise additions or deletions in comparison with the reference sequence, in order to obtain optimal alignment between two sequences. Comparisons of two sequences are usually carried out by comparing said sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Neddleman and Wunsch, 1970, J. Mol. Biol. 48, 443, and with the aid of the similarity search algorithm by Pearson and Lipman, 1988, Proc. Natl Acad. Sci. USA 85, 2444 or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.).

Percentage identity is obtained by determining the number of identical positions in which the sequences to be compared correspond, dividing this number by the number of positions compared and multiplying this result by 100.

For example, the BLAST program "BLAST 2 sequences" which is available on the website http://www.ncbi.nlm.nih.gov/blast/bl2seq/wblast2.cgi may be used.

A nucleic acid is "capable of hybridizing" or "hybridizes" to another nucleic acid if the two sequences are complementary with one another. A nucleic acid is "complementary" to another nucleic acid if the two sequences are capable of forming a stable duplex with one another. According to the invention, hybridization is preferably carried out under conditions which allow specific hybridization between polynucleotides (stringent conditions). Stringent conditions are described, for example, in Molecular Cloning: A Laboratory Manual, J. Sambrook et al., Editors, 2nd Edition, Cold Spring Harbor Laboratory press, Cold Spring Harbor, N.Y., 1989 or Current Protocols in Molecular Biology, F. M. Ausubel et al., Editors, John Wiley & Sons, Inc., New York and refer, for example, to hybridization at 65° C. in hybridization buffer (3.5×SSC, 0.02% Ficoll, 0.02% polyvinylpyrrolidone, 0.02% bovine serum albumin, 2.5 mM NaH2PO4 (pH 7), 0.5% SDS, 2 mM EDTA). SSC is 0.15 M sodium chloride/0.15 M sodium citrate, pH 7. After hybridization, the membrane to which the DNA has been transferred is washed, for example, in 2×SSC at room temperature and then in 0.1-0.5×SSC/0.1×SDS at temperatures of up to 68° C.

A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or "fully complementary" means that all the contiguous residues of a nucleic acid sequence will hydrogen bond with the same number of contiguous residues in a second nucleic acid sequence. Preferably, the degree of complementarity according to the invention is at least 70%, preferably at least 75%, preferably at least 80%, more preferably at least 85%, even more preferably at least 90% or most preferably at least 95%, 96%, 97%, 98% or 99%. Most preferably, the degree of complementarity according to the invention is 100%.

The term "derivative" comprises any chemical derivatization of a nucleic acid on a nucleotide base, on the sugar or on the phosphate. The term "derivative" also comprises nucleic acids which contain nucleotides and nucleotide analogs not occurring naturally. Preferably, a derivatization of a nucleic acid increases its stability.

Fragments or variants of specific nucleic acid sequences or nucleic acid sequences having a particular degree of identity to specific nucleic acid sequences preferably have at least one functional property of said specific sequences and preferably are functionally equivalent to said specific sequences, e.g. nucleic acid sequences exhibiting properties identical or similar to those of the specific nucleic acid sequences.

One important property is to retain or improve stability of an RNA molecule and/or translational efficiency and includes in particular the ability to increase, in a functional linkage to a nucleic acid which can be transcribed into RNA (transcribable nucleic acid sequence) or a nucleic acid sequence coding for a peptide or protein, the stability and/or translation efficiency of RNA produced from this nucleic acid or of the nucleic acid sequence coding for a peptide or protein in the complete RNA molecule.

In one embodiment, if a specific nucleic acid sequence is active so as to increase the translation efficiency and/or the stability of another nucleic acid sequence, a fragment or variant of the specific nucleic acid sequence or a nucleic acid sequence having a particular degree of identity to the specific nucleic acid sequence is also active so as to increase the translation efficiency and/or the stability of the another nucleic acid sequence (when it replace the specific nucleic acid sequence). A fragment or variant of the specific nucleic acid sequence or a nucleic acid sequence having a particular degree of identity to the specific nucleic acid sequence may be as active as or more active than the specific nucleic acid sequence or activity of a fragment or variant of the specific nucleic acid sequence or of a nucleic acid sequence having a particular degree of identity to the specific nucleic acid sequence may be at least 50%, at least 60%, at least 70%, at least 80%, or at least 90% of the activity of the specific nucleic acid sequence.

According to the invention, "functional linkage" or "functionally linked" relates to a connection within a functional relationship. A nucleic acid is "functionally linked" if it is functionally related to another nucleic acid sequence. For example, a promoter is functionally linked to a coding sequence if it influences transcription of said coding sequence. Functionally linked nucleic acids are typically adjacent to one another, where appropriate separated by further nucleic acid sequences, and, in particular embodiments, are transcribed by RNA polymerase to give a single RNA molecule (common transcript). Preferably, a sequence which is a variant with respect to a specific sequence, when it replaces the specific sequence in an RNA molecule retains RNA stability and/or translational efficiency.

According to the invention, a "nucleic acid sequence which is derived from a nucleic acid sequence" refers to a nucleic acid which is a variant of the nucleic acid from which it is derived.

"3' end of a nucleic acid" refers according to the invention to that end which has a free hydroxy group. In a diagrammatic representation of double-stranded nucleic acids, in particular DNA, the 3' end is always on the right-hand side. "5' end of a nucleic acid" refers according to the invention to that end which has a free phosphate group. In a diagrammatic representation of double-strand nucleic acids, in particular DNA, the 5' end is always on the left-hand side.

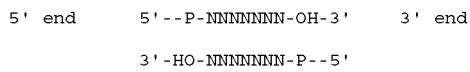

In particular embodiments, a nucleic acid is functionally linked according to the invention to expression control sequences which may be homologous or heterologous with respect to the nucleic acid.

A transcribable nucleic acid sequence, in particular a nucleic acid sequence coding for a peptide or protein, and an expression control sequence are "functionally" linked to one another, if they are covalently linked to one another in such a way that transcription or expression of the transcribable and in particular coding nucleic acid sequence is under the control or under the influence of the expression control sequence. If the nucleic acid sequence is to be translated into a functional peptide or protein, induction of an expression control sequence functionally linked to the coding sequence results in transcription of said coding sequence, without causing a frame shift in the coding sequence or the coding sequence being unable to be translated into the desired peptide or protein.

The term "expression control sequence" comprises according to the invention promoters, ribosome-binding sequences and other control elements which control transcription of a gene or translation of the derived RNA. In particular embodiments of the invention, the expression control sequences can be regulated. The precise structure of expression control sequences may vary depending on the species or cell type but usually includes 5'-untranscribed and 5'- and 3'-untranslated sequences involved in initiating transcription and translation, respectively, such as TATA box, capping sequence, CAAT sequence and the like. More specifically, 5'-untranscribed expression control sequences include a promoter region which encompasses a promoter sequence for transcription control of the functionally linked gene. Expression control sequences may also include enhancer sequences or upstream activator sequences.

The nucleic acid sequences specified herein, in particular transcribable and coding nucleic acid sequences, may be combined with any expression control sequences, in particular promoters, which may be homologous or heterologous to said nucleic acid sequences, with the term "homologous" referring to the fact that a nucleic acid sequence is also functionally linked naturally to the expression control sequence, and the term "heterologous" referring to the fact that a nucleic acid sequence is not naturally functionally linked to the expression control sequence.

The term "promoter" or "promoter region" refers to a DNA sequence upstream (5') of the coding sequence of a gene, which controls expression of said coding sequence by providing a recognition and binding site for RNA polymerase. The promoter region may include further recognition or binding sites for further factors involved in regulating transcription of said gene. A promoter may control transcription of a prokaryotic or eukaryotic gene. A promoter may be "inducible" and initiate transcription in response to an inducer, or may be "constitutive" if transcription is not controlled by an inducer. An inducible promoter is expressed only to a very small extent or not at all, if an inducer is absent. In the presence of the inducer, the gene is "switched on" or the level of transcription is increased. This is usually mediated by binding of a specific transcription factor.

Examples of promoters preferred according to the invention are promoters for SP6, T3 or T7 polymerase.

According to the invention, the term "expression" is used in its most general meaning and comprises production of RNA or of RNA and protein. It also comprises partial expression of nucleic acids. Furthermore, expression may be transient or stable. With respect to RNA, the term "expression" or "translation" relates to the process in the ribosomes of a cell by which a strand of messenger RNA directs the assembly of a sequence of amino acids to make a peptide or protein.

The term "nucleic acid sequences which can be transcribed to give a common transcript" means that said nucleic acid sequences are functionally linked to one another in such a way that, where appropriate after linearization such as restriction enzyme cleavage of the nucleic acid molecule comprising said nucleic acid sequences, in particular of a closed circular nucleic acid molecule, transcription under the control of a promoter results in an RNA molecule comprising the transcripts of said nucleic acid sequences covalently bound to one another, where appropriate separated by sequences located inbetween.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system. Preferably, cloning vectors are applied for the generation of transcripts. These cloning vectors are generally designated as transcription vectors and are according to the present invention encompassed by the term "vector". According to the present invention, RNA preferably is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

The term "nucleic acid sequence transcribed from a nucleic acid sequence" refers to RNA, where appropriate as part of a complete RNA molecule, which is a transcription product of the latter nucleic acid sequence.

The term "nucleic acid sequence which is active in order to increase the translation efficiency and/or stability of a nucleic acid sequence" means that the first nucleic acid sequence is capable of modifying, in a common transcript with the second nucleic acid sequence, the translation efficiency and/or stability of said second nucleic acid sequence in such a way that said translation efficiency and/or stability is increased in comparison with the translation efficiency and/or stability of said second nucleic acid sequence without said first nucleic acid sequence. In this context, the term "translation efficiency" relates to the amount of translation product provided by an RNA molecule within a particular period of time and the term "stability" relates to the half life of an RNA molecule.

Modification, and thereby stabilization and/or increase in translation efficiency, of RNA can be achieved according to the invention by genetically modifying expression nucleic acid molecules of the invention when used as expression vectors in such a way that they allow transcription of RNA with 3'-untranslated regions as described herein at its 3' end, and preferably between the sequence coding for a peptide or protein (open reading frame) and the poly(A) sequence The term "3'-untranslated region" relates to a region which is located at the 3' end of a gene, downstream of the termination codon of a protein-encoding region, and which is transcribed but is not translated into an amino acid sequence, or to the corresponding region in an RNA molecule.

According to the invention, a first polynucleotide region is considered to be located downstream of a second polynucleotide region, if the 5' end of said first polynucleotide region is the part of said first polynucleotide region closest to the 3' end of said second polynucleotide region.

The 3'-untranslated region typically extends from the termination codon for a translation product to the poly(A) sequence which is usually attached after the transcription process. The 3'-untranslated regions of mammalian mRNA typically have a homology region known as the AAUAAA hexanucleotide sequence. This sequence is presumably the poly(A) attachment signal and is frequently located from 10 to 30 bases upstream of the poly(A) attachment site.

3'-untranslated regions may contain one or more inverted repeats which can fold to give stem-loop structures which act as barriers for exoribonucleases or interact with proteins known to increase RNA stability (e.g. RNA-binding proteins).

5'- and/or 3'-untranslated regions may, according to the invention, be functionally linked to a transcribable and in particular coding nucleic acid, so as for these regions to be associated with the nucleic acid in such a way that the stability and/or translation efficiency of the RNA transcribed from said transcribable nucleic acid are increased.

The 3'-untranslated regions of immunoglobulin mRNAs are relatively short (fewer than about 300 nucleotides), while the 3'-untranslated regions of other genes are relatively long. For example, the 3'-untranslated region of tPA is about 800 nucleotides in length, that of factor VIII is about 1800 nucleotides in length and that of erythropoietin is about 560 nucleotides in length.

It can be determined according to the invention, whether a 3'-untranslated region or a nucleic acid sequence derived therefrom increases the stability and/or translation efficiency of RNA, by incorporating the 3'-untranslated region or the nucleic acid sequence derived therefrom into the 3'-untranslated region of a gene and measuring whether said incorporation increases the amount of protein synthesized.

The above applies accordingly to the case in which according to the invention a nucleic acid comprises two or more 3'-untranslated regions which are preferably coupled sequentially with or without a linker inbetween, preferably in a "head-to-tail relationship" (i.e. the 3'-untranslated regions have the same orientation, preferably the orientation naturally occurring in a nucleic acid).

According to the invention, the term "gene" refers to a particular nucleic acid sequence which is responsible for producing one or more cellular products and/or for achieving one or more intercellular or intracellular functions. More specifically, said term relates to a DNA section which comprises a nucleic acid coding for a specific protein or a functional or structural RNA molecule.

Polyadenylation is the addition of a poly(A) sequence or tail to a primary transcript RNA. The poly(A) sequence consists of multiple adenosine monophosphates. In other words, it is a stretch of RNA that has only adenine bases. In eukaryotes, polyadenylation is part of the process that produces mature messenger RNA (mRNA) for translation. It, therefore, forms part of the larger process of gene expression. The process of polyadenylation begins as the transcription of a gene finishes, or terminates. The 3'-most segment of the newly made pre-mRNA is first cleaved off by a set of proteins; these proteins then synthesize the poly(A) sequence at the RNA's 3' end. The poly(A) sequence is important for the nuclear export, translation, and stability of mRNA. The sequence is shortened over time, and, when it is short enough, the mRNA is enzymatically degraded.

The terms "polyadenyl sequence", "poly(A) sequence" or "poly(A) tail" refer to a sequence of adenyl residues which is typically located at the 3' end of an RNA molecule. The invention provides for such a sequence to be attached during RNA transcription by way of a DNA template on the basis of repeated thymidyl residues in the strand complementary to the coding strand, whereas said sequence is normally not encoded in the DNA but is attached to the free 3' end of the RNA by a template-independent RNA polymerase after transcription in the nucleus. According to the invention, in one embodiment, a poly(A) sequence has at least 20, preferably at least 40, preferably at least 80, preferably at least 100 and preferably up to 500, preferably up to 400, preferably up to 300, preferably up to 200, and in particular up to 150, A nucleotides, preferably consecutive A nucleotides, and in particular about 120 A nucleotides (SEQ ID NO: 229). The term "A nucleotides" or "A" refers to adenyl residues.

In a preferred embodiment, a nucleic acid molecule according to the invention is a vector. The term "vector" is used here in its most general meaning and comprises any intermediate vehicles for a nucleic acid which, for example, enable said nucleic acid to be introduced into prokaryotic and/or eukaryotic host cells and, where appropriate, to be integrated into a genome. Such vectors are preferably replicated and/or expressed in the cell. Vectors comprise plasmids, phagemids or virus genomes. The term "plasmid", as used herein, generally relates to a construct of extrachromosomal genetic material, usually a circular DNA duplex, which can replicate independently of chromosomal DNA.

The nucleic acids described herein may be recombinant and/or isolated molecules.

An "isolated molecule" as used herein, is intended to refer to a molecule which is substantially free of other molecules such as other cellular material. The term "isolated nucleic acid" means according to the invention that the nucleic acid has been (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid available to manipulation by recombinant DNA techniques.

The term "recombinant" in the context of the present invention means "made through genetic engineering". Preferably, a "recombinant object" such as a recombinant cell in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

According to the invention, the term "host cell" refers to any cell which can be transformed or transfected with an exogenous nucleic acid. The term "host cell" comprises, according to the invention, prokaryotic (e.g. *E. coli*) or eukaryotic cells (e.g. yeast cells and insect cells). Particular preference is given to mammalian cells such as cells from humans, mice, hamsters, pigs, goats, primates. The cells may be derived from a multiplicity of tissue types and comprise primary cells and cell lines. Specific examples include keratinocytes, peripheral blood leukocytes, bone marrow stem cells and embryonic stem cells. In other embodiments, the host cell is an antigen-presenting cell, in particular a dendritic cell, a monocyte or a macrophage. A nucleic acid may be present in the host cell in a single or in several copies and, in one embodiment is expressed in the host cell.

*E. coli* is a gram-negative, facultatively anaerobic, rod-shaped bacterium of the genus *Escherichia* that is commonly found in the lower intestine of warm-blooded organisms. The bacterium can be grown easily and inexpensively in a laboratory setting, and has been intensively investigated for over 60 years. *E. coli* is the most widely studied prokaryotic model organism, and an important species in the fields of biotechnology and microbiology, where it has served as the host organism for the majority of work with recombinant DNA. *E. coli* strains according to the invention include: AG1, AB1157, B2155, BL21, BNN93, BNN97, BW26434, C600, CSH50, D1210, DB3.1, DH1, DH5a, DH10B, DH12S, DM1, *E. cloni*(r), *E. coli* K12 ER2738, ER2566, ER2267, HB101, IJ1126, IJ1127, JM83, JM101, JM103, JM105, JM106, JM107, JM108, JM109, JM110, JM2.300, LE392, Mach1, MC1061, MC4100, MFDpir, MG1655, OmniMAX2, RR1, RV308, SOLR, SS320, STBL2, STBL3, STBL4, SURE, SURE2, TG1, TOP10, Top10F', W3110, WM3064, XL1-Blue, XL2-Blue, XL1-Red and XL10-Gold.

According to the present invention, the term "peptide" comprises oligo- and polypeptides and refers to substances which comprise two or more, preferably 3 or more, preferably 4 or more, preferably 6 or more, preferably 8 or more, preferably 10 or more, preferably 13 or more, preferably 16 or more, preferably 20 or more, and up to preferably 50, preferably 100 or preferably 150, consecutive amino acids linked to one another via peptide bonds. The term "protein" refers to large peptides, preferably peptides having at least 151 amino acids, but the terms "peptide" and "protein" are used herein usually as synonyms.

The terms "peptide" and "protein" comprise according to the invention substances which contain not only amino acid components but also non-amino acid components such as sugars and phosphate structures, and also comprise substances containing bonds such as ester, thioether or disulfide bonds.

According to the present invention, a nucleic acid such as RNA may encode a peptide or protein. Accordingly, a transcribable nucleic acid sequence or a transcript thereof may contain an open reading frame (ORF) encoding a peptide or protein. Said nucleic may express the encoded peptide or protein. For example, said nucleic acid may be a nucleic acid encoding and expressing an antigen or a pharmaceutically active peptide or protein such as an immunologically active compound (which preferably is not an antigen).

According to the invention, the term "nucleic acid encoding a peptide or protein" means that the nucleic acid, if present in the appropriate environment, preferably within a cell, can direct the assembly of amino acids to produce the peptide or protein during the process of translation. Preferably, RNA according to the invention is able to interact with the cellular translation machinery allowing translation of the peptide or protein.

According to the invention, in one embodiment, RNA comprises or consists of pharmaceutically active RNA. A "pharmaceutically active RNA" may be RNA that encodes a pharmaceutically active peptide or protein.

A "pharmaceutically active peptide or protein" has a positive or advantageous effect on the condition or disease state of a subject when administered to the subject in a therapeutically effective amount. Preferably, a pharmaceutically active peptide or protein has curative or palliative properties and may be administered to ameliorate, relieve, alleviate, reverse, delay onset of or lessen the severity of one or more symptoms of a disease or disorder. A pharmaceutically active peptide or protein may have prophylactic properties and may be used to delay the onset of a disease or to lessen the severity of such disease or pathological condition. The term "pharmaceutically active peptide or protein" includes entire proteins or polypeptides, and can also refer to pharmaceutically active fragments thereof. It can also include pharmaceutically active analogs of a peptide or protein. The term "pharmaceutically active peptide or protein" includes peptides and proteins that are antigens, i.e., the peptide or protein elicits an immune response in a subject which may be therapeutic or partially or fully protective.

Examples of pharmaceutically active proteins include, but are not limited to, cytokines and immune system proteins such as immunologically active compounds (e.g., interleukins, colony stimulating factor (CSF), granulocyte colony stimulating factor (G-CSF), granulocyte-macrophage colony stimulating factor (GM-CSF), erythropoietin, tumor necrosis factor (TNF), interferons, integrins, addressins, seletins, homing receptors, T cell receptors, immunoglobulins, soluble major histocompatibility complex antigens, immunologically active antigens such as bacterial, parasitic, or viral antigens, allergens, autoantigens, antibodies), hormones (insulin, thyroid hormone, catecholamines, gonadotrophines, trophic hormones, prolactin, oxytocin, dopamine, bovine somatotropin, leptins and the like), growth hormones (e.g., human grown hormone), growth factors (e.g., epidermal growth factor, nerve growth factor, insulin-like growth factor and the like), growth factor receptors, enzymes (tissue plasminogen activator, streptokinase, cholesterol biosynthetic or degradative, steriodogenic enzymes, kinases, phosphodiesterases, methylases, de-methylases, dehydrogenases, cellulases, proteases, lipases, phospholipases, aromatases, cytochromes, adenylate or guanylaste cyclases, neuramidases and the like), receptors (steroid hormone receptors, peptide receptors), binding proteins (growth hormone or growth factor binding proteins and the like), transcription and translation factors, tumor growth suppressing proteins (e.g., proteins which inhibit angiogenesis), structural proteins (such as collagen, fibroin, fibrinogen, elastin, tubulin, actin, and myosin), blood proteins (thrombin, serum albumin, Factor VII, Factor VIII, insulin, Factor IX, Factor X, tissue plasminogen activator, protein C, von Wilebrand factor, antithrombin III, glucocerebrosidase, erythropoietin granulocyte colony stimulating factor (GCSF) or modified Factor VIII, anticoagulants and the like.

In one embodiment, the pharmaceutically active protein according to the invention is a cytokine which is involved in regulating lymphoid homeostasis, preferably a cytokine which is involved in and preferably induces or enhances development, priming, expansion, differentiation and/or survival of T cells. In one embodiment, the cytokine is an interleukin. In one embodiment, the pharmaceutically active protein according to the invention is an interleukin selected from the group consisting of IL-2, IL-7, IL-12, IL-15, and IL-21.

The term "immunologically active compound" relates to any compound altering an immune response, preferably by inducing and/or suppressing maturation of immune cells, inducing and/or suppressing cytokine biosynthesis, and/or altering humoral immunity by stimulating antibody production by B cells. Immunologically active compounds possess potent immunostimulating activity including, but not limited to, antiviral and antitumor activity, and can also down-regulate other aspects of the immune response, for example shifting the immune response away from a TH2 immune response, which is useful for treating a wide range of TH2 mediated diseases. Immunologically active compounds can be useful as vaccine adjuvants.

If, according to the present invention, it is desired to induce or enhance an immune response by using RNA as described herein, the immune response may be triggered or enhanced by the RNA. For example, proteins or peptides encoded by the RNAs or procession products thereof may be presented by major histocompatibility complex (MHC) proteins expressed on antigen presenting cells. The MHC peptide complex can then be recognized by immune cells such as T cells leading to their activation.

In one embodiment, RNA that codes for an antigen such a disease-associated antigen is administered to a mammal, in particular if treating a mammal having a disease involving the antigen is desired. The RNA is taken up into the mammal's antigen-presenting cells (monocytes, macrophages, dendritic cells or other cells). An antigenic translation product of the RNA is formed and the product is displayed on the surface of the cells for recognition by T cells. In one embodiment, the antigen is displayed on the cell surface for recognition by CAR-engineered T cells directed to the antigen. In one embodiment, the antigen or a product produced by optional procession thereof is displayed on the cell surface in the context of MHC molecules for recognition by T cells through their T cell receptor.

Alternatively, the present invention envisions embodiments wherein RNA expressing an antigen is introduced into antigen-presenting cells ex vivo, e.g. antigen-presenting cells taken from a patient, and the antigen-presenting cells, optionally clonally propagated ex vivo, are transplanted back into the same patient. Transfected cells may be reintroduced into the patient using any means known in the art, preferably in sterile form by intravenous, intracavitary, intraperitoneal or intratumor administration.

The methods of the invention may involve an antigen presenting cell for expressing the RNA encoding the antigen. To this end, the methods of the invention may involve introduction of RNA encoding antigens into antigen presenting cells such as dendritic cells. For transfection of antigen presenting cells such as dendritic cells a pharmaceutical composition comprising RNA encoding the antigen may be used. A delivery vehicle that targets the RNA to a dendritic or other antigen presenting cell may be administered to a patient, resulting in transfection that occurs in vivo.

According to the invention it is preferred to use formulations of the RNA encoding an antigen which deliver the RNA with high selectivity to antigen presenting cells such as dendritic cells (DCs) in the spleen after systemic administration. For example, nanoparticulate RNA formulations with defined particle size wherein the net charge of the particles is close to zero or negative, such as electro-neutral or negatively charged lipoplexes from RNA and liposomes, e.g. lipoplexes comprising DOTMA and DOPE or DOTMA and Cholesterol, lead to substantial RNA expression in spleen DCs after systemic administration. A strong expression in the target cells (spleen) was determined while the expression in other organs was low.

As used herein, the term "nanoparticle" refers to any particle having a diameter making the particle suitable for systemic, in particular parenteral, administration, of, in particular, nucleic acids, typically a diameter of less than 1000 nanometers (nm). In some embodiments, a nanoparticle has a diameter of less than 600 nm. In some embodiments, a nanoparticle has a diameter of less than 400 nm.

As used herein, the term "nanoparticulate formulation" or similar terms refer to any substance that contains at least one nanoparticle. In some embodiments, a nanoparticulate composition is a uniform collection of nanoparticles. In some embodiments, nanoparticulate compositions are dispersions or emulsions. In general, a dispersion or emulsion is formed when at least two immiscible materials are combined.

The term, "lipoplex" or "nucleic acid lipoplex", in particular "RNA lipoplex", refers to a complex of lipids and nucleic acids, in particular RNA. Lipoplexes are formed spontaneously when cationic liposomes, which often also include a neutral "helper" lipid, are mixed with nucleic acids.

If the present invention refers to a charge such as a positive charge, negative charge or neutral charge or a cationic compound, negative compound or neutral compound this generally means that the charge mentioned is present at a selected pH, such as a physiological pH. For example, the term "cationic lipid" means a lipid having a net positive charge at a selected pH, such as a physiological pH. The term "neutral lipid" means a lipid having no net positive or negative charge and can be present in the form of a non-charged or a neutral amphoteric ion at a selected pH, such as a physiological pH. By "physiological pH" herein is meant a pH of about 7.5.

The nanoparticulate carriers such as lipid carriers contemplated for use in the present invention include any substances or vehicles with which nucleic acid such as RNA can be associated, e.g. by forming complexes with the nucleic acid or forming vesicles in which the nucleic acid is enclosed or encapsulated. This may result in increased stability of the nucleic acid compared to naked nucleic acid. In particular, stability of the nucleic acid in blood may be increased.

Cationic lipids, cationic polymers and other substances with positive charges may form complexes with negatively charged nucleic acids. These cationic molecules can be used to complex nucleic acids, thereby forming e.g. so-called lipoplexes or polyplexes, respectively, and these complexes have been shown to deliver nucleic acids into cells.

Nanoparticulate nucleic acid preparations for use in the present invention can be obtained by various protocols and from various nucleic acid complexing compounds. Lipids, polymers, oligomers, or amphipiles are typical complexing agents. In one embodiment, the complexing compound comprises at least one agent selected from the group consisting protamine, polyethyleneimine, a poly-L-lysine, a poly-L-arginine or a histone.

According to the invention, protamine is useful as cationic carrier agent. The term "protamine" refers to any of various strongly basic proteins of relatively low molecular weight that are rich in arginine and are found associated especially with DNA in place of somatic histones in the sperm cells of various animals (as fish). In particular, the term "protamine" refers to proteins found in fish sperm that are strongly basic, are soluble in water, are not coagulated by heat, and yield chiefly arginine upon hydrolysis. In purified form, they are used in a long-acting formulation of insulin and to neutralize the anticoagulant effects of heparin.

According to the invention, the term "protamine" as used herein is meant to comprise any protamine amino acid sequence obtained or derived from native or biological sources including fragments thereof and multimeric forms of said amino acid sequence or fragment thereof. Furthermore, the term encompasses (synthesized) polypeptides which are artificial and specifically designed for specific purposes and cannot be isolated from native or biological sources.

The protamine used according to the present invention can be sulfated protamine or hydrochloride protamine.

In a preferred embodiment, the protamine source used for the production of the nanoparticles described herein is protamine 5000 which contains protamine at more than 10 mg/ml (5000 heparin-neutralizing units per ml) in an isotonic salt solution.

Liposomes are microscopic lipidic vesicles often having one or more bilayers of a vesicle-forming lipid, such as a phospholipid, and are capable of encapsulating a drug. Different types of liposomes may be employed in the context of the present invention, including, without being limited thereto, multilamellar vesicles (MLV), small unilamellar vesicles (SUV), large unilamellar vesicles (LUV), sterically stabilized liposomes (SSL), multivesicular vesicles (MV), and large multivesicular vesicles (LMV) as well as other bilayered forms known in the art. The size and lamellarity of the liposome will depend on the manner of preparation and the selection of the type of vesicles to be used will depend on the preferred mode of administration. There are several other forms of supramolecular organization in which lipids may be present in an aqueous medium, comprising lamellar phases, hexagonal and inverse hexagonal phases, cubic phases, micelles, reverse micelles composed of monolayers. These phases may also be obtained in the combination with DNA or RNA, and the interaction with RNA and DNA may substantially affect the phase state. The described phases may be present in the nanoparticulate nucleic acid formulations of the present invention.

For formation of nucleic acid lipoplexes from nucleic acid and liposomes, any suitable method of forming liposomes can be used so long as it provides the envisaged nucleic acid lipoplexes. Liposomes may be formed using standard methods such as the reverse evaporation method (REV), the ethanol injection method, the dehydration-rehydration method (DRV), sonication or other suitable methods.

After liposome formation, the liposomes can be sized to obtain a population of liposomes having a substantially homogeneous size range.

Bilayer-forming lipids have typically two hydrocarbon chains, particularly acyl chains, and a head group, either polar or nonpolar. Bilayer-forming lipids are either composed of naturally-occurring lipids or of synthetic origin, including the phospholipids, such as phosphatidylcholine, phosphatidylethanolamine, phosphatide acid, phosphatidylinositol, and sphingomyelin, where the two hydrocarbon chains are typically between about 14-22 carbon atoms in length, and have varying degrees of unsaturation. Other suitable lipids for use in the composition of the present invention include glycolipids and sterols such as cholesterol and its various analogs which can also be used in the liposomes.

Cationic lipids typically have a lipophilic moiety, such as a sterol, an acyl or diacyl chain, and have an overall net positive charge. The head group of the lipid typically carries the positive charge. The cationic lipid preferably has a positive charge of 1 to 10 valences, more preferably a positive charge of 1 to 3 valences, and more preferably a positive charge of 1 valence. Examples of cationic lipids include, but are not limited to 1,2-di-O-octadecenyl-3-trimethylammonium propane (DOTMA); dimethyldioctadecylammonium (DDAB); 1,2-dioleoyl-3-trimethylammonium-propane (DOTAP); 1,2-dioleoyl-3-dimethylammonium-propane (DODAP); 1,2-diacyloxy-3-dimethylammonium propanes; 1,2-dialkyloxy-3-dimethylammonium propanes; dioctadecyldimethyl ammonium chloride (DODAC), 1,2-dimyristoyloxypropyl-1,3-dimethylhydroxyethyl ammonium (DMRIE), and 2,3-dioleoyloxy-N-[2(spermine carboxamide)ethyl]-N,N-dimethyl-1-propanamium trifluoroacetate (DOSPA). Preferred are DOTMA, DOTAP, DODAC, and DOSPA. Most preferred is DOTMA.

In addition, the nanoparticles described herein preferably further include a neutral lipid in view of structural stability and the like. The neutral lipid can be appropriately selected in view of the delivery efficiency of the nucleic acid-lipid complex. Examples of neutral lipids include, but are not limited to, 1,2-di-(9Z-octadecenoyl)-sn-glycero-3-phosphoethanolamine (DOPE), 1,2-dioleoyl-sn-glycero-3-phosphocholine (DOPC), diacylphosphatidyl choline, diacylphosphatidyl ethanol amine, ceramide, sphingoemyelin, cephalin, sterol, and cerebroside. Preferred is DOPE and/or DOPC. Most preferred is DOPE. In the case where a cationic liposome includes both a cationic lipid and a neutral lipid, the molar ratio of the cationic lipid to the neutral lipid can be appropriately determined in view of stability of the liposome and the like.

According to one embodiment, the nanoparticles described herein may comprise phospholipids. The phospholipids may be a glycerophospholipid. Examples of glycerophospholipid include, without being limited thereto, three types of lipids: (i) zwitterionic phospholipids, which include, for example, phosphatidylcholine (PC), egg yolk phosphatidylcholine, soybean-derived PC in natural, partially hydrogenated or fully hydrogenated form, dimyristoyl phosphatidylcholine (DMPC) sphingomyelin (SM); (ii) negatively charged phospholipids: which include, for example, phosphatidylserine (PS), phosphatidylinositol (PI), phosphatidic acid (PA), phosphatidylglycerol (PG) dipalmipoyl PG, dimyristoyl phosphatidylglycerol (DMPG); synthetic derivatives in which the conjugate renders a zwitterionic phospholipid negatively charged such is the case of methoxy-polyethylene, glycol-distearoyl phosphatidylethanolamine (mPEG-DSPE); and (iii) cationic phospholipids, which include, for example, phosphatidylcholine or sphingomyelin of which the phosphomonoester was O-methylated to form the cationic lipids.

Association of nucleic acid to the lipid carrier can occur, for example, by the nucleic acid filling interstitial spaces of the carrier, such that the carrier physically entraps the nucleic acid, or by covalent, ionic, or hydrogen bonding, or by means of adsorption by non-specific bonds. Whatever the mode of association, the nucleic acid must retain its therapeutic, i.e. antigen-encoding, properties.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases.

According to the invention, the term "disease" also refers to cancer diseases. The terms "cancer disease" or "cancer" (medical term: malignant neoplasm) refer to a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor, i.e. a swelling or lesion formed by an abnormal growth of cells (called neoplastic cells or tumor cells), but some, like leukemia, do not. Examples of cancers include, but are not limited to, carcinoma, lymphoma, blastoma, sarcoma, glioma and leukemia. More particularly, examples of such cancers include bone cancer, blood cancer, lung cancer, liver cancer, pancreatic cancer, skin cancer, cancer of the head or neck, cutaneous or intraocular malignant melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases.

The term "infectious disease" refers to any disease which can be transmitted from individual to individual or from organism to organism, and is caused by a microbial agent (e.g. common cold). Examples of infectious diseases include viral infectious diseases, such as AIDS (HIV), hepatitis A, B or C, herpes, herpes zoster (chicken-pox), German measles (rubella virus), yellow fever, dengue etc. flaviviruses, influenza viruses, hemorrhagic infectious diseases (Marburg or Ebola viruses), and severe acute respiratory syndrome (SARS), bacterial infectious diseases, such as Legionnaire's disease (*Legionella*), sexually transmitted diseases (e.g. *chlamydia* or gonorrhea), gastric ulcer (*Helicobacter*), cholera (*Vibrio*), tuberculosis, diphtheria, infections by *E. coli*, Staphylococci, *Salmonella* or Streptococci (tetanus); infections by protozoan pathogens such as malaria, sleeping sickness, leishmaniasis; toxoplasmosis, i.e. infections by *Plasmodium, Trypanosoma, Leishmania* and *Toxoplasma*; or fungal infections, which are caused e.g. by *Cryptococcus neoformans, Histoplasma capsulatum, Coccidioides immitis, Blastomyces dermatitidis* or *Candida albicans*.

The term "autoimmune disease" refers to any disease in which the body produces an immunogenic (i.e. immune system) response to some constituent of its own tissue. In other words, the immune system loses its ability to recognize some tissue or system within the body as self and targets and attacks it as if it were foreign. Autoimmune diseases can be classified into those in which predominantly one organ is affected (e.g. hemolytic anemia and anti-immune thyroiditis), and those in which the autoimmune disease process is diffused through many tissues (e.g. systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

According to the invention, an immune response may be stimulated by introducing into a subject a suitable mRNA which codes for an antigen or a fragment thereof, e.g., a disease-associated antigen.

The term "antigen" relates to an agent comprising an epitope against which an immune response is to be generated. The term "antigen" includes in particular proteins, peptides, polysaccharides, nucleic acids, especially RNA and DNA, and nucleotides. The term "antigen" also includes agents, which become antigenic—and sensitizing—only through transformation (e.g. intermediately in the molecule or by completion with body protein). An antigen is preferably presentable by cells of the immune system such as antigen presenting cells like dendritic cells or macrophages. In addition, an antigen or a processing product thereof is preferably recognizable by a T or B cell receptor, or by an immunoglobulin molecule such as an antibody. In a preferred embodiment, the antigen is a disease-associated antigen, such as a tumor-associated antigen, a viral antigen, or a bacterial antigen.

The term "disease-associated antigen" is used in it broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen may therefore be used for therapeutic purposes. Disease-associated antigens are preferably associated with infection by microbes, typically microbial antigens, or associated with cancer, typically tumors.

The term "disease involving an antigen" refers to any disease which implicates an antigen, e.g. a disease which is characterized by the presence and/or expression of an antigen. The disease involving an antigen can be an infectious disease, an autoimmune disease, or a cancer disease or simply cancer. As mentioned above, the antigen may be a disease-associated antigen, such as a tumor-associated antigen, a viral antigen, or a bacterial antigen.

In one embodiment, a disease-associated antigen is a tumor-associated antigen. In this embodiment, the present invention may be useful in treating cancer or cancer metastasis. Preferably, the diseased organ or tissue is characterized by diseased cells such as cancer cells expressing a disease-associated antigen and/or being characterized by association of a disease-associated antigen with their surface. Immunization with intact or substantially intact tumor-associated antigens or fragments thereof such as MHC class I and class II peptides or nucleic acids, in particular mRNA, encoding such antigen or fragment makes it possible to elicit a MHC class I and/or a class II type response and, thus, stimulate T cells such as CD8+ cytotoxic T lymphocytes which are capable of lysing cancer cells and/or CD4+ T cells. Such immunization may also elicit a humoral immune response (B cell response) resulting in the production of antibodies against the tumor-associated antigen. Furthermore, antigen presenting cells (APC) such as dendritic cells (DCs) can be loaded with MHC class I-presented peptides by transfection with nucleic acids encoding tumor antigens in vitro and administered to a patient. In one embodiment, the term "tumor-associated antigen" refers to a constituent of cancer cells which may be derived from the cytoplasm, the cell surface and the cell nucleus. In particular, it refers to those antigens which are produced, preferably in large quantity, intracellularly or as surface antigens on tumor cells. Examples for tumor antigens include HER2, EGFR, VEGF, CAMPATH1-antigen, CD22, CA-125, HLA-DR, Hodgkin-lymphoma or mucin-1, but are not limited thereto.

According to the present invention, a tumor-associated antigen preferably comprises any antigen which is characteristic for tumors or cancers as well as for tumor or cancer cells with respect to type and/or expression level. In one embodiment, the term "tumor-associated antigen" relates to proteins that are under normal conditions, i.e. in a healthy subject, specifically expressed in a limited number of organs and/or tissues or in specific developmental stages, for example, the tumor-associated antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2 or 1. The tumor-associated antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor-associated antigen is preferably not or only rarely expressed in normal tissues or is mutated in tumor cells. Preferably, the tumor-associated antigen or the aberrant expression of the tumor-associated antigen identifies cancer cells. In the context of the present invention, the tumor-associated antigen that is expressed by a cancer cell in a subject, e.g., a patient suffering from a cancer disease, is preferably a self-protein in said subject. In preferred embodiments, the tumor-associated antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, a tumor-associated antigen is presented in the context of MHC molecules by a cancer cell in which it is expressed.

Examples for differentiation antigens which ideally fulfill the criteria for tumor-associated antigens as contemplated by the present invention as target structures in tumor immunotherapy, in particular, in tumor vaccination are the cell surface proteins of the Claudin family, such as CLDN6 and CLDN18.2. These differentiation antigens are expressed in tumors of various origins, and are particularly suited as target structures in connection with antibody-mediated cancer immunotherapy due to their selective expression (no expression in a toxicity relevant normal tissue) and localization to the plasma membrane.

Further examples for antigens that may be useful in the present invention are p53, ART-4, BAGE, beta-catenin/m, Bcr-abL CAMEL, CAP-1, CASP-8, CDC27/m, CDK4/m, CEA, CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Pm1/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT, preferably WT-1.

The term "viral antigen" refers to any viral component having antigenic properties, i.e. being able to provoke an immune response in an individual. The viral antigen may be a viral ribonucleoprotein or an envelope protein.

The term "bacterial antigen" refers to any bacterial component having antigenic properties, i.e. being able to provoke an immune response in an individual. The bacterial antigen may be derived from the cell wall or cytoplasm membrane of the bacterium.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, preferably antigen presenting cells to specific T cells.

The term "immune response", as used herein, relates to a reaction of the immune system such as to immunogenic organisms, such as bacteria or viruses, cells or substances. The term "immune response" includes the innate immune response and the adaptive immune response. Preferably, the immune response is related to an activation of immune cells, an induction of cytokine biosynthesis and/or antibody production. It is preferred that the immune response comprises the steps of activation of antigen presenting cells, such as dendritic cells and/or macrophages, presentation of an antigen or fragment thereof by said antigen presenting cells and activation of cytotoxic T cells due to this presentation.

The term "treat" or "treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

In particular, the term "treatment of a disease" includes curing, shortening the duration, ameliorating, slowing down or inhibiting progression or worsening of a disease or the symptoms thereof.

The term "immunotherapy" relates to a treatment preferably involving a specific immune reaction and/or immune effector function(s).

The term "immunization" or "vaccination" describes the process of treating a subject for therapeutic or prophylactic reasons.

The term "subject" or "individual", as used herein, preferably relates to mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity, such as animals of zoos. In a preferred embodiment, the subject is a human.

The term "antigen presenting cell" (APC) relates to a cell of a variety of cells capable of displaying, acquiring, and/or presenting at least one antigen or antigenic fragment on (or at) its cell surface. Antigen-presenting cells can be distinguished in professional antigen presenting cells and non-professional antigen presenting cells.

The term "professional antigen presenting cells" relates to antigen presenting cells which constitutively express the Major Histocompatibility Complex class II (MHC class II) molecules required for interaction with naive T cells. If a T cell interacts with the MHC class II molecule complex on the membrane of the antigen presenting cell, the antigen presenting cell produces a co-stimulatory molecule inducing activation of the T cell. Professional antigen presenting cells comprise dendritic cells and macrophages.

The term "non-professional antigen presenting cells" relates to antigen presenting cells which do not constitutively express MHC class II molecules, but upon stimulation by certain cytokines such as interferon-gamma. Exemplary, non-professional antigen presenting cells include fibroblasts, thymic epithelial cells, thyroid epithelial cells, glial cells, pancreatic beta cells or vascular endothelial cells.

The term "major histocompatibility complex" and the abbreviation "MHC" include MHC class I and MHC class II molecules and relate to a complex of genes which occurs in all vertebrates. MHC proteins or molecules are important for signaling between lymphocytes and antigen presenting cells or diseased cells in immune reactions, wherein the MHC proteins or molecules bind peptides and present them for recognition by T cell receptors. The proteins encoded by the MHC are expressed on the surface of cells, and display both self antigens (peptide fragments from the cell itself) and nonself antigens (e.g., fragments of invading microorganisms) to a T cell.

According to the invention the term "chimeric antigen receptor (CAR)" is synonymous with the terms "chimeric T cell receptor" and "artificial T cell receptor".

These terms relate to engineered receptors, which confer an arbitrary specificity such as the specificity of a monoclonal antibody onto an immune effector cell such as a T cell. In this way, a large number of cancer-specific T cells can be generated for adoptive cell transfer. Thus, a CAR may be present on T cells, e.g. instead of or in addition to the T cell's own T cell receptor. Such T cells do not necessarily require processing and presentation of an antigen for recognition of the target cell but rather may recognize preferably with specificity any antigen present on a target cell. Preferably, said CAR is expressed on the surface of the cells. For the purpose of the present invention T cells comprising a CAR are comprised by the term "T cell" as used herein.

According to the invention, the term "CAR" (or "chimeric antigen receptor") relates to an artificial receptor comprising a single molecule or a complex of molecules which recognizes, i.e. binds to, a target structure (e.g. an antigen) on a target cell such as a cancer cell (e.g. by binding of an antigen binding domain to an antigen expressed on the surface of the target cell) and may confer specificity onto an immune effector cell such as a T cell expressing said CAR on the cell surface. Preferably, recognition of the target structure by a CAR results in activation of an immune effector cell expressing said CAR. A CAR may comprise one or more protein units said protein units comprising one or more domains as described herein. The term "CAR" does not include T cell receptors.

In one embodiment, a single-chain variable fragment (scFv) derived from a monoclonal antibody is fused to CD3-zeta transmembrane and endodomain. Such molecules result in the transmission of a zeta signal in response to recognition by the scFv of its antigen target on a target cell and killing of the target cell that expresses the target antigen. Antigen recognition domains which also may be used include among others T cell receptor (TCR) alpha and beta single chains. In fact almost anything that binds a given target with high affinity can be used as an antigen recognition domain.

Following antigen recognition, receptors cluster and a signal is transmitted to the cell. In this respect, a "T cell signaling domain" is a domain, preferably an endodomain, which transmits an activation signal to the T cell after antigen is bound. The most commonly used endodomain component is CD3-zeta.

Adoptive cell transfer therapy with CAR-engineered T cells expressing chimeric antigen receptors is a promising anti-cancer therapeutic as CAR-modified T cells can be engineered to target virtually any tumor antigen. For example, patient's T cells may be genetically engineered (genetically modified) to express CARs specifically directed towards antigens on the patient's tumor cells, then infused back into the patient.

According to the invention a CAR may replace the function of a T cell receptor and, in particular, may confer reactivity such as cytolytic activity to a cell such as a T cell. However, in contrast to the binding of the T cell receptor to an antigen peptide-MHC complex, a CAR may bind to an antigen, in particular when expressed on the cell surface.

According to the invention, CARs may generally comprise three domains.

The first domain is the binding domain which recognizes and binds antigen.

The second domain is the co-stimulation domain. The co-stimulation domain serves to enhance the proliferation and survival of the cytotoxic lymphocytes upon binding of the CAR to a targeted moiety. The identity of the co-stimulation domain is limited only in that it has the ability to enhance cellular proliferation and survival upon binding of the targeted moiety by the CAR. Suitable co-stimulation domains include CD28, CD137 (4-1BB), a member of the tumor necrosis factor (TNF) receptor family, CD134 (OX40), a member of the TNFR-superfamily of receptors, and CD278 (ICOS), a CD28-superfamily co-stimulatory molecule expressed on activated T cells. The skilled person will understand that sequence variants of these noted co-stimulation domains can be used without adversely impacting the invention, where the variants have the same or similar activity as the domain on which they are modeled. Such variants will have at least about 80% sequence identity to the amino acid sequence of the domain from which they are derived. In some embodiments of the invention, the CAR constructs comprise two co-stimulation domains. While the particular combinations include all possible variations of the four noted domains, specific examples include CD28+ CD137 (4-1BB) and CD28+CD134 (OX40).

The third domain is the activation signaling domain (or T cell signaling domain). The activation signaling domain serves to activate cytotoxic lymphocytes upon binding of the CAR to antigen. The identity of the activation signaling domain is limited only in that it has the ability to induce activation of the selected cytotoxic lymphocyte upon binding of the antigen by the CAR. Suitable activation signaling domains include the T cell CD3[zeta] chain and Fc receptor [gamma]. The skilled artisan will understand that sequence variants of these noted activation signaling domains can be used without adversely impacting the invention, where the variants have the same or similar activity as the domain on which they are modeled. Such variants will have at least about 80% sequence identity to the amino acid sequence of the domain from which they are derived.

CARs may comprise the three domains, together in the form of a fusion protein. Such fusion proteins will generally comprise a binding domain, one or more co-stimulation domains, and an activation signaling domain, linked in a N-terminal to C-terminal direction. However, CARs are not limited to this arrangement and other arrangements are acceptable and include a binding domain, an activation signaling domain, and one or more co-stimulation domains. It will be understood that because the binding domain must be free to bind antigen, the placement of the binding domain in the fusion protein will generally be such that display of the region on the exterior of the cell is achieved. In the same manner, because the co-stimulation and activation signaling domains serve to induce activity and proliferation of the cytotoxic lymphocytes, the fusion protein will generally display these two domains in the interior of the cell. The CARs may include additional elements, such as a signal peptide to ensure proper export of the fusion protein to the cells surface, a transmembrane domain to ensure the fusion protein is maintained as an integral membrane protein, and a hinge domain (or spacer region) that imparts flexibility to the binding domain and allows strong binding to antigen.

The cells used in connection with the CAR system of the present invention are preferably T cells, in particular cytotoxic lymphocytes, preferably selected from cytotoxic T cells, natural killer (NK) cells, and lymphokine-activated killer (LAK) cells. Upon activation, each of these cytotoxic lymphocytes triggers the destruction of target cells. For example, cytotoxic T cells trigger the destruction of target cells by either or both of the following means. First, upon activation T cells release cytotoxins such as perforin, granzymes, and granulysin. Perforin and granulysin create pores in the target cell, and granzymes enter the cell and trigger a caspase cascade in the cytoplasm that induces apoptosis (programmed cell death) of the cell. Second, apoptosis can be induced via Fas-Fas ligand interaction between the T cells and target cells. The cytotoxic lymphocytes will preferably be autologous cells, although heterologous cells or allogenic cells can be used.

A variety of methods may be used to introduce CAR constructs into T cells including non-viral-based DNA transfection, transposon-based systems and viral-based systems. Non-viral-based DNA transfection has low risk of insertional mutagenesis. Transposon-based systems can integrate transgenes more efficiently than plasmids that do not contain an integrating element. Viral-based systems include the use of γ-retroviruses and lentiviral vectors. γ-Retroviruses are relatively easy to produce, efficiently and permanently transduce T cells, and have preliminarily proven safe from an integration standpoint in primary human T cells. Lentiviral vectors also efficiently and permanently transduce T cells but are more expensive to manufacture. They are also potentially safer than retrovirus based systems.

The RNA described herein (e.g. obtained using a nucleic acid molecule described herein as a transcription template) is also useful in reprogramming or de-differentiating somatic cells into stem-like cells, i.e. cells having stem cell characteristics, in vitro or in vivo. This may involve the transient expression of reprogramming factors in vitro or in vivo in order to initiate reprogramming or de-differentiation processes in cells. Thus, in one embodiment, the peptide or protein encoded by a nucleic acid such as RNA described herein is a factor allowing the reprogramming of somatic cells to cells having stem cell characteristics. Stem-like cells can be provided according to the invention without generating embryos or fetuses. De-differentiation of somatic cells to cells having stem cell characteristics, in particular pluripotency, can be effected by introducing RNA encoding factors inducing the de-differentiation of somatic cells into the somatic cells (also termed reprogramming transcription factors (rTF)) and culturing the somatic cells allowing the cells to de-differentiate. After being de-differentiated, the cells could be induced to re-differentiate into the same or a different somatic cell type such as neuronal, hematopoietic, muscle, epithelial, and other cell types. Thus, such stem-like cells have medical applications for treatment of degenerative diseases by "cell therapy" and may be utilized in novel therapeutic strategies in the treatment of cardiac, neurological, endocrinological, vascular, retinal, dermatological, muscular-skeletal disorders, and other diseases.

Accordingly, the invention also relates to a method for providing cells having stem cell characteristics comprising the steps of (i) providing a cell population comprising somatic cells, (ii) introducing RNA of the invention capable of expressing one or more factors allowing the reprogramming of the somatic cells to cells having stem cell characteristics into the somatic cells, and (iii) allowing the development of cells having stem cell characteristics. In one embodiment, the method further comprises introducing into the somatic cells miRNA enhancing reprogramming of the somatic cells to cells having stem cell characteristics.

In one embodiment, the one or more factors comprise OCT4 and SOX2. The one or more factors may further comprise KLF4 and/or c-MYC and/or NANOG and/or LIN28. In one embodiment, the one or more factors comprise OCT4, SOX2, KLF4 and c-MYC and may further comprise LIN28 and optionally NANOG. In one embodiment, the one or more factors comprise OCT4, SOX2, NANOG and LIN28.

In one embodiment, the method further comprises the step of culturing the somatic cells in the presence of at least one histone deacetylase inhibitor, wherein the at least one histone deacetylase inhibitor preferably comprises valproic acid, sodium butyrate, trichostatin A and/or scriptaid.

In one embodiment, step (iii) comprises culturing the somatic cells under embryonic stem cell culture conditions.

In one embodiment, the stem cell characteristics comprise an embryonic stem cell morphology.

In one embodiment, the cells having stem cell characteristics have normal karyotypes, express telomerase activity, express cell surface markers that are characteristic for embryonic stem cells and/or express genes that are characteristic for embryonic stem cells.

In one embodiment, the cells having stem cell characteristics exhibit a pluripotent state.

In one embodiment, the cells having stem cell characteristics have the developmental potential to differentiate into advanced derivatives of all three primary germ layers.

In one embodiment, the somatic cells are fibroblasts such as lung fibroblasts, foreskin fibroblasts or dermal fibroblasts. Preferably, the somatic cells are human cells.

In one embodiment, the RNA is introduced into the somatic cells by electroporation or lipofection. In one embodiment, the RNA is introduced into the somatic cells repetitively.

In one embodiment, introduction of RNA capable of expression certain factors as disclosed herein into somatic cells results in expression of said factors for an extended period of time, preferably for at least 10 days, preferably for at least 11 days and more preferably for at least 12 days. To achieve such long term expression, RNA is preferably periodically (i.e. repetitively) introduced into the cells more than one time, preferably using electroporation. Preferably, RNA is introduced into the cells at least twice, more preferably at least 3 times, more preferably at least 4 times, even more preferably at least 5 times up to preferably 6 times, more preferably up to 7 times or even up to 8, 9 or 10 times, preferably over a time period of at least 10 days, preferably for at least 11 days and more preferably for at least 12 days to ensure expression of one or more factors for an extended period of time. Preferably, the time periods elapsing between the repeated introductions of the RNA are from 24 hours to 120 hours, preferably 48 hours to 96 hours. In one embodiment, time periods elapsing between the repeated introductions of the RNA are not longer than 72 hours, preferably not longer than 48 hours or 36 hours. In one embodiment, prior to the next electroporation, cells are allowed to recover from the previous electroporation. In any case, the conditions should be selected so that the factors are expressed in the cells in amounts and for periods of time which support the reprogramming process.

A "stem cell" is a cell with the ability to self-renew, to remain undifferentiated, and to become differentiated. A stem cell can divide without limit, for at least the lifetime of the animal in which it naturally resides. A stem cell is not terminally differentiated; it is not at the end stage of a differentiation pathway. When a stem cell divides, each daughter cell can either remain a stem cell or embark on a course that leads toward terminal differentiation.

Totipotent stem cells are cells having totipotential differentiation properties and being capable of developing into a complete organism. This property is possessed by cells up to the 8-cell stage after fertilization of the oocyte by the sperm. When these cells are isolated and transplanted into the uterus, they can develop into a complete organism.

Pluripotent stem cells are cells capable of developing into various cells and tissues derived from the ectodermal, mesodermal and endodermal layers. Pluripotent stem cells which are derived from the inner cell mass located inside of blastocysts, generated 4-5 days after fertilization are called "embryonic stem cells" and can differentiate into various other tissue cells but cannot form new living organisms.

Multipotent stem cells are stem cells differentiating normally into only cell types specific to their tissue and organ of origin. Multipotent stem cells are involved not only in the growth and development of various tissues and organs during the fetal, neonatal and adult periods but also in the maintenance of adult tissue homeostasis and the function of inducing regeneration upon tissue damage. Tissue-specific multipotent cells are collectively called "adult stem cells".

An "embryonic stem cell" or "ESC" is a stem cell that is present in or isolated from an embryo. It can be pluripotent, having the capacity to differentiate into each and every cell present in the organism, or multipotent, with the ability to differentiate into more than one cell type.

As used herein, "embryo" refers to an animal in the early stages of it development. These stages are characterized by implantation and gastrulation, where the three germ layers are defined and established and by differentiation of the germs layers into the respective organs and organ systems. The three germ layers are the endoderm, ectoderm and mesoderm.

A "blastocyst" is an embryo at an early stage of development in which the fertilized ovum has undergone cleavage, and a spherical layer of cells surrounding a fluid-filled cavity is forming, or has formed. This spherical layer of cells is the trophectoderm. Inside the trophectoderm is a cluster of cells termed the inner cell mass (ICM). The trophectoderm is the precursor of the placenta, and the ICM is the precursor of the embryo.

An adult stem cell, also called a somatic stem cell, is a stem cell found in an adult. An adult stem cell is found in a differentiated tissue, can renew itself, and can differentiate, with some limitations, to yield specialized cell types of its tissue of origin. Examples include mesenchymal stem cells, hematopoietic stem cells, and neural stem cells.

A "differentiated cell" is a mature cell that has undergone progressive developmental changes to a more specialized form or function. Cell differentiation is the process a cell undergoes as it matures to an overtly specialized cell type. Differentiated cells have distinct characteristics, perform specific functions, and are less likely to divide than their less differentiated counterparts.

An "undifferentiated" cell, for example, an immature, embryonic, or primitive cell, typically has a nonspecific appearance, may perform multiple, non-specific activities, and may perform poorly, if at all, in functions typically performed by differentiated cells.

"Somatic cell" refers to any and all differentiated cells and does not include stem cells, germ cells, or gametes. Preferably, "somatic cell" as used herein refers to a terminally differentiated cell.

As used herein, "committed" refers to cells which are considered to be permanently committed to a specific function. Committed cells are also referred to as "terminally differentiated cells".

As used herein, "differentiation" refers to the adaptation of cells for a particular form or function. In cells, differentiation leads to a more committed cell.

As used herein, "de-differentiation" refers to loss of specialization in form or function. In cells, de-differentiation leads to a less committed cell.

As used herein "reprogramming" refers to the resetting of the genetic program of a cell. A reprogrammed cell preferably exhibits pluripotency.

The terms "de-differentiated" and "reprogrammed" or similar terms are used interchangeably herein to denote somatic cell-derived cells having stem cell characteristics. However, said terms are not intended to limit the subject-matter disclosed herein by mechanistic or functional considerations.

The term "RNA inducing the development of stem cell characteristics" or "RNA capable of expressing one or more factors allowing the reprogramming of the somatic cells to cells having stem cell characteristics" refers to RNA which when introduced into a somatic cell induces the cell to de-differentiate.

As used herein, "germ cell" refers to a reproductive cell such as a spermatocyte or an oocyte, or a cell that will develop into a reproductive cell.

As used herein, "pluripotent" refers to cells that can give rise to any cell type except the cells of the placenta or other supporting cells of the uterus.

Terms such as "cell having stem cell characteristics", "cell having stem cell properties" or "stem like cell" are used herein to designate cells which, although they are derived from differentiated somatic non-stem cells, exhibit one or more features typical for stem cells, in particular embryonic stem cells. Such features include an embryonic stem cell morphology such as compact colonies, high nucleus to cytoplasm ratio and prominent nucleoli, normal karyotypes, expression of telomerase activity, expression of cell surface markers that are characteristic for embryonic stem cells, and/or expression of genes that are characteristic for embryonic stem cells. The cell surface markers that are characteristic for embryonic stem cells are, for example, selected from the group consisting of stage-specific embryonic antigen-3 (SSEA-3), SSEA-4, tumor-related antigen-1-60 (TRA-1-60), TRA-1-81, and TRA-2-49/6E. The genes that are characteristic for embryonic stem cells are selected, for example, from the group consisting of endogenous OCT4, endogenous NANOG, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, and telomerase reverse transcriptase (TERT). In one embodiment, the one or more features typical for stem cells include pluripotency.

In one embodiment of the invention, the stem cell characteristics comprise an embryonic stem cell morphology, wherein said embryonic stem cell morphology preferably comprises morphological criteria selected from the group consisting of compact colonies, high nucleus to cytoplasm ratio and prominent nucleoli. In certain embodiments, the cells having stem cell characteristics have normal karyotypes, express telomerase activity, express cell surface markers that are characteristic for embryonic stem cells and/or express genes that are characteristic for embryonic stem cells. The cell surface markers that are characteristic for embryonic stem cells may be selected from the group consisting of stage-specific embryonic antigen-3 (SSEA-3), SSEA-4, tumor-related antigen-1-60 (TRA-1-60), TRA-1-81, and TRA-2-49/6E and the genes that are characteristic for embryonic stem cells may be selected from the group consisting of endogenous OCT4, endogenous NANOG, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, and telomerase reverse transcriptase (TERT).

Preferably, the cells having stem cell characteristics are de-differentiated and/or reprogrammed somatic cells. Preferably, the cells having stem cell characteristics exhibit the essential characteristics of embryonic stem cells such as a pluripotent state. Preferably, the cells having stem cell characteristics have the developmental potential to differentiate into advanced derivatives of all three primary germ layers. In one embodiment, the primary germ layer is endoderm and the advanced derivative is gut-like epithelial tissue. In a further embodiment, the primary germ layer is mesoderm and the advanced derivative is striated muscle and/or cartilage. In an even further embodiment, the primary germ layer is ectoderm and the advanced derivative is neural tissue and/or epidermal tissue. In one preferred embodiment, the cells having stem cell characteristics have the developmental potential to differentiate into neuronal cells and/or cardiac cells.

In one embodiment, the somatic cells are embryonic stem cell derived somatic cells with a mesenchymal phenotype. In a preferred embodiment, the somatic cells are fibroblasts such as fetal fibroblasts or postnatal fibroblasts or keratinocytes, preferably hair follicle derived keratinocytes. In further embodiments, the fibroblasts are lung fibroblasts, foreskin fibroblasts or dermal fibroblasts. In particular embodiments, the fibroblasts are fibroblasts as deposited at the American Type Culture Collection (ATCC) under Catalog No. CCL-186, as deposited at the American Type Culture Collection (ATCC) under Catalog No. CRL-2097 or as deposited at the American Type Culture Collection (ATCC) under Catalog No. CRL-2522, or as distributed by System Biosciences under the catalog no. PC501A-HFF. In one embodiment, the fibroblasts are adult human dermal fibroblasts. Preferably, the somatic cells are human cells. According to the present invention, the somatic cells may be genetically modified.

The term "factor" according to the invention when used in conjunction with the expression thereof by RNA includes proteins and peptides as well as derivatives and variants thereof. For example, the term "factor" comprises OCT4, SOX2, NANOG, LIN28, KLF4 and c-MYC.

The factors can be of any animal species; e.g., mammals and rodents. Examples of mammals include but are not limited to human and non-human primates. Primates include but are not limited to humans, chimpanzees, baboons, cynomolgus monkeys, and any other New or Old World monkeys. Rodents include but are not limited to mouse, rat, guinea pig, hamster and gerbil.

According to the present invention, one or more factors capable of allowing the reprogramming of somatic cells to cells having stem cell characteristics comprise an assembly of factors selected from the group consisting of (i) OCT4 and SOX2, (ii) OCT4, SOX2, and one or both of NANOG and LIN28, (iii) OCT4, SOX2 and one or both of KLF4 and c-MYC. In one embodiment, said one or more factors capable of being expressed by the RNA comprise OCT4, SOX2, NANOG and LIN28 or OCT4, SOX2, KLF4 and c-MYC. Preferably, the RNA is introduced into said somatic cells by electroporation or microinjection. Preferably, the invention further comprises allowing the development of cells having stem cell characteristics, e.g. by culturing the somatic cell under embryonic stem cell culture conditions, preferably conditions suitable for maintaining pluripotent stem cells in an undifferentiated state. OCT4 is a transcription factor of the eukaryotic POU transcription factors and an indicator of pluripotency of embryonic stem cells. It is a maternally expressed Octomer binding protein. It has been observed to be present in oocytes, the inner cell mass of blastocytes and also in the primordial germ cell. The gene POU5F1 encodes the OCT4 protein. Synonyms to the gene name include OCT3, OCT4, OTF3 and MGC22487. The presence of OCT4 at specific concentrations is necessary for embryonic stem cells to remain undifferentiated. Preferably, "OCT4 protein" or simply "OCT4" relates to human OCT4.

Sox2 is a member of the Sox (SRY-related HMG box) gene family that encode transcription factors with a single HMG DNA-binding domain. SOX2 has been found to control neural progenitor cells by inhibiting their ability to differentiate. The repression of the factor results in delamination from the ventricular zone, which is followed by an exit from the cell cycle. These cells also begin to lose their progenitor character through the loss of progenitor and early neuronal differentiation markers. Preferably, "SOX2 protein" or simply "SOX2" relates to human SOX2.

NANOG is a NK-2 type homeodomain gene, and has been proposed to play a key role in maintaining stem cell pluripotency presumably by regulating the expression of genes critical to embryonic stem cell renewal and differentiation. NANOG behaves as a transcription activator with two unusually strong activation domains embedded in its C terminus. Reduction of NANOG expression induces differentiation of embryonic stem cells. Preferably, "NANOG protein" or simply "NANOG" relates to human NANOG.

LIN28 is a conserved cytoplasmic protein with an unusual pairing of RNA-binding motifs: a cold shock domain and a pair of retroviral-type CCHC zinc fingers. In mammals, it is abundant in diverse types of undifferentiated cells. In pluripotent mammalian cells, LIN28 is observed in RNase-sensitive complexes with Poly(A)-Binding Protein, and in polysomal fractions of sucrose gradients, suggesting it is associated with translating mRNAs. Preferably, "LIN28 protein" or simply "LIN28" relates to human LIN28.

Krueppel-like factor (KLF4) is a zinc-finger transcription factor, which is strongly expressed in postmitotic epithelial cells of different tissues, e.g. the colon, the stomach and the skin. KLF4 is essential for the terminal differentiation of these cells and involved in the cell cycle regulation. Preferably, "KLF4 protein" or simply "KLF4" relates to human KLF4.

MYC (cMYC) is a protooncogene, which is overexpressed in a wide range of human cancers. When it is specifically-mutated, or overexpressed, it increases cell proliferation and functions as an oncogene. MYC gene encodes for a transcription factor that regulates expression of 15% of all genes through binding on Enhancer Box sequences (E-boxes) and recruiting histone acetyltransferases (HATs). MYC belongs to MYC family of transcription factors, which also includes N-MYC and L-MYC genes. MYC-family transcription factors contain the bHLH/LZ (basic Helix-Loop-Helix Leucine Zipper) domain. Preferably, "cMYC protein" or simply "cMYC" relates to human cMYC.

A reference herein to specific factors such as OCT4, SOX2, NANOG, LIN28, KLF4 or c-MYC is to be understood so as to also include all variants of these factors. In particular, it is to be understood so as to also include all splice variants, posttranslationally modified variants, conformations, isoforms and species homologs of these factors which are naturally expressed by cells.

The term "miRNA" (microRNA) relates to 21-23-nucleotide-long noncoding RNAs found in eukaryotic cells that, by inducing degradation and/or preventing translation of target mRNAs, modulate a plethora of cell functions, including those related to ESC self-renewal/differentiation and cell cycle progression. miRNAs are post-transcriptional regulators that bind to complementary sequences on target messenger RNA transcripts (mRNAs), usually resulting in translational repression or target degradation and gene silencing. It has been found that miRNAs in the right combination are capable of inducing direct cellular reprogramming of somatic cells to cells having stem cell characteristics in vitro. For example, it has been observed that miRNA cluster 302-367 enhances somatic cell reprogramming.

Preferably, the step of allowing the development of cells having stem cell characteristics comprises culturing the somatic cells under embryonic stem cell culture conditions, preferably conditions suitable for maintaining pluripotent stem cells in an undifferentiated state.

Preferably, to allow the development of cells having stem cell characteristics, cells are cultivated in the presence of one or more DNA methyltransferase inhibitors and/or one or more histone deacetylase inhibitors. Preferred compounds are selected from the group consisting of 5'-azacytidine (5'-azaC), suberoylanilide hydroxamic acid (SAHA), dexamethasone, trichostatin A (TSA), sodium butyrate (NaBu), Scriptaid and valproic acid (VPA). Preferably, cells are cultivated in the presence of valproic acid (VPA), preferably in a concentration of between 0.5 and 10 mM, more preferably between 1 and 5 mM, most preferably in a concentration of about 2 mM.

The methods of the present invention can be used to effect de-differentiation of any type of somatic cell. Cells that may be used include cells that can be de-differentiated or reprogrammed by the methods of the present invention, in particular cells that are fully or partially differentiated, more preferably terminally differentiated. Preferably, the somatic cell is a diploid cell derived from pre-embryonic, embryonic, fetal, and post-natal multi-cellular organisms. Examples of cells that may be used include but are not limited to fibroblasts, such as fetal and neonatal fibroblasts or adult fibroblasts, keratinocytes, in particular primary keratinocytes, more preferably keratinocytes derived from hair, adipose cells, epithelial cells, epidermal cells, chondrocytes, cumulus cells, neural cells, glial cells, astrocytes, cardiac cells, esophageal cells, muscle cells, melanocytes, hematopoietic cells, osteocytes, macrophages, monocytes, and mononuclear cells.

The cells with which the methods of the invention can be used can be of any animal species; e.g., mammals and rodents. Examples of mammalian cells that can be de-differentiated and re-differentiated by the present invention include but are not limited to human and non-human primate cells. Primate cells with which the invention may be performed include but are not limited to cells of humans, chimpanzees, baboons, cynomolgus monkeys, and any other New or Old World monkeys. Rodent cells with which the invention may be performed include but are not limited to mouse, rat, guinea pig, hamster and gerbil cells.

De-differentiated cells prepared according to the present invention are expected to display many of the same requirements as pluripotent stem cells and can be expanded and maintained under conditions used for embryonic stem cells, e.g. ES cell medium or any medium that supports growth of the embryonic cells. Embryonic stem cells retain their pluripotency in vitro when maintained on inactivated fetal fibroblasts such as irradiated mouse embryonic fibroblasts or human fibroblasts (e.g., human foreskin fibroblasts, human skin fibroblasts, human endometrial fibroblasts, human oviductal fibroblasts) in culture. In one embodiment, the human feeder cells may be autologous feeder cells derived from the same culture of reprogrammed cells by direct differentiation.

Furthermore, human embryonic stem cells can successfully be propagated on Matrigel in a medium conditioned by mouse fetal fibroblasts. Human stem cells can be grown in culture for extended period of time and remain undifferentiated under specific culture conditions.

In certain embodiments, the cell culture conditions may include contacting the cells with factors that can inhibit differentiation or otherwise potentiate de-differentiation of cells, e.g., prevent the differentiation of cells into non-ES cells, trophectoderm or other cell types.

De-differentiated cells prepared according to the present invention can be evaluated by methods including monitoring changes in the cells' phenotype and characterizing their gene and protein expression. Gene expression can be determined by RT-PCR, and translation products can be determined by immunocytochemistry and Western blotting. In particular, de-differentiated cells can be characterized to determine the pattern of gene expression and whether the reprogrammed cells display a pattern of gene expression similar to the expression pattern expected of undifferentiated, pluripotent control cells such as embryonic stem cells using techniques well known in the art including transcriptomics.

The expression of the following genes of de-differentiated cells can be assessed in this respect: OCT4, NANOG, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, telomerase reverse transcriptase (TERT), embryonic antigen-3 (SSEA-3), SSEA-4, tumor-related antigen-1-60 (TRA-1-60), TRA-1-81, and TRA-2-49/6E.

The undifferentiated or embryonic stem cells to which the reprogrammed cells may be compared may be from the same species as the differentiated somatic cells. Alternatively, the undifferentiated or embryonic stem cells to which the reprogrammed cells may be compared may be from a different species as the differentiated somatic cells.

In some embodiments, a similarity in gene expression pattern exists between a reprogrammed cell and an undifferentiated cell, e.g., embryonic stem cell, if certain genes specifically expressed in an undifferentiated cell are also expressed in the reprogrammed cell. For example, certain genes, e.g., telomerase, that are typically undetectable in differentiated somatic cells may be used to monitor the extent of reprogramming. Likewise, for certain genes, the absence of expression may be used to assess the extent of reprogramming.

Self-renewing capacity, marked by induction of telomerase activity, is another characteristic of stem cells that can be monitored in de-differentiated cells.

Karyotypic analysis may be performed by means of chromosome spreads from mitotic cells, spectral karyotyping, assays of telomere length, total genomic hybridization, or other techniques well known in the art.

Using the present invention, RNA encoding appropriate factors is incorporated into one or more somatic cells, e.g. by electroporation. After incorporation, cells are preferably cultured using conditions that support maintenance of de-differentiated cells (i.e. stem cell culture conditions). The de-differentiated cells can then be expanded and induced to re-differentiate into different type of somatic cells that are needed for cell therapy. De-differentiated cells obtained according to the present invention can be induced to differentiate into one or more desired somatic cell types in vitro or in vivo.

Preferably, the de-differentiated cells obtained according to the present invention may give rise to cells from any of three embryonic germ layers, i.e., endoderm, mesoderm, and ectoderm. For example, the de-differentiated cells may differentiate into skeletal muscle, skeleton, dermis of skin, connective tissue, urogenital system, heart, blood (lymph cells), and spleen (mesoderm); stomach, colon, liver, pancreas, urinary bladder; lining of urethra, epithelial parts of trachea, lungs, pharynx, thyroid, parathyroid, intestine (endoderm); or central nervous system, retina and lens, cranial and sensory, ganglia and nerves, pigment cells, head connective tissue, epidermis, hair, mammary glands (ectoderm). The de-differentiated cells obtained according to the present invention can be re-differentiated in vitro or in vivo using techniques known in the art.

In one embodiment of the present invention, the reprogrammed cells resulting from the methods of this invention are used to produce differentiated progeny. Thus, in one aspect, the present invention provides a method for producing differentiated cells, comprising: (i) obtaining reprogrammed cells using the methods of this invention; and (ii) inducing differentiation of the reprogrammed cells to produce differentiated cells. Step (ii) can be performed in vivo or in vitro. Furthermore, differentiation can be induced through the presence of appropriate differentiation factors which can either be added or are present in situ, e.g. in a body, organ or tissue into which the reprogrammed cells have been introduced. The differentiated cells can be used to derive cells, tissues and/or organs which are advantageously used in the area of cell, tissue, and/or organ transplantation. If desired, genetic modifications can be introduced, for example, into somatic cells prior to reprogramming. The differentiated cells of the present invention preferably do not possess the pluripotency of an embryonic stem cell, or an embryonic germ cell, and are, in essence, tissue-specific partially or fully differentiated cells.

One advantage of the methods of the present invention is that the reprogrammed cells obtained by the present invention can be differentiated without prior selection or purification or establishment of a cell line. Accordingly in certain embodiments, a heterogeneous population of cells comprising reprogrammed cells are differentiated into a desired cell type. In one embodiment, a mixture of cells obtained from the methods of the present invention is exposed to one or more differentiation factors and cultured in vitro.

Methods of differentiating reprogrammed cells obtained by the methods disclosed herein may comprise a step of permeabilization of the reprogrammed cell. For example, cells generated by the reprogramming techniques described herein, or alternatively a heterogeneous mixture of cells comprising reprogrammed cells, may be permeabilized before exposure to one or more differentiation factors or cell extract or other preparation comprising differentiation factors.

For example, differentiated cells may be obtained by culturing undifferentiated reprogrammed cells in the presence of at least one differentiation factor and selecting differentiated cells from the culture. Selection of differentiated cells may be based on phenotype, such as the expression of certain cell markers present on differentiated cells, or by functional assays (e.g., the ability to perform one or more functions of a particular differentiated cell type).

In another embodiment, the cells reprogrammed according to the present invention are genetically modified through the addition, deletion, or modification of their DNA sequence(s).

The reprogrammed or de-differentiated cells prepared according to the present invention or cells derived from the reprogrammed or de-differentiated cells are useful in research and in therapy. Reprogrammed pluripotent cells may be differentiated into any of the cells in the body including, without limitation, skin, cartilage, bone skeletal muscle, cardiac muscle, renal, hepatic, blood and blood forming, vascular precursor and vascular endothelial, pancreatic beta, neurons, glia, retinal, neuronal, intestinal, lung, and liver cells.

The reprogrammed cells are useful for regenerative/reparative therapy and may be transplanted into a patient in need thereof. In one embodiment, the cells are autologous with the patient.

The reprogrammed cells provided in accordance with the present invention may be used, for example, in therapeutic strategies in the treatment of cardiac, neurological, endocrinological, vascular, retinal, dermatological, muscular-skeletal disorders, and other diseases.

For example, and not intended as a limitation, the reprogrammed cells of the present invention can be used to replenish cells in animals whose natural cells have been depleted due to age or ablation therapy such as cancer radiotherapy and chemotherapy. In another non-limiting example, the reprogrammed cells of the present invention are useful in organ regeneration and tissue repair. In one embodiment of the present invention, reprogrammed cells can be used to reinvigorate damaged muscle tissue including dystrophic muscles and muscles damaged by ischemic events such as myocardial infarcts. In another embodiment of the present invention, the reprogrammed cells disclosed herein can be used to ameliorate scarring in animals, including humans, following a traumatic injury or surgery. In this embodiment, the reprogrammed cells of the present invention are administered systemically, such as intravenously, and migrate to the site of the freshly traumatized tissue recruited by circulating cytokines secreted by the damaged cells. In another embodiment of the present invention, the reprogrammed cells can be administered locally to a treatment site in need or repair or regeneration.

In one embodiment of the invention, nucleic acids such as RNA are administered to a patient by ex vivo methods, i.e. by removing cells from a patient, genetically modifying said cells and reintroducing the modified cells into the patient. Transfection and transduction methods are known to the skilled worker.

The term "transfection" relates to the introduction of nucleic acids, in particular RNA, into a cell. For purposes of the present invention, the term "transfection" also includes the introduction of a nucleic acid into a cell or the uptake of a nucleic acid by such cell, wherein the cell may be present in a subject, e.g., a patient. Thus, according to the present invention, a cell for transfection of a nucleic acid described herein can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. RNA can be transfected into cells to transiently express its coded protein. According to the present invention, any technique useful for introducing, i.e. transferring or transfecting, nucleic acids into cells may be used. Preferably, RNA is transfected into cells by standard techniques. Such techniques include electroporation, lipofection and microinjection. In one particularly preferred embodiment of the present invention, RNA is introduced into cells by electroporation. Electroporation or electropermeabilization relates to a significant increase in the electrical conductivity and permeability of the cell plasma membrane caused by an externally applied electrical field. It is usually used in molecular biology as a way of introducing some substance into a cell. According to the invention it is preferred that introduction of nucleic acid encoding a protein or peptide into cells results in expression of said protein or peptide.

According to the invention, nucleic acids may be directed to particular cells. In such embodiments, a carrier used for administering a nucleic acid to a cell (e.g. a retrovirus or a liposome) may have a bound targeting molecule. For example, a molecule such as an antibody specific to a surface membrane protein on the target cell, or a ligand for a receptor on the target cell may be incorporated into or bound to the nucleic acid carrier. If administration of a nucleic acid by liposomes is desired, proteins binding to a surface membrane protein associated with endocytosis may be incorporated into the liposome formulation in order to enable targeting and/or absorption. Such proteins include capsid proteins or fragments thereof which are specific to a particular cell type, antibodies to proteins that are internalized, proteins targeting an intracellular site, and the like.

"Reporter" relates to a molecule, typically a peptide or protein, which is encoded by a reporter gene and measured in a reporter assay. Conventional systems usually employ an enzymatic reporter and measure the activity of said reporter.

The term "multiple cloning site" refers to a nucleic acid region containing restriction enzyme sites, any one of which may be used for cleavage of, for example, a vector and insertion of a nucleic acid.

According to the invention, two elements such as nucleotides or amino acids are consecutive, if they are directly adjacent to one another, without any interruption. For example, a sequence of x consecutive nucleotides N refers to the sequence $(N)_x$.

"Restriction endonuclease" or "restriction enzyme" refers to a class of enzymes that cleave phosphodiester bonds in both strands of a DNA molecule within specific base sequences. They recognize specific binding sites, referred to as recognition sequences, on a double-stranded DNA molecule. The sites at which said phosphodiester bonds in the DNA are cleaved by said enzymes are referred to as cleavage sites. In the case of type IIS enzymes, the cleavage site is located at a defined distance from the DNA binding site. According to the invention, the term "restriction endonuclease" comprises, for example, the enzymes SapI, EciI, BpiI, AarI, AloI, BaeI, BbvCI, PpiI and PsrI, BsrD1, BtsI, EarI, BmrI, BsaI, BsmBI, FauI, BbsI, BciVI, BfuAI, BspMI, BseRI, EciI, BtgZI, BpuEI, BsgI, MmeI, CspCI, BaeI, BsaMI, Mva1269I, PctI, Bse3DI, BseMI, Bst6I, Eam1104I, Ksp632I, BfiI, Bso31I, BspTNI, Eco31I, Esp3I, BfuI, Acc36I, AarI, Eco57I, Eco57MI, GsuI, AloI, Hin4I, PpiI, and PsrI.

The term "stability" of RNA relates to the "half-life" of RNA. "Half-life" relates to the period of time which is needed to eliminate half of the activity, amount, or number of molecules. In the context of the present invention, the half-life of a RNA is indicative for the stability of said RNA.

The nucleic acids such as RNA described herein, in particular when used for the treatments described herein, may be present in the form of a pharmaceutical composition or kit comprising the nucleic acid and optionally one or more pharmaceutically acceptable carriers, diluents and/or excipients.

Pharmaceutical compositions are preferably sterile and contain an effective amount of the nucleic acid.

Pharmaceutical compositions are usually provided in a uniform dosage form and may be prepared in a manner known in the art. The pharmaceutical composition may, e.g., be in the form of a solution or suspension.

The pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interfere with the action of the active component(s) of the pharmaceutical composition.

Salts which are not pharmaceutically acceptable may be used for preparing pharmaceutically acceptable salts and are included in the invention. Pharmaceutically acceptable salts of this kind comprise, in a non-limiting way, those prepared from the following acids:

hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in the pharmaceutical composition include acetic acid in a salt, citric acid in a salt, boric acid in a salt and phosphoric acid in a salt.

Suitable preservatives for use in the pharmaceutical composition include benzalkonium chloride, chlorobutanol, paraben and thimerosal.

The term "carrier" refers to an organic or inorganic component, of a natural or non-natural (synthetic) nature, with which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are, e.g., sterile water, glucose solutions, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxy-propylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavoring agents, or colorants.

The pharmaceutical compositions described herein may be administered via any conventional route, such as by parenteral administration including by injection or infusion. Administration is preferably parenterally, e.g. intravenously, intraarterially, subcutaneously, in the lymph node, intradermally or intramuscularly.

Compositions suitable for parenteral administration usually comprise a sterile aqueous or non-aqueous preparation of the active compound, which is preferably isotonic to the blood of the recipient. Examples of compatible carriers and solvents are Ringer's solution and isotonic sodium chloride solution. In addition, usually sterile, fixed oils are used as solution or suspension medium.

The agents and compositions described herein are preferably administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on several of these parameters. In the case that a reaction in a patient is insufficient with an initial dose, higher doses (or effectively higher doses achieved by a different, more localized route of administration) may be used.

The present invention is described in detail by the following figures and examples which should be construed by way of illustration only and not by way of limitation. On the basis of the description and the examples, further embodiments are accessible to the skilled worker and are likewise within the scope of the invention.

FIGURES

FIG. 1: Overview of the in vivo selection process

To prepare the starting library, human immature dendritic cells were grown in the presence of Actinomycin D, an inhibitor of transcription, for five hours to preselect stable RNAs. The remaining cellular mRNA was extracted and purified using the Poly(A)Purist Kit (Ambion) and next fragmented with Nuclease P1 (Roche). For this, 10 µg RNA were incubated for 45 min with 0.3 U NP-1 in 8 µL 50 mM NaAc buffer (pH 5.5) in a total reaction volume of 24 µL. After purification with RNeasy columns (Qiagen) the fragments were ready to be reverse transcribed into cDNA. First and second strand synthesis were done using and following the protocol of the RevertAid Premium 1st strand cDNA synthesis Kit (Fermentas) and a hexamer-primer with a defined primer sequence and a NotI-restriction site. To fill-in 5'-overhangs and remove 3'-overhangs the cDNA was next incubated with 12.5 U T4 DNA polymerase for 5 min at 15° C. Reaction was terminated adding 5 µL 0.5 mM EDTA, pH 8.0 and cDNA was purified using NucleoBond columns (Macherey-Nagel). Digest of cDNA-library with NotI (NEB) produced fragments with a blunt and sticky end. Fragments were additionally size selected via gel preparation to ensure removal of all fragments smaller 150 bps. For the cloning of the library the vector as shown in panel A was digested with EcoRV and NotI leaving a blunt and sticky end respectively. In the next step the library was ligated into the vector using the T4 DNA ligase (Fermentas). The ligation mixture was directly used as template for PCR as given in Tab. 4 using the Phusion™ Hot Start High-Fidelity DNA Polymerase (Finnzymes). After purification, PCR-product was used as template for T7-transcription as shown in Tab. 5. Incubation was done at 37° C. After every 30 min 0.75 µL 100 mM GTP were added to the reaction. Reaction was stopped after 2.5 h by adding TURBO DNase (2 U/µL, Ambion) and incubating for another 15 min at 37° C. Reaction was finally cleaned up via RNeasy columns (Qiagen). The RNA-library could then be used for the selection procedure starting with electroporation of the RNA into hiDCs as described previously (Kuhn et al, 2010). After the cultivation for selection, extraction and purification of the RNA was done using RNeasy columns (Qiagen) and following manufacturer's instructions. RNA was next used as template for cDNA synthesis using the Superscript II Reverse transcriptase (Invitrogen) and following manufacturer's instructions and a dT18-primer (SEQ ID NO: 230). cDNA was next used as template for PCR as described above. Finally, the PCR products could be used as template for T7-transcription (see above) to start the next selection round (panel B). Quality controls of DNA/cDNA and RNA samples were done via agarose gel and AGILENT 2100 bioanalyzer respectively. FIG. 1 discloses "poly(T)60" as SEQ ID NO: 224 and "poly(A)60" as SEQ ID NO: 223.

FIG. 2: Schematic of sample appearance within the luc2CPmut-vector (A) A single element or two (upstream and downstream) elements were cloned as 3'-UTRs into the vector as given. Shown are also control samples NEG (negative control without insertion of a 3' UTR), hBg and 2hBg. Preparation of RNA for selection rounds. (B) For electroporation in hiDCs vector was used as template for PCR using elongated primers comprising the T7-promotor and the poly(A)-tail. PCR-product was next used as template for T7-in vitro synthesis to produce the respective IVT-RNA. FIG. 2 discloses "poly(A)60" as SEQ ID NO: 223.

FIG. 3: Effect of the selected sequences on the stability of RNAs encoding luc2CPmut Results showing luciferase activity, half-life and total protein over time of RNAs containing the selected sequences as 3' UTRs compared to our gold-standard 2hBg upon electroporation into human immature dendritic cells (NEG is as defined in FIG. 2). The upper panel gives the time courses of three exemplary RNAs with 3' UTRs as indicated. In the lower left panel, the half-life of the RNAs with the respective 3' UTR as indicated relative to an RNA with 2hBg is shown. Similarly, the relative total protein expression compared to an RNA with 2hBG is given in the lower right panel.

FIG. 4: Representative luciferase activity using luc2mut as reporter gene and newly selected 3'-UTRs After electroporation of RNAs with 3' UTRs as indicated into human immature dendritic cells, luciferase activity was measured over 72 h.

FIG. 5: Representative results of electroporation with IVT-RNAs into fibroblasts left panel: luc2CPmut based vector. right panel: luc2mut based vector FIG. 6: Representative results of electroporation with IVT-RNAs into T cells The leftmost panel gives the relative total protein expression of an RNA with the FI 3' UTR compared to an RNA with 2hBG in CD4+ and CD8+ T cells. Similarly, the relative translation efficiency and mRNA half-life of an RNA with the FI 3' UTR compared to an RNA with 2hBG in CD4+ and CD8+ T cells is given in the middle and rightmost panel, respectively.

FIG. 7: RNA architecture and integrity for testing RNAs with modified nucleotides A: The RNAs used in the Luciferase assays were constructed as depicted here. As 5' cap β-S-ARCA(D2) was used. As 5'UTR the human alpha globin 5'UTR was used, including a Kozak sequence. After the Firefly Luciferase gene, the two 3'UTRs to be compared were cloned. As polyA-tail, an A30L70 sequence was used.

B: Before transfection, the RNAs were checked for their integrity on a 2100 Bioanalyzer (Agilent). All RNAs had a sufficiently high and also comparable integrity and could therefore be used in the experiments.

FIG. 8: Effect of the FI 3' UTR an RNA stability and functionality in vivo

Luciferase and gp70 mRNA containing the FI 3'UTR or the 2hBg 3'UTR were formulated with F12 and administered i.v. into BALB/c mice. After Luciferase mRNA administration, expression was monitored after 6 h and 24 h; gp70 mRNA was administered at day 0 and day 6 and immune activation was analyzed at day 10 via CD8 and gp70 tet+ staining.

A) Shows the Luciferase Expression levels at 6 h and 24 h post injection of unmodified and m1Y modified mRNA containing the FI 3'UTR or the 2hBg 3'UTR. Both unmodified and m1Y modified Luciferase mRNA containing the FI 3'UTR show comparable expression levels as the corresponding mRNA containing the 2hBg 3'UTR.

B) Shows the percentage of gp70-specific CD8 T cells in response to gp70 mRNA containing the FI 3'UTR or the 2hBg 3'UTR. The two 3'UTRs perform equally well in inducing antigen-specific immunity after two immunizations, with a significant increase of antigen-specific CD8 T cells in the spleen of those mice that had received gp70 mRNA containing the FI 3'UTR.

Statistics: One-way ANOVA and Tukey's post test, *p<0.05.

FIG. 9: Effect of stabilizing UTRs on stability of self-replicating RNA

Destabilized Luciferase (Luc2CP) was cloned immediately upstream of the 3'conserved sequence element of a non-cytotoxic Semliki Forest virus derived self-replicating (replicon) RNA. Replicon RNA was prepared by in vitro transcription from a corresponding linearized plasmid and electroporated into cells. Luciferase expression was measured by adding luminescent substrate for 96 h to 120 h. (A) Time course of luciferase expression in a representative experiment with BHK21 cells. (B) Time course of luciferase expression in a representative experiment with human foreskin fibroblasts (HFF). To reduce cytotoxicity of released type I interferons, Vaccinia virus Bl8R mRNA was cotransfected in each sample. To inhibit protein kinase R activation and increase the overall level of translation, Vaccinia virus E3 mRNA was cotransfected in each sample.

FIG. 10: homology stretches in the FI Element (SEQ ID NO: 174).

The underlined sequence stretches were predicted to base-pair with each other. For the "8 nt mutation" construct, the first element was mutated to aaagggcu to disrupt interactions with the second element.

FIG. 11: Artefacts in PCR-template based IVT using 2hBgUTR.

A: Schematic representation of IVT template generation via PCR. The 5' primer anneals upstream of the T7 Promoter, the 3' primer contains a 120 nt polyA tail (SEQ ID NO: 222) and anneals to the plasmid-encoded polyA and part of the 3'UTR. In case of the 2hBgUTR, mispriming by annealing to the first repeat can occur. FIG. 11A also discloses "A50" as SEQ ID NO: 225. B: PCR products from a plasmid containing the 2hBgUTR. The red arrow depicts the side product, representing a 1hBg truncation. C: The RNA transcribed from such a PCR product thus also presents a shortened by-product (arrow). D: PCR products from a plasmid containing the FI element as 3'UTR. No side product is visible. E: The resulting mRNA is of the expected high integrity without any additional side-peaks.

FIG. 12: Schematic representation of the truncated UTR elements and half-life of corresponding mRNA constructs.

The upper panel of figure A shows a schematic representation of the truncated UTR elements in reference to the nucleic acid positions of the full length sequence of the F-element SEQ ID NO: 86 covered by those truncated variants.

The lower panel of figure A shows the relative half-life of mRNA comprising the truncated UTR in reference to mRNA comprising the full length sequence of the F-element SEQ ID NO: 86. The mRNAs encoding a Luciferase reporter were electroporated into hiDCs and their expression was followed over time by Luciferase measurements to determine relative RNA half-life.

The upper panel of figure B shows a schematic representation of the truncated UTR elements in reference to the nucleic acid positions of the full length sequence of the I-element SEQ ID NO: 115 covered by those truncated variants.

The lower panel of figure B shows the relative half-life of mRNA comprising the truncated UTR in reference to mRNA comprising the full length sequence of the I-element SEQ ID NO: 115. The mRNAs encoding a Luciferase reporter were electroporated into hiDCs and their expression was followed over time by Luciferase measurements to determine relative RNA half-life.

FIG. 13: Relative half-life and protein expression from mRNA constructs comprising of F, I or FI elements towards random UTRs.

FIG. 13 shows the relative half-life and protein expression from mRNA constructs comprising of F, I or FI elements towards random UTRs. For this full length individual F and I elements as well as the FI combination were compared towards a random 3' UTR (257 nt in length). All elements were cloned into luciferase-encoding constructs, in vitro transcribed to mRNA, electroporated into hiDCs, luciferase expression measured over time, and the relative half-lifes and total protein expression calculated.

FIG. 14: UTR elements for cellular reprogramming.

FIG. 14A shows the timeline for the reprogramming of primary human foreskin fibroblasts. 40,000 cells were plated into a 12-well-plate and lipofected for three (3×) or four (4×) consecutive days with mRNA mixtures that were composed of 0.33 µg unmodified in vitro transcribed (IVT)-RNA encoding the reprogramming TF OCT4, SOX2, KLF4, cMYC, NANOG and LIN28 (OSKMNL) (1:1:1:1:1:1) with 0.08 µg of each B18R, E3 and K3 (EKB) and 0.17 µg of a miRNA mixture composed of miRNAs 302a-d and 367 (1:1:1:1:1:1). The RNA-constructs thereby only differed in their 3'UTR consisting of a tandem repeat of the human β-globin 3'UTR (2hBg), the F-I-element (FI) or I-F-element (IF). From day 9 on, colony formation was observed and analysis of colonies were performed on d11.

EXAMPLES

Figure 1:
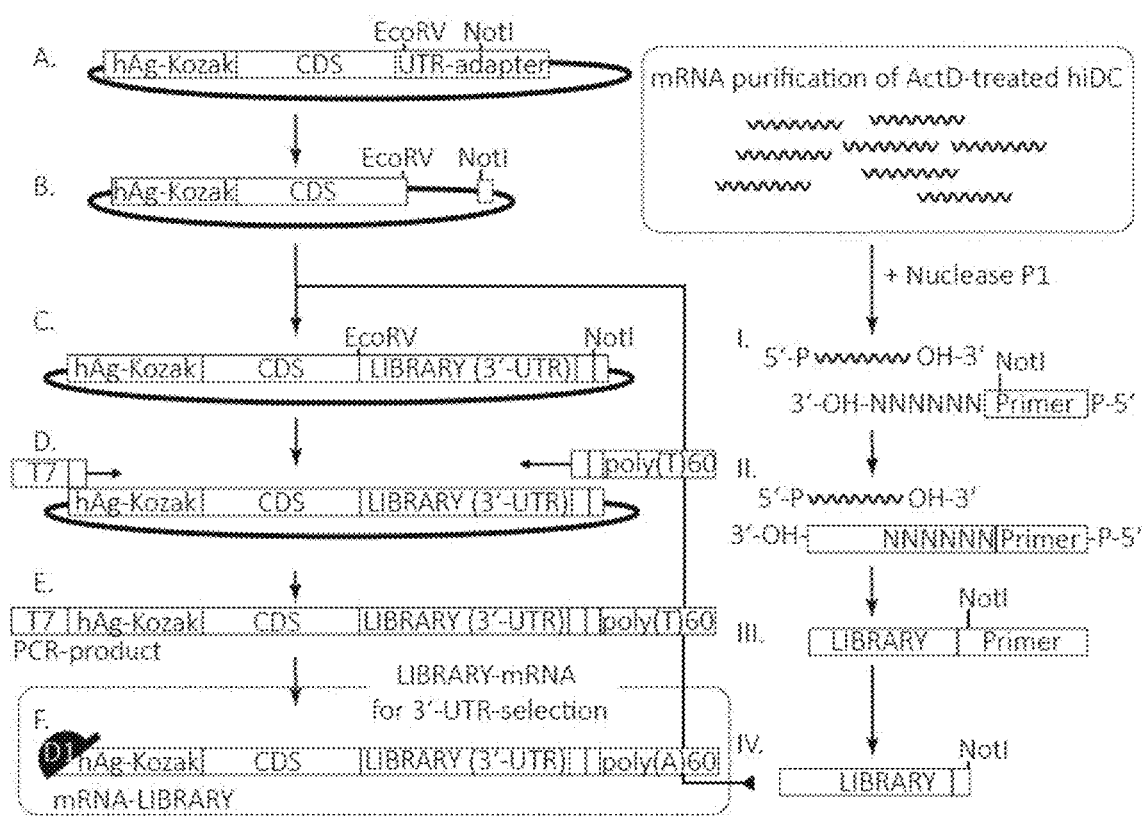
Figure 1:
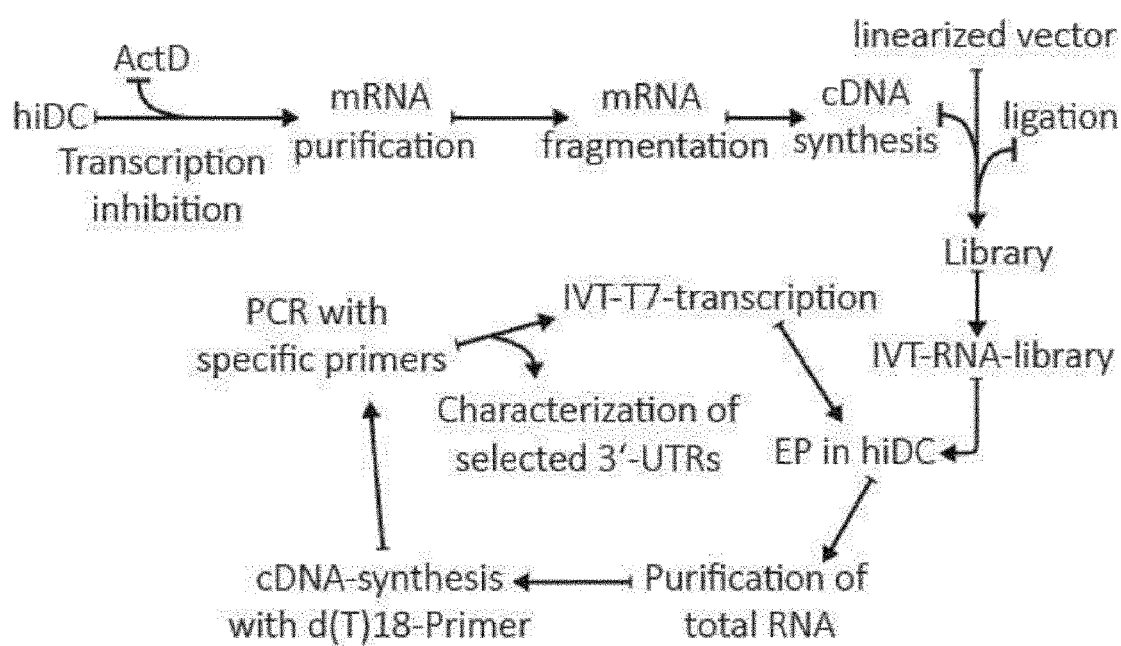

Example 1: Identification of Sequence Elements that stabilize mRNAs

To identify novel sequence elements that stabilize mRNAs, we have developed an in vivo selection process using hiDCs as selective environment for the in vitro transcribed RNA. The starting RNA-library was built using naturally occurring mRNA sequences derived from hiDCs. Prior to RNA isolation, the cells were grown for 5 hours in the presence of the transcription inhibitor Actinomycin D (ActD) to preselect stable RNAs. The remaining mRNA was then extracted and reduced to fragments of 200-800 nucleotides, reverse transcribed, and cloned as 3'-UTR in a vector bearing a hAg 5'UTR sequence and a reporter gene, which was chosen as the basis of the selection process. The DNA template used for subsequent library mRNA transcription was amplified via PCR, during which a T7 promotor was introduced via the 5'- and an A60 polyA-tail (SEQ ID NO: 223) via the 3' primer. The transcribed mRNA was then introduced in the in vivo selection process, which is comprised of several rounds of in vitro transcription of the library, electroporation of the corresponding RNAs into hiDCs, and extraction and amplification of stable sequences after defined time points. Amplification of the selected sequences was performed via PCR with specific primers, after cDNA synthesis. The resulting PCR products were subsequently used as templates for the new mRNA library. This was done for six rounds, with extraction of the remaining RNAs after 24 hours in round 1, 48 hours in rounds 2 and 3, 72 hours in rounds 4 and 5, and finally 96 hours as well as one and two weeks in round 6 (upon electroporation, the cells were split into three parts and then harvested individually at the time points given).

Monitoring of the selection process after rounds 1 through 5 demonstrated a significant increase of the average half-life of the corresponding RNA pool, which is indicative for an enrichment of stabilizing 3'-UTR-elements (Tab. 1). Nevertheless, the increase in stability was less pronounced with higher rounds. Therefore, the selection process was stopped after a final sixth round, in which the RNA was extracted from cells after 96 hours, one week, and two weeks. To characterize the selected sequences, more than 350 individual clones were sequenced, 108 from round 5, 88 from round %6 hours, 110 from round 6/1 week, and 96 from round 6/2 weeks. All sequences were compared to each other as well as BLASTed to identify their genomic origin. Here, it was especially looked at, whether the sequences were derived from endogenous 5'- or 3'-UTRs or from the coding region. Finally, their expression level in hiDCs was downloaded from NextBio (Illumina). In total, seven groups could be identified, (i) for which multiple sequences were found, (ii) which originated from the 3'-UTRs of endogenous RNAs or from an endogenous non-coding RNA, and (iii) which were clearly expressed in hiDCs (Tab. 2). These are derived from the following genes: Fc fragment of IgG, receptor, transporter, alpha (B, FCGRT, NM 001136019), Lymphocyte specific protein 1 (D, LSP1, NM 002339), Chemokine ligand 22 (E, CCL22, NM 002990), Amino-terminal enhancer of split (F, AES, NM_198969), Phospholipase D family member 3 (G, PLD3, NM 001031696), Mitochondrially encoded 12S RNA (I, MT_RNR1, NC_012920), Major histocompatibility complex class II DR beta 4 (J, HLA-DRB4, NM_021983). Note that for simplicity the capital letters B to I given in parentheses are used in the following as abbreviations for these elements. Importantly, in all cases the clones for one sequence differ in their exact 5'- and 3'-ends, demonstrating that these come from different starting clones and are not simply artificially enriched during the process (see appendices for a complete listing of all sequences identified in the screening).

Example 2: Characterization of Individual Sequence Elements Identified

For characterization of the identified sequence elements, a representative candidate of each group was chosen (detailed sequences are marked in the appendix). This sequence was then cloned as 3'-UTR in a vector with a luciferase reporter gene, whose expression level can be analyzed over time upon transfer into cells. It has been previously demonstrated that from the expression pattern observed for the protein the relative stability and translational efficiency of the RNA can be accurately inferred (Kuhn 2010 Gene Ther.). The specific reporter used in this experiment, luc2CPmut, is a destabilized form of luciferase (Promega). This allows detecting even small changes in the stability of the RNA. The in vitro transcribed RNA coming from these vectors was then compared with our gold-standard-mRNA, i.e. containing the 2hBg 3'-UTR, regarding RNA stability and translational efficiency. As control samples an in vitro transcribed RNA without a 3'-UTR (i.e. only containing sequences used for cloning the inserts) and one with only a single Beta-globin element (1hB) were used.

Starting with the UTR containing vectors, the region to be transcribed was amplified by PCR using a 5' primer containing the T7 promoter and a 3' primer with a poly(A)-tail of 60 nucleotides (SEQ ID NO: 223). Cleanup of PCR fragments was done using AGENCOURT AMPURE XP (Beckman Coulter). 0.6 volume of beads were added to each PCR reaction and mixed. After a 15 min incubation at RT PCR, PCR products bound to the beads were separated via magnetic stand from excess primers, nucleotides, salts, and enzymes. Beads were washed twice for 30 s with 80% ethanol to further remove contaminants. The desired PCR products were finally eluted twice with 30 µL ddH2O and used as template for in vitro transcription of the corresponding RNAs. For in vitro transcriptions T7 RNA polymerase (Fermentas), the respective reaction buffer and 6 mM NTPs were used. For efficient capping of the RNA the GTP concentration was lowered to 1.5 mM and 6 mM of β-S-ARCA(D2) were added to the reaction and incubated for 2.5 h at 37° C. RNA was purified via carboxylated magnetic beads (Invitrogen) and RNA concentration and quality were assessed by spectrophotometry and analysis on a 2100 Bionanalyzer (Agilent).

Figure 3:
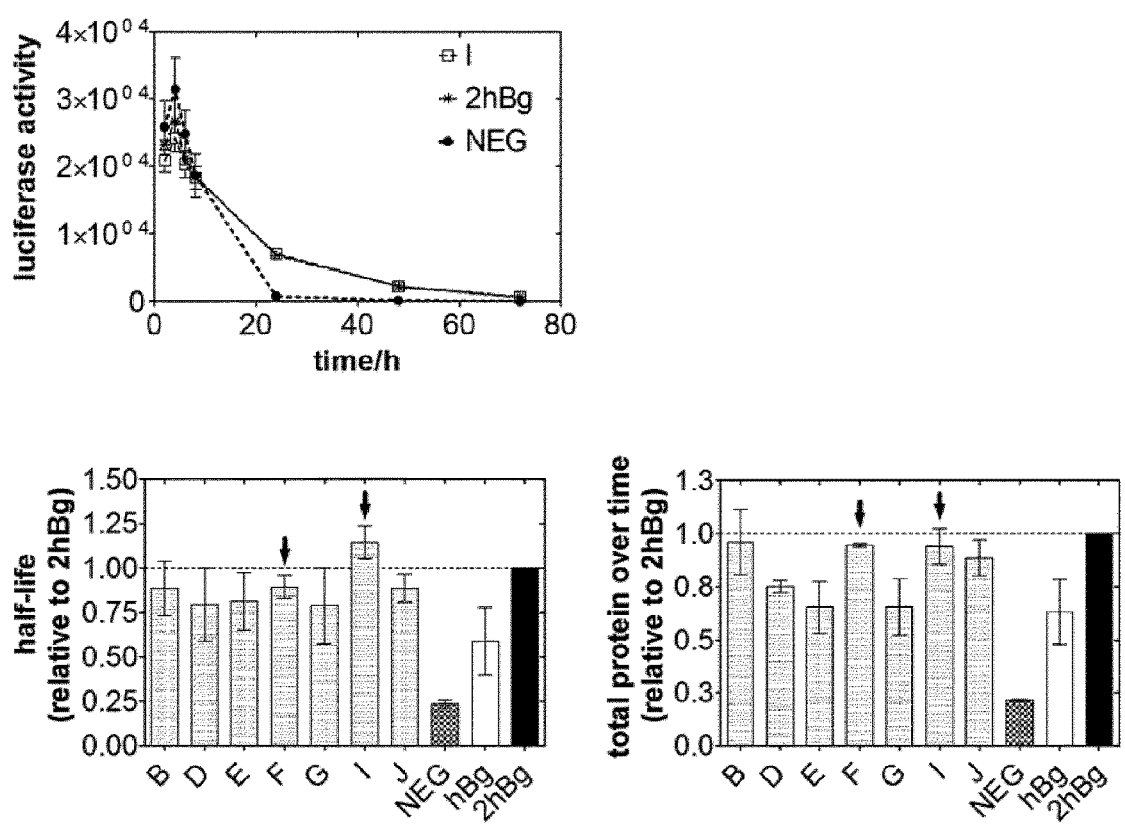

Consistent with their identification in the screening approach, all of the new sequences showed very similar characteristics compared to 2hBg regarding RNA stability with group I (mtRNR1) as the best (FIG. 3; Tab. 3). Importantly, each individual element conferred RNA stabilization compared to the RNA without a 3'-UTR and even compared to the RNA with only a single copy of the Beta-globin element. The translation efficiency was not significantly affected, as observed by the direct correlation between RNA stability and total protein expressed over time.

Example 3: Combination of Individual Sequence Elements

Figure 2:
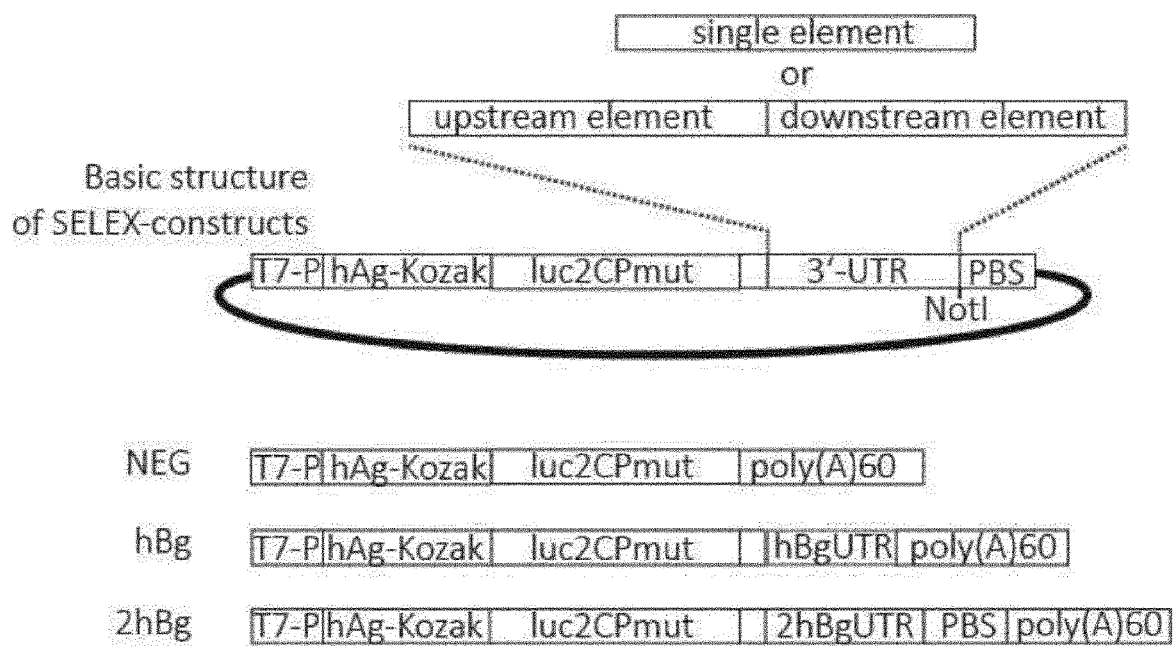
Figure 2:
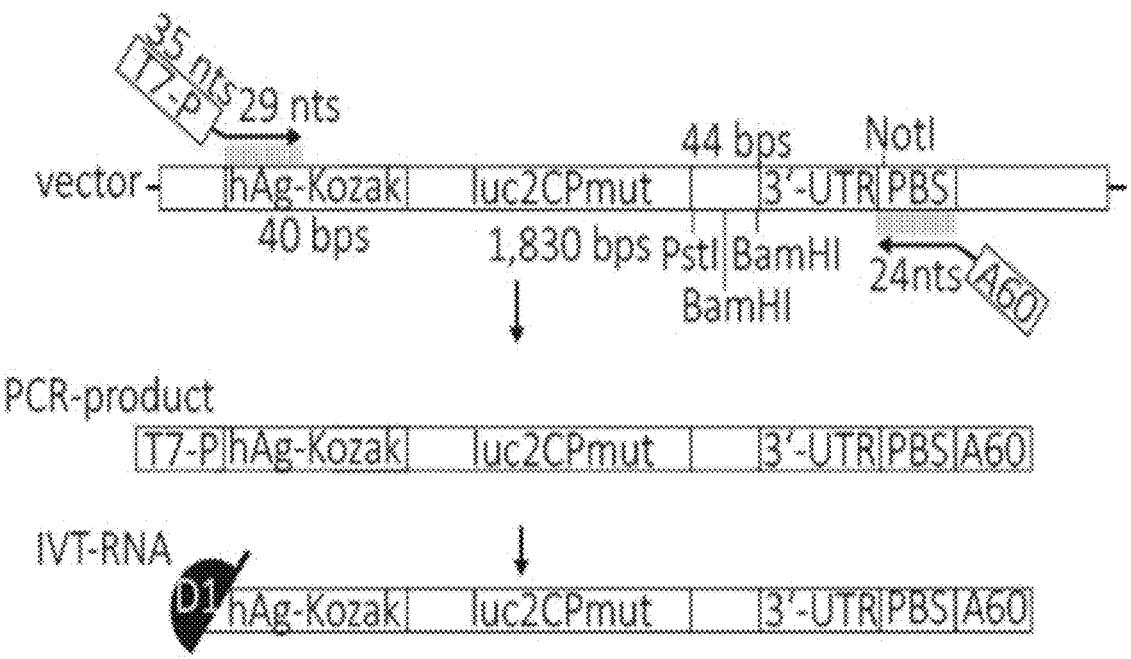

In a further experiment, single sequences of each group were combined with each other in a pair-wise manner (FIG. 2). The rationale behind this was our previous observation that the combination of two 3'-UTRs had an additional effect on the stability and translational efficiency of the RNA (Holtkamp et al. 2006). Stability and translational efficiency of the RNA were calculated in R by interpolating the measured Luciferase values with a spline, from which the steepest rising slope was defined as translational efficiency and the half-life of the signal as stability. The integral of the interpolated spline is interpreted as total protein expression. In total 64 combinations were cloned, i.e. all possible combinations of the seven newly identified sequences and of the human beta-globin 3'-UTR (Tab. 6). As described above, RNA was prepared from these template DNAs, and then electroporated in hiDCs. As controls, RNAs containing the individual elements were also included. For the majority of the seven new elements it was observed that at least one combination with another element gives an RNA with a higher stability than with just the single element (Tab. 7 to Tab. 13). Interestingly, in most cases the combination with the I element (mtRNR1) increased the half-life of the RNA. Here, the stability of the RNA was generally even higher compared to an RNA with the 2hBg 3'-UTR (Tab. 7 to Tab. 13). Almost all combinations had a positive effect on the translational efficiency of the RNA. In total, the combined effects on RNA stability and translational efficiency result in an increase of the total protein expression of up to 1.74-fold. Thus, we could identify single elements (with lengths below 233 nucleotides) as well as combinations of two different elements that give rise to RNAs with increased stability and/or translational efficiency, but at the same time avoiding the problems with having two identical copies of one element as described above for 2hBg.

Figure 4:
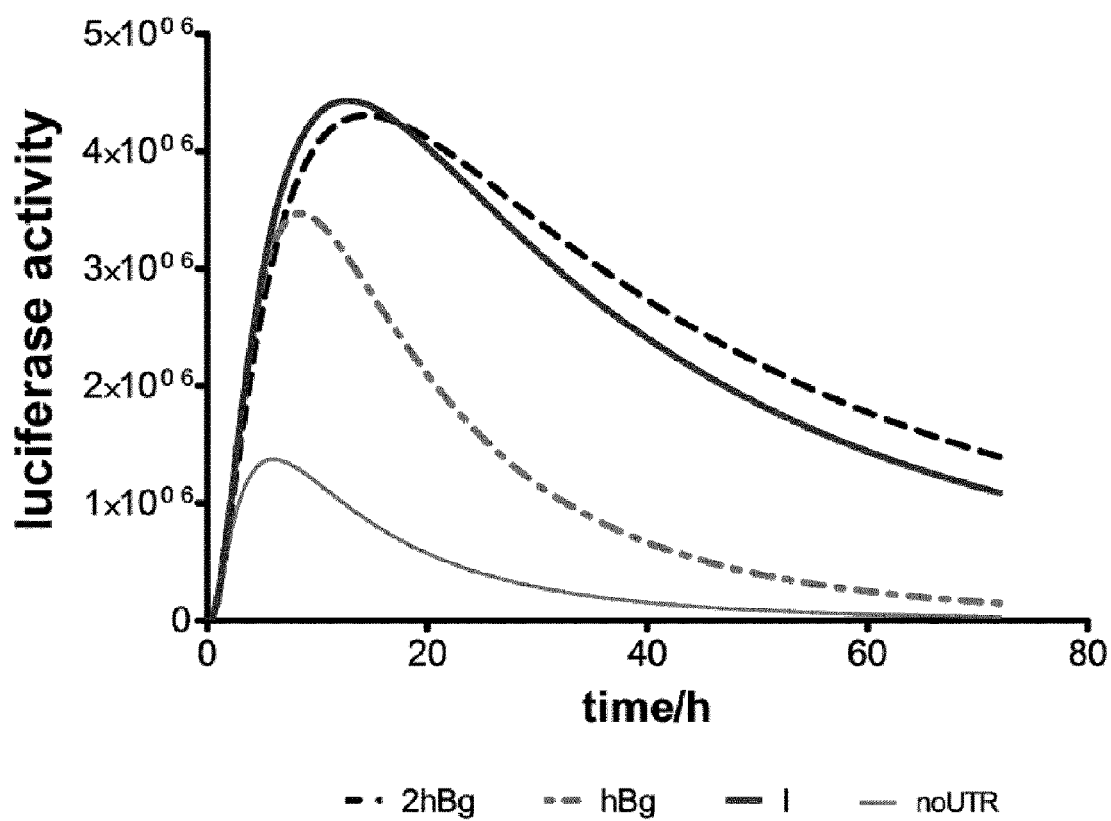

To verify the results obtained with the destabilized form of luciferase, the previous experiments were repeated with RNAs bearing the standard luciferase (Promega), and the following selected 3'-UTRs: mtRNR1 (I), mtRNR1-AES (IF), AES-mtRNR1 (FI), mtRNR1-hBg (IhBg) and hBg-mtRNR1 (IhBg). As shown in FIG. 4 and Tab. 14, equivalent results as observed above could be obtained, verifying that the new elements, individually or in combination, increase mRNA stability and/or translational efficiency similarly as the 2hBg element.

Figure 5:
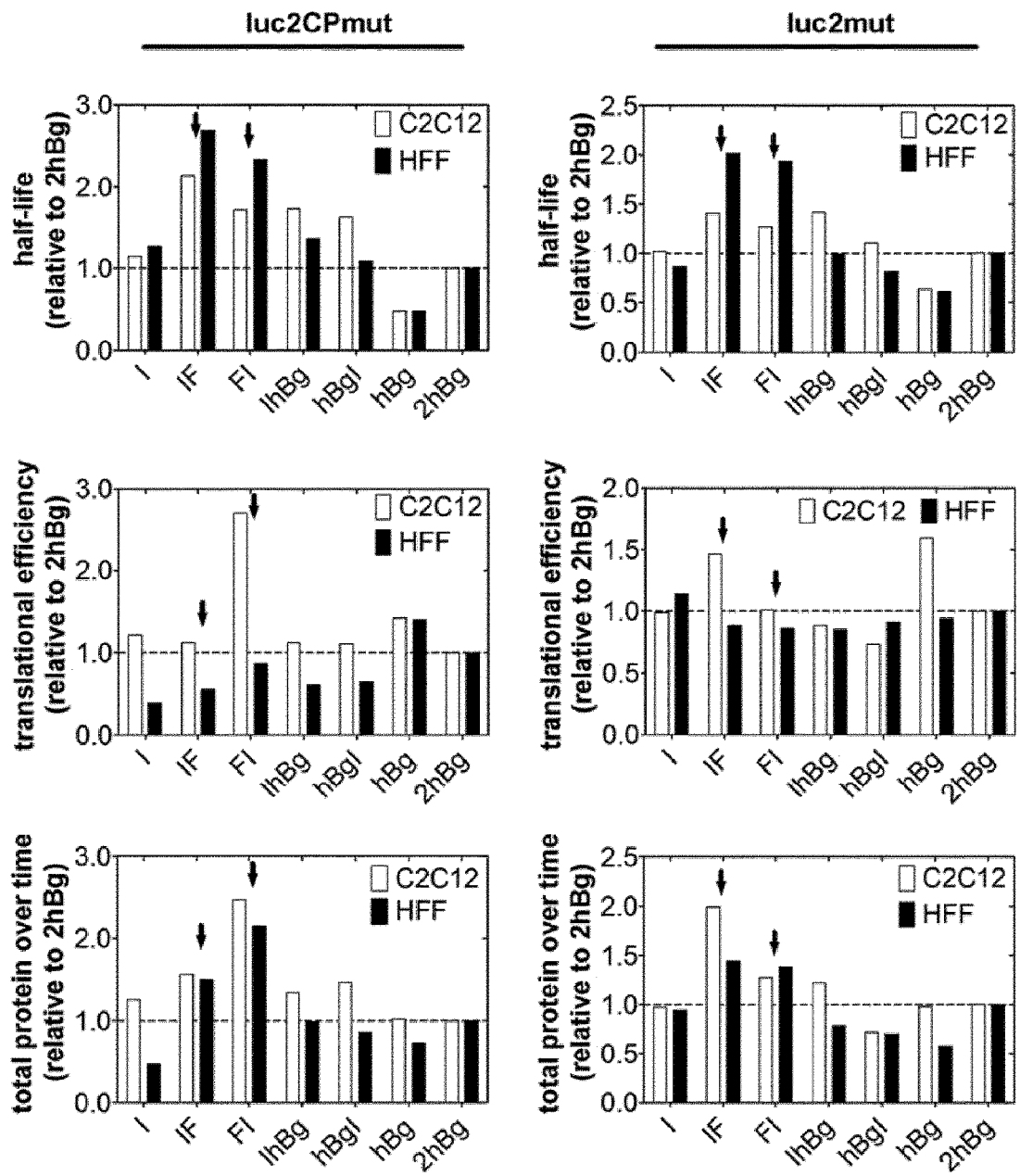
Figure 6:
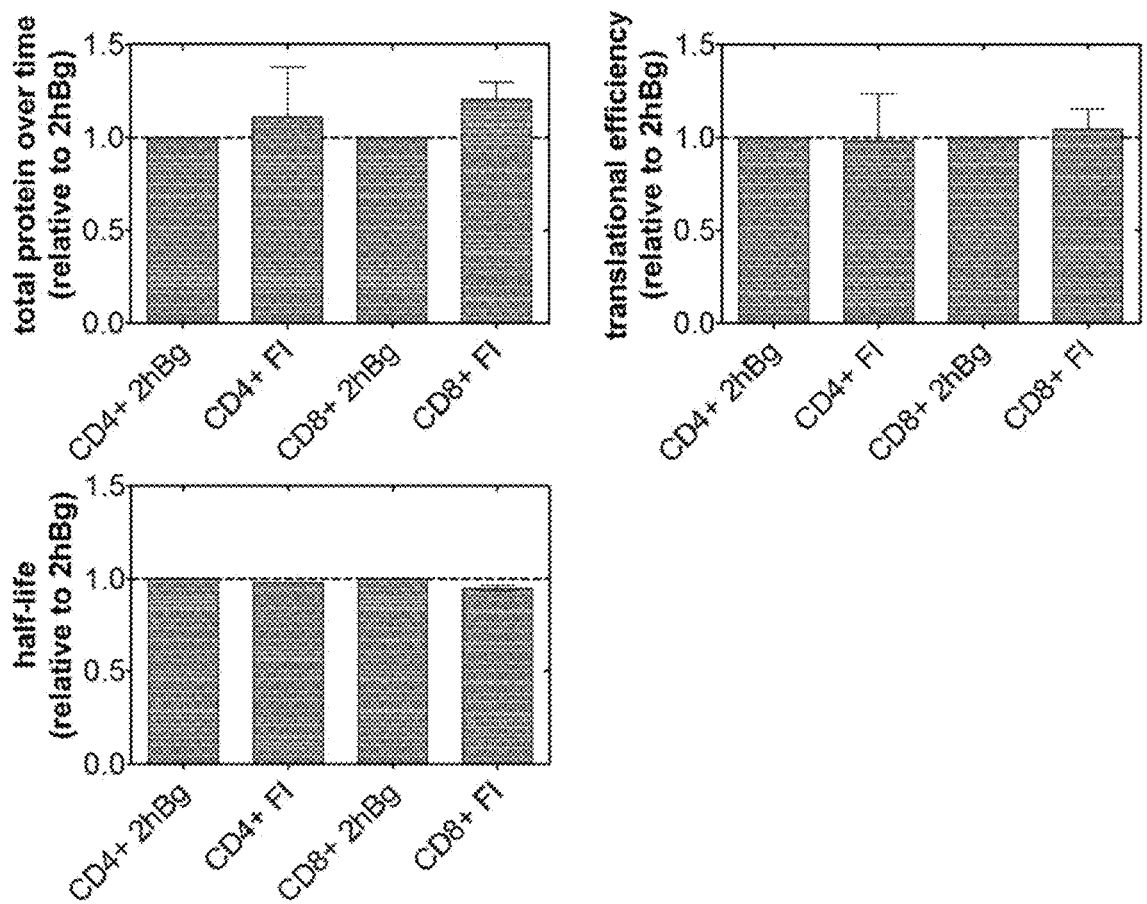

Example 4: Analysis of mRNAs Bearing Selected Sequence Elements in Other Cell Types The newly selected 3'-UTRs mtRNR1 and AES were also tested in different cell types and cell lines to see if there is a hiDC-specificity. The sequences were tested in human fibroblasts (HFF), murine myoblasts (C2C12) (FIG. 5) and T cells (FIG. 6) to assess whether they are also stabilizing in these cells.

HFF and C2C12 cells were harvested and prepared for electroporation. 2.0 µg IVT-RNA were next electroporated together with 1.0 µg GFP encoding RNA containing the indicated 3'UTRs. After electroporation cells were splitted. 5000 cells per well were distributed into a 96-well plate in triplicates for in total 7 time points (2, 4, 8, 24, 48 and 72 h) to measure luciferase activity. 2E+05 cells per well were plated into 6-well plates to harvest for FACS after 24 h (GFP-signal). This allowed monitoring of transfection efficiencies. These differed between 72 and 90% and could be included into calculation of half-life. Results obtained with HFF and C2C12 as well as T cells confirmed results obtained previously with hiDC. The combination of I with F was in particular 2- to 3-fold better in half-life compared to 2hBg. Moreover, FI showed a 3-fold better translational efficiency in C2C12 cells and a 2-fold better protein production over time compared to our gold-standard. These results showed, that I and F are not hiDC-specific, but do also enhance mRNA stability and translational efficiency in other cells.

Example 5: The FI 3'UTR Increases Expression from Modified mRNA

For some applications, including protein replacement therapy, mRNAs with modified nucleotides are preferable to unmodified ones due to their decreased immunogenicity (Kariko et al., 2008). However, base modifications might have an effect on the stability of an mRNA either by directly influencing the interaction with a corresponding RNA binding protein or by altering secondary structure formation of the RNA. Accordingly, the selected 3' UTRs might behave differently in the context of modified mRNAs. Therefore, we compared the combination of F and I with the 2hBgUTR in the context of m1Y modified mRNA in hiDCs, HFFs, CD8+ and CD4+ T-cells and in murine MEFs, C2C12 and bmDCs. As reporter, Luciferase was used (see FIG. 7A for construct design). For generation of modified mRNAs, U was completely replaced by m1Y in the IVT reaction. In all experiments, unmodified RNA was included as a control. The integrities of the obtained mRNAs were not affected by the exchange of UTP for m1YTP (FIG. 7B). Cells were electroporated using the settings described in Tab. 15, and Luciferase levels were measured at 3, 6, 12, 24, 48, 72 and 96 h.

Electroporation of unmodified Luciferase mRNA could reproduce the effects seen before: In all cell types the FI element was equal to or superior to the 2hBg control in conveying RNA stability (Tab.16A). Whereas in murine DCs and human T-cells the mRNA half-lifes were comparable between the two 3'UTR, the FI element increased mRNA half-lifes up to 1.69-fold in HFF cells. The total protein amount was increased in all cell lines, most prominently in HFF cells (2.45 fold).

With modified mRNA, the FI element also led to an increase in mRNA half-life compared to 2hBg in hiDCs, the total protein amount was increased more than two-fold (Tab. 16B). The results in other cell types are also similar to the ones obtained with unmodified mRNA: The FI element was superior to 2hBg in all experiments involving HFF, MEF and C2C12 cells and comparable in T-cells and murine DCs (Tab. 16B). Therefore, U modification does not alter the ability of the FI element to stabilize the mRNA.

Example 6: The FI 3'UTR Increases Expression from mRNA Irrespective of the Transfection Method So far, all experiments were done with electroporation as transfection method. With electroporation, the delivered mRNA arrives directly in the cytoplasm, under circumvention of an endosomal uptake route, which is taken upon transfection via lipofection. To see whether the FI element also functions under these conditions, cells were lipofected with the same FI and 2hBg containing Luciferase mRNAs as used in previous experiments using RNAiMAX as a transfection reagent. Also upon lipofection, the FI element increased Luciferase expression, though the increase was less pronounced compared to experiments where the RNA was delivered via electroporation (Tab. 16C). Therefore, the transfection method does not have an impact on the stabilizing effect of the FI element.

Figure 8:
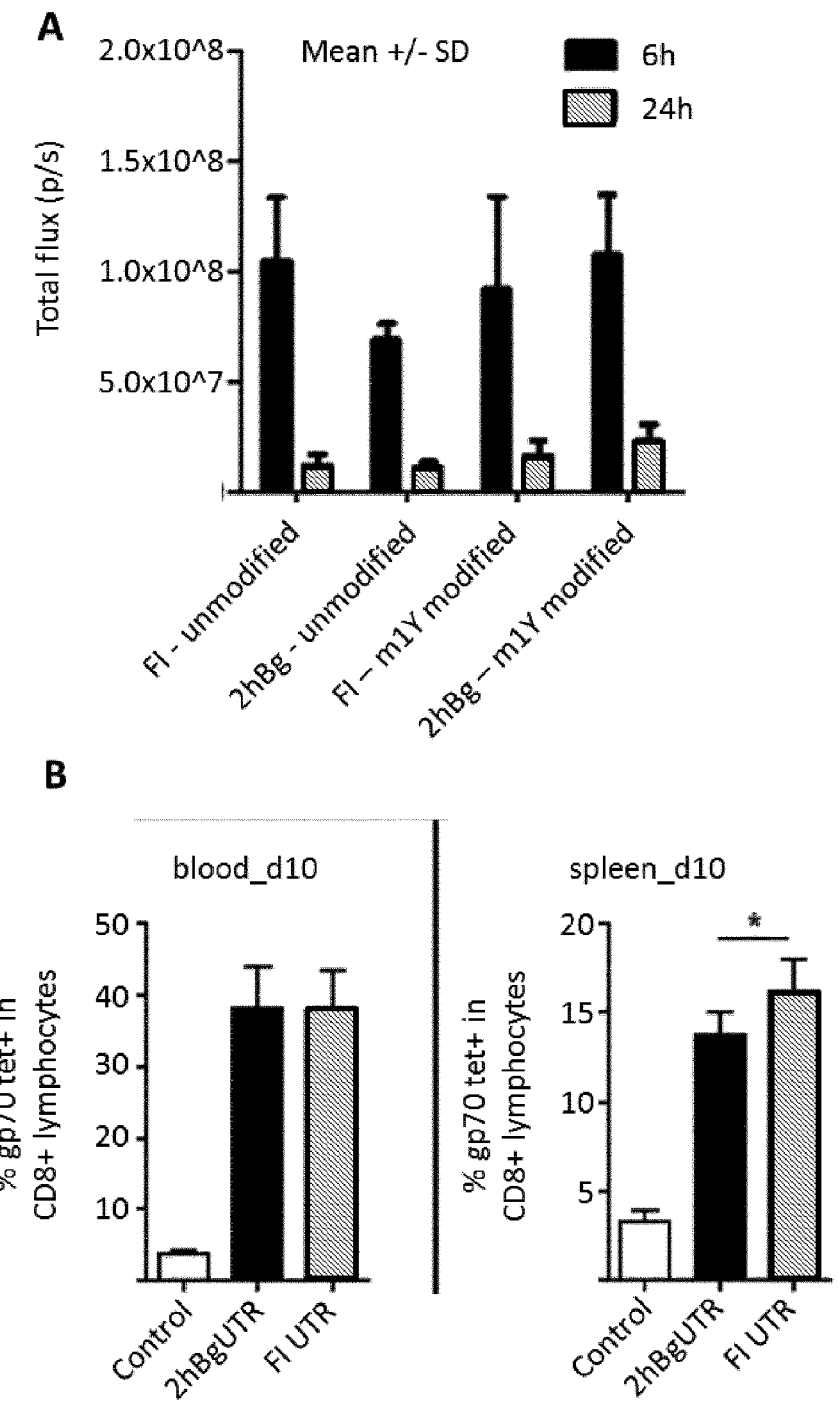

Example 7: FI 3'UTR and the 2hBgUTR Containing mRNA Lead to Comparable Protein Expression and Immune Activation In Vivo To assess protein expression from mRNA containing the FI 3'UTR in vivo, the same FI and 2hBg containing Luciferase mRNAs as used in previous experiments were formulated with F12 and administered i.v. into BALB/c mice. As shown in FIG. 8, luciferase expression was comparable for both 3'UTRs. Antigen specific immune response was also induced to a comparable extent, with the effect of the FI 3'UTR containing mRNA being slightly stronger in the spleen.

Example 8: IF UTR Leads to Increased Stability of Self-Replicating RNA In Vitro

In vitro transcribed self-replicating RNA (replicon RNA) derived from alphaviral genomes are potent vaccine vectors. Replicon RNA encodes on the first two thirds the enzyme complex necessary for cytoplasmic replication (replicase) of the replicon RNA. This replicase recognizes an internal RNA structure that acts as subgenomic promoter for the replicase-dependent synthesis of subgenomic RNAs. Transgenes or antigens for vaccination are encoded on this subgenomic RNA which is significantly shorter than the whole replicon. Overall, both genomic (i.e. the full length replicon RNA) and subgenomic RNA ressembles cellular mRNA. Both are flanked by UTRs, both are capped and poly-adenylated. The enzymes responsible for capping and poly-adenylation are contained in the replicase enzyme complex. Conserved sequence elements (CSE) within the UTRs—overlapping with the ORF of the replicase in case of the 5'CSE—are required for binding of replicase and act as promoters for minus strand synthesis (3'CSE) or plus-strand synthesis (5'CSE).

Figure 9:
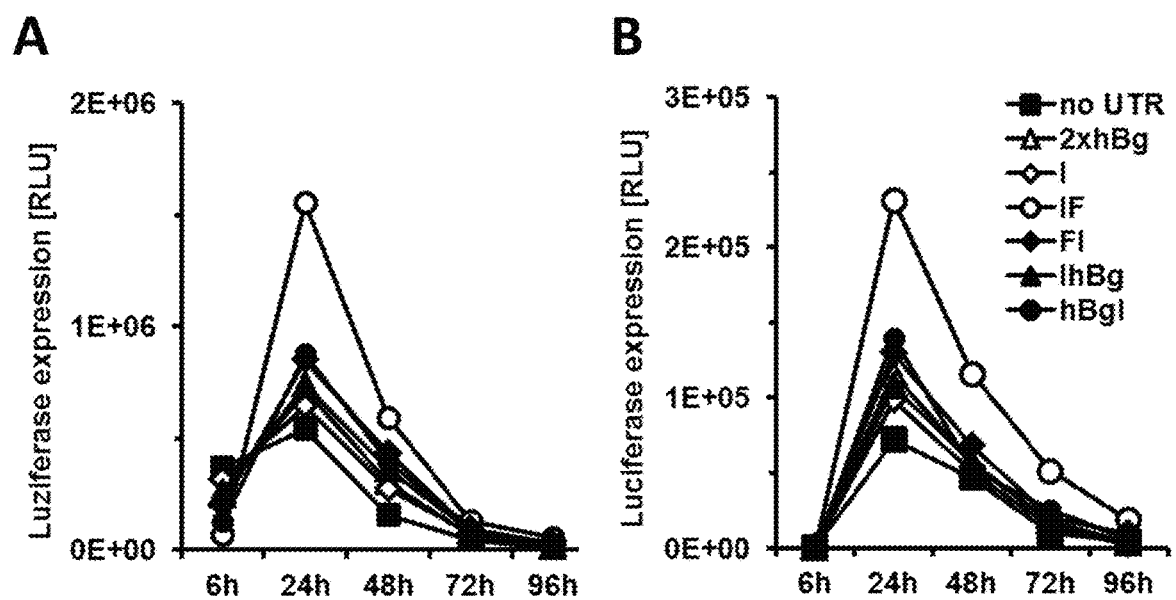

To assess whether the novel stabilizing UTRs identified and validated for non-replicating in vitro transcribed mRNA provide greater stability, and thereby higher transgene expression, of replicon RNA, we cloned the respective sequences into replicon RNA template vectors. As the 3'CSE needs to be located immediately adjacent to the poly-A tail we inserted the novel UTRs immediately upstream of the 3'CSE of a replicon encoding destabilized luciferase (Luc2CP). Replicon RNA was synthesized by in vitro transcription of linearized template plasmids similar to IVT mRNA. The replicon RNA was introduced into cells (BHK2l and HFF) by electroporation, and luciferase expression was assessed. As shown in FIG. 9, all inserted UTRs increased the translation of Luc2CP in both cell lines used. Interestingly the "IF" UTR combination resulted in an outstanding increase of translation.

Example 9: Nucleotide Exchanges Up to 90% Homology have No Impact on the Stabilizing Properties of the FI Element Due to the selection procedure that was applied to identify novel stabilizing UTR elements, sequences in a certain size range were obtained. The identification of the same sequences with prolonged 5' and 3' ends gave a first indication for the minimal length required. However, the minimal region required for each element to exert its stabilizing effect might be even shorter. In addition, slight variations of the sequences might still be functional, i.e. identity of any individual nucleotide might not be of the utmost importance to the stabilizing properties of the FI element. To see to which degree the elements are robust against nucleotide exchanges, 3' UTR sequences with 97.5%, 95.0%, 92.5% and 90.0% homology to the original FI element were tested for total protein expression and mRNA half-life in hiDCs. The nucleotides that were changed were chosen randomly over the whole sequence length (sequences 208-211, random modifications). Luciferase mRNAs with these modified elements as 3'UTR were in vitro transcribed, electroporated in hiDCs and their expression was followed over time by Luciferase measurements after 3, 6, 24, 48, and 72 h. Luciferase mRNAs with the modified FI element yielded the same overall protein amount and had approximately the same half-life (Tab. 17).

In addition to the random substitutions with increasing degrees as described above, another set of modified FI elements were generated by rationally introducing nucleotide substitutions which are likely to disrupt the secondary structure of the FI element. For multiple natural 3' UTR sequences it is known that their secondary structure is of importance because it provides binding sites for regulatory proteins, which influence mRNA stability (Addess et al., 1997; Putland et al., 2002; Crucs et al., 2000; Adams et al., 2003) Two 8 nt sequences which are perfectly complementary to each other are present in the FI element, one in the F and the other in the I element (FIG. 10). Base pairing of these two regions can also be seen in most mfold predictions. mFold (Zuker, 2003) is a computer program allowing secondary structure predictions of input sequences. To check for the importance of this specific secondary structure element, the sequence was changed in a way that abolishes base pairing (sequence 212, 8 nt mutation). Besides this rather long complementary sequences, mfold predictions for the FI 3'UTR were screened for structure elements present in most of the output folds, which should therefore have a high probability of forming in vivo. The nucleotides involved in base-pairing of these folds were changed to 97.5%, 95.0%, 92.5% and 90.0% homology to the original FI sequences by swapping them with their base-pairing partners, thereby retaining the secondary structure of the sequence (sequences 217-220, structure retaining modifications). In addition, the same sequences were exchanged on only one strand of the double-stranded part, thereby deliberately destroying the secondary structure. In these cases, the identity to the original sequence was 98.75%, 97.50%, 96.25%, and 95.00%, respectively (sequences 213-216, structure destabilizing modifications).

Luciferase RNAs with the described modified 3' UTR elements were in vitro transcribed, electroporated in hiDCs and their expression was followed over time by Luciferase measurements after 3, 6, 24, 48 and 72 h.

With neither modification strategy any significant impact on mRNA half-life could be observed. Therefore, the stabilizing properties of the FI element seem to be robust against changes in its nucleotide sequence or secondary structure at least up to 10.0% varied nucleotides. Also, no decline in total protein amount could be observed upon modification of the FI sequence (Tab. 18 A and B).

Example 10: Using the FI Element Instead of 2hBg Avoids Mispriming in PCR-Based Amplification of the RNA-Encoding Region As has been shown, the FI element is equal or superior to the 2hBg 3'UTR with regard to mRNA stability and translation efficiency. Another advantage of the FI Element is its non-repetitive sequence, whereas the two copies of the hBg 3'UTR can cause problems in some instances.

Figure 11:
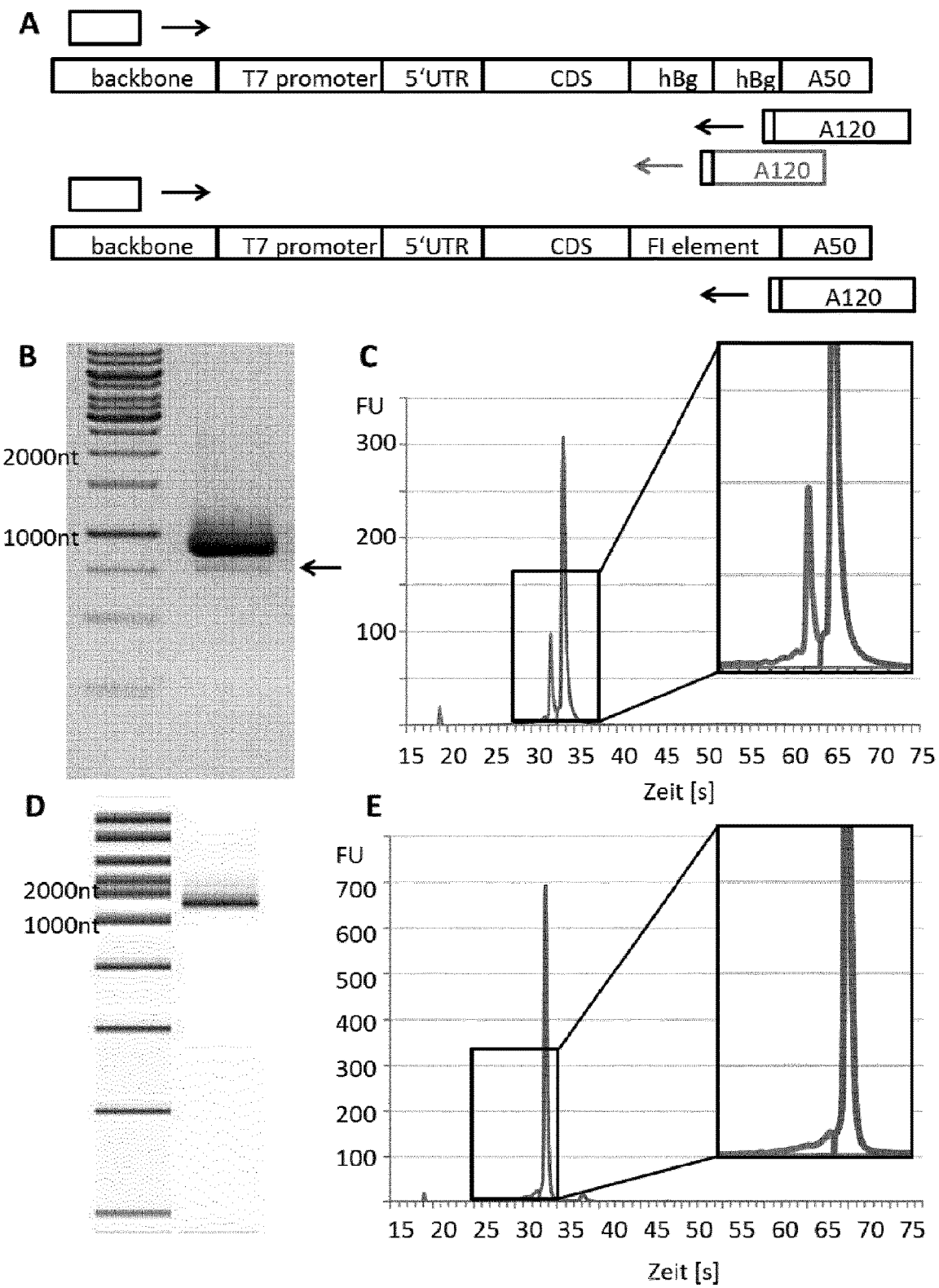

This is most obvious, when the DNA template for RNA transcription is amplified by PCR. In such cases, the full-length polyA-tail is added with the 3' primer oligo that binds at the very 3' end of the 3' UTR (FIG. 11A). In the case of the 2hBgUTR, truncated side-products emerge during the PCR, which after sequencing turned out to consist of mRNA with only 1hBg repeat in the UTR (FIG. 11 B). After transcription, the truncation is also visible in the mRNA (FIG. 11C). This phenomenon occurs in the majority of PCR reactions with constructs containing the 2hBgUTR element and cannot be abolished completely via optimization efforts including primer annealing temperature, buffer composition, primer sequence or alternative polymerases. Even after insertion of an unique linker sequence between the 3' UTR and the polyA-tail, the problem remains. Importantly, the strength of the side-peak correlated with the PCR reaction yield, indicating mispriming of short truncated PCR fragments, which increase with each PCR cycle, as probable cause of the problem. Therefore, no satisfactory conditions could be identified for DNA templates coding for RNAs with the 2hBg 3'-UTR.

In contrast, PCR of DNA templates with the FI element did not yield any truncated side-products (FIG. 11 D), and also the resulting mRNA showed no additional peak in the Bioanalyzer profile (FIG. 11 E). Therefore, the FI element constitutes a considerable improvement as a 3'UTR compared with the 2hBgUTR with regard to PCR template integrity and corresponding RNA quality.

Example 11: RNA-Stabilizing Properties of Subfragments of the Fund I Elements

Figure 12:
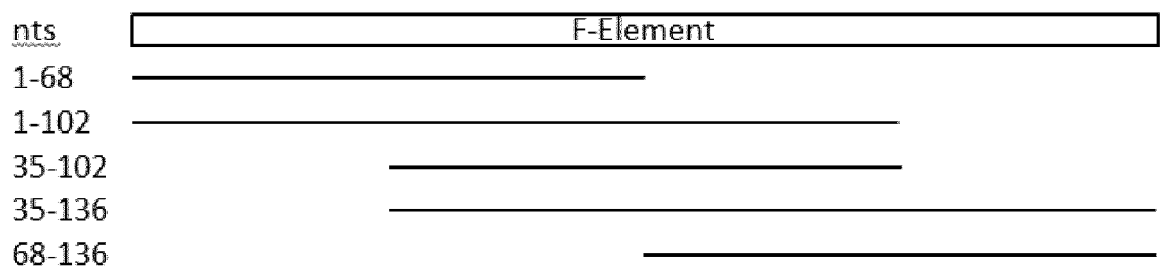
Figure 12:
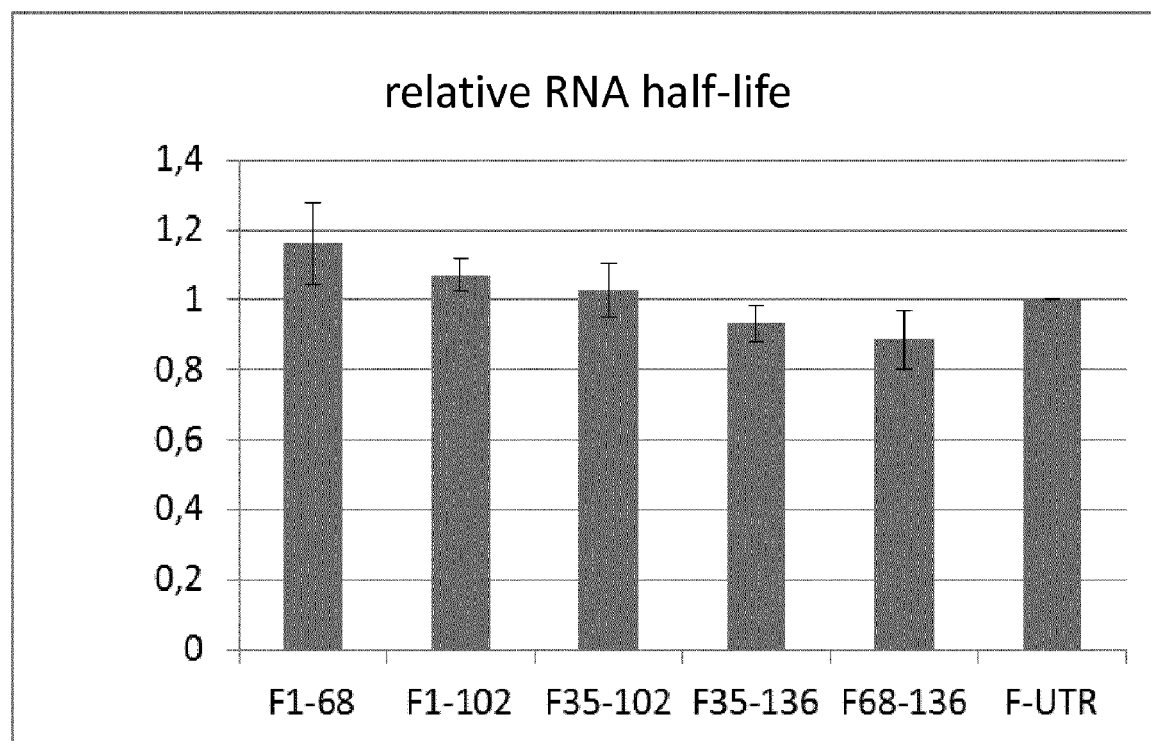
Figure 12:
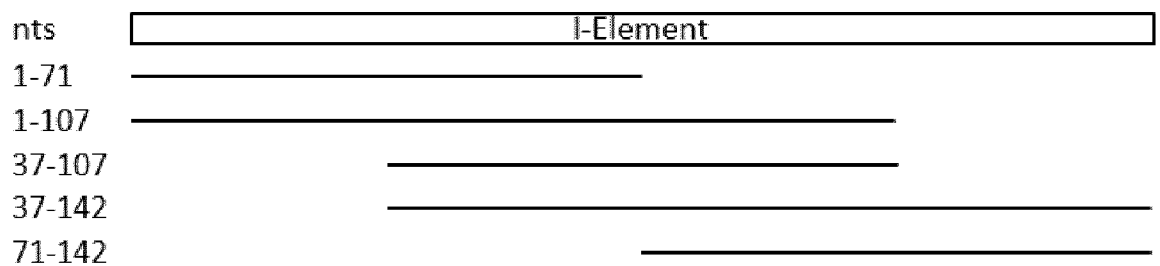
Figure 12:
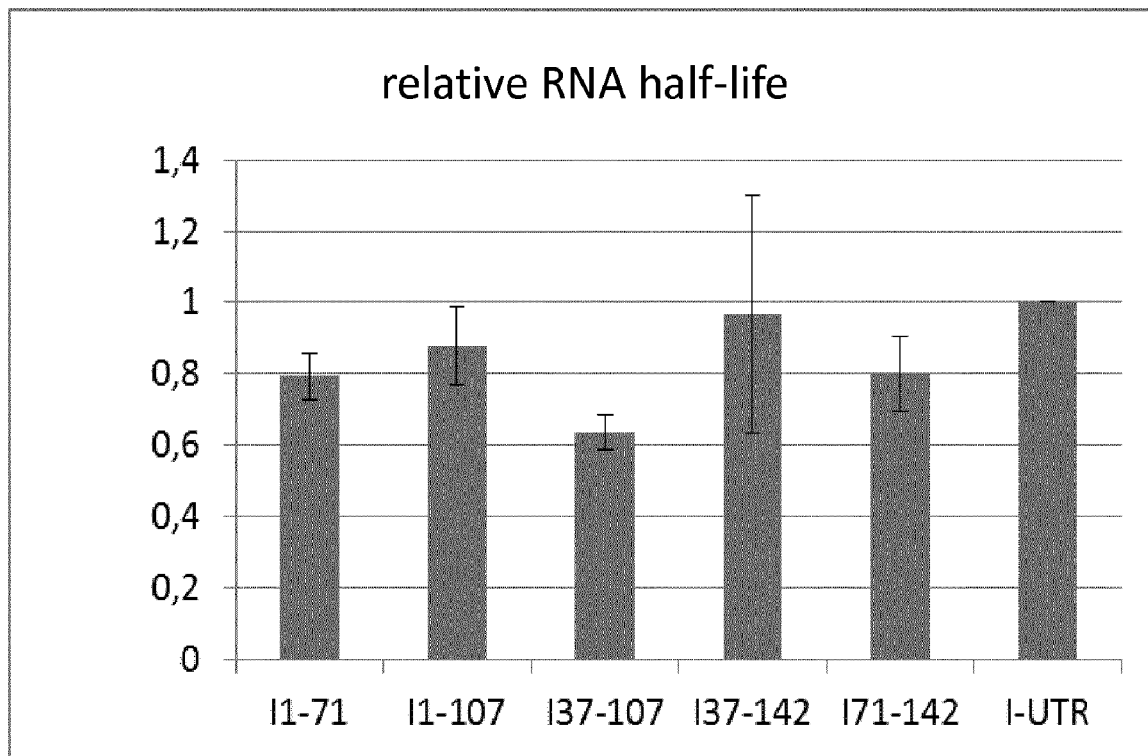

Due to the selection procedure that was applied to identify novel stabilizing UTR elements, sequences in a certain size range were obtained. The identification of the same sequences with prolonged 5' and 3' ends gave a first indication for the minimal length required. However, the minimal region required for each element to exert its stabilizing effect might even be shorter. To this end, for both the F and I element five Luciferase reporter constructs were designed, each containing a shortened UTR covering a different fragment of the original element shortened at the 5' and/or 3' end (see FIG. 12 upper panels A and B, respectively). These reporter constructs were in vitro transcribed, electroporated into hiDCs and their expression was followed over time by Luciferase measurements 3, 6, 24, 48 and 72 h after electroporation. The resulting expression curves were analyzed for relative RNA half-life with the RNA containing the respective full-length set to 1 (see FIG. 12 lower panels A and B, respectively).

For the F-element, no significantly decreased mRNA half-life could be observed for any subsequence tested, indicating a redundant, non-cooperative involvement of various subsequences along the F-element in its stabilizing role. A similar result could be obtained for the I-element, though here a slight drop in performance could be observed when only the central region (nt37-107) was used as 3'UTR.

Figure 13:
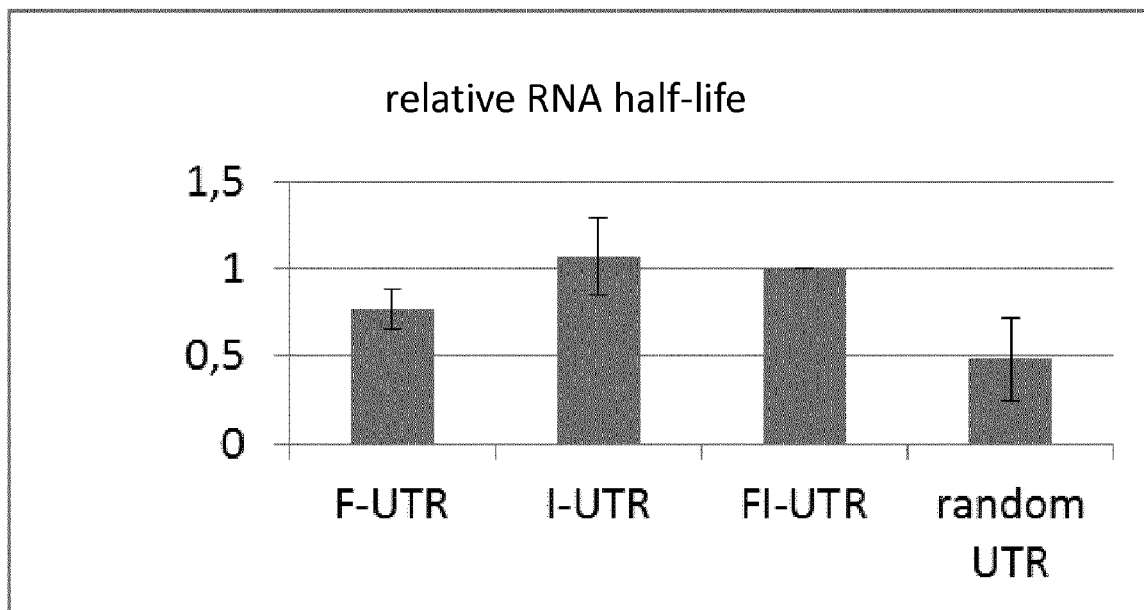
Figure 13:
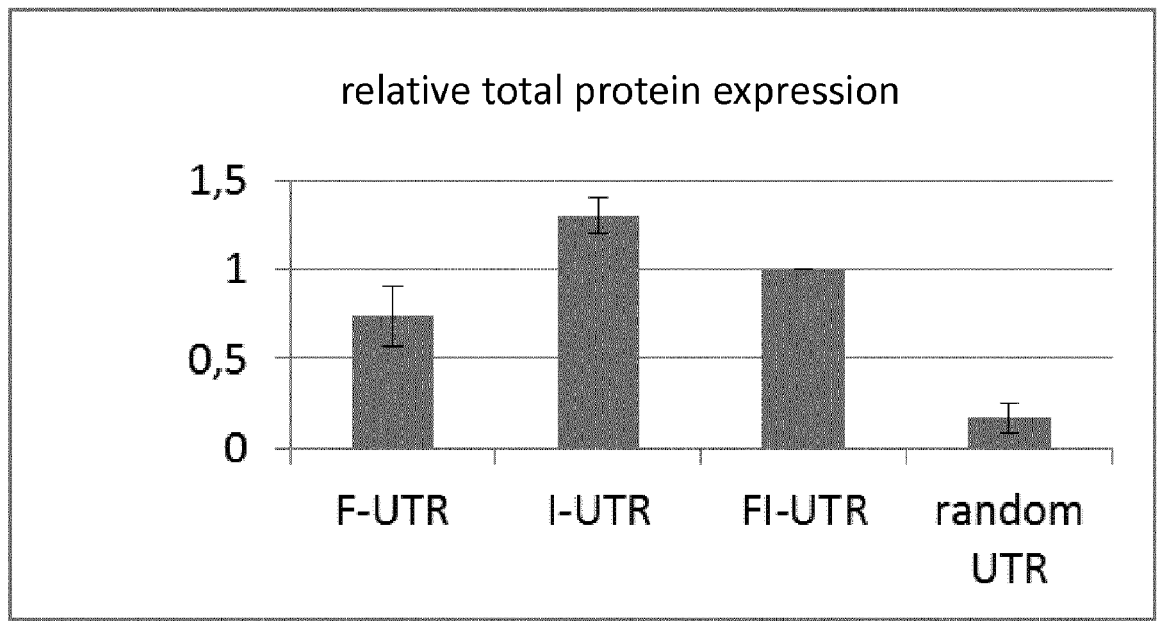

To put these results into perspective, full length individual F and I elements as well as the FI combination were compared to a randomly selected 3' UTR from the starting library (257 nt in length) This was obtained by cloning the starting DNA pool and selecting a single random clone. As described above luciferase-encoding RNAs with the respective UTR sequences were electroporated into hiDCs, luciferase expression measured over time, and the relative half-lifes and total protein expression calculated. Compared to the F, I, and FI elements, the RNA with the randomly selected 3' UTR is significantly less stable (FIG. 13, upper panel). The effect of the selected UTRs is even more pronounced for the total protein expression (FIG. 13, lower panel). This clearly indicates that the effect of the fragments of the F and I elements as described above are specific for the selected sequences and not simply caused by the presence of a 3' UTR sequence. This is in-line with the observed increase in RNA stability of the pool during selection (see above).

Figure 14:
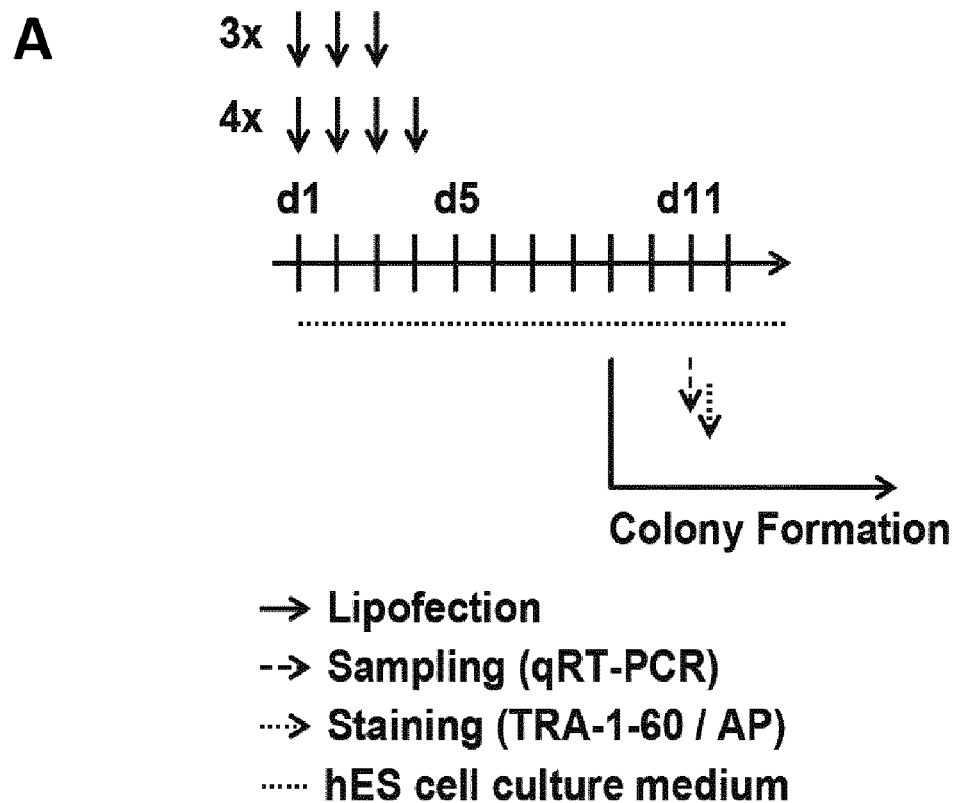
FIG. 14B shows a alkaline phosphatase (AP) staining of the established colonies and FIG. 14C shows a corresponding bar chart representing the counted numbers of the AP positive colonies.
FIG. 14D shows the morphology of resulting iPS-cell colonies using RNAs containing the FI-UTR. It was hES cell-like with tightly packed small cells in distinct colonies and well-defined borders.
FIG. 14E shows the colonies prepared as in D stained positive for AP in four- and tenfold magnification.
FIG. 14F shows colonies prepared as in D in a live staining of the hES cell surface marker TRA-1-60.
FIG. 14G shows the mRNA-expression of the hES-markers OCT4 (endogenous), NANOG (endogenous), LIN28 (endogenous), TERT and REX1 evaluated by pelleting the colonies, isolating total RNA and quantifying by qRT-PCR.
Figure 14:
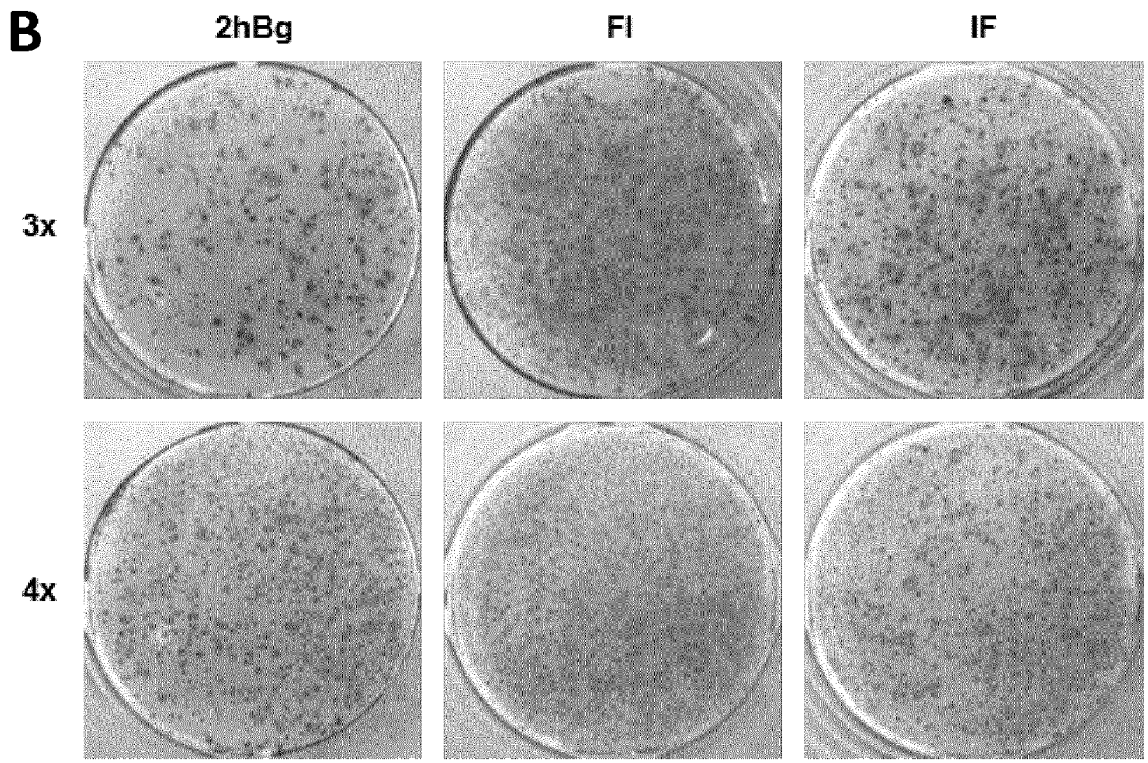
Figure 14:
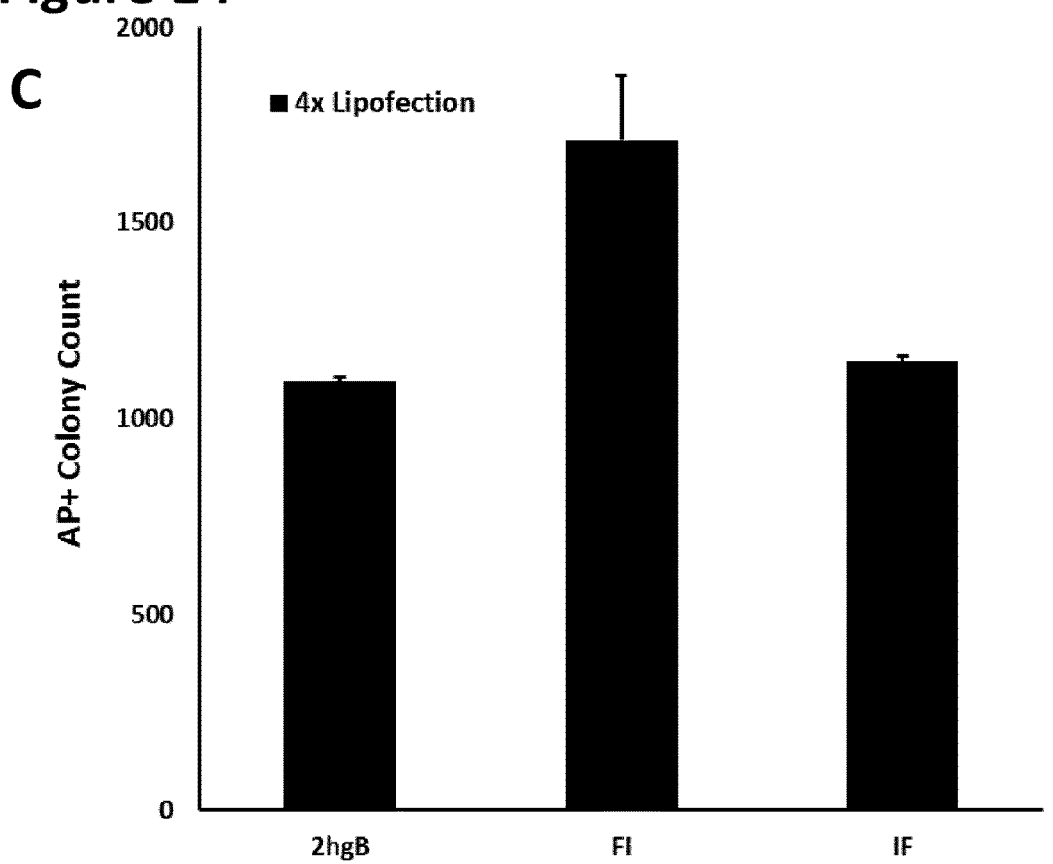
Figure 14:
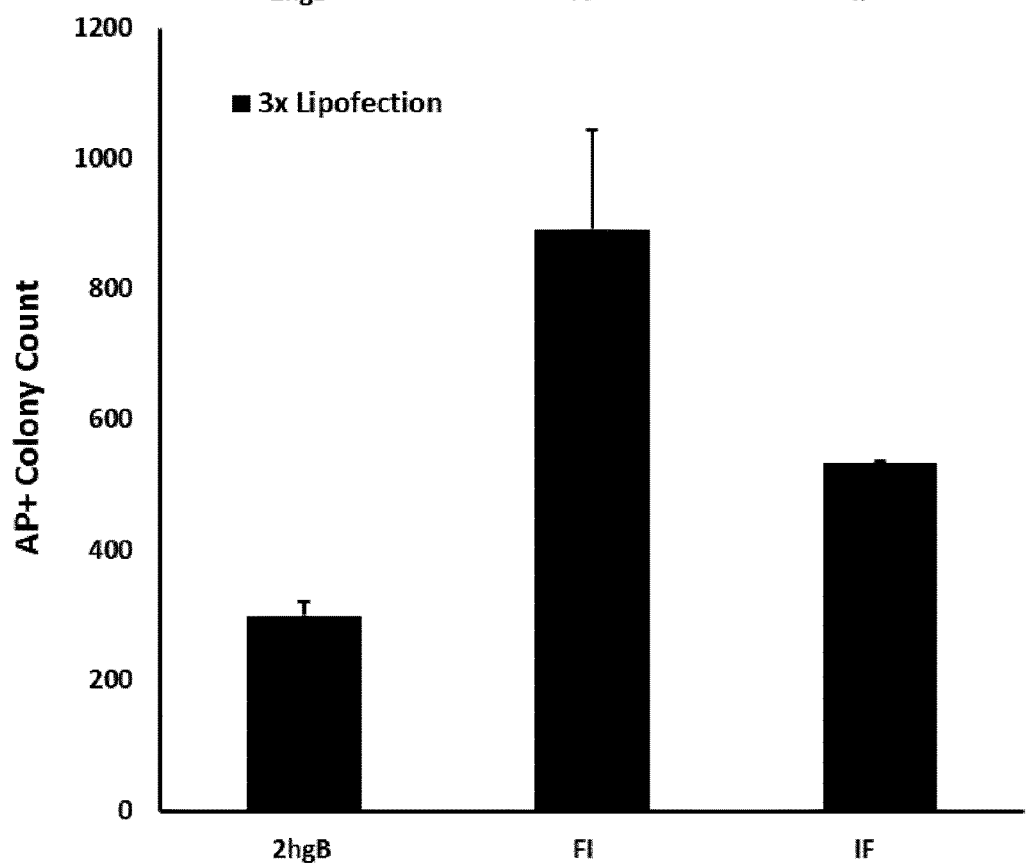
Figure 14:
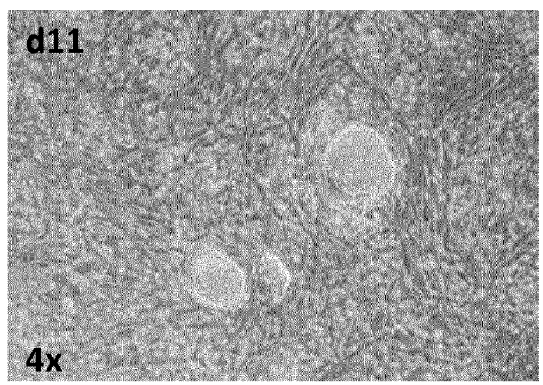
Figure 14:
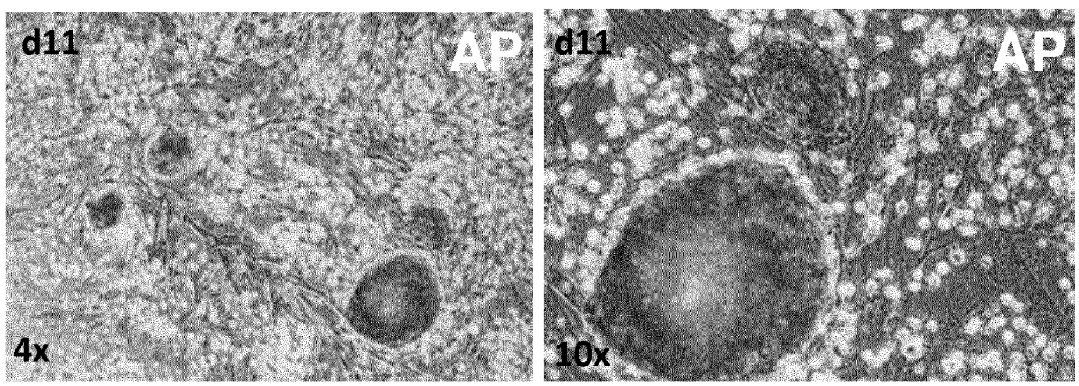
Figure 14:
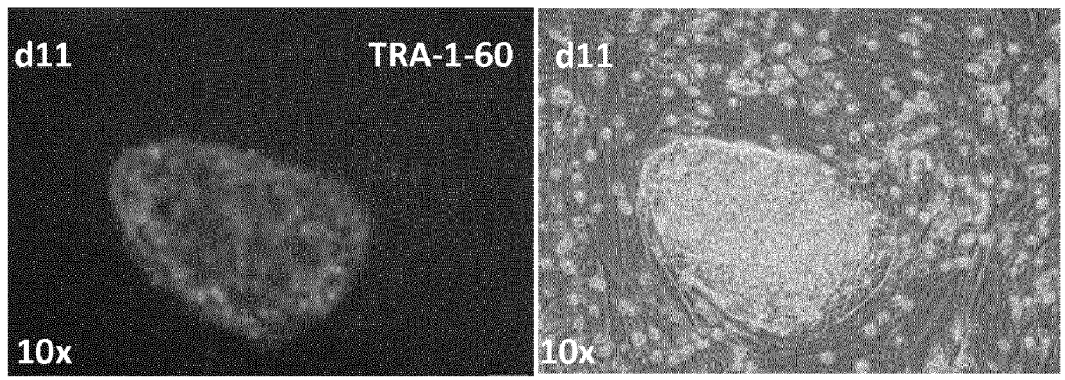
Figure 14:
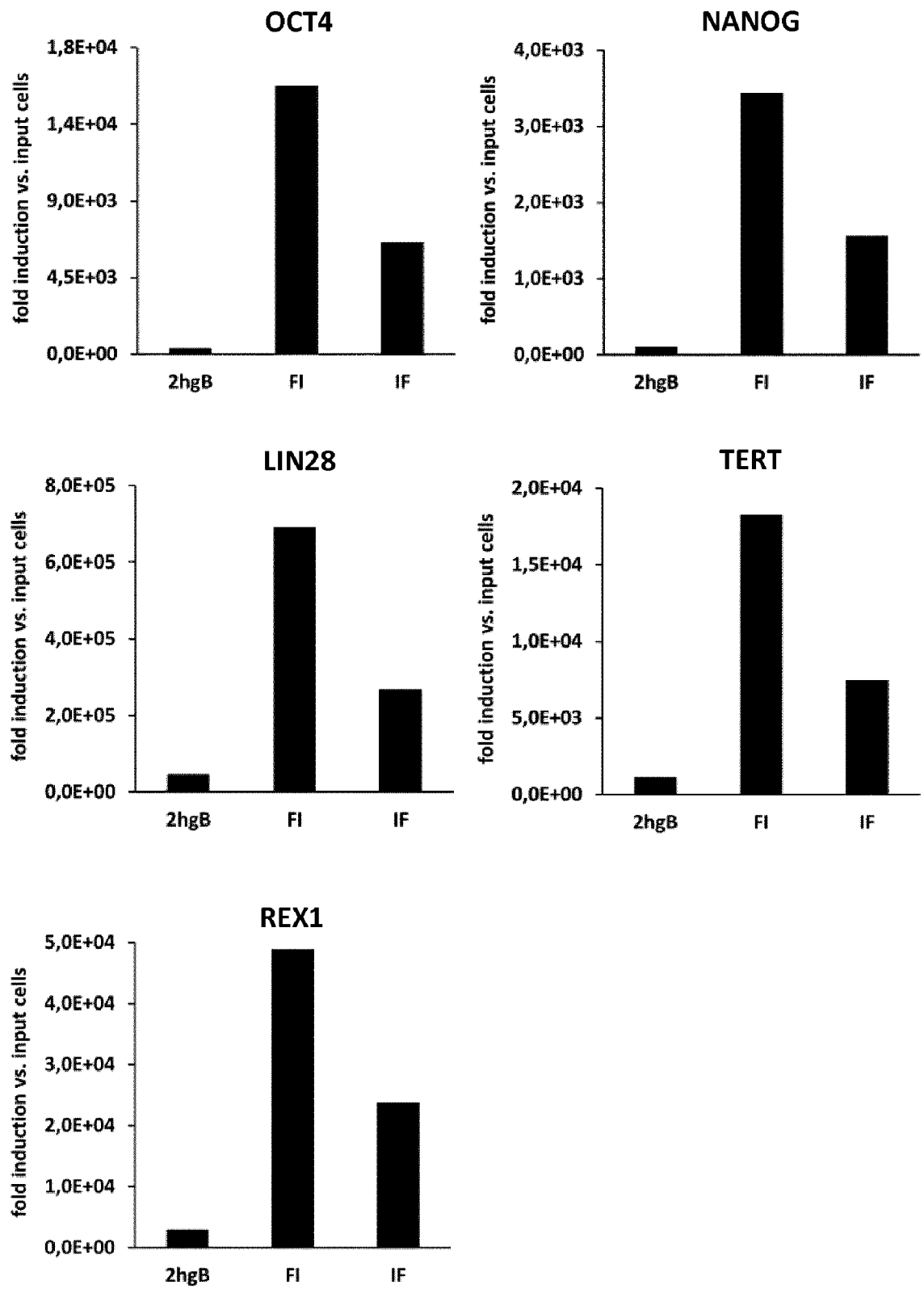

Example 12: Use of Stabilizing UTR Elements for Stem Cell Reprogramming 40,000 cells were plated into a 12-well-plate and lipofected for three (3×) or four (4×) consecutive days with mRNA mixtures that were composed of 0.33 µg unmodified in vitro transcribed (IVT)-RNA encoding the reprogramming TF OCT4, SOX2, KLF4, cMYC, NANOG and LIN28 (OSKMNL) (1:1:1:1:1:1) with 0.08 µg of each B18R, E3 and K3 (EKB) and 0.17 µg of a miRNA mixture composed of miRNAs 302a-d and 367 (1:1:1:1:1:1). The RNA-constructs thereby only differed in their 3'UTR consisting of a tandem repeat of the human β-globin 3'UTR (2hBg), the F-I-element (FI) or I-F-element (IF). Cells were cultivated in human embryonic stem (hES) cell medium and lipofections using RNAiMAX were performed according to the manufacturers instructions. From day 9 on, colony formation was observed and analysis of colonies were performed on d11 (see FIG. 14A for timeline overview). Established colonies were stained for alkaline phosphatase (AP) on day 11 using an AP Staining Kit. For an overview representative stainings are shown in FIG. 14B. It became obvious that the incorporation of the FI-element results in higher amounts of AP positive colonies (dark). Colonies stained for AP were counted and results from the overview was confirmed: In comparison to the previously used 2hBg-UTR, replacement with the FI-UTR leads to a 3-4 fold excess of colonies when cells were lipofected 3 times. Replacement with the IF-UTR results in an 2 fold excess. With four transfections these effects are less pronounced. No improvement is here observed with the IF-UTR. On one side the process seems to be in a saturation with four transfections whereas on the other side counting of colonies is here to some extent biased due to overgrowth of colonies (see FIG. 14C). Colony morphology of resulting iPS-cell colonies using RNAs containing the FI-UTR was hES cell-like with tightly packed small cells in distinct colonies and well-defined borders (FIG. 14D). These colonies could be stained positive for AP (FIG. 14E) and the hES cell surface marker TRA-1-60 (FIG. 14F). TRA-1-60 live staining was performed with the Stain-Alive TRA-1-60 antibody (Stemgent) according to the manufacturers instructions. Representative pictures of colonies are shown. To further assess pluripotency of colonies, cells were pelleted, total RNA isolated and mRNA-expression of the hES-markers OCT4 (endogenous), NANOG (endogenous), LIN28 (endogenous), TERT and REX1 was quantified by qRT-PCR. mRNA expression was normalized to that of HPRT and is shown as fold induction compared to the transcript levels of input cells. Analysis of colonies after 3 lipofections is shown in FIG. 14G. All analyzed markers were highly expressed compared to input cells indicating pluripotency of reprogrammed cells. Superiority of FI-containing synthetic mRNA was confirmed by a higher endogenous marker expression compared to reprogramming with the 2hBg- and IF-containing mRNAs.

These results show, that replacement of the 2hBg-UTR with the FI-UTR results in a more rapid and efficient RNA-based reprogramming technology. This is probably based on the longer and higher expression of reprogramming transcription factors resulting from the substitution with the FI-element. Orientation of the FI element seems thereby indispensable since the benefit was not observed with the IF-constructs. Successful reprogramming of cells by FI-containing mRNAs was confirmed by hES-cell like morphology, AP-activity and the expression of hES-cell surface and endogenous markers of resulting iPS-cell colonies.

TABLES

TABLE 1 mRNA half-life in hours (h) calculated from data of real-time reverse transcriptase-PCR (RT-PCR) experiments to monitor progress of selection. mRNAs were quantified 8, 24, and 48 hours after electroporation. In experiment I (left), each sample was analysed only once. Accordingly, no standard deviation is given.

| Sample | mRNA half life | Sample | mRNA half life |
|---|---|---|---|
| 2hBg | 7.5 h | 2hBg | 13.5 ± 0.2 h |
| lib | 4.5 h | Rn4 | 13.9 ± 0.7 h |
| Rn1 | 4.9 h | Rn5 | 16.5 ± 0.7 h |
| Rn2 | 6.7 h | | |
| Rn3 | 7.5 h | | |

TABLE 2

Overview of the 7 main groups with the binding region (BR) within the 3'-UTR of the BLASTed sequence. Shown are group abbreviation, number of clones identified for the group (no.), genomic origin with respective abbreviation (Abbr.), NCBI code and position within the sequence with respect to the coding region. According to NextBio all sequences are upregulated in hiDC.

| Group | no. | BLAST-result with representative sequence of each group. *Homo Sapiens* | Abbr. | NCBI code | BR |
|---|---|---|---|---|---|
| B | 50 | Fc fragment of IgG. receptor. transporter. alpha. mRNA (cDNA clone) | FCGRT | NM_001136019 | 3'-UTR |
| D | 22 | Lymphocyte-specific protein 1. mRNA | LSP1 | NM_002339 | 3'-UTR |
| E | 13 | Chemokine (C-C motif) ligand 22. mRNA | CCL22 | NM_002990 | 3'-UTR |
| F | 4 | Amino-terminal enhancer of split. mRNA | AES | NM_198969 | 3'-UTR |
| G | 15 | Phospholipase D family. member 3. mRNA | PLD3 | NM_001031696 | CDS + 3'-UTR |
| I | 17 | Mitochondrially encoded 12S RNA | MT-RNR1 | NC_012920 | ncRNA |
| J | 22 | Major histocompatibility complex. class II. DR beta 4. mRNA | HLA-DRB4 | NM_021983 | 3'-UTR |

TABLE 3

Values calculated relative to our gold-standard 2hBg for half-life and total protein over time. Shown are group-name and respective gene.

| | | Relative to 2hBg ||
|---|---|---|---|
| Gene | RefSeq | Half-life | Total protein over time |
| Fc fragment of IgG, receptor, transporter, alpha | NM_001136019 | 0.89 ± 0.15 | 0.96 ± 0.15 |
| Lymphocyte specific protein 1 | NM_002339 | 0.80 ± 0.21 | 0.75 ± 0.03 |
| Chemokine ligand 22 | NM_002990 | 0.82 ± 0.16 | 0.66 ± 0.12 |
| Amino-terminal enhancer of split | NM_198969 | 0.90 ± 0.06 | 0.95 ± 0.01 |
| Phospholipase D family member 3 | NM_001031696 | 0.79 ± 0.21 | 0.66 ± 0.13 |
| Mitochondrially encoded 12S RNA | NC_012920 | 1.15 ± 0.09 | 0.94 ± 0.08 |
| Major histocompatibility complex class II DR beta 4 | NM_021983 | 0.89 ± 0.08 | 0.89 ± 0.09 |

TABLE 4

PCR-conditions for amplification of library and subsequent selection rounds.

| Time | Temperature | Step |
|---|---|---|
| 1 min 30 s | 98 °C | Initial denaturation |
| 20 s | 98 °C | Denaturation |
| 30 s | 65 °C | Annealing |
| 45 s | 72 °C | Extension |
| 5 min | 72 °C | Final Extension |
| ∞ | 4 °C | Hold |

TABLE 5

IVT-T7-transcription reaction.

| | Conc./Vol. | End Conc. |
|---|---|---|
| ddH2O | | Ad 50 µL |
| D1 cap | Variabel | 6.0 mM |
| ATP/CTP/UTP | 100 mM | 7.5 mM |
| GTP | 100 mM | 1.5 mM |
| T7 buffer | 10x | 1x |
| PCR-product | Variabel | 0.05 µg/µL |
| T7 enzyme mix HC | 10x | 1x |

TABLE 6

Combinations cloned and compared with our gold-standard 2hBg (lower right corner). Single elements cloned twice are shown in bold.

| | I | G | B | D | J | E | F | hBg |
|---|---|---|---|---|---|---|---|---|
| I | II | GI | BI | DI | JI | EI | FI | hBgI |
| G | IG | GG | BG | DG | JG | EG | FG | hBgG |
| B | IB | GB | BB | DB | JB | EB | FB | hBgB |
| D | ID | GD | BD | DD | JD | ED | FD | hBgD |
| J | IJ | GJ | BJ | DJ | JJ | EJ | FJ | hBgJ |
| E | IE | GE | BE | DE | JE | EE | FE | hBgE |
| F | IF | GF | BF | DF | JF | EF | FF | hBgF |
| hBg | IhBg | GhBg | BhBg | DhBg | JhBg | EhBg | FhBg | 2hBg |

TABLE 7

Result of FCGRT (group B) cloned as single or upstream element combined with one of the other group sequences as downstream element. Bold values are >1.0. Values are relative to 2hBg

| | Relative to 2hBg | | |
|---|---|---|---|
| Sample | Half-life | Translational efficiency | Total protein over time |
| B | 0.840 | 1.320 | 1.300 |
| BB | 0.580 | 1.530 | 0.900 |
| BI | 0.920 | 1.750 | 1.410 |
| BG | 0.780 | 2.300 | 1.430 |
| BD | 0.730 | 1.970 | 1.220 |
| BJ | 0.710 | 1.910 | 1.190 |
| BE | 0.720 | 1.500 | 1.030 |
| BF | 0.760 | 1.720 | 1.220 |
| BhBg | 0.970 | 2.200 | 1.740 |
| hBgB | 0.640 | 1.750 | 1.030 |
| 2hBg | 1.000 | 1.000 | 1.000 |

TABLE 8

Result of LSP1 (group D) cloned as single or upstream element combined with one of the other group sequences as downstream element. Bold values are >1.0. Values are relative to 2hBg.

| | Relative to 2hBg | | |
|---|---|---|---|
| Sample | Half-life | Translational efficiency | Total protein over time |
| D | 0.770 | 0.860 | 1.250 |
| DD | 0.680 | 1.130 | 1.000 |
| DI | 0.960 | 1.440 | 1.270 |
| DG | 0.700 | 1.530 | 1.110 |
| DB | 0.640 | 0.900 | 0.760 |
| DJ | 0.640 | 1.040 | 0.890 |
| DE | 0.690 | 1.000 | 0.970 |
| DF | 0.750 | 1.080 | 1.000 |
| DhBg | 0.840 | 1.120 | 1.020 |
| hBgD | 0.820 | 1.490 | 1.160 |
| 2hBg | 1.000 | 1.000 | 1.000 |

TABLE 9

Result of CCL22 (group E) cloned as single or upstream element combined with one of the other group sequences as downstream element. Bold values are >1.0. Values are relative to 2hBg.

| | Relative to 2hBg | | |
|---|---|---|---|
| Sample | Half-life | Translational efficiency | Total protein over time |
| E | 0.760 | 0.970 | 0.940 |
| EE | 0.600 | 0.950 | 0.670 |
| EI | 0.890 | 1.120 | 0.960 |
| EG | 0.680 | 1.590 | 0.940 |
| EB | 0.570 | 1.470 | 0.850 |
| ED | 0.650 | 1.350 | 0.950 |
| EJ | 0.600 | 1.230 | 0.760 |
| EF | 0.760 | 1.100 | 0.860 |
| EhBg | 0.690 | 1.190 | 0.780 |
| hBgE | 0.880 | 1.630 | 1.050 |
| 2hBg | 1.000 | 1.000 | 1.000 |

TABLE 10

Result of AES (group F) cloned as single or upstream element combined with one of the other group sequences as downstream element. Bold values are >1.0. Values are relative to 2hBg.

| | Relative to 2hBg | | |
|---|---|---|---|
| Sample | Half-life | Translational efficiency | Total protein over time |
| F | 0.500 | 1.760 | 0.970 |
| FF | 0.910 | 1.770 | 1.410 |
| FI | 1.100 | 1.490 | 1.290 |
| FG | 0.850 | 1.680 | 0.980 |
| FB | 0.720 | 1.360 | 0.860 |
| FD | 0.490 | 1.350 | 0.620 |
| FJ | 0.780 | 1.720 | 1.090 |
| FE | 0.730 | 1.660 | 1.080 |
| FhBg | 1.050 | 1.900 | 1.530 |
| hBgF | 0.940 | 2.250 | 1.500 |
| 2hBg | 1.000 | 1.000 | 1.000 |

TABLE 11

Result of PLD3 (group G) cloned as single or upstream element combined with one of the other group sequences as downstream element. Bold values are >1.0. Values are relative to 2hBg.

| | Relative to 2hBg | | |
|---|---|---|---|
| Sample | Half-life | Translational efficiency | Total protein over time |
| G | 0.740 | 1.260 | 1.110 |
| GG | 0.480 | 1.080 | 0.690 |
| GI | 0.990 | 1.010 | 1.000 |
| GB | 0.520 | 0.970 | 0.620 |
| GD | 0.630 | 1.170 | 0.780 |
| GJ | 0.520 | 0.940 | 0.640 |
| GE | 0.500 | 0.730 | 0.550 |
| GF | 0.620 | 0.790 | 0.680 |
| GhBg | 0.740 | 0.990 | 0.860 |
| hBgG | 0.720 | 1.160 | 0.910 |
| 2hBg | 1.000 | 1.000 | 1.000 |

TABLE 12

Result of mtRNR1 (group I) cloned as single or upstream element combined with one of the other group sequences as downstream element. Bold values are. Values are relative to 2hBg.

| | Relative to 2hBg | | |
|---|---|---|---|
| Sample | Half-life | Translational efficiency | Total protein over time |
| I | 1.080 | 1.020 | 1.440 |
| II | 1.170 | 0.830 | 1.030 |
| IG | 1.040 | 1.250 | 1.310 |
| IB | 1.100 | 1.200 | 1.180 |
| ID | 1.190 | 1.580 | 1.510 |
| IJ | 1.080 | 1.430 | 1.330 |
| IE | 1.060 | 1.000 | 1.070 |
| IF | 1.220 | 1.130 | 1.290 |
| IhBg | 1.230 | 1.110 | 1.210 |
| hBgI | 1.210 | 1.420 | 1.270 |
| 2hBg | 1.000 | 1.000 | 1.000 |

TABLE 13

Result of HLA-DRB4 (group J) cloned as single or upstream element combined with one of the other group sequences as downstream element. Bold values are >1.0. Values are relative to 2hBg.

| | Relative to 2hBg | | |
|---|---|---|---|
| Sample | Half-life | Translational efficiency | Total protein over time |
| J | 0.790 | 0.930 | 0.920 |
| JJ | 0.490 | 0.960 | 0.540 |
| JI | 0.880 | 1.110 | 0.900 |
| JG | 0.420 | 1.280 | 0.630 |
| JB | 0.480 | 1.000 | 0.520 |
| JD | 0.500 | 1.370 | 0.830 |
| JE | 0.420 | 0.950 | 0.520 |
| JF | 0.570 | 1.190 | 0.800 |
| JhBg | 0.730 | 1.100 | 0.800 |
| hBgJ | 0.770 | 1.530 | 1.080 |
| 2hBg | 1.000 | 1.000 | 1.000 |

TABLE 14

Representative results using luc2mut as reporter gene and newly selected 3'-UTRs after electroporation into hiDC. Luciferase activity was measured over 96 h. Values are relative to 2hBg.

| | Relative to 2hBg | | |
|---|---|---|---|
| Sample | Half-life | Translational efficiency | Total protein over time |
| noUTR | 0.300 | 0.694 | 0.139 |
| hBg | 0.360 | 1.216 | 0.437 |
| I | 0.800 | 1.132 | 0.936 |
| IF | 1.110 | 1.050 | 1.133 |
| FI | 1.020 | 0.818 | 0.847 |
| IhBg | 0.880 | 0.860 | 0.792 |
| hBgI | 0.840 | 0.776 | 0.681 |
| 2hBg | 1.000 | 1.000 | 1.000 |

TABLE 15

Electroporation settings
The table summarizes the details of the electroporation protocol for all cell types used. The amount of cells stated under cell count was mixed with the amount of RNA stated either in μg or pmol either in electroporation cuvettes or 96-well electroporation plates (as indicated under format) in X-VIVO15 media (Lonza). Electroporation was performed by applying a pulse with the designated length and the voltage listed under V. Afterwards, the cell suspension was diluted in growth medium and distributed in 96-wells with the density listed under cells/time point.

| | Format | gap size | cell count | RNA [μg] | RNA [pmol] | cells/time point | V | pulse |
|---|---|---|---|---|---|---|---|---|
| hiDCs | cuvette | 4 mm | 1.00E+06 | | 10 | 5.00E+04 | 300 | 1 × 12 ms |
| HFF | 96-well | 4 mm | 7.00E+04 | 2 | | 1.00E+04 | 200 | 1 × 24 ms |
| CD8+ | cuvette | 4 mm | 2.50E+06 | | 10 | 1.67E+05 | 500 | 1 × 3 ms |
| CD4+ | cuvette | 4 mm | 2.50E+06 | | 10 | 1.67E+05 | 500 | 1 × 3 ms |
| MEF | 96-well | 4 mm | 7.00E+04 | 2 | | 1.00E+04 | 200 | 5 × 6 ms/400 ms |
| C2C12 | 96-well | 4 mm | 7.00E+04 | 2 | | 1.00E+04 | 240 | 5 × 5 ms/400 ms |
| bmDCs | cuvette | 4 mm | 1.00E+06 | | 10 | 5.00E+04 | 400 | 1 × 5 ms |

TABLE 16

Half-lifes and total protein of FI-element relative to 2hBgUTR containing unmodified and modified mRNA upon electroporation and unmodified RNA upon lipofection. Plasmids coding for the firefly luciferase gene containing either FI or 2hBg as 3'UTR were linearized downstream of the poly(dA:dT) with a classIIS restriction enzyme thereby generating a template with no additional nucleotide past the poly(dA:dT). Linearized plasmid DNA was purified using carboxylated magnetic beads (Invitrogen), quantified spectrophotometrically and subjected to in vitro transcriptions. For in vitro transcriptions home-made T7 RNA polymerase supplemented with RNase inhibitors and pyrophosphatase was used with 7.5 mM NTPs in a 125 mM Hepes pH 8.35, 34 mM MgOAc2, 10 mM DTT and 2 mM Spermidin buffer. For efficient capping of the RNA 6 mM of β-S-ARCA(D2) was added to the reaction and the initial GTP concentration was lowered to 1.5 mM, which was adjusted to 7.5 mM in a fed-batch process during 2.5 h at 37° C. RNA was purified via carboxylated magnetic beads (Invitrogen) and RNA concentration and quality were assessed by spectrophotometry and analysis on a 2100 Bioanalyzer (Agilent).

| | A Unmodified mRNA relative to 2hBg | | B m1Y modified mRNA relative to 2hBg | | C Lipofection relative to 2hBg | |
|---|---|---|---|---|---|---|
| | Half-life | total protein | Half-life | total protein | Half-life | total protein |
| hiDCs | | | 1.29 | 2.24 | | |
| C2C12 | 1.64 | 2.24 | 1.58 | 2.32 | 1.09 | 1.82 |
| HFF | 1.69 | 2.45 | 1.83 | 2.21 | 1.14 | 2.22 |
| MEF | 1.39 | 2.15 | 1.18 | 1.52 | 1.11 | 2.24 |
| CD4+ | 1.04 | 1.32 | 1.02 | 1.46 | | |
| CD8+ | 0.96 | 1.29 | 1.05 | 1.33 | | |
| bmDC | 0.87 | 1.98 | 1.09 | 1.34 | | |

A) Shows that the Half-lifes of unmodified mRNAs containing the FI element are higher or comparable to those containing the 2hBg 3'UTR in several human and murine cell lines. The amount of human fibroblasts (HFFs), CD8+ and CD4+ T-cells, murine embryonic fibroblast (MEF), myoblastoma cells (C2C12) and murine DCs as listed in Tab. 15 were mixed with the respective amount of RNA (Tab. 15) in X-VIVO15 media (Lonza) and subjected to electroporation. The indicated number of cells was plated in 96 well dishes in 100 μl of appropriate growth medium with additives. At 2, 6, 24, 48, 72 and 96 hours after seeding firefly luciferase activities were determined by addition of Luciferin (Promega) in a fluorescence reader (TECAN).
B) Shows that the Half-lifes of m1Y modified mRNAs containing the FI element are higher or comparable to those containing the 2hBg 3'UTR in different human and murine cell lines. The amount of human immature dendritic cells (iDC), fibroblasts (HFFs), CD8+ and CD4+ T-cells, murine embryonic fibroblast (MEF), myoblastoma cells (C2C12) and murine DCs as listed in Tab. 15 were mixed with the respective amount of m1Y modified RNA (Tab. 15) in X-VIVO15 media (Lonza) and subjected to electroporation. The indicated number of cells was plated in 96 well dishes in 100 μl of appropriate growth medium with additives. At 2, 6, 24, 48, 72 and 96 hours after seeding firefly luciferase activities were determined by addition of Luciferin (Promega) in a fluorescence reader (TECAN).
C) Shows that the Half-lifes of unmodified mRNAs containing the FI element are higher or comparable to those containing the 2hBg 3'UTR in different cell lines also when the RNA was transfected via lipofection. 50 ng RNA was incubated for 15-30 min with 0.2 μl RNAiMAX and given on 1E04 HFF, MEF or C2C12 cells in 96wells. Luciferase levels were measured at 3, 6, 12, 24, 48, 72 and 96 h by addition of Luciferin (Promega) in a fluorescence reader (TECAN).

TABLE 17

10 μg RNA coding for firefly luciferase containing either the FI element or variations of the FI element with the designated homology to the original FI sequence as 3'UTRs were electroporated into hiDCs in a 96-well format. Luciferase expression was followed over time at 3, 6, 24, 48, and 72 h, and from the resulting expression curve the mRNA half-life and the total protein amount translated from the RNA were calculated.

| | relative to FI sequence | |
|---|---|---|
| % Homology | Half-life | total protein |
| 97.5 | 1.0 +/- 0.1 | 1.3 +/- 0.2 |
| 95.0 | 1.0 +/- 0.0 | 1.2 +/- 0.2 |
| 92.5 | 1.1 +/- 0.1 | 1.4 +/- 0.1 |
| 90.0 | 0.9 +/- 0.1 | 1.1 +/- 0.2 |

TABLE 18

10 μg RNA coding for firefly luciferase containing either the FI element or variations of the FI element containing structure retaining or destroying mutations and with the designated homology to the original FI sequence as 3'UTRs were electroporated in hiDCs in a 96-well format. Luciferase expression was followed over time at 3, 6, 24, 48, and 72 h, and from the resulting expression curve the mRNA half-life and the total protein amount were calculated.

| A Structure retaining modifications | | | B Structure destabilizing modifications | | |
|---|---|---|---|---|---|
| | relative to FI sequence | | | relative to FI sequence | |
| % Homology | Half-life | total protein | % Homology | Half-life | total protein |
| 97.5 | 1.2 +/- 0.1 | 1.6 +/- 0.3 | 98.75 | 1.1 +/- 0.1 | 1.5 +/- 0.1 |
| 95.0 | 1.1 +/- 0.1 | 1.7 +/- 0.3 | 97.50 | 1.1 +/- 0.1 | 1.4 +/- 0.1 |
| 92.5 | 1.1 +/- 0.1 | 1.5 +/- 0.3 | 96.25 | 1.0 +/- 0.1 | 1.5 +/- 0.1 |
| 90.0 | 1.1 +/- 0.2 | 1.4 +/- 0.1 | 95.00 | 1.0 +/- 0.0 | 1.1 +/- 0.2 |
| | | | 8nt mutation | 0.9 +/- 0.0 | 1.3 +/- 0.4 |

Sequences Described Herein are as Follows:

```
Group B
>Rn5-2p1-A4_For2 (SEQ ID NO: 1)
CAUCCUGCUGCUGCUGCUGCUGCUGCGGGUCUUCCUGGAAUCUGACCAUUCGUUGUC

UGCUAUGCCCGUCCUCACCAAGACUGACUGCCUGCUGCUUUGCUACUGCCCGGGCCCAUG

AGACUGACUUCCCACUGCUCUGCCUGCCUCUCCCCACUGCACUGGCACAGCCCCGCCUUG

CCGCUGCUGAUCCAUUGCCGGUGUGACC

>Rn5-2p1-A3_For2 (SEQ ID NO: 2)
GCUGCUGCUGCUGCUGCUGCGGGUCUUCCUGGAAUCUGACCAUUCGUUGUCUGCUAU

GCCCGUCCUCACCAAGACUGACUGCCUGCUGCUUUGCUACUGCCCGGGCCCAUGAGACUG

ACUUCCCACUGCUCUGCCUGCCUCUCCCCACUGCACUGGCACAGCCCCGCCUUGCCGCUG

CUGAUCCAUUGCCGGUGUGACC

>Rn5C5_For2 (SEQ ID NO: 3)
UUCCUGCUGCUGCUGCUGCUGCUGCUGCGGGUCUUCCUAGAAUCUGACCAUUCGUUG

UCUGCUAUGCCCGUCCUCACCAAGACUGACUGCCUGCUGCUUUGCUACUGCCCGGGCCCA

UGAGACUGACUUCCCACUGCUCUGCCUGCCUCUCCCCACUGCACUGGCACAGCCCCGCCU

UGCCGCUGCUGAUCCAUUGCCGGUGAGACC

>Rn5E6_For2 (SEQ ID NO: 4)
UGCUGCUGCUGCUGCGGGUCUUCCUGGAAUCUGACCAUUCGUUGUCUGCUAUGCCCGUCC

UCACCAAGACUGACUGCCUGCUGCUUUGCUACUGCCCGGGCCCAUGAGACUGACUUCCCA

CUGCUCUGCCUGCCUCUCCCCACUGCACUGGCACAGCCCCGCCUUGCCGCUGCUGAUCCA

UUGCCGGCGGACA

>Rn6-1WoC3_For2 (SEQ ID NO: 5)
GCUGCUGCGGGUCUUCCUGGAAUCUGACCAUUCGUUGUCUGCUAUGCCCGUCCUCACCAA

GACUGACUGCCUGCUGCUUUGCUACUGCCCGGGCCCAUGAGACUGACUUCCCACUGCUCU

GCCUGCCUCUCCCCACUGCACUGGCACAGCCCCGCCUUGCCGCUGCUGAUCCAUUGCCGG

CGUACC

>Rn6-1WoB12_For2 (SEQ ID NO: 6)
CUGGAAUCUGACCAUUCGUUGUCUGCUAUGCCCGUCCUCACCAAGACUGACUGCCUGCUG

CUUUGCUACUGCCCGGGCCCAUGAGACUGACUUCCCACUGCUCUGCCUGCCUCUCCCCAC

UGCACUGGCACAGCCCCGCCUUGCCGCUGCUGAUCCAUUGCCGGCGGACC

>Rn6-1WoB1_For2 (SEQ ID NO: 7)
UCCUGCUGCUGCUGCUGCUGCUGCUGCGGGUCUUCCUGGAAUCUGACCAUUCGUUGUCUG

CUAUGCCCGUCCUCACCAAGACUGACUGCCUGCUGCUUUGCUACUGCCCGGGCCCAUGAG

ACUGACUUCCCACUGCUCUGCCUGCCUCUCCCCACUGCACUGGCACAGCCCCGCCUUGCC

GCUGCUGAUCCAUUGCCGGUGGGACC

>Rn6-1WoF3_For2 (SEQ ID NO: 8)
CUGCCUGCUGCUUUGCUACUGCCCGGGCCCAUGAGACUGACUUCCCACUGCUCUGCCUGC

CUCUCCCCACUGCACUGGCACAGCCCCGCCUUGCCGCUGCUGAUCCAUUGCCGGUAGAAC

C

>Rn6-1Wo_H11_b (SEQ ID NO: 9)
UCCUGCUGCUGCUGCUGCUGCUGCUGCGGGUCUUCCUGGAAUCUGACCAUUUGUUGUCUG

CUAUGCCCGUCCUCACCAAGACUGACUGCCUGCUGCUUUGCUACUGCCCGGGCCCAUGAG

ACUGACUUCCCACUGCUCUGCCUGCCUCUCCCCACUGCACUGGCACAGCCCCGCCUUGCC

GCUGCUGAUCCAUUGCCGGUGGGACC
```

-continued

>Rn6-2WoG8_b (SEQ ID NO: 10)
GCUGCUGCUGCUGCUGCGGGUCUUCCUGGAAUCUGACCAUUCGUUGUCUGCUAUGCCCGU

CCUCACCAAGACUGACUGCCUGCUGCUUUGCUACUGCCCGGGCCCAUGAGACUGACUUCC

CACUGCUCUGCCUGCCUCUCCCCACUGCACUGGCACAGCCCCGCCUUGCCGCUGCUGAUC

CAUUGCCGGUGUGACC

>Rn5-2pl-B3_For2 (SEQ ID NO: 11)
UCUGGCCUCACUGAGUCUGAAGAGCUGUUAACUACCAUGGCCAGUCCUCCCUGAGUCUGA

CCAUCUUCCAUCCUGCUGCUGCUGCUGCUGCUGCGGGUCUUCCUGGAAUCUGACCAU

UCGUUGUCUGCUAUGCCCGUCCUCACCAAGACUGACUGCCUGCUGCUUUGCUACUGCCCG

GGCCCAUGAGACUGACUUCCCACUGCUCUGCCUGCCUCUCCCCACUGCACUGGCACAGCC

CCGCCUUGCCGCUGCUGAUCCAUUGCCGGUGUGACC

>Rn5_F5_b (SEQ ID NO: 12)
UCUGGCCUCACUGAGUCUGAAGAGCUGUUAACUACCAUGGCCAGUCCUCCCUGAGUCUGA

CCAUCUUCCAUCCUGCUGCUGCUGCUGCUGCUGCGGGUCUUCCUGGAAUCUGACCAU

UCGUUGUCUGCUAUGCCCGUCCUCACCAAGACUGACUGCCUGCUGCUUUGCUACUGCCCG

GGCCCAUGAGACUGACUUCCCACUGCUCUGCCUGCCUCUCCCCACUGCACUGGCACAGCC

CCGCCUUGCCGCUGCUGAUCCAUUGCCGGUGUGACC

>Rn5B8_For2 (SEQ ID NO: 13)
CUACCAUGGCCAGUCCUCCCUGAGUCUGACCAUCUUCCAUCCUGCUGCUGCUGCUGCUGC

UGCUGCGGGUCUUCCUGGAAUCUGACCAUUCGUUGUCUGCUAUGCCCGUCCUCACCAAGA

CUGACUGCCUGCUGCUUUGCUACUGCCCGGGCCCAUGAGACUGACUUCCCACUGCUCUGC

CUGCCUUUCCCCACUGCACUGGCACAGCCCCGCCUUGCCGCUGCUGAUCCAUUGCCGGUG

UGACC

>Rn6-1WoH9_For2 (SEQ ID NO: 14)
GUCCUCCCUGAGUCUGACCAUCUUCCAUCCUGCUGCUGCUGCUGCUGCUGCGGGUCU

UCCUGGAAUCUGACCAUUCGUUGUCUGCUAUGCCCGUCCUCACCAAGACUGACUGCCUGC

UGCUUUGCUACUGCCCGGGCCCAUGAGACUGACUUCCCACUGCUCUGCCUGCCUCUCCCC

ACUGCACUGGCACAGCCCCGCCUUGCCGCUGCUGAUCCAUUGCCGGUCUGACA

>Rn6-2WoC11_For2 (SEQ ID NO: 15)
GUCCUCCCUGAGUCUGACCAUCUUCCAUCCUGCUGCUGCUGCUGCUGCUGCUGCGGGUCU

UCCUGGAAUCUGACCAUUUGUUGUCUGCUAUGCCCCUCCUCACCAAGACUGACUGCCUGC

UGCUUUGCUACUGCCCGGGCCCAUGAGACUGACUUCCCACUGCUCUGCCUGCCUUCCCCA

CUGCACUGGCACAGCCCCGCCUUGCCGCUGCUGAUCCAUUGCCGGUGUGACC

>Rn5_C3_b (SEQ ID NO: 16)
CCAUCCUGCUGCUGCUGCUGCUGCUGCGGGUCUUCCUGGAAUCUGACCAUUCGUUGU

CUGCUAUGCCCGUCCUCACCAAGACUGACUGCCUGCUGCUUUGCUACUGCCCGGGCCCAUG

AGACUGACUUCCCACUGCUCUGCCUGCCUCUCCCCACUGCACUGGCACAGCCCCGCCUUG

CCGCUGCUGAUCCAUUGCCGGUGUGACC

>Rn6-2WoH5_For2 (SEQ ID NO: 17)
GCCAGUCCUCCCUGAGUCUGACCAUCUUCCAUCCUGCUGCUGCUGCUGCUGCUGCGG

GUCUUCCUGGAAUCUGACCAUUCGUUGUCUGCUAUGCCCGUCCUCACCAAGACUGACUGC

CUGCUGAUUUGCUACUGCCCGGGCCCAUGAGACUGACUUCCCACUGCUCUGCCUGCCUCU

CCCCACUGCACUGGCACAGCCCCGCCUUGCCGCUGCUGAUCCAUUGCCGGUGUGACC

>Rn6-96hE12_For2 (SEQ ID NO: 18)
UGCCUUCCGUCUCCUGCUGCUUCUGGCCUCACUGAGUCUGAAGAGCUGUUAACUACCAUG

GCCAGUCCUCCCUGAGUCUGACCAUCUUCCAUCCUGCUGCUGCUGCUGCUGCUGCUGCGG

GUCUUCCUGGAAUCUGACCAUUCGUUGUCUGCUAUGCCCGUCCUCACCAAGACUGACUGC

CUGCUGCUUUGCUACUGCCCGGGCCCAUGAGACUGACUUCCCACUGCUCUGCCUGCCUCU

CCCCACUGCACUGGCACAGCCCCGCCUUGCCGCUGCUGAUCCAUUGCCGGUGUGACC

>Rn6-96h-2pl-E9_F (SEQ ID NO: 19)
GGCCAGUCCUCCCUGAGUCUGACCAUCUUCCAUCCUGCUGCUGCUGCUGCUGCUGCUGCG

GGUCUUCCUGGAAUCUGACCAUUCGUUGUCUGCUAUGCCCGUCCUCACCAAGACUGACUG

CCUGCUGCUUUGCUACUGCCCGGGCCCAUGAGACUGACUUCCCACUGCUCUGCCUGCCUC

UCCCCACUGCACUGGCACAGCCCCGCCUUGCCGCUGCUGAUCCAUUGCCGGUGUGACC

>Rn6-96h-2pl-H10_ (SEQ ID NO: 20)
GGCCAGUCCUCCCUGAGUCUGACCAUCUUCCAUCCUGCUGCUGCUGCUGCUGCUGCUGCG

GGUCUUCCUGGAAUCUGACCAUUCGUUGUCUGCUAUGCCCGUCCUCACCAAGACUGACUG

CCUGCUGCUUUGCUACUGCCCGGGCCCAUGAGACUGACUUCCCACUGCUCUGCCUGCCUC

UCCCCACUGCACUGGCACAGCCCCGCCUUGCCGCUGCUGAUCCAUUGCCGGUGUGACC

>Rn6-1WoB11_For2 (SEQ ID NO: 21)
UGACCAUCUUCCAUCCUGCUGCUGCUGCUGCUGCUGCUGGGUCUUCCUGGAAUCUGAC

CAUUCGUUGUCUGCUAUGCCCGUCCUCACCAAGACUGACUGCCUGCUGCUUUGCUACUGC

CCGGGCCCAUGAGACUGACUUCCCACUGCUCUGCCUGCCUCUCCCCACUGCACUGGCACA

GCCCCGCCUUGCCGCUGCUGAUCCAUUGCCGGUGUGACC

>Rn6-1WoF7_For2 (SEQ ID NO: 22)
CCAGUCCUCCCUGAGUCUGACCAUCUUCCAUCCUGCUGCUGCUGCUGCUGCUGCUGCGGG

UCUUCCUGGAAUCUGACCAUUCGUUGUCUGCUAUGCCCGUCCUCACCAAGACUGACUGCC

UGCUGCUUUGCUACUGCCCGGGCCCAUGAGACUGACUUCCCUCUGCUCUGCCUGCCUCUC

CCCACUGCACUGGCACAGCCCCGCCUUGCCGCUGCUGAUCCAUUGCCUGUGUGACCA

>Rn6-1WoA7_For2 (SEQ ID NO: 23)
UGACCAUCUUCCAUCCUGCUGCUGCUGCUGCUGCGGGUCUUCCUGGAAUCUGACCAUUCG

UUGUCUGCUAUGCCCGUCCUUACCAAGACUGACUGCCUGCUGCUUUGCUACUGCCCGGGC

CCAUGAGACUGACUUCCCACUGCUCUGCCUGCCUCUCCCCACUGCACUGGCACAGCCCCG

CCUUGUCGCUGCUGAUCCAUUGCCGGUGUGACAC

>Rn6-2WoD11_b (SEQ ID NO: 24)
GACUGACUGCCUGCUGCUUUGCUACUGCCCGGGCCCAUGAGACUGACUUCCCACUGCUCU

GCCUGCCUCUCCCCACUGCACUGGCACAGCCCCGCCUUGCCGCUGCUGAUCCAUUGCCGG

UGUGACCC

>Rn6-2WoG3_For2 (SEQ ID NO: 25)
CUCCCUGAGUCUGACCAUCUUCCAUCCUGCUGCUGCUGCUGCUGCUGCGGGUCUUCC

UGGAAUCUGACCAUUCGUUGUCUGCUAUGCCCGUCCUCACCAAGACUGACUGCCUGCUGC

UUUGCUACUGCCCGGGCCCAUGAGACUGACUUCCCACUGCUCUGCCUGCCUCUCCCCACU

GCACUGGCACAGCCCCGCCUUGCCGCUGCUGAUCCAUUGCCGGUGUGACC

>Rn6-2WoC2_For2 (SEQ ID NO: 26)
UUCCAUCCUGCUGCUGCUGCUGCUGCUGCGGGUCUUCCUGGAAUCUGACCAUUCGUU

GUCUGCUAUGCCCGUCCUCACCAAGACUGACUGCCUGCUGCUUUGCUACUGCCCGGGCCC

AUGAGACUGACUUCCCACUGCUCUGCCUGCCUCUCCCCACUGCACUGGCACAGCCCCGCC

UUGCCGCUGCUGAUCCAUUGCCGGUGUGACC

>Rn6-1WoD6_For2 (SEQ ID NO: 27)
UGCCCGUCCUCACCAAGACUGACUGCCUGCUGCUUUGCUACUGCCCGGGCCCAUGAGACU

GACUUCCCACUGCUCUGCCUGCCUCUCCCCACUGCACUGGCACAGCCCCGCCUUGCCGCU

GCUGAUCCAUUGCCGGUGUGACC

>Rn6-1WoD10_For2 (SEQ ID NO: 28)
UGCCCGUCCUCACCAAGACUGACUGCCUGCUGCUUUGCUACUGCCCGGGCCCAUGAGACU

GACUUCCCACUGCUCUGCCUGCCUCUCCCCACUGCACUGGCACAGCCCCGCCUUGCCGCU

GCUGAUCCAUUGCCGGUGUGACC

>Rn6-2WoG5_For2 (SEQ ID NO: 29)
GCGGGUCUUCCUGGAAUCUGAACAUUCGUUGUCUGCUAUGCCCGUCCUCACCAAGACUGA

CUGCCUGCUGCUUUGCUACUGCCCGGGCCCAUGAGACUGACUUCCCACUGCUCUGCCUGC

CUCUCCCCACUGCACUGGCACAGCCCCGCCUUGCCGCUGCUGAUCCAUUGCCGGUGUGAC

C

>Rn6-96h-2p1-G8_F (SEQ ID NO: 30)
GUUGUCUGCUAUGCCCGUCCUCACCAAGACUGACUGCCUGCUGCUUUGCUACUGCCCGGG

CCCAUGAGACUGACUUCCCACUGCUCUGCCUGCCUCUCCCCACUGCACUGGCACAGCCCC

GCCUUGCCGCUGCUGAUCCAUUGCCGGUGUGACC

>Rn6-1WoE7_For2 (SEQ ID NO: 31)
CAAGACUGACUGCCUGCUGCUUUGCUACUGCCCGGGCCCAUGAGACUGACUUCCCACUGC

UCUGCCUGCCUCUCCCCACUGCACUGGCACAGCCCCGCCUUGCCGCUGCUGAUCCAUUGC

CGGUGUGACC

>Rn6-1Wo_A12_b (SEQ ID NO: 32)
CCUCACCAAGACUGACUGCCUGCUGCUUUGCUACUGCCCGGACCCAUGAGACUGACUUCC

CACUGCUCUGCCUGCCUCUCCCCACUGCACUGGCACAGCCCCGCCUUGCCGCUGCUGAUC

CAUUGCCGGUGUGACUGC

>Rn6-1WoG11_For2 (SEQ ID NO: 33)
CUUCCAUCCUGCUGCUGCUGCUGCUGCUGCGGGUCUUCCUGGAAUCUGACCAUUCGU

UGUCUGCUAUGCCCGUCCUCACCAAGACUGACUGCCUGCUGCUUUGCUACUGCCCGGGCC

CAUGAGACUGACUUCCCACUGCUCUGCCUGCCUCUCCCCACUGCACUGGCACAGCCCCGC

CUUGCCGCUGCUGAUCCAUUGCCGGUGUGACCCC

>Rn6-1WoH5_For2 (SEQ ID NO: 34)
CUCACCAAGACUGACUGCCUGCUGCUUUGCUACUGCCCGGGCCCAUGAGACUGACUUCCC

ACUGCUCUGCCUGCCUCUCCCCACUGCACUGGCACAGCCCCGCCUUGCCGCUGCUGAUCC

AUUGCCGGUGUGACC

>Rn6-1WoH4_For2 (SEQ ID NO: 35)
AAGACUGACUGCCUGCUGCUUUGCUACUGCCCGGGCCCAUGAGACUGACUUCCCACUGCU

CUGCCUGCCUCUCCCCACUGCACUGGCACAGCCCCGCCUUGCCGCUGCUGAUCCAUUGCC

GGUGUGACC

>Rn6-2WoB4_For2 (SEQ ID NO: 36)
CUCCAGCUCGCUUCCAUUUGCUUGCAGAAGUUCUCGCUGUGCUCACGAAGCUUGCGCUCC

UUGGAGGCCUCAGCAACAGCAUCAUCAAGCUGAGCUUCCAGCUCUUUCCUGAGCUUCUCA

GCUCUCCGCAUUUCCUGCCGCAUGGCGUCCACCUUCGCGUGGCCACCUCCAUCUCCUCC

UCCUUGUCUCGCAGCUGCCGGGACACCUUCUGCGCUAAGAUGGGAUACGGCAUUGAGGGA

UCAAUGUGUAAGGAUCCGAUCUGCUUCUGGCCUCACUGAGUCUGAAGAGCUGUUAACUAC

CAUGGCCAGUCCUCCCUGAGUCUGACCAUCUUCCAUCCUGCUGCUGCUGCUGCUGCUGCU

-continued
GCGGGUCUUCCUGGAAUCUGACCAUUCGUUGUCUGCUAUGUCCGUCCUCACCAAGACUGA

CUGCCUGCUGCUUUGCUACUGCCCGGGCCCAUGAGACUGACUUCCCACUGCUCUGCCUGC

CUCUCCCCACUGCACUGGCACAGCCCCGCCUUGCCGCUGCUGAUCCAUUGCCGGUGUGAC

C

>Rn6-96h-2pl-A5_F (SEQ ID NO: 37)
CUGACUGCCUGCUGCUUUGCUACUGCCCGGGCCCAUGAGACUGACUUCCCACUGCUCUGC

CUGCCUCUCCCCACUGCACUGGCACAGCCCCGCCUUGCCGCUGCUGAUCCAUUGCCGGUG

UGACC

>Rn6-1WoC8_For2 (SEQ ID NO: 38)
CCAAGACUGACUGCCUGCUGCUUUGCUACUGCCCGGGCCCAUGAGACUGACUUCCCACUG

CUCUGCCUGCCUCUCCCCACUGCACUGGCACAGCCCCGCCUUGCCGCUGCUGAUCCAUUG

ACGGUGUGACC

>Rn5D1_For2 (SEQ ID NO: 39)
UAACUACCAUGGCCAGUCCUCCCUGAGUCUGACCAUCUUCCAUCCUGCUGCUGCUGCUGC

UGCUGCGGGUCUUCCUGGAAUCUGACCAUUCGUUGUCUGCUAUGCCCGUCCUCACCAAGA

CUGACUGCCUGCUGCUUUGCUACUGCCCGGGCCCAUGAGACUGACUUCCCACUGCUCUGC

CUGCCUCUCCCCACUGCACUGGCACAGCCCCGCCUUGCCGCUGUUGAUCCAUUGCCGGUG

UGACC

>Rn6-2WoG10_For2 (SEQ ID NO: 40)
CCAAGACUGACUGCCUGCUGCUUUGCUACUGCCCGGGCCCAUGAGACUGACUUCCCACUG

CUCUGCCUGCCUCUCCCCACUGCACUGGCACAGCCCCGCCUUGCCGCUGUUGAUCCAUUG

UCGGUGUGACC

>Rn6-1Wo_E4_b (SEQ ID NO: 41)
CCAAGACUGACUGCCUGCUGCUUUGCUACUGCCCGGGCCCAUGAGACUGACUUCCCACUG

CUCUGCCUGCCUCUCCCCACUGCACUGGCACAGCCCCGCCUUGCCGCUGCUGAUCCAUUG

CCGGUGUGACC

>Rn6-2WoF3_For2 (SEQ ID NO: 42)
CUGCUAUGCCCGUCCUCACCAAGACUGACUGCCUGCUGCUUUGCUACUGCCCGGGCCCAU

GAGACUGACUUCCCACUGCUCUGCCUGCCUCUCCCCAAUGCACUGGCACAGCCCCGCCUU

GCCGCUGCUGAUCCAUUGCCGGUGUGACC

>Rn6-96h-2pl-B10 (SEQ ID NO: 43)
CUGCUAUGCCCGUCCUCACCAAGACUGACUGCCUGCUGCUUUGCUACUGCCCGGGCCCAU

GAGACUGACUUCCCACUGCUCUGCCUGCCUCUCCCCACUGCACUGGCACAGCCCCGCCUU

GCCGCUGCUGAUCCAUUGCCGGUGUGACC

>Rn6-96h-2pl-C10 (SEQ ID NO: 44)
GCUAUGCCCGUCCUCACCAAGACUGACUGCCUGCUGCUUUGCUACUGCCCGGGCCCAUGA

GACUGACUUCCCACUGCUCUGCCUGCCUCUCCCCACUGCACUGGCACAGCCCCGCCUUGC

CGCUGCUGAUCCAUUGCCGGUGUGACC

>Rn6-1WoB6_For2 (SEQ ID NO: 45)
UCUUCCUGGAAUCUGACCAUUCGUUGUCUGCUAUGCCCGUCCUCACCAAGACUGACUGCC

UGCUGCUUUGCUACUGCCCGGGCCCAUGAGACUGACUUCCCACUGCUCUGCCUGCCUCUC

CCCACUGCACUGGCACAGCCCCGCCUUGCCGCUGCUGAUCCAUUGCCGGUGUGACC

>Rn6-96h-2pl-D6_F (SEQ ID NO: 46)
CUGGAAUCUGACCAUUCGUUGUCUGCUAUGCCCGUCCUCACCAAGACUGACUGCCUGCUG

CUUUGCUACUGCCCGGGCCCAUGAGACUGACUUCCCACUGCUCUGCCUGCCUCUCCCCAC

UGCACUGGCACAGCCCCGCCUUGCCGCUGCUGAUCCAUUGCCGGUGUGACC

```
>Rn6-96h-2p1-E6_F (SEQ ID NO: 47)
CUGGAAUCUGACCAUUCGUUGUCUGCUAUGCCCGUCCUCACCAAGACUGACUGCCUGCUG

CUUUGCUACUGCCCGGGCCCAUGAGACUGACUUCCCACUGCUCUGCCUGCCUCUCCCCAC

UGCACUGGCACAGCCCCGCCUUGCCGCUGCUGAUCCAUUGCCGGUGUGACC

>Rn6-2WoF10_For2 (SEQ ID NO: 48)
GGAAUCUGACCAUUCGUUGUCUGCUAUGCCCGUCCUCACCAAGACUGACUGCCUGCUGCU

UUGCUACUGCCCGGGCCCAUGAGACUGACUUCCCACUGCUCUGCCUGCCUCUCCCCACUG

CACUGGCACAGCCCCGCCUUGCCGCUGCUGAUCCAUUGCCGGUGUGACC

>Rn6-1WoG9_For2 (SEQ ID NO: 49)
CCAAGACUGACUGCCUGCUGCUUUGCUACUGCCCGGGCCCAUGAGACUGACUUCCCACUG

CUCUGCCUGCCUCUCCCCACUGCACUGGCAUAGCCCCGCCUUGCCGCUGCUGAUCCAUUG

CCGGUGUGACC

>Rn6-96hC12_For2 (SEQ ID NO: 50)
CUUCCUGGAAUCUGACCAUUCGUUGUCUGCUAUGCCCGUCCUCACCAAGACUGACUGCCU

GCUGCUUUGCUACUGCCCGGGCCCAUGAGACUGACUUCCCACUGCUCUGCCUGCCUCUCC

CCACUGCACUGGCAUAGCCCCGCCUUGCCGCUGCUGAUCCAUUUCCGGUGUGACC

Group D
>Rn6-1WoF2_For2 (SEQ ID NO: 51)
CAGACACCCGCCCCCGGCCCUGGCUAAGAAUUUGCUUCCUGUUGCCAGCAUGACCUACC

CUCGCCUCUUUGAUGCCAUCCGCUGCCACCUCCUUUUGCUCCUGGACCCUUUAGCCUCUC

UGCCCUUCCACUCUCUGACC

>Rn6-2WoD8_For2 (SEQ ID NO: 52)
UUCCAGCCAGACACCCGCCCCCCGGCCCUGGCUAAGAAGUUGCUUCCUGUUGCCAGCAUG

ACCUACCCUCGCCUCUUUGAUGCCAUCCGCUGCCACCUCCUUUUGCUCCUGGACCCUUUA

GCCUCUCUGCCCUUCCACUCUCUGACCCC

>Rn6-1WoD5_For2 (SEQ ID NO: 53)
CUCGCUUCCUGGGUCUGCAGGUCCAGCCGGCUGGCACCCUCCAUGUACCCAGGGGAGAUU

CCAGCCAGACACCCGCCCCCCGGCCCUGGCUAAGAAGUUGCUUCCUGUUGCCAGCAUGAC

CUACCCUCGCCUCUUUGAUGCCAUCCGCUGCCACCUCCUUUUGCUCCUGGACCCUUUAGC

CUCUCUGCCCUUCCACUCUCUGACCACCGCCC

>Rn5-2p1-D3_For2 (SEQ ID NO: 54)
UCCAGCCAGACACCCGCCCCCCGGCCCUGGCUAAGAAGUUGCUUCCUGUUGCCAGCAUGA

CCUACCCUCGCCUCUUUGAUGCCAUCCGCUGCCACCUCCUUUUGCUCCUGGACCCUUUAG

CUUCUCUGCCCUUCCACUCUCUGG

>Rn6-2WoA8_For2 (SEQ ID NO: 55)
CGCUUCCUGGGUCUGCAGGUCCAGCCGGCUGGCACCCUCCACGUACCCAGGGGAGAUUCC

AGCCAGACACCCGCCCCCCGGCCCUGGCUAAGAAGUUGCUUCCUGUUGCCAGCAUGACCU

ACCCUCGCCUCUUUGAUGCCAUCCGCUGCCACCUCCUUUUGCUCCUGGACCCUUUAGCCU

CUCUGCCCUUCCACUCUCUGACCACCG

>Rn6-2WoD7_For2 (SEQ ID NO: 56)
CAUGUACCCAGGGGAGAUUCCAGCCAGACACCCGCCCCCCGGCCCUGGCUAAGAAGUUGC

UUCCUGUUGCCAGCAUGACCUACCCUCGCCUCUUUGAUGCCAUCCGCUGCCACCUCCUUU

UGCUCCUGGACCCUUUAGCCUCUCUGCCCUUCCACUCG

>Rn6-2WoB8_For2 (SEQ ID NO: 57)
CUCGCUUCCUGGGUCUGCAGGUCCAGCCGGCUGGCACCCUCCAUGUACCCAGGGGAGAUU

CCAGCCAGACACCCGCCCCCCGGCCCUGGCUAAGAAGUUGCUUCCUGUUGCCAGCAUGAC
```

CUACCCUCGCCUCUUUGAUGCCAUCCGCUGCCACCUCCUUUUGCUCCUGGACCCUUUAGC

CUCUCUGCCCCCCGAU

>Rn6-96h-2p1-H6_F (SEQ ID NO: 58)
CCCAGCUCCCUAGGCGUCCCAUCUCGCUUCCUGGGUCUGCAGGUCCAGCCGGCUGGCACC

CUCCAUGUACCCAGGGGAGAUUCCAGCCAGACACCCGCCCCCCGGCCCUGGCUAAGAAGU

UGCUUCCUGUUGCCAGCAUGACCUACCCUCGCCUCUUUGAUGCCAUCCGCUGCCACCUCC

UUUUGCUCCUGGACCCUUUAGCCUCUCUGCCCUUCCACUCUUUGACCCCCAUCUUA

>Rn6-96h-2p1-F10 (SEQ ID NO: 59)
GGCCACCGGGCAUGGGAAGUAUGAGAAGGUGCUUGUGGAAGGGGCCCGGCUCCCUAGGC

GUCCCAUCUCGCUUCCUGGGUCUGCAGGUCCAGCCGGCUGGCACCCUCCAUGUACCCAGG

GAGAUUCCAGCCAGACACCCGCCCCCCGGCCCUGGCUAAGAAGUUGCUUCCUGUUGCCAG

CAUGACCUACCCUCGCCUCUUUGAUGCCAUCCGCUGCCACCUCCUUUUGCUCCUGGACCC

UUUAGCCUCUCUGCCCUUCCACUCUCUGACCCC

>Rn5H3_For2 (SEQ ID NO: 60)
UGUACCCAGGGGAGAUUCCAGCCAGACACCCGCCCCCCGGCCCUGGCUAAGAAGUUGCUU

CCUGUUGCCAGCAUGACCUACCCUCGCCUCUUUGAUGCCAUCCGCUGCCACCUCCUUUUG

CUCCUGGACCCUUUAGCCUCUCUGCCCUUCCACUCUCUGACCACCACCCCC

>Rn5G7_For2 (SEQ ID NO: 61)
CCGGCCCUGGCUAAGAAGUUGCUUCCUGUUGCCAGCAUGACCUACCCUCGCCUCUUUGAU

GCCAUCCGCUGCCACCUCCUUUUGCUCCUGGACCCUUUAGCCUCUCUGCCCUUCCACUCU

CUGACCACAGCCCC

>Rn6-1WoG5_For2 (SEQ ID NO: 62)
CCCCGGCCCUGGCUAAGAAGUUGCUUCCUGUUGCCAGCAUGACCUACCCUCGCCUCUUUG

AUGCCAUCCGCUGCCACCUCCUUUUGCUCCUGGACCCUUUAGCCUCUCUGCCCUUCCACU

CUCUGACCACCGCCCCCGCC

>Rn6-1WoA8_For2 (SEQ ID NO: 63)
CCGGCUGGCACCCUCCAUGUACCCAGGGGAGAUUCCAGCCAGACACCCGCCCCCCGGCCC

UGGCUAAGAAGUUGCUUCCUGUUGCCAGCAUGACCUACCCUCGCCUCUUUGAUGCCAUCC

GCUGCCACCUCCUUUUGCUCCUGGACCCUUUAGCCUCUCUGCCCUUCCACUCUCUGACCA

CCGCCCCC

>Rn6-96h_D3_b (SEQ ID NO: 64)
GCCGGCUGGCACCCUCCAUGUACCCAGGGGAGAUUCCAGCCAGACACCCGCCCCCCGGCC

CUGGCUAAGAAGUUGCUUCCUGUUGCCAGCAUGACCUACCCUAGCCUCUUUGAUGCCAUC

CGCUGCCACCUCCUUUUUGCUCCUGGACCCUUUAGCCUCUCUGCCCUUCCACUCUCUGAC

CACCGCCCCC

>Rn6-96hC11_For2 (SEQ ID NO: 65)
UCCAGCCAGACACCCGCCCCCCGGCCCUGGCUAAGAAGUUGCUUCCUGUUGCCAGCAUGA

CCUACCCUCGCCUCUUUGAUGCCAUCCGCUGCCACCUCCUUUUGCUCCUGGACCCUUUAG

CCUCUCUGCCCUUCCACUCUCUGACCACCACCCCC

>Rn5H1_For2 (SEQ ID NO: 66)
GCCAGACACCCGCCCCCCGGCCCUGGCUAAGAAGUUGCUUCCUGUUGCCAGCAUGACCUA

CCCUCGCCUCUUUGAUGCCAUCCGCUGCCACCUCCUUUUGCUCCUGGACCCUUUAGCCUC

UCUGCCCUUCCACUCUCUGACCCCCC

>Rn6-1WoG2_For2 (SEQ ID NO: 67)
UCCAGCCAGACACCCGCCCCCGGCCCUGGCUAAGAAGUUGCUUCCUGUUGCCAGCAUGA

CCUACCCUCGCCUCUUUGAUGCCAUCCGCUGCCACCUCCUUUUGCUCCUGGACCCUUUAG

CCUCUCUGCCCUUCCACUCUCUGACCCCCC

>Rn6-1WoG7_For2 (SEQ ID NO: 68)
CGGCUCCCUAGGCGUCCCAUCUCGCUUCCUGGGUCUGCAGGUCCAGCCGGCUGGCACCCU

CCAUGUACCCAGGGGAGAUUCCAGCCAGACACCCGCCCCCGGCCCUGGCUAAGAAGUUG

CUUCCUGUUGCCAGCAUGACCUACCCUCGCCUCUUUGAUGCCAUCCGCUGCCACCUCCUU

UUGCUCCUGGACCCUUUAGCCUCUCUGCCCUUCCACUCUCUGACCACUGCCCC

>Rn6-96hB11_For2 (SEQ ID NO: 69)
UGCAGGUCCAGCCGGCUGGCACCCUCCAUGUACCCAGGGGAGAUUCCAGCCAGACACCCA

CCCCCCGGCCCUGGCUAAGAAGUUGCUCCUGUUGCCAGCAUGACCUACCCUCGCCUCUUU

GAUGCCAUCCGCUGCCACCUCCUUUUGCUCCUGGACCCUUUAGCCUCUCUGCCCUUCCAC

UCUCUGACCACUACCCC

>Rn6-2WoF8_For2 (SEQ ID NO: 70)
UUCCAGCCAGACACCCGCCCCCCGGCCCUGGCUAAGAAGUUGCUUCCUGUUGCCAGCAUG

ACCUACCCUCGCCUCUUUGAUGCCAUCCGCUGCCACCUCCUUUUGCUCCUGGACCCUUUA

GCCUCUCUGCCCUUCCACUCUCUGACCACUGCCCC

>Rn6-96h_A9_b (SEQ ID NO: 71)
CCCGCCCCCGGCCCUGGCUAAGAAGUUGCUUCCUGUUGCCAGCAUGACCUACCCUCGCC

UCUUUGAUGCCAUCCGCUGCCACCUCCUUUUGCUCCUGGACCCUUUAGCCUCUCUGCCCU

UCCACUCUCUGACC

>Rn6-1WoH3_For2 (SEQ ID NO: 72)
CAGCCAGACACCCGCCCCCGGCCCUGGCUAAGAAGUUGCUUCCUGUUGCCAGCAUGACC

UACCCUCGCCUCUUUGAUGCCAUCCGCUGCCACCUCCUUUUGCUCCUGGACCCUUUAGCC

UCUCUGCCCUUCCACUCUCUGAACACC

Group E
>Rn6-2WoE2_For2 (SEQ ID NO: 73)
GAGCCUACUCUGAUGACCGUGGCCUUGGCUCCUCCAGGAAGGCUCAGGAGCCCUACCUCC

CUGCCAUUAUAGCUGCUCCCCGCCAGAAGCCUGUGCCAACUCUCUGCAUUCCCUGAUCUC

CUGUGGCUGUCACCCUUGGUCACCUCCGUGCUGUCACUGCCAUCUCCCCCUGACCCCUC

GAACCCAUCCUA

>Rn6-1WoD3_For2 (SEQ ID NO: 74)
GAGCCUACUCUGAUGACCGUGGCCUUGGCUCCUCCAGGAAGGCUCAGGCGCCCUACCUCC

CUGCCAUUAUAGCUGCUCCCCGCCAGAAGCCUGUGCCAACUCUCUGCAUUCCCUGAUCUC

CAUCCCUGUGGCUGUCACCCUUGGUCACCUCCGUGCUGUCACUGCCAUCUCCCCCUGAC

CCCUCUAACCC

>Rn6-2WoG7_For2 (SEQ ID NO: 75)
GCCUACUCUGAUGACCGUGGCCUUGGCUCCUCCAGGAAGGCUCAGGAGCCCUACCUCCCU

GCCAUUAUAGCUGCUCCCCGCCAGAAGCCUGUGCCAACUCUCUGCAUUCCCUGAUCUCCA

UCCCUGUGGCUGUCACCCUUGGUCCACUGCCAUCUCCCCCCC

>Rn6-2WoH2_For2 (SEQ ID NO: 76)
GAGCCUACUCUGAUGACCGUGGCCUUGGCUCCUCCAGGAAGGCUCAGGAGCCCUACCUCC

CUGCCAUUAUAGCUGCUCCCCGCCAGAAGCCUGUGCCAACUCUCUGCAUUCCCUGAUCUC

CAUCCCUGUGGCUGUCACCCUUGGUCACCUCCGUGCUGUUACUGCCAUCUCCCCCCUGAC

CCC

```
>Rn6-2WoC1_For2 (SEQ ID NO: 77)
GAAGAGCCUACUCUGAUGACCGUGGCCUUGGCUCCUCCAGGAAGGCUCAGGAGCCCUACC

UCCCUGCCAUUAUAGCUGCUCCCCGCCAGAAGCCUGUGCCAACUCUCUGCAUUCCCUGAU

CUCCAUCCCUGUGGCUGUCAUCCUUGGUCACCUCCGUGCUGUCACUGCCAUCUCCCCCCU

GACCCCUCUAACCCAUCCUCUGCCUCCCUCCCUGCAGUCAGAGGGUCCUGUUCCCAACCA

>Rn6-1Wo_C12_b (SEQ ID NO: 78)
UGUGGCUUGGCUCCUCCAGGAAGGCUAAGGAGCCCUACCUCCCUGCCAUUAUAGCUGCU

CCCCGCCAGAAGCCUGUGCCAACUCUCUGCAUUCCCUGAUCUCCAUCCCUGUGGCUGUCA

CCCUUGGUCACCUCCGUGCUGUCACUGCCAUCUCCCCCCUGACCCC

>Rn6-1WoE12_For2 (SEQ ID NO: 79)
GCCUUGGCUCCUCCAGGAAGGCUCAGGAGCCCUACCUCCCUGCCAUUAUAGCUGCUCCCC

GCCAGAAGCCUGUGCCAACUCUCUGCAUUCCCUGAUCUCCAUCCCUGUGGCUGUCACCCU

UGGUCACCUCCGUGCUGUCACUGCCAUCUCCCCCC

>Rn6-2WoF5_For2 (SEQ ID NO: 80)
AGAGCCUACUCUGAUGACCGUGGCCUUGGCUCCUCCAGGAAGGCUCAGGAGCCCUACCUC

CCUGCCAUUAUAGCUGCUCCCCGCCAGAAGCCUGUGCCAACUCUCUGCAUUCCCUGAUCU

CCAUCCCUGUGGCUGUCACCCUUGGUCACCUCCGUGCUGUCACUGCCAUCUCCCCCCUGA

CCCCUCUAACCCAUCCUCUGCCUCCCUCCCUGCAGUCAGAGGGUCCUGUUCCCAUCAGCG

AUUCCCCUGCUUAAACCCUUCCAUGACUCCCCACUGCCCUAAGCUGAGGUCAGUCUCCCA

AGCCUGACAU

>Rn5-2pl-H3_For2 (SEQ ID NO: 81)
UAUAGCUGCUCCCCGCCAGAAGCCUGUGCCAACUCUCUGCAUUCCCUGAUCUCCAUCCCU

GUGGCUGUCACCCUUGGUCACCUCCGUGCUGUCACUGCCAUCUCCCCCCUGACCCCUCUA

ACCCAUCCUCUGCCUCCCUCCCUGCAGUCAGAGGGUCCUGUUCCCAUCAGCGAUUCCCCU

GCUUAAACCCUUCCAUGACAGCCC

>Rn6-2WoA3_For2 (SEQ ID NO: 82)
UCUGCAUUCCCUGAUCUCCAUCCCUGUGGCUGUCACCCUUGGUCACCUCCGUGCUGUCAC

UGCCAUCUCCCCCCUGACCCCUCUAACCCAUCCUCUGCCUCCCUCCCUGCAGUCAGAGGG

UCCUGUUCCCAUCAGCGAUUCCCCUGCUUAAGCCCUUCCAUGACUCCCC

>Rn6-96hF12_For2 (SEQ ID NO: 83)
CUCCCUGCCAUUAUAGCUGCUCCCCGCCAGAAGCCUGUGCCAACUCUCUGCAUUCCCUGA

UCUCCAUCCCUGUGGCUGUCACCCUUGGUCACCUCCGUGCUGUCACUGCCAUCUCCCCCC

UGACCCCUCUAACCCAUCCUCUGCCUCCCUCCCUGCAGUCAGAGGGUCCUGUUCCCAUCA

GCGAUUCCCCUGCUUAAACCCUUCCAUGACUCCCCAA

>Rn6-96hE11_For2 (SEQ ID NO: 84)
GCCUACUCUGAUGACCGUGGCCUUGGGUCCUCCAGGAAGGCUCAGGAGCCCUACCUCCCU

GCCAUUAUAGCUGCUCCCCGCCAGAAGUCUGUGCCAACUCUCUGCAUUCCCUGAUCUCCA

UCCCUGUGGCUGUCACCCUUGGUCACCUCCGUGCUGUCACUGCCAUCUCCCCCCUGACCC

CUCUAACCCAUCCUCUGCCUCCCUCCCUGCAGUCAGAGGGUCCUGUUCCCAUCAGCGAUU

CCCCUGCUUAAACCCUUCCAUGACUCCCCUCU

>Rn6-96h-2pl-A11 (SEQ ID NO: 85)
CUACCUCCCUGCCAUUAUAGCUGCUCCCCGCCAGAAGCCUGUGCCAACUCUCUGCAUUCC

CUGAUCUCCAUCCCUGUGGCUGUCACCCUUGGUCACCUCCGUGCUGUCACUGCCAUCUCC

CCCCUGACCCC
```

-continued

Group F
>Rn6-1WoB5_For2 (SEQ ID NO: 86)
CUGGUACUGCAUGCACGCAAUGCUAGCUGCCCCUUUCCCGUCCUGGGUACCCCGAGUCUC

CCCCGACCUCGGGUCCCAGGUAUGCUCCCACCUCCACCUGCCCCACUCACCACCUCUGCU

AGUUCCAGACACCUCC

>Rn6-2WoE11_a (SEQ ID NO: 87)
CCGGCCCUUCCCCCGUUUUGAACAUGUGUAACCGACAGUCUGCCUGGGCCACAGCCCUCU

CACCCUGGUACUGCAUGCACGCAAUGCUAGCUGCCCCUUUCCCGUCCUGGGCACCCCGAG

UCUCCCCCGACCCCGGGUCCCAGGUAUGCUCCCACCUCCACCUGCCCCACUCACCACCUC

UGCUAGUUCCAGACACCCCCGCG

>Rn6-96h_E3_b (SEQ ID NO: 88)
CCUUCCCCCGUUUUGAACAUGUGUAACCGACAGUCUGCCUGGGCCACAGCCCUCUCACCC

UGGUACUGCAUGCACGCAAUGCUAGCUGCCCCUUUCCCGCCCUGGGCACCCCGAGUCUCC

CCCGACCCCGGGUCCCAGGUAUGCUCCCACCUCCACCUGCCCCACUCACCACCUCUGCUA

GUUCCAGACACCUCCAC

>Rn6-96h-2p1-B6_F (SEQ ID NO: 89)
UCUGCCUGGGCCACAGCCCUCUCACCCUGGUACUGCAUGCACGCAAUGCUAGCUGCCCCU

UUCCCGUCCUGGGCACCCCGAGUCUCCCCCGACCCCGGGUCCCAGGUAUGCUCCCACCUC

CACCUGCCCCACUCACCACCUCUGCUAGUUCCAGACACCUCCACGCCCACCUGGUCCUCU

CCCAUCGCCCACAAAAGGGGGGCACGAGGGACGAGCUUAGCUGAGCUGGGAGGAGCAGG

GUGAGGGUGGGCGACCCAGGAUUCCCCCACCCC

Group G
>Rn5_D5_b (SEQ ID NO: 90)
UGACACCUCAGCUGACAGCGUGGGCAACGCCUGCCGCCUGCUCUGAGGCCCGAUCCAGUG

GGCAGGCCAAGGCCUGCUGGGCCCCCGCGGACCCAGGUGCUCUGGGUCACGGUCCCUGUC

CCCGCACCCCCGCUUCUGUCUGCCCCAUUGUGGCUCCUCAGGCUCUCUCCCCUGCUCUCC

CACCUCUACCUCCACCCCA

>Rn5B2_For2 (SEQ ID NO: 91)
CUCAGCUGACAGCGUGGGCAACGCCUGCCGCCUGCUCUGAGGCCCGAUCCAGUGGGCAGG

CCAAGGCCUGCUGGGCCCCCGCGGACCCAGGUGCUCUGGGUCACGGUCCCUGUCCCCGCA

CCCCCGCUUCUGUCUGCCCCAUUGUGGCUCCUCAGGCUCUCUCCCCUGCUCUCCCACCUC

UACCUCCACUCCC

>Rn5G3_For2 (SEQ ID NO: 92)
UCUGAGGCCCGAUCCAGUGGGCAGGCCAAGGCCUGCUGGGCCCCCGCGGACCCAGGUGCU

CUGGGUCACGGUCCCUGUCCCCGCACCCCCGCUUCUGUCUGCCCCAUUGUGGCUCCUCAG

GCUCUCUCCCCUGCUCUCCCACCUCUACCUCCACCCCC

>Rn6-96hF11_For2 (SEQ ID NO: 93)
GGCCCGAUCCAGUGGGCAGGCCAAGGCCUGCUGGGCCCCCGCGGACCCAGGUGCUCUGGG

UCACGGUCCCUGUCCCCGCACCCCCGCUUCUGUCUGCCCCAUUGUGGCUCCUCAGGCUCU

CUCCCCUGCUCUCCCACCUCUACCUCCACCCCC

>Rn6-96h-2p1-D8_F (SEQ ID NO: 94)
GCCUGCUGGGCCCCCGCGGACCCAGGUGCUCUGGGUCACGGUCCCUGUCCCCGCACCCCC

GCUUCUGUCUGCCCCAUUGUGGCUCCUCAGGCUCUCUCCCCUGCUCUCCCACCUCUACCU

CCGCCCCC

>Rn5C4_For2 (SEQ ID NO: 95)
CGCGGACCCAGGUGCUCUGGGUCACGGUCCCUGUCCCCGCACCCCCGCUUCUGUCUGCCC

CAUUGUGGCUCCUUAGGCUCUCUCCCCUGCUCUCCCACCUUUACCUCCACCCCUAC

>Rn6-2WoD3_For2 (SEQ ID NO: 96)
CUGACAGCGUGGGCAACGCCUGCCGCCUGCUCUGAGGCCCGAUCCAGUGGGCAGGCCAAG

GCCUGCUGGGCCCCGCGGACCCAGGUGCUCUGGGUCACGGUCCCUGUCCCCGCACCCCC

GCUUCUGUCUGCCCAUUGUGGCUCCUCAGGCUCUCUCCCCUGCUCUCCCACCUCUACCU

CCACCCCCAC

>Rn6-96h-2p1-C6_F (SEQ ID NO: 97)
CUGACAGCGUGGGCAACGCCUGCCGCCUGCUCUGAGGCCCGAUCCAGUGGGCAGGCCAAG

GCCUGCUGGGCCCCGCGGACCCAGGUGCUCUGGGUCACGGUCCCUGUCCCCGCACCCCC

GCUUCUGUCUGCCCAUUGUGGCUCCUCAGGCUCUCUCCCCUGCUCUCCCACCUCUACCU

CCACCCCCAAC

>Rn6-96h-2p1-C7_F (SEQ ID NO: 98)
CUGACAGCGUGGGCAACGCCUGCCGCCUGCUCUGAGGCCCGAUCCAGUGGGCAGGCCAAG

GCCUGCUGGGCCCCGCGGACCCAGGUGCUCUGGGUCACGGUCCCUGUCCCCGCACCCCC

GCUUCUGUCUGCCCAUUGUGGCUCCUCAGGCUCUCUCCCCUGCUCUCCCACCUCUACCU

CCACCCCCAAC

>Rn6-96h-2p1-F8_F (SEQ ID NO: 99)
CGUGGGCAACGCCUGCCGCCUGCUCUGAGGCCCGAUCCAGUGGGCAGGCCAAGGCCUGCU

GGGCCCCGCGGACCCAGGUGCUCUGGGUCACGGUCCCUGUCCCCGCACCCCCGCUUCUG

UCUGCCCCAUUGUGGCUCCUCAGGCUCUCUCCCCUGCUCUCCCACCUCUACCUCCACCCA

CACC

>Rn6-96hH9_For2 (SEQ ID NO: 100)
UCCUGAGGGACUGGGACUCCCCUUACAGCCAUGACCUUGACACCUCAGCUGACAGCGUGG

GCAACGCCUGCCGCCUGCUCUGAGGCCCGAUCCAGUGGGCAGGCCAAGGCCUGCUGGGCC

CCCGCGGACCCAGGUGCUCUGGGUCACGGUCCCUGUCCCCGCACCCCCGCUUCUGUCUGC

CCCAUUGUGGCUCCUCAGGCUCUCUCCCCUGCUCUCCCACCUCUACCUCCACGCCCAC

>Rn5_F10_b (SEQ ID NO: 101)
CUGAGGGACUGGGACUCCCCUUACAGCCAUGACCUUGACACCUCAGCUGACAGCGUGGGC

AACGCCUGCCGCCUGCUCUGAGGCCCGAUCCAGUGGGCAGGCCAAGGCCUGCUGGGCCCC

CGCGGACCCAGGUGCUCUGGGUCACGGUCCCUGUCCCCGCACCCCCGCUUCUGUCUGCCC

CAUUGUGGCUCCUCAGGCUCUCUCCCCUGCUCUCCCACCUCUACCUCCACACCU

>Rn6-2WoF11_For2 (SEQ ID NO: 102)
UGCGGAGCCAGCUGGAGGCCAUUUUCCUGAGGGACUGGGACUCCCCUUACAGCCAUGACC

UUGACACCUCAGCUGACAGCGUGGGCAACGCCUGCCGCCUGCUCUGAGGCCCGAUCCAGU

GGGCAGGCCAAGGCCUGCUGGGCCCCGCGGACCCAGGUGCUCUGGGUCACGGUCCCUGU

CCCCGCACCCCCGCUUCUGUCUGCCCCAUUGUGGCUCCUCAGGCUCUCUCCCCUGCUCUC

CCACCUCUACCUCCACCC

>Rn6-1WoA9_For2 (SEQ ID NO: 103)
CUGGAGGCCAUUUUCCUGAGGGACUGGGACUCCCCUUACAGCCAUGACCUUGACACCUCA

GCUGACAGCGUGGGCAACGCCUGCCGCCUGCUCUGAGGCCCGAUCCAGUGGGCAGGCCAA

GGCCUGCUGGGCCCCGCGGACCCAGGUGCUCUGGGUCACGGUCCCUGUCCCCGCACCCCC

GCUUCUGUCUGCCCCAUUGUGGCUCCUCAGGCUCUCUCCCCUGCUCUCCCACCUCUACC

UCCCCCCAC

>Rn6-1WoF9_For2 (SEQ ID NO: 104)
CUGGGACUCCCCUUACAGCCAUGACCUUGACACCUCAGCUGACAGCGUGGGCAACGCCUG

CCGCCUGCUCUGAGGCCCAAUCCAGUGGGCAGGCCAAGGCCUGCUGGGCCCCCGCGGACC

CAGGUGCUCUGGGUCACGGUCCCUGUCCCCGCACCCCCGCUUCUGUCUGCCCCAUUGUGC

CUCCUUAGGCUCUCUCCCCUGCUCUCCCACCUCUACCUCCACCCCC

Group I
>Rn5_A7_b (SEQ ID NO: 105)
GCAGCAAUGCAGCUCAAAACGCUUAGCCUAGCCACACCCCCACGGUAAACAGCAGUGAUU

AACUUUUAGCAAUAAACGAAAGUUUAACUAAGCUAUACUAACCCCAGGGUUGGUCAAUUU

CGUGCCAGCCACC

>Rn5_B6_b (SEQ ID NO: 106)
CUUUCUAUUAGCUCUUAGUAAGAUUACACAUGCAAGCAUCCCCGUUCCAGUGAGUUCACC

CUCUAAAUCACCACGAUAAAAAGGGACAAGCAUCAAGCACGCAGCAAUGCAGCUCAAAAC

GCUUAGCCUAGCCACACCCCCACGGGAAACAGCAGUGAUUAACCUUUAGCAAUAAACGAA

AGUUUAACUAAGCUAUACUAACCCCAGGGUUGGUCAAUUUCGUGCCAGCUACC

>Rn5D4_For2 (SEQ ID NO: 107)
GUUCCAGUGAGUUCACCCUCUAAAUCACCACGAUCAAAAGGGACAAGCAUCAAGCACGCA

GCAAUGCAGCUCAAAACGCUUAGCCUAGCCACACCCCCACGGGAAACAGCAGUGAUUAAC

CUUUAGCAAUAAACGAAAGUUUAACUAAGCUAUACUAACCCCAGGGUUGGUCAAUUUCGU

GCCAGCCACC

>Rn5D2_For2 (SEQ ID NO: 108)
AAAGGGACAAGCAUCAAGCACGCAGCAAUGCAGCUCAAAACGCUUAGCCUAGCCACACCC

CCACGGGAAACAGCAGUGAUUAACCUUUAGCAAUAAACGAAAGUUUAACUAAGCUAUACU

AACCCCAGGGUUGGUCAAUUUCGUGCCAGCCACC

>Rn6-1Wo_D7_b (SEQ ID NO: 109)
UCAAAAGGGACAAGCAUCAAGCACGCAACAAUGCAGCUCAAAAACGCUUAGCCUAGCCAC

ACCCCCACGGGAAACAGCAGUGAUUAACCUUUAGCAAUAAACGAAAGUUUAACUAAGCUA

CACUAACCCCAGGGUUGGUCAAUUUCGUGCCAGCCACC

>Rn6-96h-2pl-A9_F (SEQ ID NO: 110)
UACACAUGCAAGCAUCCCCGUUCCAGUGAGUUCACCCUCUAAAUCACCACGAUCAAAAGG

GACAAGCAUCAAGCACGCAGCAAUGCAGCUCAAAAACGCUUAGCCUAGCCACACCCCCAC

GGGAAACAGCAGUGAUUAACCUUUAGCAAUAAACGAAAGUUUAACUAAGCUAUACUAACC

CCAGGGUUGGUCAAUUUCGUGCCAGCCACC

>Rn6-2WoH3_For2 (SEQ ID NO: 111)
CAUCAAGCACGCAGCAAUGCAGCUCAAAACGCUUAGCCUAGCCACACCCCCACGGGAAAC

AGCAGUGAUUAACCUUUAGCAAUAAACGAAAGUUUAACUAAGCUAUACUAACCCCAGGGU

UGGUCAAUUUCGUGCCAACCACC

>Rn6-96hG11_For2 (SEQ ID NO: 112)
AAAGGGACAAGCAUCAAGCACGCAGCAAUGCAGCUCAAAACGCUUAGCCUAGCCACACCC

CCACGGGAAACAGCAGUGAUUAACCUUUAGCAAUAAACGAAAGUUUAACUAAGCUAUACU

AACCCCAGGGUUGGUCAAUUUCGUGCCAACCACC

>Rn5E1_For2 (SEQ ID NO: 113)
CAAGCACGCAACAAUGCAGCUCAAAACGCUUAGCCUAGCCACACCCCCACGGGAAACAGC

AGUGAUUAACCUUUAGCAAUAAACGAAAGUUUAACUAAGCUAUACUAACCCCAGGGUUGG

UCAAUUUCGUGCCAACCACC

-continued

>Rn6-1WoA11_For2 (SEQ ID NO: 114)
CAUCAAGCACGCAGCAAUGCAGCUCAAAACGCUUAGCCUAGCCACACCCCCAUGGGAAAC

AGCAGUGAUUAACCUUUAGCAAUAAACGAAAGUUUAACUAAGCUAUACUAACCCCAGGGU

UGGUCAAUUUCGUGCCAGCUCACC

>Rn6-2WoE7_For2 (SEQ ID NO: 115)
CAAGCACGCAGCAAUGCAGCUCAAAACGCUUAGCCUAGCCACACCCCCACGGGAAACAGC

AGUGAUUAACCUUUAGCAAUAAACGAAAGUUUAACUAAGCUAUACUAACCCCAGGGUUGG

UCAAUUUCGUGCCAGCCACACC

>Rn6-96h-2p1-B5_F (SEQ ID NO: 116)
CAAGCACGCAGCAAUGCAGCUCAAAACGCUUAGCCUAGCCACACCCCCACGGGAAACAGC

AGUGAUUAACCUUUAGCAAUAAACGAAAGUUUAACUAAGCUAUACUAACCCCAGGGUUGG

UCAAUUUCGUGCCAGCCACC

>Rn5H2_For2 (SEQ ID NO: 117)
CACGAUCAAAAGGGACAAGCAUCAAGCACGCAGCAAUGCAGCUCAAAACGCUUAGCCUAG

CCACACCCCCACGGGAAACAGCAGUGAUUAACCUUUAGCAAUAAACGAAAGUUUAACUAA

GCUAUACUAACCCCAGGGUUGGUCAAUUUCGUGCCAGCCACC

>Rn6-1WoF11_For2 (SEQ ID NO: 118)
UAAAUCACCACGAUCAAAAGGGACAAGCAUCAAGCACGCAGCAAUGCAGCUCAAAACGCU

UAGCCUAGCCACACCCCCACGGGAAACAGCAGUGAUUAACCUUUAGCAAUAAACGAAAGU

UUAACUAAGCUAUACUAACCCCAGGGUUGGUCAAUUUCGUGCCAGCCACC

>Rn6-2WoB11_For2 (SEQ ID NO: 119)
AGCCUUUCUAUUAGCUCUUAGUAAGAUUACACAUGCAAGCAUCCCCGUUCCAGUGAGUUC

ACCCUCUAAAUCACCACGAUCAAAAGGGACAAGCAUCAAGCACGCAGCAAUGCAGCUCAA

AACGCUUAGCCUAGCCACACCCCCACGGGAAACAGCAGUGAUUAACCUUUAGCAAUAAAC

GAAAGUUUAACUAAGCUAUACUAACCCCAGGGUUGGUCAAUUUCGUGCCAGCCACC

>Rn6-1WoA3_For2 (SEQ ID NO: 120)
GGGACAAGCAUCAAGCACGCAGCAAUGCAGCUCAAAACGCUUAGCCUAGCCACACCCCCA

CGGGAAACAGCAGUGAUUAACCUUUAGCAAUAAACGAAAGUUUAACUAAGCUAUACUAAC

CCCAGGGUUGGUCAAUUUCGUGCCAGCCACC

>Rn6-1Wo_D2_b (SEQ ID NO: 121)
GGGACAAGCAUCAAGCACGCAGCAAUGCAGCUCAAAACGCUUAGCCUAGCCACACCCCCA

CGGGAAACAGCAGUGAUUAACCUUUAGCAAUAAACGAAAGUUUAACUAAGCUAUACUAAC

CCCAGGGUUGGUCAAUUUCGUGCCAGCCACC

Group J
>Rn5A1_For2 (SEQ ID NO: 122)
UUCUGCCCCAGCUUUGCAGGAUGAAACACUUCCCCGCUUGGCUCUCAUUCUUCCACAAGA

GAGACCUUUCUCCGGACCUGGUUGCUACUGGUUCAGCAACUCUGCAGAAAAUGUCCUCCC

CUGUGGCUGCCUCAGCUCAUGCCUUUGGCCUGAAGUCCCAGCAUUGAUGGCAGCCCCUCA

UCUUCCAAGUUUUGUGCUCCCCUUUACCUAACGCUUCCUGCCUCCCAUGCAUCUGUACUC

CUUCUGUGCCACU

>Rn5B1_For2 (SEQ ID NO: 123)
UUCUGCCCCAGCUUUGCAGGAUGAAACACUUCCCCGCUUGGCUCUCAUUCUUCCACAAGA

GAGACCUUUCUCCGGACCUGGUUGCUACUGGUUCAGCAACUCUGCAGAAAAUGUCCUCCC

CUGUGGCUGCCUCAGCUCAUGCCUUUGGCCUGAAGUCCCAGCAUUGAUGGCAGCCCCUCA

UCUUCCAAGUUUUGUGCUCCCCUUUACCUAACGCUUCCUGCCUCCCAUGCAUCUGUACUC

CUUCUGUGCCACU

```
>Rn5_A10_b (SEQ ID NO: 124)
CCCCAGCUUUGCAGGAUGAAACACUUCCCCGCUUGGCUCUCAUUCUUCCACAAGAGAGAC
CUUUCUCCGGACCUGGUUGCUACUGGUUCAGCAACUCUGCAGAAAAUGUCCUCCCCUGUG
GCUGCCUCAGCUCAUGCCUUUGGCCUGAAGUCCCAGCAUUGAUGGCAGCCCCUCAUCUUC
CAAGUUUUGUGCUCCCCUUUACCUAACGCUUCCUGCCUCCCAUGCAUCUGUACUCCUCCU
GUGCCACAAA

>Rn5_G1_b (SEQ ID NO: 125)
CCCCAGCUUUGCAGGAUGAAACACUUCCCCGCUUGGCUCUCAUUCUUCCACAAGAGAGAC
CUUUCUCCGGACCUGGUUGCUACUGGUUCAGCAACUCUGCAGAAAAUGUCCUCCCCUGUG
GCUGCCUCAGCUCAUGCCUUUGGCCUGAAGUCCCAGCAUUGAUGGCAGCCCCUCAUCUUC
CAAGUUUUGUGCUCCCCUUUACCUAACGCUUCCUGCCUCCCAUGCAUCUGUACUCCUCCU
GUGCCACAAA

>Rn6-1WoF5_For2 (SEQ ID NO: 126)
CUUUGCAGGAUGAAACACUUCCCCGCUUGGCUCUCAUUCUUCCACAAGAGAGACCUUUCU
CCGGACCUGGUUGCUACUGGUUCAGCAACUCUGCAGAAAAUGUCCUCCCCUGUGGCUGCC
UCAGCUCAUGCCUUUGGCCUGAAGUCCCAGCAUUGAUGGCAGCCCCUCAUCUUCCAAGUU
UUGUGCUCCCCUUUACCUAACGCUUCCUGCCUCCCAUGCAUCUGUACUCCUCC

>Rn6-2WoA5_For2 (SEQ ID NO: 127)
UGCAGGAUGAAACACUUCCCCGCUUGGCUCUCAUUCUUCCACAGGAGAGACCUUUCUCCG
GACCUGGUUGCUACUGGUUCAGCAACUCUGCAGAAAAUGUCCUCCCCUGUGGCUGCCUCA
GCUCAUGCCUUUGGCCUGAAGUCCCAGCAUUGAUGGCAGCCCCUCAUCUUCCAAGUUUUG
UGCUCCCCUUUACCUAACGCUUCCUGCCUCCCAUGCAUCUGUACUCCA

>Rn6-2WoA7_For2 (SEQ ID NO: 128)
GUGAAGAUGACCACAUUCAAGGAAGAACCUUCUGCCCCAGCUUUGCAGGAUGAAACACUU
CCCCGCUUGGCUCUCCUUCUUCCACAAGAGAGACCUUUCUCCGGACCUGGUUGCUACUGG
UUCAGCAGCUCUGCAGAAAAUGUCCUCCCUUGUGGCUGCCUCAGCUCGUACCUUUGGCCU
GAAGUCCCAGCAUUAAUGGCAGCCCCUCAUCUUCCAAGUUUUGUGCUCCCCUUUACCUAA
UGCUUCCUGCCUCCCAUGCAUCUGUACUCCUGCUGUGCCA

>Rn6-2WoG2_For2 (SEQ ID NO: 129)
UCCACAAGAGAGACCUUUCUCCGGACCUGGCUGCUACUGGUUCAGCAGCUCUGCAGAAAA
UGUCCUCCCUUGUGGCUGCCUCAGCUCGUACCUUUGGCCUGAAGUCCCAGCAUUAAUGGC
AGCCCCUCAUCUUCCAAGUUUUGUGCUCCCCUUUACCUAAUGCUUCCUGCCUCCCAUGCA
UCUGUACUCCUGCUGUGCCACAAACAC

>Rn6-2WoH10_For2 (SEQ ID NO: 130)
UCCACAAGAGAGACCUUUCUCCGGACCUGGCUGCUACUGGUUCAGCAGCUCUGCAGAAAA
UGUCCUCCCUUGUGGCUGCCUCAGCUCGUACCUUUGGCCUGAAGUCCCAGCAUUAAUGGC
AGCCCCUCAUCUUCCAAGUUUUGUGCUCCCCUUUACCUAAUGCUUCCUGCCUCCCAUGCA
UCUGUACUCCUGCUGUGCCACAAACAC

>Rn6-96h-2pl-G7_F (SEQ ID NO: 131)
GCUACUGGUUCAGCAGCUCUGCAGAAAAUGUCCUCCCUUGUGGCUGCCUCAGCUCGUACC
UUUGGCCUGAAGUCCCAGCAUUAAUGGCAGCCCCUCAUCUUCCAAGUUUUGUGCUCCCCU
UUACCUAAUGCUUCCUGCCUCCCAUGCAUCUGUACUCCUGCGU

>Rn5-2pl-B2_For2 (SEQ ID NO: 132)
AGAACCUUCUGCCCCAGCUUUGCAGGAUGAAACACUUCCCCGCUUGGCUCUCAUUCUUCC
ACAAGAGAGACCUUUCUCCGGACCUGGUUGCUACUGGUUCAGCAGCUCUGCAGAAAAUGU
```

-continued

CCUCCCUUGUGGCUGCCUCAGCUCGUACCUUUGGCCUGAAGUCCCAGCAUUAAUGGCAGC

CCCUCAUCUUCCAAGUUUUGUGCUCCCCUUUACCUAAUGCUUCCUGCCUCCCAUGCAUCU

GUACUCCUG

>Rn5-2pl-D1_For2 (SEQ ID NO: 133)
AGAACCUUCUGCCCCAGCUUUGCAGGAUGAAACACUUCCCCGCUUGGCUCUCAUUCUUCC

ACAAGAGAGACCUUUCUCCGGACCUGGUUGCUACUGGUUCAGCAGCUCUGCAGAAAAUGU

CCUCCCUUGUGGCUGCCUCAGCUCGUACCUUUGGCCUGAAGUCCCAGCAUUAAUGGCAGC

CCCUCAUCUUCCAAGUUUUGUGCUCCCCUUUACCUAAUGCUUCCUGCCUCCCAUGCAUCU

GUACUCCUG

>Rn6-1WoA5_For2 (SEQ ID NO: 134)
UGAAGAUGACCACAUUCAAGGAAGAACCUUCUGCCCCAGCUUUGCAGGAUGAAACACUUC

CCCGCUUGGCUCUCAUUCUUCCACAAGAGAGACCUUUCUCCGGACCUGGUUGUUCAGCAG

CUCUGCAGAAAAUGUCCUCCCUUGUGGCUGCCUCAGCUCGUACCUUUGGCCUGAAGUCCC

AGCAUUAAUGGCAGCCCCUCAUCUUCCAAGUUUUGUGCUCCCCUUUACCUAAUGCUUCCU

GCCUCCCAUGCAUCUGUACUCCUG

>Rn6-1Wo_G10_b (SEQ ID NO: 135)
UGAAGAUGACCACAUUCAAGGAAGAACCUUCUGCCCCAGCUUUGCAGGAUGAAACACUUC

CCCGCUUGGCUCUCAUUCUUCCACAAGAGAGACCUUUCUCCGGACCUGGUUGCUACUGGU

UCAGCAGCUCUGCAGAAAAUGUCCUCCCUUGUGGCUGCCUCAGCUCGUACCUUUGGCCUG

AAGUCCCAGCAUUAAUGGCAGCCCCUCAUCUUCCAAGUUUUGUGCUCCCCUUUACCUAAU

GCUUCCUGCCUCCCAUGCAUCUGUACUCCC

>Rn6-2WoE4_For2 (SEQ ID NO: 136)
CCACAUUCAAGGAAGAACCUUCUGCCCCAGCUUUGCAGGAUGAAACACUUCCCCGCUUGG

CUCUCAUUCUUCCACAAGAGAGACCUUUCUCCGGACCUGGUUGCUACUGGUUCAGCAGCU

CUGCAGAAAAUGUCCUCCCUUGUGGCUGCCUCAGCUCGUACCUUUGGCCUGAAGUCCCAG

CAUUAAUGGCAGCCCCUCAUCUUCCAAGUUUUGUGCUCCCCUUUACCUAAUGCUUCCUGC

CCCCC

>Rn6-96hG12_For2 (SEQ ID NO: 137)
GUGAAGAUGACCACAUUCAAGGAAGAACCUUCUGCCCCAGCUUUGCAGGAUGAAACACUU

CCCCGCUUGGCUCUCAUUCUUCCACAAGAGAGACCUUUCUCCGGACCUGGUUGCUACUGG

UUCAGCAGCUCUGCAGAAAAUGUCCUCCCUUGUGGCUGCCUCAGCUCGUACCUUUGGCCU

GAAGUCCCAGCAUUAAUGGCAGCCCCUCAUCUUCCAAGUUUUGUGCUCCCCUUUACCUAA

UGCUUCCUGCCCCCCAU

>Rn6-96h-2pl-C12 (SEQ ID NO: 138)
AGAACCUUCUGCCCCAGCUUUGCAGGAUGAAACACUUCCCCGCUUGGCUCUCAUUCUUCC

ACAAGAGAGACCUUUCUCCGGACCUGGUUGCUACUGGUUCAGCAGCUCUGCAGAAAAUGU

CCUCCCUUGUGGCUGCCUCAGCUCGUACCUUUGGCCUGAAGUCCCAGCAUUAAUGGCAGC

CCCUCAUCUUCCAAGUUUUGUGCUCCCCC

>Rn6-96h-2pl-A6_F (SEQ ID NO: 139)
CUGAAGUGAAGAUGACCACAUUCAAGGAAGAACCUUCUGCCCCAGCUUUGCAGGAUGAAA

CACUUCCCCGCUUGGCUCUCAUUCUUCCACAAGAGAGACCUUUCUCCGGACCUGGUUGCU

ACUGGUUCAGCAGCUCUGCAGAAAAUGUCCUCCCUUGUGGCUGCCUCAGCUCGUACCUUU

GGCCUGAAGUCCCAGCAUUAAUGGCAGCCCCUCAUCUUCCAAGUUUUGUGCUCCCCUUUA

CCUAAUGCUUCCUGCCUCCCAUGCAUCUGUACUCCU

>Rn6-96h-2pl-H5_F (SEQ ID NO: 140)
CUGAAGUGAAGAUGACCACAUUCAAGGAAGAACCUUCUGCCCCAGCUUUGCAGGAUGAAA

CACUUCCCCGCUUGGCUCUCAUUCUUCCACAAGAGAGACCUUUCUCCGGACCUGGUUGCU

ACUGGUUCAGCAGCUCUGCAGAAAAUGUCCUCCCUUGUGGCUGCCUCAGCUCGUACCUUU

GGCCUGAAGUCCCAGCAUUAAUGGCAGCCCCUCAUCUUCCAAGUUUUGUGCUCCCCUUUA

CCUAAUGCUUCCUGCCUCCCAUGCAUCUGUACUCCU

>Rn6-2WoG1_For2 (SEQ ID NO: 141)
AAGAUGACCACAUUCAAGGAAGAACCUUCUGCCCCAGCUUUGCAGGAUGAAACACUUCCC

CGCUUGGCUCUCAUUCUUCCACAAGAGAGACCUUUCUCCGGACCUGGUUGCUACUGGUUC

AGCAGCUCUGCAGAAAAUGUCCUCCCUUGUGGCUGCCUCAGCUCGUACCUUUGGCCUGAA

GUCCCAGCAUUAAUGGCAGCCCCUCAUCUUCCAAGUUUUGUGCUCCCCUUUACCUAAUGC

UUCCUGCCUCCCAUGCAUCUGUACUCCUGC

>Rn6-96h-2pl-D11 (SEQ ID NO: 142)
CCCCGCUUGGCUCUCAUUCUUCCACAAGAGAGACCUUUCUCCGGACCUGGUUGCUACUGG

UUCAGCAGCUCUGCAGAAAAUGUCCUCCCUUGUGGCUGCCUCAGCUCGUACCUUUGGCCU

GAAGUCCCAGCAUUAAUGGCAGCCCCUCAUCUUCCAAGUUUUGUGCUCCCCUUUACCUAA

UGCUUCCUGCCUCCCAUGCAUCUGUACUCCU

>Rn6-96h-2pl-F9_F (SEQ ID NO: 143)
CCCCGCUUGGCUCUCAUUCUUCCACAAGAGAGACCUUUCUCCGGACCUGGUUGCUACUGG

UUCAGCAGCUCUGCAGAAAAUGUCCUCCCUUGUGGCUGCCUCAGCUCGUACCUUUGGCCU

GAAGUCCCAGCAUUAAUGGCAGCCCCUCAUCUUCCAAGUUUUGUGCUCCCCUUUACCUAA

UGCUUCCUGCCUCCCAUGCAUCUGUACUCCU

>hBg: (SEQ ID NO: 221)
GAGAGCUCGCUUUCUUGCUGUCCAAUUUCUAUUAAAGGUUCCUUUGUUCCCUAAGUCCAA

CUACUAAACUGGGGGAUAUUAUGAAGGGCCUUGAGCAUCUGGAUUCUGCCUAAUAAAAAA

CAUUUAUUUUCAUUGCUGCGUC noUTR:
>

>BB (SEQ ID NO: 144)
UGCCCGUCCUCACCAAGACUGACUGCCUGCUGCUUUGCUACUGCCCGGGCCCAUGAGACU

GACUUCCCACUGCUCUGCCUGCCUCUCCCCACUGCACUGGCACAGCCCCGCCUUGCCGCU

GCUGAUCCAUUGCCGGUGUGACCUGCCCGUCCUCACCAAGACUGACUGCCUGCUGCUUUG

CUACUGCCCGGGCCCAUGAGACUGACUUCCCACUGCUCUGCCUGCCUCUCCCCACUGCAC

UGGCACAGCCCCGCCUUGCCGCUGCUGAUCCAUUGCCGGUGUGACC

>BD (SEQ ID NO: 145)
UGCCCGUCCUCACCAAGACUGACUGCCUGCUGCUUUGCUACUGCCCGGGCCCAUGAGACU

GACUUCCCACUGCUCUGCCUGCCUCUCCCCACUGCACUGGCACAGCCCCGCCUUGCCGCU

GCUGAUCCAUUGCCGGUGUGACCUUCCAGCCAGACACCCGCCCCCCGGCCCUGGCUAAGA

AGUUGCUUCCUGUUGCCAGCAUGACCUACCCUCGCCUCUUUGAUGCCAUCCGCUGCCACC

UCCUUUUGCUCCUGGACCCUUUAGCCUCUCUGCCCUUCCACUCUCUGACCCC

>BE (SEQ ID NO: 146)
UGCCCGUCCUCACCAAGACUGACUGCCUGCUGCUUUGCUACUGCCCGGGCCCAUGAGACU

GACUUCCCACUGCUCUGCCUGCCUCUCCCCACUGCACUGGCACAGCCCCGCCUUGCCGCU

GCUGAUCCAUUGCCGGUGUGACCGCCUUGGCUCCUCCAGGAAGGCUCAGGAGCCCUACCU

-continued

CCCUGCCAUUAUAGCUGCUCCCCGCCAGAAGCCUGUGCCAACUCUCUGCAUUCCCUGAUC

UCCAUCCCUGUGGCUGUCACCCUUGGUCACCUCCGUGCUGUCACUGCCAUCUCCCCCC

>BF (SEQ ID NO: 147)
UGCCCGUCCUCACCAAGACUGACUGCCUGCUGCUUUGCUACUGCCCGGGCCCAUGAGACU

GACUUCCCACUGCUCUGCCUGCCUCUCCCCACUGCACUGGCACAGCCCCGCCUUGCCGCU

GCUGAUCCAUUGCCGGUGUGACCCUGGUACUGCAUGCACGCAAUGCUAGCUGCCCCUUUC

CCGUCCUGGGUACCCCGAGUCUCCCCCGACCUCGGGUCCCAGGUAUGCUCCCACCUCCAC

CUGCCCCACUCACCACCUCUGCUAGUUCCAGACACCUCC

>BG (SEQ ID NO: 148)
UGCCCGUCCUCACCAAGACUGACUGCCUGCUGCUUUGCUACUGCCCGGGCCCAUGAGACU

GACUUCCCACUGCUCUGCCUGCCUCUCCCCACUGCACUGGCACAGCCCCGCCUUGCCGCU

GCUGAUCCAUUGCCGGUGUGACCCUGACAGCGUGGGCAACGCCUGCCGCCUGCUCUGAGG

CCCGAUCCAGUGGGCAGGCCAAGGCCUGCUGGGCCCCCGCGGACCCAGGUGCUCUGGGUC

ACGGUCCCUGUCCCCGCACCCCCGCUUCUGUCUGCCCCAUUGUGGCUCCUCAGGCUCUCU

CCCCUGCUCUCCCACCUCUACCUCCACCCCCAC

>BhBg (SEQ ID NO: 149)
UGCCCGUCCUCACCAAGACUGACUGCCUGCUGCUUUGCUACUGCCCGGGCCCAUGAGACU

GACUUCCCACUGCUCUGCCUGCCUCUCCCCACUGCACUGGCACAGCCCCGCCUUGCCGCU

GCUGAUCCAUUGCCGGUGUGACCGAGAGCUCGCUUUCUUGCUGUCCAAUUUCUAUUAAAG

GUUCCUUUGUUCCCUAAGUCCAACUACUAAACUGGGGGAUAUUAUGAAGGGCCUUGAGCA

UCUGGAUUCUGCCUAAUAAAAAACAUUUAUUUUCAUUGCUGCGUC

>BI (SEQ ID NO: 150)
UGCCCGUCCUCACCAAGACUGACUGCCUGCUGCUUUGCUACUGCCCGGGCCCAUGAGACU

GACUUCCCACUGCUCUGCCUGCCUCUCCCCACUGCACUGGCACAGCCCCGCCUUGCCGCU

GCUGAUCCAUUGCCGGUGUGACCCAAGCACGCAGCAAUGCAGCUCAAAACGCUUAGCCUA

GCCACACCCCCACGGGAAACAGCAGUGAUUAACCUUUAGCAAUAAACGAAAGUUUAACUA

AGCUAUACUAACCCCAGGGUUGGUCAAUUUCGUGCCAGCCACACC

>BJ (SEQ ID NO: 151)
UGCCCGUCCUCACCAAGACUGACUGCCUGCUGCUUUGCUACUGCCCGGGCCCAUGAGACU

GACUUCCCACUGCUCUGCCUGCCUCUCCCCACUGCACUGGCACAGCCCCGCCUUGCCGCU

GCUGAUCCAUUGCCGGUGUGACCCUUUGCAGGAUGAAACACUUCCCCGCUUGGCUCUCAU

UCUUCCACAAGAGAGACCUUUCUCCGGACCUGGUUGCUACUGGUUCAGCAACUCUGCAGA

AAAUGUCCUCCCCUGUGGCUGCCUCAGCUCAUGCCUUUGGCCUGAAGUCCCAGCAUUGAU

GGCAGCCCCUCAUCUUCCAAGUUUUGUGCUCCCCUUUACCUAACGCUUCCUGCCUCCCAU

GCAUCUGUACUCCUCC

>DB (SEQ ID NO: 152)
UUCCAGCCAGACACCCGCCCCCCGGCCCUGGCUAAGAAGUUGCUUCCUGUUGCCAGCAUG

ACCUACCCUCGCCUCUUUGAUGCCAUCCGCUGCCACCUCCUUUUGCUCCUGGACCCUUUA

GCCUCUCUGCCCUUCCACUCUCUGACCCCUGCCCGUCCUCACCAAGACUGACUGCCUGCU

GCUUUGCUACUGCCCGGGCCCAUGAGACUGACUUCCCACUGCUCUGCCUGCCUCUCCCCA

CUGCACUGGCACAGCCCCGCCUUGCCGCUGCUGAUCCAUUGCCGGUGUGACC

>DD (SEQ ID NO: 153)
UUCCAGCCAGACACCCGCCCCCCGGCCCUGGCUAAGAAGUUGCUUCCUGUUGCCAGCAUG

ACCUACCCUCGCCUCUUUGAUGCCAUCCGCUGCCACCUCCUUUUGCUCCUGGACCCUUUA

-continued

GCCUCUCUGCCCUUCCACUCUCUGACCCCUUCCAGCCAGACACCCGCCCCCCGGCCCUGG

CUAAGAAGUUGCUUCCUGUUGCCAGCAUGACCUACCCUCGCCUCUUUGAUGCCAUCCGCU

GCCACCUCCUUUUGCUCCUGGACCCUUUAGCCUCUCUGCCCUUCCACUCUCUGACCCC

>DE (SEQ ID NO: 154)
UUCCAGCCAGACACCCGCCCCCCGGCCCUGGCUAAGAAGUUGCUUCCUGUUGCCAGCAUG

ACCUACCCUCGCCUCUUUGAUGCCAUCCGCUGCCACCUCCUUUUGCUCCUGGACCCUUUA

GCCUCUCUGCCCUUCCACUCUCUGACCCCGCCUUGGCUCCUCCAGGAAGGCUCAGGAGCC

CUACCUCCCUGCCAUUAUAGCUGCUCCCCGCCAGAAGCCUGUGCCAACUCUCUGCAUUCC

CUGAUCUCCAUCCCUGUGGCUGUCACCCUUGGUCACCUCCGUGCUGUCACUGCCAUCUCC

CCCC

>DF (SEQ ID NO: 155)
UUCCAGCCAGACACCCGCCCCCCGGCCCUGGCUAAGAAGUUGCUUCCUGUUGCCAGCAUG

ACCUACCCUCGCCUCUUUGAUGCCAUCCGCUGCCACCUCCUUUUGCUCCUGGACCCUUUA

GCCUCUCUGCCCUUCCACUCUCUGACCCCUGGUACUGCAUGCACGCAAUGCUAGCUGCC

CCUUUCCCGUCCUGGGUACCCCGAGUCUCCCCCGACCUCGGGUCCCAGGUAUGCUCCCAC

CUCCACCUGCCCCACUCACCACCUCUGCUAGUUCCAGACACCUCC

>DG (SEQ ID NO: 156)
UUCCAGCCAGACACCCGCCCCCCGGCCCUGGCUAAGAAGUUGCUUCCUGUUGCCAGCAUG

ACCUACCCUCGCCUCUUUGAUGCCAUCCGCUGCCACCUCCUUUUGCUCCUGGACCCUUUA

GCCUCUCUGCCCUUCCACUCUCUGACCCCCUGACAGCGUGGGCAACGCCUGCCGCCUGCU

CUGAGGCCCGAUCCAGUGGGCAGGCCAAGGCCUGCUGGGCCCCGCGGACCCAGGUGCUC

UGGGUCACGGUCCCUGUCCCCGCACCCCCGCUUCUGUCUGCCCCAUUGUGGCUCCUCAGG

CUCUCUCCCCUGCUCUCCCACCUCUACCUCCACCCCAC

>DhBg (SEQ ID NO: 157)
UUCCAGCCAGACACCCGCCCCCCGGCCCUGGCUAAGAAGUUGCUUCCUGUUGCCAGCAUG

ACCUACCCUCGCCUCUUUGAUGCCAUCCGCUGCCACCUCCUUUUGCUCCUGGACCCUUUA

GCCUCUCUGCCCUUCCACUCUCUGACCCCGAGAGCUCGCUUUCUUGCUGUCCAAUUUCUA

UUAAAGGUUCCUUUGUUCCCUAAGUCCAACUACUAAACUGGGGGAUAUUAUGAAGGGCCU

UGAGCAUCUGGAUUCUGCCUAAUAAAAAACAUUUAUUUUCAUUGCUGCGUC

>DI (SEQ ID NO: 158)
UUCCAGCCAGACACCCGCCCCCCGGCCCUGGCUAAGAAGUUGCUUCCUGUUGCCAGCAUG

ACCUACCCUCGCCUCUUUGAUGCCAUCCGCUGCCACCUCCUUUUGCUCCUGGACCCUUUA

GCCUCUCUGCCCUUCCACUCUCUGACCCCCAAGCACGCAGCAAUGCAGCUCAAAACGCUU

AGCCUAGCCACACCCCACGGGAAACAGCAGUGAUUAACCUUUAGCAAUAAACGAAAGUU

UAACUAAGCUAUACUAACCCCAGGGUUGGUCAAUUUCGUGCCAGCCACACC

>DJ (SEQ ID NO: 159)
UUCCAGCCAGACACCCGCCCCCCGGCCCUGGCUAAGAAGUUGCUUCCUGUUGCCAGCAUG

ACCUACCCUCGCCUCUUUGAUGCCAUCCGCUGCCACCUCCUUUUGCUCCUGGACCCUUUA

GCCUCUCUGCCCUUCCACUCUCUGACCCCCUUUGCAGGAUGAAACACUUCCCCGCUUGGC

UCUCAUUCUUCCACAAGAGAGACCUUUCUCCGGACCUGGUUGCUACUGGUUCAGCAACUC

UGCAGAAAAUGUCCUCCCCUGUGGCUGCCUCAGCUCAUGCCUUUGGCCUGAAGUCCCAGC

AUUGAUGGCAGCCCCUCAUCUUCCAAGUUUUGUGCUCCCCUUUACCUAACGCUUCCUGCC

UCCCAUGCAUCUGUACUCCUCC

-continued

>EB (SEQ ID NO: 160)
GCCUUGGCUCCUCCAGGAAGGCUCAGGAGCCCUACCUCCCUGCCAUUAUAGCUGCUCCCC

GCCAGAAGCCUGUGCCAACUCUCUGCAUUCCCUGAUCUCCAUCCCUGUGGCUGUCACCCU

UGGUCACCUCCGUGCUGUCACUGCCAUCUCCCCCUGCCCGUCCUCACCAAGACUGACUG

CCUGCUGCUUUGCUACUGCCCGGGCCCAUGAGACUGACUUCCCACUGCUCUGCCUGCCUC

UCCCCACUGCACUGGCACAGCCCCGCCUUGCCGCUGCUGAUCCAUUGCCGGUGUGACC

>ED (SEQ ID NO: 161)
GCCUUGGCUCCUCCAGGAAGGCUCAGGAGCCCUACCUCCCUGCCAUUAUAGCUGCUCCCC

GCCAGAAGCCUGUGCCAACUCUCUGCAUUCCCUGAUCUCCAUCCCUGUGGCUGUCACCCU

UGGUCACCUCCGUGCUGUCACUGCCAUCUCCCCCUUCCAGCCAGACACCCGCCCCCCGG

CCCUGGCUAAGAAGUUGCUUCCUGUUGCCAGCAUGACCUACCCUCGCCUCUUUGAUGCCA

UCCGCUGCCACCUCCUUUUGCUCCUGGACCCUUUAGCCUCUCUGCCCUUCCACUCUCUGA

CCCC

>EE (SEQ ID NO: 162)
GCCUUGGCUCCUCCAGGAAGGCUCAGGAGCCCUACCUCCCUGCCAUUAUAGCUGCUCCCC

GCCAGAAGCCUGUGCCAACUCUCUGCAUUCCCUGAUCUCCAUCCCUGUGGCUGUCACCCU

UGGUCACCUCCGUGCUGUCACUGCCAUCUCCCCCGCCUUGGCUCCUCCAGGAAGGCUCA

GGAGCCCUACCUCCCUGCCAUUAUAGCUGCUCCCCGCCAGAAGCCUGUGCCAACUCUCUG

CAUUCCCUGAUCUCCAUCCCUGUGGCUGUCACCCUUGGUCACCUCCGUGCUGUCACUGCC

AUCUCCCCCC

>EF (SEQ ID NO: 163)
GCCUUGGCUCCUCCAGGAAGGCUCAGGAGCCCUACCUCCCUGCCAUUAUAGCUGCUCCCC

GCCAGAAGCCUGUGCCAACUCUCUGCAUUCCCUGAUCUCCAUCCCUGUGGCUGUCACCCU

UGGUCACCUCCGUGCUGUCACUGCCAUCUCCCCCCUGGUACUGCAUGCACGCAAUGCUA

GCUGCCCCUUUCCCGUCCUGGGUACCCCGAGUCUCCCCCGACCUCGGGUCCCAGGUAUGC

UCCCACCUCCACCUGCCCCACUCACCACCUCUGCUAGUUCCAGACACCUCC

>EG (SEQ ID NO: 164)
>GCCUUGGCUCCUCCAGGAAGGCUCAGGAGCCCUACCUCCCUGCCAUUAUAGCUGCUCCCC

GCCAGAAGCCUGUGCCAACUCUCUGCAUUCCCUGAUCUCCAUCCCUGUGGCUGUCACCC

UUGGUCACCUCCGUGCUGUCACUGCCAUCUCCCCCCUGACAGCGUGGGCAACGCCUGCC

GCCUGCUCUGAGGCCCGAUCCAGUGGGCAGGCCAAGGCCUGCUGGGCCCCCGCGGACCCA

GGUGCUCUGGGUCACGGUCCCUGUCCCCGCACCCCCGCUUCUGUCUGCCCCAUUGUGGCU

CCUCAGGCUCUCUCCCCUGCUCUCCCACCUCUACCUCCACCCCCAC

>EhBg (SEQ ID NO: 165)
GCCUUGGCUCCUCCAGGAAGGCUCAGGAGCCCUACCUCCCUGCCAUUAUAGCUGCUCCCC

GCCAGAAGCCUGUGCCAACUCUCUGCAUUCCCUGAUCUCCAUCCCUGUGGCUGUCACCCU

UGGUCACCUCCGUGCUGUCACUGCCAUCUCCCCCGAGAGCUCGCUUUCUUGCUGUCCAA

UUUCUAUUAAAGGUUCCUUUGUUCCCUAAGUCCAACUACUAAACUGGGGGAUAUUAUGAA

GGGCCUUGAGCAUCUGGAUUCUGCCUAAUAAAAAACAUUUAUUUUCAUUGCUGCGUC

>EI (SEQ ID NO: 166)
GCCUUGGCUCCUCCAGGAAGGCUCAGGAGCCCUACCUCCCUGCCAUUAUAGCUGCUCCCC

GCCAGAAGCCUGUGCCAACUCUCUGCAUUCCCUGAUCUCCAUCCCUGUGGCUGUCACCCU

UGGUCACCUCCGUGCUGUCACUGCCAUCUCCCCCCCAAGCACGCAGCAAUGCAGCUCAAA

-continued

ACGCUUAGCCUAGCCACACCCCCACGGGAAACAGCAGUGAUUAACCUUUAGCAAUAAACG

AAAGUUUAACUAAGCUAUACUAACCCCAGGGUUGGUCAAUUUCGUGCCAGCCACACC

>EJ (SEQ ID NO: 167)
GCCUUGGCUCCUCCAGGAAGGCUCAGGAGCCCUACCUCCCUGCCAUUAUAGCUGCUCCCC

GCCAGAAGCCUGUGCCAACUCUCUGCAUUCCCUGAUCUCCAUCCCUGUGGCUGUCACCCU

UGGUCACCUCCGUGCUGUCACUGCCAUCUCCCCCCUUUGCAGGAUGAAACACUUCCCCG

CUUGGCUCUCAUUCUUCCACAAGAGAGACCUUUCUCCGGACCUGGUUGCUACUGGUUCAG

CAACUCUGCAGAAAAUGUCCUCCCCUGUGGCUGCCUCAGCUCAUGCCUUUGGCCUGAAGU

CCCAGCAUUGAUGGCAGCCCCUCAUCUUCCAAGUUUUGUGCUCCCCUUUACCUAACGCUU

CCUGCCUCCCAUGCAUCUGUACUCCUCC

>FB (SEQ ID NO: 168)
CUGGUACUGCAUGCACGCAAUGCUAGCUGCCCCUUUCCCGUCCUGGGUACCCCGAGUCUC

CCCCGACCUCGGGUCCCAGGUAUGCUCCCACCUCCACCUGCCCCACUCACCACCUCUGCU

AGUUCCAGACACCUCCUGCCCGUCCUCACCAAGACUGACUGCCUGCUGCUUUGCUACUGC

CCGGGCCCAUGAGACUGACUUCCCACUGCUCUGCCUGCCUCUCCCCACUGCACUGGCACA

GCCCCGCCUUGCCGCUGCUGAUCCAUUGCCGGUGUGACC

>FD (SEQ ID NO: 169)
CUGGUACUGCAUGCACGCAAUGCUAGCUGCCCCUUUCCCGUCCUGGGUACCCCGAGUCUC

CCCCGACCUCGGGUCCCAGGUAUGCUCCCACCUCCACCUGCCCCACUCACCACCUCUGCU

AGUUCCAGACACCUCCUUCCAGCCAGACACCCGCCCCCCGGCCCUGGCUAAGAAGUUGCU

UCCUGUUGCCAGCAUGACCUACCCUCGCCUCUUUGAUGCCAUCCGCUGCCACCUCCUUUU

GCUCCUGGACCCUUUAGCCUCUCUGCCCUUCCACUCUCUGACCCC

>FE (SEQ ID NO: 170)
CUGGUACUGCAUGCACGCAAUGCUAGCUGCCCCUUUCCCGUCCUGGGUACCCCGAGUCUC

CCCCGACCUCGGGUCCCAGGUAUGCUCCCACCUCCACCUGCCCCACUCACCACCUCUGCU

AGUUCCAGACACCUCCGCCUUGGCUCCUCCAGGAAGGCUCAGGAGCCCUACCUCCCUGCC

AUUAUAGCUGCUCCCCGCCAGAAGCCUGUGCCAACUCUCUGCAUUCCCUGAUCUCCAUCC

CUGUGGCUGUCACCCUUGGUCACCUCCGUGCUGUCACUGCCAUCUCCCCCC

>FF (SEQ ID NO: 171)
CUGGUACUGCAUGCACGCAAUGCUAGCUGCCCCUUUCCCGUCCUGGGUACCCCGAGUCUC

CCCCGACCUCGGGUCCCAGGUAUGCUCCCACCUCCACCUGCCCCACUCACCACCUCUGCU

AGUUCCAGACACCUCCCUGGUACUGCAUGCACGCAAUGCUAGCUGCCCCUUUCCCGUCCU

GGGUACCCCGAGUCUCCCCCGACCUCGGGUCCCAGGUAUGCUCCCACCUCCACCUGCCCC

ACUCACCACCUCUGCUAGUUCCAGACACCUCC

>FG (SEQ ID NO: 172)
CUGGUACUGCAUGCACGCAAUGCUAGCUGCCCCUUUCCCGUCCUGGGUACCCCGAGUCUC

CCCCGACCUCGGGUCCCAGGUAUGCUCCCACCUCCACCUGCCCCACUCACCACCUCUGCU

AGUUCCAGACACCUCCCUGACAGCGUGGGCAACGCCUGCCGCCUGCUCUGAGGCCCGAUC

CAGUGGGCAGGCCAAGGCCUGCUGGGCCCCCGCGGACCCAGGUGCUCUGGGUCACGGUCC

CUGUCCCCGCACCCCCGCUUCUGUCUGCCCCAUUGUGGCUCCUCAGGCUCUCUCCCCUGC

UCUCCCACCUCUACCUCCACCCCCAC

>FhBg (SEQ ID NO: 173)
CUGGUACUGCAUGCACGCAAUGCUAGCUGCCCCUUUCCCGUCCUGGGUACCCCGAGUCUC

CCCCGACCUCGGGUCCCAGGUAUGCUCCCACCUCCACCUGCCCCACUCACCACCUCUGCU

-continued

AGUUCCAGACACCUCCGAGAGCUCGCUUUCUUGCUGUCCAAUUUCUAUUAAAGGUUCCUU

UGUUCCCUAAGUCCAACUACUAAACUGGGGGAUAUUAUGAAGGGCCUUGAGCAUCUGGAU

UCUGCCUAAUAAAAAACAUUUAUUUUCAUUGCUGCGUC

>FI (SEQ ID NO: 174)
CUGGUACUGCAUGCACGCAAUGCUAGCUGCCCCUUUCCCGUCCUGGGUACCCCGAGUCUC

CCCCGACCUCGGGUCCCAGGUAUGCUCCCACCUCCACCUGCCCCACUCACCACCUCUGCU

AGUUCCAGACACCUCCCAAGCACGCAGCAAUGCAGCUCAAAACGCUUAGCCUAGCCACAC

CCCCACGGGAAACAGCAGUGAUUAACCUUUAGCAAUAAACGAAAGUUUAACUAAGCUAUA

CUAACCCCAGGGUUGGUCAAUUUCGUGCCAGCCACACC

>FJ (SEQ ID NO: 175)
CUGGUACUGCAUGCACGCAAUGCUAGCUGCCCCUUUCCCGUCCUGGGUACCCCGAGUCUC

CCCCGACCUCGGGUCCCAGGUAUGCUCCCACCUCCACCUGCCCCACUCACCACCUCUGCU

AGUUCCAGACACCUCCCUUUGCAGGAUGAAACACUUCCCCGCUUGGCUCUCAUUCUUCCA

CAAGAGAGACCUUUCUCCGGACCUGGUUGCUACUGGUUCAGCAACUCUGCAGAAAAUGUC

CUCCCCUGUGGCUGCCUCAGCUCAUGCCUUUGGCCUGAAGUCCCAGCAUUGAUGGCAGCC

CCUCAUCUUCCAAGUUUUGUGCUCCCCUUUACCUAACGCUUCCUGCCUCCCAUGCAUCUG

UACUCCUCC

>GB (SEQ ID NO: 176)
CUGACAGCGUGGGCAACGCCUGCCGCCUGCUCUGAGGCCCGAUCCAGUGGGCAGGCCAAG

GCCUGCUGGGCCCCGCGGACCCAGGUGCUCUGGGUCACGGUCCCUGUCCCCGCACCCCC

GCUUCUGUCUGCCCCAUUGUGGCUCCUCAGGCUCUCUCCCCUGCUCUCCCACCUCUACCU

CCACCCCCACUGCCCGUCCUCACCAAGACUGACUGCCUGCUGCUUUGCUACUGCCCGGGC

CCAUGAGACUGACUUCCCACUGCUCUGCCUGCCUCUCCCCACUGCACUGGCACAGCCCCG

CCUUGCCGCUGCUGAUCCAUUGCCGGUGUGACC

>GD (SEQ ID NO: 177)
CUGACAGCGUGGGCAACGCCUGCCGCCUGCUCUGAGGCCCGAUCCAGUGGGCAGGCCAAG

GCCUGCUGGGCCCCGCGGACCCAGGUGCUCUGGGUCACGGUCCCUGUCCCCGCACCCCC

GCUUCUGUCUGCCCCAUUGUGGCUCCUCAGGCUCUCUCCCCUGCUCUCCCACCUCUACCU

CCACCCCCACUUCCAGCCAGACACCCGCCCCCCGGCCCUGGCUAAGAAGUUGCUUCCUGU

UGCCAGCAUGACCUACCCUCGCCUCUUUGAUGCCAUCCGCUGCCACCUCCUUUUGCUCCU

GGACCCUUUAGCCUCUCUGCCCUUCCACUCUCUGACCCC

>GE (SEQ ID NO: 178)
CUGACAGCGUGGGCAACGCCUGCCGCCUGCUCUGAGGCCCGAUCCAGUGGGCAGGCCAAG

GCCUGCUGGGCCCCGCGGACCCAGGUGCUCUGGGUCACGGUCCCUGUCCCCGCACCCCC

GCUUCUGUCUGCCCCAUUGUGGCUCCUCAGGCUCUCUCCCCUGCUCUCCCACCUCUACCU

CCACCCCCACGCCUUGGCUCCUCCAGGAAGGCUCAGGAGCCCUACCUCCCUGCCAUUAUA

GCUGCUCCCCGCCAGAAGCCUGUGCCAACUCUCUGCAUUCCCUGAUCUCCAUCCCUGUGG

CUGUCACCCUUGGUCACCUCCGUGCUGUCACUGCCAUCUCCCCCC

>GF (SEQ ID NO: 179)
CUGACAGCGUGGGCAACGCCUGCCGCCUGCUCUGAGGCCCGAUCCAGUGGGCAGGCCAAG

GCCUGCUGGGCCCCGCGGACCCAGGUGCUCUGGGUCACGGUCCCUGUCCCCGCACCCCC

GCUUCUGUCUGCCCCAUUGUGGCUCCUCAGGCUCUCUCCCCUGCUCUCCCACCUCUACCU

CCACCCCCACCUGGUACUGCAUGCACGCAAUGCUAGCUGCCCCUUUCCCGUCCUGGGUAC

-continued

CCCGAGUCUCCCCCGACCUCGGGUCCCAGGUAUGCUCCCACCUCCACCUGCCCCACUCAC

CACCUCUGCUAGUUCCAGACACCUCC

>GG (SEQ ID NO: 180)
CUGACAGCGUGGGCAACGCCUGCCGCCUGCUCUGAGGCCCGAUCCAGUGGGCAGGCCAAG

GCCUGCUGGGCCCCCGCGGACCCAGGUGCUCUGGGUCACGGUCCCUGUCCCCGCACCCCC

GCUUCUGUCUGCCCCAUUGUGGCUCCUCAGGCUCUCUCCCCUGCUCUCCCACCUCUACCU

CCACCCCCACCUGACAGCGUGGGCAACGCCUGCCGCCUGCUCUGAGGCCCGAUCCAGUGG

GCAGGCCAAGGCCUGCUGGGCCCCCGCGGACCCAGGUGCUCUGGGUCACGGUCCCUGUCC

CCGCACCCCGCUUCUGUCUGCCCCAUUGUGGCUCCUCAGGCUCUCUCCCCUGCUCUCCC

ACCUCUACCUCCACCCCCAC

>GhBg (SEQ ID NO: 181)
CUGACAGCGUGGGCAACGCCUGCCGCCUGCUCUGAGGCCCGAUCCAGUGGGCAGGCCAAG

GCCUGCUGGGCCCCCGCGGACCCAGGUGCUCUGGGUCACGGUCCCUGUCCCCGCACCCCC

GCUUCUGUCUGCCCCAUUGUGGCUCCUCAGGCUCUCUCCCCUGCUCUCCCACCUCUACCU

CCACCCCCACGAGAGCUCGCUUUCUUGCUGUCCAAUUUCUAUUAAAGGUUCCUUUGUUCC

CUAAGUCCAACUACUAAACUGGGGGAUAUUAUGAAGGGCCUUGAGCAUCUGGAUUCUGCC

UAAUAAAAACAUUUAUUUUCAUUGCUGCGUC

>GI (SEQ ID NO: 182)
CUGACAGCGUGGGCAACGCCUGCCGCCUGCUCUGAGGCCCGAUCCAGUGGGCAGGCCAAG

GCCUGCUGGGCCCCCGCGGACCCAGGUGCUCUGGGUCACGGUCCCUGUCCCCGCACCCCC

GCUUCUGUCUGCCCCAUUGUGGCUCCUCAGGCUCUCUCCCCUGCUCUCCCACCUCUACCU

CCACCCCCACCAAGCACGCAGCAAUGCAGCUCAAAACGCUUAGCCUAGCCACACCCCCAC

GGGAAACAGCAGUGAUUAACCUUUAGCAAUAAACGAAAGUUUAACUAAGCUAUACUAACC

CCAGGGUUGGUCAAUUUCGUGCCAGCCACACC

>GJ (SEQ ID NO: 183)
CUGACAGCGUGGGCAACGCCUGCCGCCUGCUCUGAGGCCCGAUCCAGUGGGCAGGCCAAG

GCCUGCUGGGCCCCCGCGGACCCAGGUGCUCUGGGUCACGGUCCCUGUCCCCGCACCCCC

GCUUCUGUCUGCCCCAUUGUGGCUCCUCAGGCUCUCUCCCCUGCUCUCCCACCUCUACCU

CCACCCCCACCUUUGCAGGAUGAAACACUUCCCCGCUUGGCUCUCAUUCUUCCACAAGAG

AGACCUUUCUCCGGACCUGGUUGCUACUGGUUCAGCAACUCUGCAGAAAAUGUCCUCCCC

UGUGGCUGCCUCAGCUCAUGCCUUUGGCCUGAAGUCCCAGCAUUGAUGGCAGCCCCUCAU

CUUCCAAGUUUUGUGCUCCCCUUUACCUAACGCUUCCUGCCUCCCAUGCAUCUGUACUCC

UCC

>hBgB (SEQ ID NO: 184)
GAGAGCUCGCUUUCUUGCUGUCCAAUUUCUAUUAAAGGUUCCUUUGUUCCCUAAGUCCAA

CUACUAAACUGGGGGAUAUUAUGAAGGGCCUUGAGCAUCUGGAUUCUGCCUAAUAAAAA

CAUUUAUUUUCAUUGCUGCGUCUGCCCGUCCUCACCAAGACUGACUGCCUGCUGCUUUGC

UACUGCCCGGGCCCAUGAGACUGACUUCCACUGCUCUGCCUGCCUCUCCCACUGCACU

GGCACAGCCCCGCCUUGCCGCUGCUGAUCCAUUGCCGGUGUGACC

>hBgD (SEQ ID NO: 185)
GAGAGCUCGCUUUCUUGCUGUCCAAUUUCUAUUAAAGGUUCCUUUGUUCCCUAAGUCCAA

CUACUAAACUGGGGGAUAUUAUGAAGGGCCUUGAGCAUCUGGAUUCUGCCUAAUAAAAA

CAUUUAUUUUCAUUGCUGCGUCUUCCAGCCAGACACCCGCCCCCCGGCCCUGGCUAAGAA

-continued

GUUGCUUCCUGUUGCCAGCAUGACCUACCCUCGCCUCUUUGAUGCCAUCCGCUGCCACCU

CCUUUUGCUCCUGGACCCUUUAGCCUCUCUGCCCUUCCACUCUCUGACCCC

>hBgE (SEQ ID NO: 186)
GAGAGCUCGCUUUCUUGCUGUCCAAUUUCUAUUAAAGGUUCCUUUGUUCCCUAAGUCCAA

CUACUAAACUGGGGAUAUUAUGAAGGGCCUUGAGCAUCUGGAUUCUGCCUAAUAAAAAA

CAUUUAUUUUCAUUGCUGCGUCGCCUUGGCUCCUCCAGGAAGGCUCAGGAGCCCUACCUC

CCUGCCAUUAUAGCUGCUCCCCGCCAGAAGCCUGUGCCAACUCUCUGCAUUCCCUGAUCU

CCAUCCCUGUGGCUGUCACCCUUGGUCACCUCCGUGCUGUCACUGCCAUCUCCCCCC

>hBgF (SEQ ID NO: 187)
GAGAGCUCGCUUUCUUGCUGUCCAAUUUCUAUUAAAGGUUCCUUUGUUCCCUAAGUCCAA

CUACUAAACUGGGGAUAUUAUGAAGGGCCUUGAGCAUCUGGAUUCUGCCUAAUAAAAAA

CAUUUAUUUUCAUUGCUGCGUCCUGGUACUGCAUGCACGCAAUGCUAGCUGCCCCUUUCC

CGUCCUGGGUACCCCGAGUCUCCCCCGACCUCGGGUCCCAGGUAUGCUCCCACCUCCACC

UGCCCCACUCACCACCUCUGCUAGUUCCAGACACCUCC

>hBgG (SEQ ID NO: 188)
GAGAGCUCGCUUUCUUGCUGUCCAAUUUCUAUUAAAGGUUCCUUUGUUCCCUAAGUCCAA

CUACUAAACUGGGGAUAUUAUGAAGGGCCUUGAGCAUCUGGAUUCUGCCUAAUAAAAAA

CAUUUAUUUUCAUUGCUGCGUCCUGACAGCGUGGGCAACGCCUGCCGCCUGCUCUGAGGC

CCGAUCCAGUGGGCAGGCCAAGGCCUGCUGGGCCCCGCGGACCCAGGUGCUCUGGGUCA

CGGUCCCUGUCCCCGCACCCCGCUUCUGUCUGCCCCAUUGUGGGCUCCUCAGGCUCUCUC

CCCUGCUCUCCCACCUCUACCUCCACCCCCAC

>hBghBg (SEQ ID NO: 189)
GAGAGCUCGCUUUCUUGCUGUCCAAUUUCUAUUAAAGGUUCCUUUGUUCCCUAAGUCCAA

CUACUAAACUGGGGAUAUUAUGAAGGGCCUUGAGCAUCUGGAUUCUGCCUAAUAAAAAA

CAUUUAUUUUCAUUGCUGCGUCGAGAGCUCGCUUUCUUGCUGUCCAAUUUCUAUUAAAGG

UUCCUUUGUUCCCUAAGUCCAACUACUAAACUGGGGAUAUUAUGAAGGGCCUUGAGCAU

CUGGAUUCUGCCUAAUAAAAAACAUUUAUUUUCAUUGCUGCGUC

>hBgI (SEQ ID NO: 190)
GAGAGCUCGCUUUCUUGCUGUCCAAUUUCUAUUAAAGGUUCCUUUGUUCCCUAAGUCCAA

CUACUAAACUGGGGAUAUUAUGAAGGGCCUUGAGCAUCUGGAUUCUGCCUAAUAAAAAA

CAUUUAUUUUCAUUGCUGCGUCCAAGCACGCAGCAAUGCAGCUCAAAACGCUUAGCCUAG

CCACACCCCACGGGAAACAGCAGUGAUUAACCUUUAGCAAUAAACGAAAGUUUAACUAA

GCUAUACUAACCCCAGGGUUGGUCAAUUUCGUGCCAGCCACACC

>hBgJ (SEQ ID NO: 191)
GAGAGCUCGCUUUCUUGCUGUCCAAUUUCUAUUAAAGGUUCCUUUGUUCCCUAAGUCCAA

CUACUAAACUGGGGAUAUUAUGAAGGGCCUUGAGCAUCUGGAUUCUGCCUAAUAAAAAA

CAUUUAUUUUCAUUGCUGCGUCCUUUGCAGGAUGAAACACUUCCCCGCUUGGCUCUCAUU

CUUCCACAAGAGAGACCUUUCUCCGGACCUGGUUGCUACUGGUUCAGCAACUCUGCAGAA

AAUGUCCUCCCCUGUGGCUGCCUCAGCUCAUGCCUUUGGCCUGAAGUCCCAGCAUUGAUG

GCAGCCCCUCAUCUUCCAAGUUUUGUGCUCCCCUUUACCUAACGCUUCCUGCCUCCCAUG

CAUCUGUACUCCUCC

>IB (SEQ ID NO: 192)
CAAGCACGCAGCAAUGCAGCUCAAAACGCUUAGCCUAGCCACACCCCACGGGAAACAGC

AGUGAUUAACCUUUAGCAAUAAACGAAAGUUUAACUAAGCUAUACUAACCCCAGGGUUGG

-continued

UCAAUUUCGUGCCAGCCACACCUGCCCGUCCUCACCAAGACUGACUGCCUGCUGCUUUGC

UACUGCCCGGGCCCAUGAGACUGACUUCCCACUGCUCUGCCUGCCUCUCCCCACUGCACU

GGCACAGCCCCGCCUUGCCGCUGCUGAUCCAUUGCCGGUGUGACC

>ID (SEQ ID NO: 193)
CAAGCACGCAGCAAUGCAGCUCAAAACGCUUAGCCUAGCCACACCCCCACGGGAAACAGC

AGUGAUUAACCUUUAGCAAUAAACGAAAGUUUAACUAAGCUAUACUAACCCCAGGGUUGG

UCAAUUUCGUGCCAGCCACACCUUCCAGCCAGACACCCGCCCCCCGGCCCUGGCUAAGAA

GUUGCUUCCUGUUGCCAGCAUGACCUACCCUCGCCUCUUUGAUGCCAUCCGCUGCCACCU

CCUUUUGCUCCUGGACCCUUUAGCCUCUCUGCCCUUCCACUCUCUGACCCC

>IE (SEQ ID NO: 194)
CAAGCACGCAGCAAUGCAGCUCAAAACGCUUAGCCUAGCCACACCCCCACGGGAAACAGC

AGUGAUUAACCUUUAGCAAUAAACGAAAGUUUAACUAAGCUAUACUAACCCCAGGGUUGG

UCAAUUUCGUGCCAGCCACACCGCCUUGGCUCCUCCAGGAAGGCUCAGGAGCCCUACCUC

CCUGCCAUUAUAGCUGCUCCCCGCCAGAAGCCUGUGCCAACUCUCUGCAUUCCCUGAUCU

CCAUCCCUGUGGCUGUCACCCUUGGUCACCUCCGUGCUGUCACUGCCAUCUCCCCCC

>IF (SEQ ID NO: 195)
CAAGCACGCAGCAAUGCAGCUCAAAACGCUUAGCCUAGCCACACCCCCACGGGAAACAGC

AGUGAUUAACCUUUAGCAAUAAACGAAAGUUUAACUAAGCUAUACUAACCCCAGGGUUGG

UCAAUUUCGUGCCAGCCACACCCUGGUACUGCAUGCACGCAAUGCUAGCUGCCCCUUUCC

CGUCCUGGGUACCCGAGUCUCCCCCGACCUCGGGUCCCAGGUAUGCUCCCACCUCCACC

UGCCCCACUCACCACCUCUGCUAGUUCCAGACACCUCC

>IG (SEQ ID NO: 196)
CAAGCACGCAGCAAUGCAGCUCAAAACGCUUAGCCUAGCCACACCCCCACGGGAAACAGC

AGUGAUUAACCUUUAGCAAUAAACGAAAGUUUAACUAAGCUAUACUAACCCCAGGGUUGG

UCAAUUUCGUGCCAGCCACACCCUGACAGCGUGGGCAACGCCUGCCGCCUGCUCUGAGGC

CCGAUCCAGUGGGCAGGCCAAGGCCUGCUGGGCCCCCGCGGACCCAGGUGCUCUGGGUCA

CGGUCCCUGUCCCCGCACCCCCGCUUCUGUCUGCCCCAUUGUGGCUCCUCAGGCUCUCUC

CCCUGCUCUCCCACCUCUACCUCCACCCCCAC

>IhBg (SEQ ID NO: 197)
CAAGCACGCAGCAAUGCAGCUCAAAACGCUUAGCCUAGCCACACCCCCACGGGAAACAGC

AGUGAUUAACCUUUAGCAAUAAACGAAAGUUUAACUAAGCUAUACUAACCCCAGGGUUGG

UCAAUUUCGUGCCAGCCACACCGAGAGCUCGCUUUCUUGCUGUCCAAUUUCUAUUAAGG

UUCCUUUGUUCCCUAAGUCCAACUACUAAACUGGGGGAUAUUAUGAAGGGCCUUGAGCAU

CUGGAUUCUGCCUAAUAAAAAACAUUUAUUUUCAUUGCUGCGUC

>II (SEQ ID NO: 198)
CAAGCACGCAGCAAUGCAGCUCAAAACGCUUAGCCUAGCCACACCCCCACGGGAAACAGC

AGUGAUUAACCUUUAGCAAUAAACGAAAGUUUAACUAAGCUAUACUAACCCCAGGGUUGG

UCAAUUUCGUGCCAGCCACACCCAAGCACGCAGCAAUGCAGCUCAAAACGCUUAGCCUAG

CCACACCCCCACGGGAAACAGCAGUGAUUAACCUUUAGCAAUAAACGAAAGUUUAACUAA

GCUAUACUAACCCCAGGGUUGGUCAAUUUCGUGCCAGCCACACC

>IJ (SEQ ID NO: 199)
CAAGCACGCAGCAAUGCAGCUCAAAACGCUUAGCCUAGCCACACCCCCACGGGAAACAGC

AGUGAUUAACCUUUAGCAAUAAACGAAAGUUUAACUAAGCUAUACUAACCCCAGGGUUGG

UCAAUUUCGUGCCAGCCACACCCUUUGCAGGAUGAAACACUUCCCCGCUUGGCUCUCAUU

-continued

CUUCCACAAGAGAGACCUUUCUCCGGACCUGGUUGCUACUGGUUCAGCAACUCUGCAGAA
AAUGUCCUCCCCUGUGGCUGCCUCAGCUCAUGCCUUUGGCCUGAAGUCCCAGCAUUGAUG
GCAGCCCCUCAUCUUCCAAGUUUUGUGCUCCCCUUUACCUAACGCUUCCUGCCUCCCAUG
CAUCUGUACUCCUCC

>JB (SEQ ID NO: 200)
CUUUGCAGGAUGAAACACUUCCCCGCUUGGCUCUCAUUCUUCCACAAGAGAGACCUUUCU
CCGGACCUGGUUGCUACUGGUUCAGCAACUCUGCAGAAAAUGUCCUCCCCUGUGGCUGCC
UCAGCUCAUGCCUUUGGCCUGAAGUCCCAGCAUUGAUGGCAGCCCCUCAUCUUCCAAGUU
UUGUGCUCCCCUUUACCUAACGCUUCCUGCCUCCCAUGCAUCUGUACUCCUCCUGCCCGU
CCUCACCAAGACUGACUGCCUGCUGCUUUGCUACUGCCCGGGCCCAUGAGACUGACUUCC
CACUGCUCUGCCUGCCUCUCCCCACUGCACUGGCACAGCCCCGCCUUGCCGCUGCUGAUC
CAUUGCCGGUGUGACC

>JD (SEQ ID NO: 201)
CUUUGCAGGAUGAAACACUUCCCCGCUUGGCUCUCAUUCUUCCACAAGAGAGACCUUUCU
CCGGACCUGGUUGCUACUGGUUCAGCAACUCUGCAGAAAAUGUCCUCCCCUGUGGCUGCC
UCAGCUCAUGCCUUUGGCCUGAAGUCCCAGCAUUGAUGGCAGCCCCUCAUCUUCCAAGUU
UUGUGCUCCCCUUUACCUAACGCUUCCUGCCUCCCAUGCAUCUGUACUCCUCCUUCCAGC
CAGACACCCGCCCCCGGCCCUGGCUAAGAAGUUGCUUCCUGUUGCCAGCAUGACCUACC
CUCGCCUCUUUGAUGCCAUCCGCUGCCACCUCCUUUUGCUCCUGGACCCUUUAGCCUCUC
UGCCCUUCCACUCUCUGACCCC

>JE (SEQ ID NO: 202)
CUUUGCAGGAUGAAACACUUCCCCGCUUGGCUCUCAUUCUUCCACAAGAGAGACCUUUCU
CCGGACCUGGUUGCUACUGGUUCAGCAACUCUGCAGAAAAUGUCCUCCCCUGUGGCUGCC
UCAGCUCAUGCCUUUGGCCUGAAGUCCCAGCAUUGAUGGCAGCCCCUCAUCUUCCAAGUU
UUGUGCUCCCCUUUACCUAACGCUUCCUGCCUCCCAUGCAUCUGUACUCCUCCGCCUUGG
CUCCUCCAGGAAGGCUCAGGAGCCCUACCUCCCUGCCAUUAUAGCUGCUCCCCGCCAGAA
GCCUGUGCCAACUCUCUGCAUUCCCUGAUCUCCAUCCCUGUGGCUGUCACCCUUGGUCAC
CUCCGUGCUGUCACUGCCAUCUCCCCCC

>JF (SEQ ID NO: 203)
CUUUGCAGGAUGAAACACUUCCCCGCUUGGCUCUCAUUCUUCCACAAGAGAGACCUUUCU
CCGGACCUGGUUGCUACUGGUUCAGCAACUCUGCAGAAAAUGUCCUCCCCUGUGGCUGCC
UCAGCUCAUGCCUUUGGCCUGAAGUCCCAGCAUUGAUGGCAGCCCCUCAUCUUCCAAGUU
UUGUGCUCCCCUUUACCUAACGCUUCCUGCCUCCCAUGCAUCUGUACUCCUCCCUGGUAC
UGCAUGCACGCAAUGCUAGCUGCCCCUUUCCCGUCCUGGGUACCCCGAGUCUCCCCCGAC
CUCGGGUCCCAGGUAUGCUCCCACCUCCACCUGCCCCACUCACCACCUCUGCUAGUUCCA
GACACCUCC

>JG (SEQ ID NO: 204)
CUUUGCAGGAUGAAACACUUCCCCGCUUGGCUCUCAUUCUUCCACAAGAGAGACCUUUCU
CCGGACCUGGUUGCUACUGGUUCAGCAACUCUGCAGAAAAUGUCCUCCCCUGUGGCUGCC
UCAGCUCAUGCCUUUGGCCUGAAGUCCCAGCAUUGAUGGCAGCCCCUCAUCUUCCAAGUU
UUGUGCUCCCCUUUACCUAACGCUUCCUGCCUCCCAUGCAUCUGUACUCCUCCCUGACAG
CGUGGGCAACGCCUGCCGCCUGCUCUGAGGCCCGAUCCAGUGGGCAGGCCAAGGCCUGCU

-continued

GGGCCCCCGCGGACCCAGGUGCUCUGGGUCACGGUCCCUGUCCCCGCACCCCCGCUUCUG

UCUGCCCCAUUGUGGCUCCUCAGGCUCUCUCCCCUGCUCUCCCACCUCUACCUCCACCCC

CAC

>JhBg (SEQ ID NO: 205)
CUUUGCAGGAUGAAACACUUCCCCGCUUGGCUCUCAUUCUUCCACAAGAGAGACCUUUCU

CCGGACCUGGUUGCUACUGGUUCAGCAACUCUGCAGAAAAUGUCCUCCCCUGUGGCUGCC

UCAGCUCAUGCCUUUGGCCUGAAGUCCCAGCAUUGAUGGCAGCCCCUCAUCUUCCAAGUU

UUGUGCUCCCCUUUACCUAACGCUUCCUGCCUCCCAUGCAUCUGUACUCCUCCGAGAGCU

CGCUUUCUUGCUGUCCAAUUUCUAUUAAAGGUUCCUUUGUUCCCUAAGUCCAACUACUAA

ACUGGGGGAUAUUAUGAAGGGCCUUGAGCAUCUGGAUUCUGCCUAAUAAAAAACAUUUAU

UUUCAUUGCUGCGUC

>JI (SEQ ID NO: 206)
CUUUGCAGGAUGAAACACUUCCCCGCUUGGCUCUCAUUCUUCCACAAGAGAGACCUUUCU

CCGGACCUGGUUGCUACUGGUUCAGCAACUCUGCAGAAAAUGUCCUCCCCUGUGGCUGCC

UCAGCUCAUGCCUUUGGCCUGAAGUCCCAGCAUUGAUGGCAGCCCCUCAUCUUCCAAGUU

UUGUGCUCCCCUUUACCUAACGCUUCCUGCCUCCCAUGCAUCUGUACUCCUCCCAAGCAC

GCAGCAAUGCAGCUCAAAACGCUUAGCCUAGCCACACCCCCACGGGAAACAGCAGUGAUU

AACCUUUAGCAAUAAACGAAAGUUUAACUAAGCUAUACUAACCCCAGGGUUGGUCAAUUU

CGUGCCAGCCACACC

>JJ (SEQ ID NO: 207)
CUUUGCAGGAUGAAACACUUCCCCGCUUGGCUCUCAUUCUUCCACAAGAGAGACCUUUCU

CCGGACCUGGUUGCUACUGGUUCAGCAACUCUGCAGAAAAUGUCCUCCCCUGUGGCUGCC

UCAGCUCAUGCCUUUGGCCUGAAGUCCCAGCAUUGAUGGCAGCCCCUCAUCUUCCAAGUU

UUGUGCUCCCCUUUACCUAACGCUUCCUGCCUCCCAUGCAUCUGUACUCCUCCCUUUGCA

GGAUGAAACACUUCCCCGCUUGGCUCUCAUUCUUCCACAAGAGAGACCUUUCUCCGGACC

UGGUUGCUACUGGUUCAGCAACUCUGCAGAAAAUGUCCUCCCCUGUGGCUGCCUCAGCUC

AUGCCUUUGGCCUGAAGUCCCAGCAUUGAUGGCAGCCCCUCAUCUUCCAAGUUUUGUGCU

CCCCUUUACCUAACGCUUCCUGCCUCCCAUGCAUCUGUACUCCUCC

>FI UTR 97.5% homology (random modifications)
(SEQ ID NO: 208)
CUGGUACUGCAUGGACGCAAUGCUAGCUGCCCCUUUCCCGUCCUGGGUACCCCGAGUCAC

CCCCGACCUCGGGUCCCAGGUAUCGUCCCACCUCCACCUGCCCCACUCACCACCUCUGCU

AGUUCCAGACACCUCCCAAGCACGCAGCAAUGCAGCUCAAAACGCUUAGCAUAGCCACAC

CCCCACGGGAAACAGCAGUGAUUAACCUUUAGCAAUAAUCGAAUGUUUAACUAAGCUAUA

CUAACCCCAGGGUUGGUCAAUUUCGUGCCAGCCACACC

>FI UTR 95% homology (random modifications) (SEQ ID NO: 209)
CUCGUACUGCAUGGACGCAAUGCUAGCUGCCCCUUUCCCGUCCUGGGUACCCCGAGUCAC

CACCGACCUCGGGUCCCAGGUAUCGUCCCACCUCCACGUGCCCCACUCACCACCUCUGCU

AGUUCCAGACACCUCCCAAGCACGCAGCAAUGCAGCUCAAAACGCUUAGCAUAGCCACAC

CCCCACGGGAAACAGUAGUGAUUAACCUUUAGCAAUAAUCGAAUGUCUAACUAAGCUAUA

CUAACCCCAGGGUUGAUCAAUUACGUGCCAGCCACACC

-continued

>FI UTR 92.5% homology (random modifications)
(SEQ ID NO: 210)
CUCGUACUGCAUGGACGCAAUGCUAGCUGCCCCUUUCCCGUCCUGGGUACCCCGAGUCAC

CACCGACCUCGGGUCCCAGGUAUCGUCCCACCUCCACGUGCCCCACUCACCACCUUUGCU

AGUUCCAGACACCUCCCAUGCACGCAGCAAUGCAGAUCAAAACGCUUAGCAUAGCCACAC

CCCCACGGGAAACAGUAGUGAUUAACCUUUAGCAAUAAUCGAAUGUCUAACUAAGCUAUA

CUAACCCCAGGGUUGAUCAAUUACGUGCCAGCCACACC

>FI UTR 90% homology (random modifications) (SEQ ID NO: 211)
GUCGUACUGCAUGGACGCAAUGCUAGCAGCACCUUUCCCGUCCUGGGUACCCCGAGUCAC

CACCGACCUCGGGUCCCAGGUAUCGUCCCACCUCCACGUGCCCCACCCACCACCUUUGCU

AGUUCCAGAGACCUCCCAUGCACGCAGCAAUGCAGAUCAAAACGCUUAGCAUAGCCACAC

CGCCACGGGAAACAGUAGUGAUCAACCUUUAGCUAUAAUCGAAUGUCUAACUAAGCUAUU

CUAACCACAGGGUUGAUCAAUUACGUGCCAGCCAGACC

>FI 8 nt mutation (SEQ ID NO: 212)
CUGGUACUGCAUGCACGCAAUGCUAGCUGCCCCAAAGGGCUCCUGGGUACCCCGAGUCUC

CCCCGACCUCGGGUCCCAGGUAUGCUCCCACCUCCACCUGCCCCACUCACCACCUCUGCU

AGUUCCAGACACCUCCCAAGCACGCAGCAAUGCAGCUCAAAACGCUUAGCCUAGCCACAC

CCCCACGGGAAACAGCAGUGAUUAACCUUUAGCAAUAAACGAAAGUUUAACUAAGCUAUA

CUAACCCCAGGGUUGGUCAAUUUCGUGCCAGCCACACC

>FI UTR 98.75% homology (structure destabilizing
modifications) (SEQ ID NO: 213)
CUGGUACUGCAUGCACGCAAUGCUAGCUGCCCCUUUCCCGUGGUCCGUACCCCGAGUCUC

CCCCGACCUCGGGUCCCAGGUAUGCUCCCACCUCCACCUGCCCCACUCACCACCUCUGCU

AGUUCCAGACACCUCCCAAGCACGCAGCAAUGCAGCUCAAAACGCUUAGCCUAGCCACAC

CCCCACGGGAAACAGCAGUGAUUAACCUUUAGCAAUAAACGAAAGUUUAACUAAGCUAUA

CUAACCCCAGGGUUGGUCAAUUUCGUGCCAGCCACACC

>FI UTR 97.5% homology (structure destabilizing
modifications) (SEQ ID NO: 214)
CUGGUACUGCAUGCACGCAAUGCUAGCUGCCCCUUUCCCGUGGACCGUACGGCGAGUCUC

CCCCGACCUCGGGUCCCAGGUAUGCUCCCACCUCCACCUGCCCCACUCACCACCUCUGCU

AGUUCCAGACACCUCCCAAGCACGCAGCAAUGCAGCUCAAAACGCUUAGCCUAGCCACAC

CCCCACGGGAAACAGCAGUGAUUAACCUUUAGCAAUAAACGAAAGUUUAACUAAGCUAUA

CUAACCCCAGGGUUGGUCAAUUUCGUGCCAGCCACACC

>FI UTR 96.25% homology (structure destabilizing
modifications) (SEQ ID NO: 215)
CUGGUACUGCAUGCACGCAAUGCUAGCUGCCCCUUUGCCGUGGACCGUACGGGCUGUCUC

CCCCGACCUCGGGUCCCAGGUAUGCUCCCACCUCCACCUGCCCCACUCACCACCUCUGCU

AGUUCCAGACACCUCCCAAGCACGCAGCAAUGCAGCUCAAAACGCUUAGCCUAGCCACAC

CCCCACGGGAAACAGCAGUGAUUAACCUUUAGCAAUAAACGAAAGUUUAACUAAGCUAUA

CUAACCCCAGGGUUGGUCAAUUUCGUGCCAGCCACACC

>FI UTR 95% homology (structure destabilizing modifications)
(SEQ ID NO: 216)
CUGGUACUGCAUGCACGCAAUGCUAGCUGCCCCUUUGGGCUGGACCGUACGGGCUGUCUC

CCCCGACCUCGGGUCCCAGGUAUGCUCCCACCUCCACCUGCCCCACUCACCACCUCUGCU

AGUUCCAGACACCUCCCAAGCACGCAGCAAUGCAGCUCAAAACGCUUAGCCUAGCCACAC

-continued

CCCCACGGGAAACAGCAGUGAUUAACCUUUAGCAAUAAACGAAAGUUUAACUAAGCUAUA

CUAACCCCAGGGUUGGUCAAUUUCGUGCCAGCCACACC

>FI UTR 97.5% homology (structure retaining modifications)
(SEQ ID NO: 217)
CUGGUACUGCAUGCACGCAAUGCUAGCUGCCCCUUUCCCGUGGUCCGUACCCCGAGUCUC

CCCCGACCUCGGGUCGGACCUAUGCUCCCACCUCCACCUGCCCCACUCACCACCUCUGCU

AGUUCCAGACACCUCCCAAGCACGCAGCAAUGCAGCUCAAAACGCUUAGCCUAGCCACAC

CCCCACGGGAAACAGCAGUGAUUAACCUUUAGCAAUAAACGAAAGUUUAACUAAGCUAUA

CUAACCCCAGGGUUGGUCAAUUUCGUGCCAGCCACACC

>FI UTR 95% (structure retaining modifications) (SEQ ID
NO: 218)
CUGGUACUGCAUGCACGCAAUGCUAGCUGCCCCUUUCCCGUGGACCGUACGGCGAGUCUC

CCCCGACCUCGCCUCGGUCCUAUGCUCCCACCUCCACCUGCCCCACUCACCACCUCUGCU

AGUUCCAGACACCUCCCAAGCACGCAGCAAUGCAGCUCAAAACGCUUAGCCUAGCCACAC

CCCCACGGGAAACAGCAGUGAUUAACCUUUAGCAAUAAACGAAAGUUUAACUAAGCUAUA

CUAACCCCAGGGUUGGUCAAUUUCGUGCCAGCCACACC

>FI UTR 92.5% (structure retaining modifications) (SEQ ID
NO: 219)
CUGGUACUGCAUGCACGCAAUGCUAGCUGCCCCUUUGCCGUGGACCGUACGGGCUGUCUC

CCCCGACCAGCCCUCGGUCCUAUGCUCCCACCUCCACCUGCCCCACUCACCACCUCUGCU

AGUUCCAGACACCUCCCAAGCACGCAGCAAUGCAGCUCAAAACGCUUAGCCUAGCCACAC

CCCCACGGCAAACAGCAGUGAUUAACCUUUAGCAAUAAACGAAAGUUUAACUAAGCUAUA

CUAACCCCAGGGUUGGUCAAUUUCGUGCCAGCCACACC

>FI UTR 90% (structure retaining modifications) (SEQ ID
NO: 220)
CUGGUACUGCAUGCACGCAAUGCUAGCUGCCCCUUUGGGCUGGACCGUACGGGCUGUCUC

CCCCGACCAGCCCUCGGUCCUAUGCUCCCACCUCCACCUGCCCCACUCACCACCUCUGCU

AGUUCCAGACACCUCCCAAGCACGCAGCAAUGCAGCUCAAAACGCUUAGCCUAGCCACAC

CCCCAGCCCAAACAGCAGUGAUUAACCUUUAGCAAUAAACGAAAGUUUAACUAAGCUAUA

CUAACCCCAGGGUUGGUCAAUUUCGUGCCAGCCACACC

---

The invention claimed is:

1. A nucleic acid molecule comprising in the 5' 3' direction of transcription relative to synthesis of a transcript:
   (a) a promoter;
   (b) a transcribable nucleic acid sequence or a nucleic acid sequence for introducing a transcribable nucleic acid sequence; and
   (c) a nucleic acid sequence which codes for a 3'-untranslated region, and is characterized in that, when the nucleic acid molecule is transcribed under the control of the promoter (a), a transcript including the 3'-untranslated region is produced, wherein said nucleic acid sequence (c) is not naturally linked to the transcribable nucleic acid sequence (b),
   wherein said 3'-untranslated region in the transcript comprises a nucleic acid sequence of the 3'-untranslated region of Amino-Terminal Enhancer Of Split (AES), which comprises:
   (A) a nucleic acid sequence selected from the group consisting of SEQ ID NOs: 86 to 89,
   (B) a fragment comprising at least 80% of any one of SEQ ID NOs: 86 to 89, or
   (C) a variant comprising a nucleic acid sequence that is at least 90% identical to the nucleic acid sequence (A) or the fragment (B) entire.

2. The nucleic acid molecule of claim 1, wherein the nucleic acid sequences (b) and (c) under the control of the promoter (a) can be transcribed to give a common transcript in which the nucleic acid sequence transcribed from the nucleic acid sequence (c) is active so as to increase the translation efficiency and/or the stability of the nucleic acid sequence transcribed from the transcribable nucleic acid sequence (b).

3. The nucleic acid molecule of claim 1, wherein the nucleic acid sequence of the 3'-untranslated region of AES in the transcript comprises
   (A) the nucleic acid sequence of SEQ ID NO: 86,
   (B) a fragment comprising at least 80% of SEQ ID NO: 86, or
   (C) a variant comprising a nucleic acid sequence that is at least 90% identical to the nucleic acid sequence (A) or the fragment (B).

4. The nucleic acid molecule of claim 3, wherein the 3'-untranslated region in the transcript further comprises a nucleic acid sequence of the non-coding RNA of MT-RNR1 as set forth in SEQ ID NO: 115.

5. The nucleic acid molecule of claim 1, wherein the 3'-untranslated region in the transcript further comprises a nucleic acid sequence of the non-coding RNA of Mitochondrially Encoded 12S RNA (MT-RNR1), which comprises:
   (A) a nucleic acid sequence selected from the group consisting of SEQ ID NOs: 105 to 121,
   (B) a fragment comprising at least 80% of any one of SEQ ID NOs: 105 to 121, or
   (C) a variant comprising a nucleic acid sequence that is at least 90% identical to the nucleic acid sequence (A) or the fragment (B).

6. The nucleic acid molecule of claim 5, wherein the nucleic acid sequence of the non-coding RNA of MT-RNR1 in the transcript comprises:
   (A) the nucleic acid sequence of SEQ ID NO: 115,
   (B) a fragment comprising at least 80% of SEQ ID NO: 115, or
   (C) a variant comprising a nucleic acid sequence that is at least 90% identical to the nucleic acid sequence (A) or the fragment (B).

7. The nucleic acid molecule of claim 6, wherein the nucleic acid sequence of the 3'-untranslated region of AES is located 5' to the nucleic acid sequence of the non-coding RNA of MT-RNR1 in the transcript.

8. The nucleic acid molecule of claim 7, wherein the 3'-untranslated region in the transcript comprises
   (A) the nucleic acid sequence of SEQ ID NO: 174
   (B) a fragment comprising at least 80% of SEQ ID NO: 174, or
   (C) a variant comprising a nucleic acid sequence that is at least 90% identical to the nucleic acid sequence (A) or the fragment (B).

9. The nucleic acid molecule of claim 6, wherein the nucleic acid sequence of the 3'-untranslated region of AES is located 3' to the nucleic acid sequence of the non-coding RNA of MT-RNR1 in the transcript.

10. The nucleic acid molecule of claim 1, further comprising (d) a nucleic acid sequence which codes for a polyadenyl sequence, wherein the nucleic acid molecule is characterized in that, when the nucleic acid molecule is transcribed under the control of the promoter (a), the transcript 3' includes the polyadenyl sequence.

11. The nucleic acid molecule of claim 10, wherein said polyadenyl sequence comprises at least 20 A nucleotides, or at least 20 consecutive A nucleotides.

12. The nucleic acid molecule of claim 10, wherein the nucleic acid sequences (b), (c) and (d) under the control of the promoter (a) can be transcribed to give a common transcript.

13. The nucleic acid molecule of claim 12, wherein the nucleic acid sequence transcribed from the nucleic acid sequence (c) is active so as to increase the translation efficiency and/or the stability of the nucleic acid sequence transcribed from the transcribable nucleic acid sequence (b).

14. The nucleic acid molecule of claim 10, wherein in the transcript the polyadenyl sequence is located at the 3' end of the transcript.

15. The nucleic acid molecule of claim 10, wherein said polyadenyl sequence comprises at least 120 A nucleotides, or at least 120 consecutive A nucleotides.

16. The nucleic acid molecule of claim 10, wherein said polyadenyl sequence is unmasked.

17. The nucleic acid molecule of claim 10, wherein the polyadenyl sequence comprises a sequence of consecutive nucleotides, which sequence contains one or more nucleotides other than A nucleotides.

18. The nucleic acid molecule of claim 17, wherein the sequence of consecutive nucleotides is located within a region from position 21 to position 80, or from position 21 to position 60, or from position 31 to position 50, of said polyadenyl sequence.

19. The nucleic acid molecule of claim 17, wherein the first and the last nucleotide of the sequence of consecutive nucleotides is a nucleotide other than an A nucleotide.

20. The nucleic acid molecule of claim 17, wherein the sequence of consecutive nucleotides within the polyadenyl sequence is preceded by at least 20 A residues and/or is followed by at least 20 A residues.

21. The nucleic acid molecule of claim 17, wherein the sequence of consecutive nucleotides has a length of at least 3, at least 4, at least 5, at least 6, at least 8, at least 10, or at least 15 nucleotides.

22. The nucleic acid molecule of claim 21, wherein the sequence of consecutive nucleotides has a length of no more than 50, no more than 30, or no more than 20 nucleotides.

23. The nucleic acid molecule of claim 17, wherein the sequence of consecutive nucleotides comprises no more than 3, no more than 2, or no consecutive A residues.

24. The nucleic acid molecule of claim 10, wherein said polyadenyl sequence comprises at least 40, at least 80, or at least 100 A nucleotides, or at least 40, at least 80, or at least 100 consecutive A nucleotides.

25. The nucleic acid molecule of claim 10, wherein said polyadenyl sequence comprises at least 80 nucleotides, at least 90 or at least 100 A nucleotides.

26. The nucleic acid molecule of claim 1, which is a closed circular molecule or a linear molecule.

27. The nucleic acid molecule of claim 1, wherein the transcribable nucleic acid sequence comprises a nucleic acid sequence coding for a peptide or protein and/or the nucleic acid sequence for introducing a transcribable nucleic acid sequence is or comprises a multiple cloning site.

28. The nucleic acid molecule of claim 27, wherein the peptide or protein is a disease antigen.

29. The nucleic acid molecule of claim 28, wherein said disease antigen is selected from the group consisting of: a tumor-associated antigen, a viral antigen, and a bacterial antigen.

30. The nucleic acid molecule of claim 28, wherein said disease-associated antigen is a tumor-associated antigen that is not expressed in normal tissues or is mutated in tumor cells.

31. The nucleic acid molecule of claim 1, further comprising one or more members selected from the group consisting of: (a) a reporter gene; (b) a selectable marker; and (c) an origin of replication.

32. The nucleic acid molecule of claim 1, which is suitable for in vitro transcription of RNA.

33. The nucleic acid molecule of claim 1, wherein the 3'-untranslated region further comprises one or more nucleic acid sequences selected from the group consisting of the following:
   a second nucleic acid sequence of the 3'-untranslated region of AES, which comprises (A) a nucleic acid sequence selected from the group consisting of SEQ ID NOs: 86 to 89, (B) a fragment comprising at least 80% of any one of SEQ ID NOs: 86 to 89, or (C) a variant comprising a nucleic acid sequence that is at least 90% identical to the nucleic acid sequence (A) or the fragment (B);
   a nucleic acid sequence of the 3'-untranslated region of Fc Fragment of IgG (FCGRT), which comprises (A) a nucleic acid sequence selected from the group consisting of SEQ ID NOs: 1 to 50, (B) a fragment comprising at least 80% of any one of SEQ ID NOs: 1 to 50, or (C) a variant comprising a nucleic acid sequence that is at least 90% identical to the nucleic acid sequence (A) or the fragment (B);
   a nucleic acid sequence of the 3'-untranslated region of Lymphocyte Specific Protein 1 (LSP1), which comprises (A) a nucleic acid sequence selected from the group consisting of SEQ ID NOs: 51 to 72, (B) a fragment comprising at least 80% of any one of SEQ ID NOs: 51 to 72, or (C) a variant comprising a nucleic acid sequence that is at least 90% identical to the nucleic acid sequence (A) or the fragment (B);
   a nucleic acid sequence of the 3'-untranslated region of Chemokine Ligand 22 (CCL22), which comprises (A) a nucleic acid sequence selected from the group consisting of SEQ ID NOs: 73 to 85, (B) a fragment comprising at least 80% of any one of SEQ ID NOs: 73 to 85, or (C) a variant comprising a nucleic acid sequence that is at least 90% identical to the nucleic acid sequence (A) or the fragment (B);
   a nucleic acid sequence of the 3'-untranslated region of Phospholipase D Family Member 3 (PLD3), which comprises (A) a nucleic acid sequence selected from the group consisting of SEQ ID NOs: 90 to 104, (B) a fragment comprising least 80% of any one of SEQ ID NOs: 90 to 104, or (C) a variant comprising a nucleic acid sequence that is at least 90% identical to the nucleic acid sequence (A) or the fragment (B);
   a nucleic acid sequence of the 3'-untranslated region of Major Histocompatibility Complex Class II DR Beta 4 (HLA-DRB4), which comprises (A) a nucleic acid sequence selected from the group consisting of SEQ ID NOs: 122 to 143, (B) a fragment comprising at least 80% of any one of SEQ ID NOs: 122 to 143, or (C) a variant comprising a nucleic acid sequence that is at least 90% identical to the nucleic acid sequence (A) or the fragment (B).

34. The nucleic acid molecule of claim 1, wherein the nucleic acid sequence of the 3'-untranslated region of AES in the transcript is set forth in SEQ ID NO: 86.

35. A method of obtaining RNA, the method comprising:
   (a) providing the nucleic acid molecule of claim 1 as a template, and
   (b) transcribing the nucleic acid molecule into RNA.

36. The method of claim 35, further comprising, prior to transcription of the nucleic acid molecule, cleavage of the nucleic acid molecule.

37. The method of claim 35, wherein transcription is carried out in vitro.

38. An RNA molecule comprising in the 5' 3' direction:
   (a) a 5'-untranslated region;
   (b) a nucleic acid sequence coding for a peptide or protein; and
   (c) a 3'-untranslated region which is not naturally linked to the nucleic acid sequence of (b), said 3'-untranslated region comprising a nucleic acid sequence of the 3'-untranslated region of AES, which comprises:

(A) a nucleic acid sequence selected from the group consisting of SEQ ID NOs: 86 to 89,
(B) a fragment comprising at least 80% of any one of SEQ ID NOs: 86 to 89, or
(C) a variant comprising a nucleic acid sequence that is at least 90% identical to the nucleic acid sequence (A) or the fragment (B).

39. The RNA molecule of claim 38, further comprising (d) a polyadenyl sequence.

40. The RNA molecule of claim 39, wherein the polyadenyl sequence (d) is located at the 3' end of said RNA molecule.

41. The RNA molecule of claim 39, wherein the polyadenyl sequence comprises a sequence of consecutive nucleotides, which sequence contains one or more nucleotides other than A nucleotides.

42. The RNA molecule of claim 39, wherein the nucleic acid sequence (c) and the polyadenyl sequence (d) are active so as to increase the translation efficiency and/or the stability of the nucleic acid sequence coding for a peptide or protein.

43. The RNA molecule of claim 39, wherein the polyadenyl sequence comprises a sequence of consecutive nucleotides, which sequence contains one or more nucleotides other than A nucleotides.

44. The RNA molecule of claim 38, wherein the nucleic acid sequence (c) is active so as to increase the translation efficiency and/or the stability of the nucleic acid sequence coding for a peptide or protein.

45. The RNA molecule of claim 38, further comprising (e) a 5' Cap.

46. The RNA molecule of claim 38, wherein said 3'-untranslated region further comprises nucleic acid sequence of the non-coding RNA of MT-RNR1, which comprises (A) a nucleic acid sequence selected from the group consisting of SEQ ID NOs: 105 to 121, (B) a fragment comprising at least 80% of any one of SEQ ID NOs: 105 to 121, or (C) a variant comprising a nucleic acid sequence that is at least 90% identical to the nucleic acid sequence (A) or the fragment (B).

47. The RNA molecule of claim 46, wherein the nucleic acid sequence of the 3'-untranslated region of AES is located 5' to the nucleic acid sequence of the non-coding RNA of MT-RNR1.

48. The RNA molecule of claim 38, wherein the 5' UTR comprises the 5' UTR of human alpha globin and a Kozak sequence.

49. The RNA molecule of claim 38, further comprising (d) a polyadenyl sequence, which comprises at least 120 A nucleotides.

50. The RNA molecule of claim 38, further comprising (d) an unmasked polyadenyl sequence.

51. The RNA molecule of claim 38, wherein the peptide or protein encoded by the nucleic acid sequence (b) is a tumor-associated antigen, which antigen is not expressed in normal tissues or is mutated in tumor cells.

52. The RNA molecule of claim 51, wherein the peptide or protein encoded by the nucleic acid sequence (b) is a disease antigen.

53. The RNA molecule of claim 52, wherein the disease antigen is selected from the group consisting of a tumor-associated antigen, a viral antigen, and a bacterial antigen.

54. The RNA molecule of claim 38, further comprising (e) a 5' cap.

55. The RNA molecule of claim 54, wherein the 5' cap is β-S-ARCA.

56. A nanoparticle comprising the RNA molecule of claim 38.

57. The RNA of claim 38, wherein the 3'-untranslated region further comprises one or more nucleic acid sequences selected from the group consisting of the following:
a second nucleic acid sequence of the 3'-untranslated region of AES, which comprises (A) a nucleic acid sequence selected from the group consisting of SEQ ID NOs: 86 to 89, (B) a fragment comprising at least 80% of any one of SEQ ID NOs: 86 to 89, or (C) a variant comprising a nucleic acid sequence that is at least 90% identical to the nucleic acid sequence (A) or the fragment (B);
a nucleic acid sequence of the 3'-untranslated region of Fc Fragment of IgG (FCGRT), which comprises (A) a nucleic acid sequence selected from the group consisting of SEQ ID NOs: 1 to 50, (B) a fragment comprising at least 80% of any one of SEQ ID NOs: 1 to 50, or (C) a variant comprising a nucleic acid sequence that is at least 90% identical to the nucleic acid sequence (A) or the fragment (B);
a nucleic acid sequence of the 3'-untranslated region of Lymphocyte Specific Protein 1 (LSP1), which comprises (A) a nucleic acid sequence selected from the group consisting of SEQ ID NOs: 51 to 72, (B) a fragment comprising at least 80% of any one of SEQ ID NOs: 1 to 50, or (C) a variant comprising a nucleic acid sequence that is at least 90% identical to the nucleic acid sequence (A) or the fragment (B);
a nucleic acid sequence of the 3'-untranslated region of Chemokine Ligand 22 (CCL22), which comprises (A) a nucleic acid sequence selected from the group consisting of SEQ ID NOs: 73 to 85, (B) a fragment comprising at least 80% of any one of SEQ ID NOs: 73 to 85, or (C) a variant comprising a nucleic acid sequence that is at least 90% identical to the nucleic acid sequence (A) or the fragment (B);
a nucleic acid sequence of the 3'-untranslated region of Phospholipase D Family Member 3 (PLD3), which comprises (A) a nucleic acid sequence selected from the group consisting of SEQ ID NOs: 90 to 104 (B) a fragment comprising at least 80% of any one of SEQ ID NOs: 90 to 104, or (C) a variant comprising a nucleic acid sequence that is at least 90% identical to the nucleic acid sequence (A) or the fragment (B);
a nucleic acid sequence of the 3'-untranslated region of Major Histocompatibility Complex Class II DR Beta 4 (HLA-DRB4), which comprises (A) a nucleic acid sequence selected from the group consisting of SEQ ID NOs: 122 to 143, (B) a fragment comprising at least 80% of any one of SEQ ID NOs: 122 to 143, or (C) a variant comprising a nucleic acid sequence that is at least 90% identical to the nucleic acid sequence (A) or the fragment (B).

58. The RNA molecule of claim 38, wherein the nucleic acid sequence of the 3'-untranslated region of AES is set forth in SEQ ID NO: 86.

59. The RNA molecule of claim 38, wherein the 3'-untranslated region further comprises a nucleic acid sequence of the non-coding RNA of MT-RNR1 as set forth in SEQ ID NO: 115.

60. A method of obtaining a peptide or protein, the method comprising translating the RNA molecule of claim 38.

61. A method comprising: transfecting a host cell with the RNA molecule of claim 38.

62. The method of claim 61, wherein the host cell is an antigen-presenting cell.

63. The method of claim 62, wherein the antigen-presenting cell is a dendritic cell, a monocyte, or a macrophage.

64. A method of obtaining RNA, the method comprising:
(A) coupling a nucleic acid sequence (b) which codes for a 3'-untranslated region to a transcribable nucleic acid sequence (a) comprising a nucleic acid sequence coding for a peptide or protein to form a nucleic acid molecule, and is characterized in that, when the nucleic acid molecule is transcribed, the nucleic acid sequence (b) is located at 3' end of the transcribable nucleic acid sequence (a), and
(B) transcribing the nucleic acid molecule from (A) to produce RNA comprising said 3'-untranslated region,
wherein said 3'-untranslated region comprises (i) a nucleic acid sequence selected from the group consisting of SEQ ID NOs: 86 to 89, (ii) a fragment comprising at least 80% of any one of SEQ ID NOs: 86 to 89, or (iii) a variant comprising a nucleic acid sequence that is at least 90% identical to the nucleic acid sequence (i) or the fragment (ii).

65. The method of claim 64, wherein the nucleic acid sequences (a) and (b) can be transcribed to give a common transcript in which the nucleic acid sequence transcribed from the nucleic acid sequence (b) is active so as to increase the translation efficiency and/or the stability of the nucleic acid sequence transcribed from the transcribable nucleic acid sequence (a).

66. The method of claim 64, further comprising coupling a nucleic acid sequence (c), which codes for a polyadenyl sequence, to the nucleic acid molecule, and is characterized in that, when the nucleic acid molecule is transcribed, the polyadenyl sequence is located at the 3' end of the transcribable nucleic acid sequence (a).

67. The method of claim 66, wherein the nucleic acid sequences (a), (b), and (c) can be transcribed to give a common transcript in which the nucleic acid sequence transcribed from the nucleic acid sequence (b) is active so as to increase the translation efficiency and/or the stability of the nucleic acid sequence transcribed from the transcribable nucleic acid sequence (a).

68. The method of claim 66, wherein the polyadenyl sequence comprises a sequence of consecutive nucleotides, which sequence contains one or more nucleotides other than A nucleotides.

69. The method of claim 66, wherein the nucleic acid sequences (a), (b), and (c) can be transcribed to give a common transcript in which the nucleic acid sequences transcribed from the nucleic acid sequences (b) and (c) are active so as to increase the translation efficiency and/or the stability of the nucleic acid sequence transcribed from the transcribable nucleic acid sequence (a).

70. The method of claim 64, wherein said 3'-untranslated region in the transcript further comprises a nucleic acid sequence of the non-coding RNA of MT-RNR1, which comprises (A) a nucleic acid sequence selected from the group consisting of SEQ ID NOs: 105 to 121, (B) a fragment comprising at least 80% of any one of SEQ ID NOs: 105 to 121, or (C) a variant comprising a nucleic acid sequence that is at least 90% identical to the nucleic acid sequence (A) or the fragment (B).

71. The method of claim 70, wherein the nucleic acid sequence of the 3'-untranslated region of AES is located 5' to the nucleic acid sequence of the non-coding RNA of MT-RNR1 in the transcript.

72. A nucleic acid molecule comprising in the 5' 3' direction of transcription relative to synthesis of a transcript:
(a) a promoter;
(b) a transcribable nucleic acid sequence or a nucleic acid sequence for introducing a transcribable nucleic acid sequence; and
(c) a nucleic acid sequence which codes for a 3'-untranslated region
wherein the nucleic acid molecule is characterized in that so that, when the nucleic acid molecule is transcribed under control of the promoter (a), a transcript is produced that includes the 3'-untranslated region (c), wherein said 3'-untranslated region (c) is not naturally linked to the transcribable nucleic acid sequence (b),
wherein said 3'-untranslated region in the transcript comprises a combination of a nucleic acid sequence of the 3'-untranslated region of Amino-Terminal Enhancer of Split (AES) and a nucleic acid sequence of the non-coding RNA of MT-RNR1, which combination has the nucleic acid sequence of SEQ ID NO: 174.

73. An RNA molecule comprising in the 5' 3' direction:
(a) a 5'-untranslated region;
(b) a nucleic acid sequence coding for a peptide or protein; and
(c) a 3'-untranslated region which is not naturally linked to the nucleic acid sequence (b), said 3'-untranslated region comprising a combination of a nucleic acid sequence of the 3'-untranslated region of Amino-Terminal Enhancer of Split (AES) and a nucleic acid sequence of the non-coding RNA of MT-RNR1, which combination has the nucleic acid sequence of SEQ ID NO: 174.

* * * * *

UNITED STATES PATENT AND TRADEMARK OFFICE
CERTIFICATE OF CORRECTION

PATENT NO. : 11,492,628 B2
APPLICATION NO. : 15/763709
DATED : November 8, 2022
INVENTOR(S) : Alexandra Orlandini Von Niessen et al.

It is certified that error appears in the above-identified patent and that said Letters Patent is hereby corrected as shown below:

On the Title Page

Item (30) Foreign Priority Application Priority Data, replace "Oct. 5, 2016 (EP) .............. PCT/EP2015/073814" with --Oct. 7, 2015 (EP) .............. PCT/EP2015/073180--

In the Specification

Column 5, Line 33, replace "preceeded" with --preceded--

Column 5, Line 37, replace "preceeded" with --preceded--

Column 5, Line 51, replace "preceeded" with --preceded--

Column 11, Line 37, replace "preceeded" with --preceded--

Column 11, Line 45, replace "preceeded" with --preceded--

Column 18, Line 44, replace "Neddleman" with --Needleman--

Column 26, Line 5, replace "guanylaste" with --guanylate--

Column 26, Line 14, replace "Wilebrand" with --Willebrand--

Column 29, Line 67 - Column 30, Line 1, replace "dipalmipoyl" with --dipalmitoyl--

Column 31, Line 47, replace "is used in it" with --is used in its--

Column 39, Line 5, replace "of it development" with --of its development--

Signed and Sealed this
Sixth Day of June, 2023

Katherine Kelly Vidal
*Director of the United States Patent and Trademark Office*

Column 57, Line 18, replace "ressembles" with --resembles--

Column 60, Lines 17-18, replace "manufacturers" with --manufacturer's--

Column 60, Line 44, replace "manufacturers" with --manufacturer's--